US009795642B2

(12) United States Patent
Stevens et al.

(10) Patent No.: US 9,795,642 B2
(45) Date of Patent: Oct. 24, 2017

(54) ENTEROCOCCUS FAECALIS BACTERIOPHAGE AND USES THEREOF

(71) Applicants: TEMPLE UNIVERSITY—OF THE COMMONWEALTH SYSTEM OF HIGHER EDUCATION, Philadelphia, PA (US); J. CRAIG VENTER INSTITUTE, INC., Rockville, MD (US)

(72) Inventors: Roy H. Stevens, Conshohocken, PA (US); Hongming Zhang, Wynnewood, PA (US); Derrick E. Fouts, Gaithersburg, MD (US); Jessica DePew, Germantown, MD (US)

(73) Assignees: TEMPLE UNIVERSITY—Of The Commonwealth System of Higher Education, Philadelphia, PA (US); J. Craig Venter Institute, Inc., Rockville, MD (US)

( * ) Notice: Subject to any disclaimer, the term of this patent is extended or adjusted under 35 U.S.C. 154(b) by 0 days.

(21) Appl. No.: 14/779,159

(22) PCT Filed: Mar. 25, 2014

(86) PCT No.: PCT/US2014/031726
§ 371 (c)(1),
(2) Date: Sep. 22, 2015

(87) PCT Pub. No.: WO2014/160710
PCT Pub. Date: Oct. 2, 2014

(65) Prior Publication Data
US 2016/0067290 A1     Mar. 10, 2016

Related U.S. Application Data

(60) Provisional application No. 61/804,922, filed on Mar. 25, 2013.

(51) Int. Cl.
| | | |
|---|---|---|
| *A61K 35/76* | (2015.01) | |
| *A01N 63/00* | (2006.01) | |
| *C12N 7/00* | (2006.01) | |
| *A61K 9/00* | (2006.01) | |
| *A61L 26/00* | (2006.01) | |

(52) U.S. Cl.
CPC .............. *A61K 35/76* (2013.01); *A01N 63/00* (2013.01); *A61K 9/0014* (2013.01); *A61L 26/0057* (2013.01); *A61L 26/0066* (2013.01); *C12N 7/00* (2013.01); *A61L 2300/404* (2013.01); *C12N 2795/00021* (2013.01); *C12N 2795/00032* (2013.01); *C12N 2795/10121* (2013.01); *C12N 2795/10122* (2013.01); *C12N 2795/10321* (2013.01); *C12N 2795/10322* (2013.01)

(58) Field of Classification Search
None
See application file for complete search history.

(56) References Cited

U.S. PATENT DOCUMENTS

| 7,582,291 B2 | 9/2009 | Yoong et al. |
| 2010/0322903 A1 | 12/2010 | Collins et al. |
| 2012/0122186 A1 | 5/2012 | Weber-Dabrowska et al. |

OTHER PUBLICATIONS

International Search Report and Written Opinion for PCT/US2014/031726 dated Sep. 5, 2014.
Stevens et al., "The annotated complete DNA sequence of Enterococcus faecalis bacteriophage φEf11 and its comparison with all available phage and predicted prophage genomes", FEMS Microbiology Letters, vol. 317, No. 1, pp. 9-26 (2011).
Yasmin, "Comparative Genomics and Transduction Potential of Enterococcus faecalis Temperate Bacteriophages", J. Bacteriol., vol. 192, No. 4, pp. 1122-1130 (2010).
Zhang et al., "Genetic modifications to temperate Enterococcus faecalis phage φEf11 that abolish the establishment of lysogeny and sensitivity to repressor, and increase host range and productivity of lytic infection", Microbiology, vol. 159, No. 6, pp. 1023-1035 (2013).
Lewis et al., "Clinical Manifestations of Enterococcal Infection", Eur. J. Clin. Microbiol. Infect. Dist., vol. 9, No. 2, pp. 111-117 (1990).
Jett et al., "Virulence of Enterococci", Clinical Microbiology Reviews, vol. 7, No. 4, pp. 462-478 (Oct. 1994).
Wright et al., "A controlled clinical trial of a therapeutic bacteriophage preparation in chronic otitis due to antibiotic-resistant Pseudomonas aeruginosa; a preliminary report of efficacy", Clin. Otolaryngology, vol. 34, pp. 349-347 (2009).
Smith et al., "Successful Treatment of Experimental *Escherichia coli* Infections in Mice Using Phage: its General Superiority over Antibiotics", Journal of General Microbiology, vol. 128, pp. 307-318 (1982).
Paisano et al., "In vitro antimicrobial effect of bacteriophages on human dentin infected with Enterococcus faecalis ATCC 29212", Oral Microbiology Immunology, vol. 19, pp. 327-330 (2004).
Moellering, "Emergence of Enterococcus as a Significant Pathogen", Clinical Infectious Diseases, vol. 14, No. 6, pp. 1173-1176 (Jun. 1992).
Megran, "Enterococcal Endocarditis", Clinical Infectious Diseases, vol. 15, No. 1, pp. 63-71 (Jul. 1992).

(Continued)

Primary Examiner — Oluwatosin Ogunbiyi
(74) Attorney, Agent, or Firm — Drinker Biddle & Reath LLP

(57) ABSTRACT

Bacteriophages are provided that infect strains of *Enterococcus faecalis*, an opportunistic bacterial pathogen that causes human disease. Also provided are methods of treating *Enterococcus faecalis* by therapeutic administration of such bacteriophages.

24 Claims, 15 Drawing Sheets

(56) References Cited

OTHER PUBLICATIONS

Biswas et a., "Bacteriophage Therapy Rescues Mice Bacteremic from a Clinical Isolate of Vancomycin-Resistant Enterococcus faecium", Infection and Immunity, vol. 70, No. 1, pp. 204-210 (Jan. 2002).

Stevens, "Bacteriophages induced from lysogenic root canal isolates of Enterococcus faecalis", Oral Microbiology Immunology', vol. 24, pp. 278-284 (2009).

Uchiyama et al., "Isolation and characterization of a novel Enterococcus faecalis bacteriophage φEF24C as a therapeutic candidate", FEMS Microbiol. Lett., vol. 278, pp. 200-206 (2008).

Uchiyama et al., "Characterization of Lytic Enzyme Open Reading Frame 9 (ORF9) Derived from Enterococcus faecalis Bacteriophage φEF24C", Applied and Environmental Microbiology, vol. 77, No. 2, pp. 200-206 (2008).

Yoong et al., "Identification of a Broadly Active Phage Lytic Enzyme with Lethal Activity against Antibiotic-Resistant Enterococcus faecalis and Enterococcus faecium", Journal of Bacteriology, vol. 186, No. 14, pp. 4808-4812 (Jul. 2004).

Son et al., "Complete genome sequence of a newly isolated lytic bacteriophage, EFAP-1 of Enterococcus faecalis, and antibacterial activity of its endolysin EFAL-1", Journal of Applied Microbiology, vol. 108, pp. 1769-1779 (2010).

Yang et al., "Construction of an Integration-Proficient Vector Based on the Site-Specific Recombination Mechanism of Enterococcal Temperate Phage φFC1", Journal of Bacteriology, vol. 184, No. 7, pp. 1859-1864 (Apr. 2002).

Nigutova et al. "Partial Characterization of Enterococcus Faecalis Bacteriophage F4", Folia Microbiology, vol. 53, No. 3, pp. 234-236 (2008).

Mazaheri Nezhad Fard et al., "Novel Bacteriophages in *Enterococcus* spp.", Curr Microbiol, vol. 60, pp. 400-406 (2010).

Rogers et al., "Characterization of Enterococcus Bacteriophages From the Small Intestine of the Rat" J. Bacteriol., vol. 85, pp. 1378-1385 (1963).

Hiriuchi et al., "Complete Genome Sequence of Bacteriophage BC-611 Specifically Infecting Enterococcus faecalis Strain NP-10011", Journal of Virology, vol. 86, No. 17, pp. 9538-9539 (Sep. 2012).

Natkin, "Isolation and Host Range of Bacteriophages Active Against Human Oral Enterococci", Archs Oral Biology, vol. 12, pp. 669-680 (1967).

Timperley et al., "A Bacteriophage Specific for *Streptococcus faecalis* Lancefield's Serotype 19", J. Pathol. Bacteriol., vol. 91, pp. 631-634 (1966).

Follett et al., "An Electron Microscope Study of a *Streptococcal bacteriophage*", Journal of General Virology, vol. 1, No. 3, pp. 281-284 (1967).

Letkiewicz et al., "Eradication of Enterococcus faecalis by Phage Therapy in Chronic Bacterial Prostatitis—case report", Folia Microbiol., vol. 54, No. 5, pp. 457-461 (2009).

Bachrach et al., "Bacteriophage isolation from human saliva", Letters in Applied Microbiology, vol. 36, pp. 50-53 (2003).

GenBank: GQ452243.1, "Enterococcus phage phiEf11, complete genome", National Center for Biotechnology Information, U.S. National Library of Medicine, 8600 Rockville Pike, Bethesda, MD (Mar. 7, 2011).

```
                    ────▶ ORF60
φEf11:   aaaatcgcaagagagaagttggctattctgaaagagaagtattcaaagaatgaatcagaagct   39367
Sp:      aaaatcgcaagagagaagttggctattctgaaagagaagtattcaaagaatgaatcagaagct    1831
φFL1C:   aagattgctagagagaagttggatattctgaaagagaagtattcaacgcatgaatcagaagct   14296
              ▲                                         ORF60
              gp39

φEf11:   ttgattgaattcgcagagagcttaccgcaatggcaaatggcaaaataattgcatataaattttg   39427
Sp:      ttgattgaattcgcagagagcttaccgcaatggcaaatggcaaaataattgcatataaattttg    1891
φFL1C:   ttgattgaattcgcggaagcttaccgcgaatggcaaaatggcaaaataattgcatatataaattttg  14356
                                                                    gp39

φEf11:   gcggttttttggcggaaagttggcggtttttatacgaatttgagtgctaatatagtaata   39487
Sp:      gcggttttttggcggaaagttggcggtttttatacgaatttgagtgctaatatagtaata    1951
φFL1C:   gcggttttttggcggaaagttggcggttttttatacgaatttgagtgctaatatagtaata  14416

φEf11:   tcgaaagtcaaagaaatggacacattacacaacacttttctcgttttagtcaccgtttgatt   39547
Sp:      tcgaaagtcaaagaaatggacacattacacaacacttttctcgttttagtcaccgtttgatt    2011
φFL1C:   tcgaaagtcaaagaaatagacacattacacaacacttttctcgttagtcaccgttcactt   14476

φEf11:   tgactttcgatggtcacttgcagacatacgttctcaataaatgaagtgaggtgaataac   39607
Sp:      tgactttcgatggtcacttgcagacatacgttctcaataaatgaagtgaggtgaataac    2071
φFL1C:   tgtctttcgatggtcacttgcagacttacgttctcaataaatgaagtgaggtgaataac  14536
```

FIG. 11A

```
φEf11:  ctcctcttttctacaagtttgcaagtgacacgttaatggaatatagctcagttggtg  39667
Sp:     ctcctcttttctacaagtttgcaagtgacacgttaatggaatatagctcagttggtg   2131
φFL1C:  ctcctcttttctacaagtttgcaaggacactttaatggaatatagctcagttggtg   14596
        ********************** *** *** ***********************

φEf11:  agcatacgactgttaatcgtagggtcatgagttcgagtctcgttattccagtaagtgca  39727
Sp:     agcgtacgactgttaatcgtagggtcatgagttcgagtctcgttattccagtaagtagct  2191
φFL1C:  agcgtacgactgttaatcgtagggtcatgagttcgagtctcgttattccagtaagtagct 14656
        *** ************************************************** ***

φEf11:  taagctgcttaaataaaatatcgtcaataattca-gtgtaactacctttacgatcgaat  39786
Sp:     -atgctacttaaataaaaatcgtcaaatcgtcaaatgtaactaccttacgatcagat  2250
φFL1C:  -atgctacttaaataaaaatcgtcaaatcgtcaaatgtaactaccttacgatcagat  14715
         * ***  **********  ****** *     ****************** ***

φEf11:  gacggttaagat-ttccctccctctcgagactgagactgcacttctgagtgtgttccttttat  39844
Sp:     gacggttaagatttttccctccctctcgagactgagactgcacttctgagtgtgttcttttttt  2310
φFL1C:  gacggttaagatttttccctccctctcgagactgagactgcacttctgagtgtgttcttttttt 14775
        ************  *********************************** ***** ******

→ORF61
φEf11:  ttaataaaattgatattatgaatgtaaaaggaggtttattatggagactaacaatacatt  39904
Sp:     aaaaattcatagctaat-----------------------------caaatttcactt   2340
φFL1C:  aaaaattcatagctaat-----------------------------caaatttcactt  14806
          *   * **                                   ** ***
```

FIG. 11B

```
φEf11:  ttcgaatctattaaaaatttc-----gactatcctagaatcgaaccatctatga-aata  39952
Sp:     ttacattctttat-attagcttatattagtagta-agtaaaaatatgaaaata         2399
φFL1C:  ttacattctttat-attagcttatattagtagta-agtaaaaatatgaaaata        14864
                  *    *         ****  **   ****     ***** ****

φEf11:  tgcggaaaaa-------------ctagagac--tggtagtaattggct---tggaga--  40091
Sp:     agtggagtgaaatttaatgagtttaaatagtctattgttgttgattttttggtggta    2459
φFL1C:  agtggagtgaaatttaatgagtttaatagtttaatagtctattgttgttattttttggtggta 14924
              *        *  *           *      *   *    **  * gp40
φEf11:  ggagcatgggaag-atggccaatttatagagtagtaatttttagtagaggtgcaaataa  41054
Sp:     gaagcgttgttcttacaataaacaatatacataaaaacaattagagagagaacatgaa   3568
φFL1C:  gaagcgtttgtcttacaataaacaatatacataaaaacaattagagagagaacatgaa  16034
           ***  *  *  *   **   **  **   * *      *  **  *   ** ***

NdeI
φEf11:  gagcat-------aggaagcccatatgaattggaacaaacagaatgctgtgaactaac   41105
Sp:     aagctattggtatcgttacacatgaatatccacagccgaaccg-ctcaactgat       3626
φFL1C:  aagctattggtatcgttacacatgaatatccacagccgaaccg-ctcaactgat      16092
           ***         ***         *****    *  * **  *  *****

φEf11:  tagggt--tgctttaaccaatcacaag------------acgtttgtatctgaaattttggc  41153
Sp:     tcagtacgtgtctaaaggccgcacaataaaagtgtagcttttattttattcctgtgtt     3686
φFL1C:  tcagtacgtgtctaaaggccgcacaataaaagtgtagcttttattttattcctgtgtt    16152
          *          *                        *** * *     *     *

FIG. 11C
```

```
φEf11:    caaagcaattaagttcctaaaagaatttaatcgaaagcatgcaattaatagtaagctatgc  41213
Sp:       gaaagaaattagtagtaattagtagtaatttcaaaaga-cagatgg-----aggtataa    3740
φFL1c:    gaaagaaattagtagtaattagtagtaatttcaaaaga-cagatgg-----aggtataa   16206
          ****** ***** *** ******** ***  *****   *** **      *** **

φEf11:    ORF61----------------------------------------------------ORF65-ORF01
Sp:       ORF40----------------------------------------------------ORF43-ORF44/ORF01
φFL1c:    ORF40----------------------------------------------------ORF43-ORF44

---------------------------------------------------------------
Downstream:
                                                    ORF1
φEf11:    ----------------------------------gaggtggtgttatatgtcagatgaaaaagaacagc   40
Sp:       gtgttaatggatggctagaaaagagatccacgtcgtgaccaggctaaagaaacttggtt   4586
φFL1c:    gtgttaatggatggctagaaaagagatccacgtcgtgaccaggctaaagaaacttggtt  17031
              gp44                                *   *

φEf11:    aaagaaatattatgaaaaaaggttgaaatacaaggatatttccgaaaagctttctgtacc   100
Sp:       aaagtcaaacgtaaaaaggttcttaaagaattagctaatgaattaaatgtttcagattc   4646
φFL1c:    aaagtcaaacgtaaaaaggttcttaaagaattagctaatgaattaaatgtttcagattc  17091
          ****                           *    **   **   **

φEf11:    tct---caacacattgaagtcatggagaaaac---gtgataaatgggaaagaggggggtgc   154
Sp:       ccaaataagaaaatcgataatgaaatcgatagataaatgggctgaattaaaaggtaatgttac   4706
φFL1c:    ccaaataagaaaatcgataatgaaatcgatagataaatgggctgaattaaaaggtaatgttac  17151
                  *                            ***        ***
```

ENTEROCOCCUS FAECALIS BACTERIOPHAGE AND USES THEREOF

CROSS-REFERENCE TO RELATED APPLICATION

The benefit of the filing date of U.S. Provisional Patent Application No. 61/804,922, filed Mar. 25, 2013, is hereby claimed. The entire disclosure of the aforesaid application is incorporated herein by reference.

REFERENCE TO GOVERNMENT GRANT

The invention was made with government support under grant no. 1R15DE021016-01 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 21, 2014, is named 035926_0479_00_WO_SL.txt and is 256,052 bytes in size.

FIELD OF INVENTION

The invention relates to bacteriophages that infect strains of *Enterococcus faecalis*, an opportunistic bacterial pathogen that causes human disease, and therapeutic uses thereof.

BACKGROUND OF THE INVENTION

*E. faecalis*, and closely related species, such as *E. faecium*, have emerged as significant human pathogens, being major etiologic agents of infectious endocarditis, nosocomial infections, burn infections, urinary tract infections, meningitis, and surgical wound infections (Lerwis & Zervos, *Eur J. Clin Microbiol Infect Dis* 9(2): 111-117, 1990; Moellering Jr., *Clin. Infect. Dis.* 14(6): 1173-1176, 1992; Megran, *Clinical Infect. Dis.* 15: 63-71, 1992; Emori & Gaynes, *Clin. Microbiol. Rev.* 6(4): 428-442, 1993; Jett et al., 1994; Edgeworth et al., *Crit. Care Med.* 28(8): 1421-1428, 1999; Richards et al., *Infection Control Hosp. Epidemiol.* 21(8): 510-515, 2000; NNIA System, *Am J Infect Control*, 32: 470-485, 2004; Biedenbach et al., *Diagn. Microbiol. Infect. Dis.* 50: 59-69 2004; Linden, *Semin. Respir. Crit. Care Med.* 28: 632-645, 2007). In terms of oral disease, *E. faecalis* is the most commonly isolated species from infected root canals of teeth that fail to heal following root canal therapy (Sundqvist et al., *Oral Surg. Oral Med. Oral Pathol. Oral Radiol. And Endod.* 85(1): 86-93, 1998; Peciuliene et al., *J. Endod.* 26(10): 593-595, 2000; Pinheiro et al., *Int. Endod. J.* 36: 1-11, 2003; Siqueira Jr. & Rôças, *Oral Surg. Oral Med. Oral Pathol. Oral Radiol. Endod.* 97: 85-94, 2004; Stuart et al., *J. Endod.* 32(2): 93-98 2006; Zoletti et al., *J Endod.* 32(8): 722-726 2006).

The existing standard treatment for infections, including those due to enterococci, continues to involve the use of antibiotics. In the case of severe enterococcal infections, the regimen typically includes a cell wall active antibiotic, such as a penicillin or cephalosporin plus an aminoglycoside such as streptomycin (Megran, *CID* 15:63-71, 1992; Noskin, *J Lab Clin Med* 130:14-20, 1997). As resistance to these drugs became more common, vancomycin replaced these antibiotics as the drug of choice for treating these infections.

Complicating management of these infections is the development of resistance among many Enterococcal strains against many of the available, previously effective antibiotics, including vancomycin (Harvard et al., *Br. Med. J.* 1: 688-689, 1959; Murray & Mederski-Samaroj, *J. Clin. Invest.*, 72: 1168-1171, 1983; Uttley et al., *Lancet*, i: 57-58, 1988; Grayson et al., *Antimicrob. Agents Chemother.*, 35: 2180-2184, 1991; Bonten et al., *Lancet Infect. Dis.* 1: 314-325, 2001; Tenover & McDonald, *Curr. Opin. Infect. Dis.* 18: 300-305, 2005). With the appearance of vancomycin resistant enterococci (VREs) that were also resistant to the previously used antibiotics, combinations of vancomycin and quinolone type antibiotics, such as ciprofloxacin, were used, however, quinolone-resistant enterococcal strains also appeared. Although a modest number of new antibiotics, such as linezolid and daptomycin, have been developed to provide treatment alternatives in cases of infection by organisms that are resistant to all previously available antibiotics, there have been numerous reports of resistance by *E. faecalis* and *E. faecium* strains to these antibiotics as well (Eliopoulos et al., *Antimicrob. Agents Chemother.*, 45(5): 1088-1092, 1998; Prystowsky et al., *Antimicrob. Agents Chemother.*, 45(7): 2154-2156, 2001; Gonzales et al., *Lancet* 357(9263): 1179, 2002; Herrero et al., *N Eng J Med* 346: 867-860, 2002; Johnson et al., *Int. J. Antimicrob. Agents* 24: 315-319, 2004; Munoz-Price et al., *Clin. Infect. Dis.*, 41: 565-566, 2005; Kanafani et al., *Scand. J. Infect. Dis.*, 39(1): 75-77, 2007; Hidron et al., *J Antimicrob. Chemother.*, 61(6): 1394-1396, 2008; Marshall et al., *Microbe*, 4(5): 231-238, 2009; Kelesidis et al., *Clin. Infect. Dis.*, 52: 228-234, 2011; Ross et al., *J. Chemother.*, 23(2): 71-76, 2011; Ntokou et al., *Antimicrob. Chemother.* 67(8): 1819-1823, 2012). Therefore, alternative approaches to manage these infections are desired.

Bacteriophages are bacterial viruses that infect bacterial cells. During their infectious cycle within a host cell, the bacterial virus produces enzymes that will lead to the lysis of the cell and release of progeny virus particles. Harnessing this capacity of the bacteriophage to lyse and kill the host cell may provide a means of controlling antibiotic resistant bacterial infections. This approach, of using bacteriophages to treat and control bacterial infections has several advantages. Bacteriophages are highly specific in that they are only infectious for bacterial cells, and have no capacity for infecting cells of higher life forms such as mammals. In fact, they are so specific that the host range of any one bacteriophage is typically a single bacterial species, or at most, a few closely related bacterial species. Therefore, the effect of any one bacteriophage is limited to a very narrow portion of a mixed bacterial population. This provides an impact on the pathogenic bacteria while leaving the normal bacterial population unaffected. Both antibiotic sensitive and antibiotic resistant bacterial strains can be vulnerable to bacteriophage infection. In addition, in contrast to conventional antibiotics which decrease in concentration in the body after administration, bacteriophage titer can increase after administration, due to proliferation of the virus in the targeted host cell.

The therapeutic potential of bacteriophages was tested in 1919 by d'Herelle, who showed that bacteriophage preparations could be used to successfully treat cases of dysentery (described in Chanishvili, *Advances in Virus Res.* 83: 3-40, 2012). Further work continued, particularly in eastern Europe, on the use of bacteriophages ("phages") to treat infectious diseases (Barrow, *J Chem Technol Biotechnol* 76: 677-682, 2001; Duckworth and Gulig *Biodrugs*, 16(1): 57-62, 2002, Petty et al. *TRENDS in Biotechnol.*, 25(1): 7-15, 2006; Chanishvili, supra). With the advent of antibiotics in the 1940s, this line of research (phage therapy) fell by the wayside in the west since antibiotics were remarkably effective in combating many bacterial infections. However, in eastern Europe, where availability of antibiotics was limited, research into phage therapy continued, particularly in the Soviet Union, Georgia, and Poland. Here, the therapeutic use of phages became an accepted modality for treating a wide variety of bacterial infections.

Since the 1980s, as antibiotic resistance in pathogenic bacteria began to develop, and become more common in the West, there has been a resurgence in interest in using phages to treat human and animal infections (Summers, *Annu. Rev. Microbiol.* 55: 437-451, 2001, Alisky et al., *J. of Infec.* 36: 5-15, 1998, Pirisi, *Lancet.* 356: 1418, 2000; Ho, *Perspectives in Biology and Medicine,* 44(1): 1-16, 2001; Merril et al., *Naure Revs. Drug Disc.* 2: 489-497, 2003; Bradbury, *Lancet.* 363: 624-625, 2004; Dixon, *Lancet Infect Dis.* 4: 186, 2004; Schoolnik et al., *Nature* 22(5): 505-506, 2004; Thiel, *Nature* 22(1): 31-36, 2004; Skurnik and Strauch, *Int. J. Med. Microbiol.* 296: 5-14, 2005).

Several recent studies report successful implementation of phage therapy (using either infectious bacteriophages or phage products) in modifying bacterial infections in animals by *Acinetobacter baumanii, Escherichia coli*, group A streptococci, *Enterococcus faecium, Bacillus anthracis*, and *Pseudomonas aeruginosa* (Soothill, *J. Med. Microbiol.* 37: 258-261, 1992; Merril et al., *Proc. Natl. Acad. Sci. USA.* 93: 3188-3192, 1996; Nelson et al., *Proc. Nat. Acad. Sci.* 98(7): 4107-4112, 2001; Biswas et al., *Infect. Immun.* 70(1): 204-210, 2002; Schuch et al., *Nature* 418: 884-889, 2002; Watanabe et al., *Antimicrob. Agents Chemother.* 51: 446-452, 2007). In this regard, it is significant to note that in a study reported by Smith and Huggins, *J Gen Microbiol* 128: 307-318 (1982), a single intramuscular (IM) dose of phage was more effective in protecting mice from normally lethal IM or intracerebral injections of *Escherichia coli* or *Salmonella enterica*, than multiple IM injections of antibiotics such as tetracycline, ampicillin, chloramphenicol, or trimethoprim plus sulfisoxazole. In addition, in the first controlled trial of phage therapy in humans, it was shown that a cocktail of six *Pseudomonas aeruginosa* bacteriophages effectively treated antibiotic-resistant chronic otitis (Wright et al, *Clin. Otolaryngol.* 34: 349-357, 2009).

In terms of phage therapy to treat *E. faecalis* infections, there has been relatively little reported. In 2004, Paisano, et al., *Oral Microbiol Immunol,* 19: 327-330 reported that they could reduce the level of infection of a single *E. faecalis* strain in an infected dental root canal (in vitro), to an undetectable level, using a bacteriophage preparation. However, the bacteriophage used in this study was not characterized in any way (no morphological description, no genomic analysis).

Isolation of a bacterial virus (phage φEF24C) that could protect mice from otherwise lethal doses of *E. faecalis* has been reported (Uchiyama et al., *FEMS Microbiol Lett.* 278: 200-206, 2008; Uchiyama et al., *Appl Environ Microbiol.* 74(13): 4149-4163, 2008). This bacteriophage was reported to have a broad range of activity against many strains of *E. faecalis*, and have no untoward effects on the mice. This phage was well characterized and could be described as follows: φEF24C has a contractile tail, giving it the morphology of a Myovirdae type bacteriophage. Its genome consisted of a linear, double stranded DNA, 142,072 by in length, with an estimated 221 ORFs and 5 tRNA genes.

Other strategies for exploiting bacteriophages for controlling *E. faecalis* infections involve the use of lytic enzymes produced by the viruses to lyse and kill the bacterial cells. The cell lysis produced by these enzymes is needed by the virus in order to allow the release of progeny viral particles from the infected cells. The strategy for exploiting these bacteriophage-specified lytic enzymes involves the cloning and expression of the genes for these enzymes, followed by the purification of the expressed proteins. One such lytic enzyme, active against strains of *E. faecalis* (as well as strains of *E. faecium*, and several *Streptococcus* species), has reportedly been isolated from *E. faecalis* bacteriophage φ1 (Yoong et al., *J Bacteria* 186(145): 4808-4812, 2004). The bacteriophage source of this enzyme, phage φ1, was described as a Myoviridae morphotype; that is, a bacteriophage with a contractile tail. A second report of a bacteriophage lytic enzyme active against strains of *E. faecalis* came from Son et al., *Appl. Microbiol.* 108: 1769-1779 (2010). Here, the gene for a putative lytic enzyme specified by *E. faecalis* bacteriophage EFAP-1 was cloned, and expressed, and the gene product was purified. The purified phage protein was found to have lytic activity against numerous strains of *E. faecalis* and *E. faecium*. Bacteriophage EFAP-1, the source of the lytic enzyme described by Son et al., had the non-contractile tail structure of a Siphovirdae morphotype. EFAP-1 had a 21,115 bp genome containing 24 ORFs.

Several other bacterial viruses that infect strains of *E. faecalis* have been reported. These include: Bacteriophages φFC1 (Yang et al., *J. Bacteriol.* 184: 1859-1864, 2002), F4 (Nigutova et al., *Folio Microbiol.* 53(3): 234-236, 2008), phages 31, 42, 54, and 70 (Mazaheri Nezhad Fard et al., *Curr Microbiol.* 60: 400-406, 2010), VD13 (Ackermann et al., *Can. J. Microbiol.,* 21: 571-574, 1975), phages 1 and 2 (Rogers and Sarles, *J. Bacteriol.* 85: 1378-1385, 1963), SAP6 (Lee and Park, *J. Virol.* 86(17): 9538-9539, 2012), BC-611 (Horiuchi et al., *J. Virol.* 86(17): 9538-9539, 2012), and phages φFL1A, φFL1B, φFL1C, φFL2A, φFL2B, φFL3A, φFL3B and φFL4A (Yasmin et al., *J. Bacteriol.* 192(4): 1122-1130, 2010). In addition several unnamed *E. faecalis* bacteriophages have been reported (Natkin, *Arch Oral Biol.* 12(5): 669-680, 1967, Timperley et al., *J. Pathol. Bacteriol.* 9: 631-634, 1966, Follett et al., *J. Gen. Virol.* 1: 281-284, 1967, Letkiewicz et al., *Folio Microbiol.* 54: 457-461, 2009, and Bachrach et al., *Lett. Appl. Microbiol.* 36: 50-53, 2003). However, none of these have been proposed for use in phage therapy.

φEf11 is a temperate bacteriophage that was induced from a lysogenic root canal isolate of *Enterococcus faecalis* (Stevens et al., *Oral Microbiol. Immunobiol.,* 24: 278-284, 2009). φEf11 prophage is widely disseminated among strains of *E. faecalis*. It is a member of the Siphoviridae family, with a long (130 nm) non-contractile tail and a small (41 nm diameter) spherical/icosahedral head. The phage produces small, turbid plaques in lawns of *E. faecalis* JH2-2. The φEf11 DNA has been sequenced and annotated, disclosing a genome of 42,822 base pairs encoding 65 Open Reading Frames (Stevens et al., *FEMS Microbiol. Lett.,* 317: 9-26, 2011, incorporated herein by reference; GenbankGQ452243.1, incorporated herein by reference).

The φEf11 genome is shown in FIG. 10. The numbered arrows indicate ORFs. The ORF numbering scheme in FIG. 10 corresponds to the numbering system contained in Stevens et al., 2011, supra. ORFs 25-29 are involved in host cell lysis.

φEf11 possesses several characteristics making it a favorable candidate virus to be used in phage therapy: There are no toxin-related genes detected in the φEf11 genome, and it encodes several (4-6) genes encoding proteins with lysis-associated functions (Stevens et al., 2011, supra). However, as a temperate virus that has a very limited host range, and is difficult to propagate, wild-type φEf11 would not be suitable as a potential therapeutic agent.

Moreover, since φEf11 is a temperate bacteriophage, it possesses a module of genes that allows it to integrate its DNA into the host cell chromosome rather than initiating a productive infection and lysing the infected cell. The bacteriophage DNA can remain in this integrated state indefinitely, and the infected cell (a lysogen) will survive and continue to multiply. Furthermore, regulatory elements in the φEf11 genome whose activation is required for the development of a productive/lytic infection within the cell, are inactivated by a protein (repressor) produced by one of the lysogeny-related genes. Therefore, lysogenic cells producing this repressor are immune to super infection by φEf11, and would consequently survive exposure to this virus. This further limits the utility of φEf11 as therapeutic agent

SUMMARY OF THE INVENTION

Provided is a bacteriophage capable of infecting and lysing an *Enterococcus faecalis* bacterium, said bacteriophage having a genome comprising:

(A) the following ORFs with the corresponding Protein ID Numbers from Genbank Accession Number GQ452243.1, or having the following nucleic acid sequence:

(a) ORF 2, encoding the amino acid sequence of SEQ ID NO: 28, corresponding to Protein ID Number YP 003358792.1;

(b) ORF 3, encoding the amino acid sequence of SEQ ID NO: 29, corresponding to Protein ID Number YP 003358793.1;

(c) ORF 4, encoding the amino acid sequence of SEQ ID NO: 30, corresponding to Protein ID Number YP 003358794.1;

(d) ORF 5, encoding the amino acid sequence of SEQ ID NO: 31, corresponding to Protein ID Number YP 003358795.1;

(e) ORF 6, encoding the amino acid sequence of SEQ ID NO: 32, corresponding to Protein ID Number YP 003358796.1;

(f) ORF 7, encoding the amino acid sequence of SEQ ID NO: 33, corresponding to Protein ID Number YP 003358797.1;

(g) ORF 8, encoding the amino acid sequence of SEQ ID NO: 34, corresponding to Protein ID Number YP 003358798.1;

(h) ORF 9, encoding the amino acid sequence of SEQ ID NO: 35, corresponding to Protein ID Number YP 003358799.1;

(i) ORF 10, encoding the amino acid sequence of SEQ ID NO: 36, corresponding to Protein ID Number YP 003358800.1;

(j) ORF 11, encoding the amino acid sequence of SEQ ID NO: 37, corresponding to Protein ID Number YP 003358801.1;

(k) ORF 12, encoding the amino acid sequence of SEQ ID NO: 38, corresponding to Protein ID Number YP 003358802.1;

(l) ORF 13, encoding the amino acid sequence of SEQ ID NO: 39, corresponding to Protein ID Number YP 003358803.1;

(m) ORF 14, encoding the amino acid sequence of SEQ ID NO: 40, corresponding to Protein ID Number YP 003358804.1;

(n) ORF 15, encoding the amino acid sequence of SEQ ID NO: 41, corresponding to Protein ID Number YP 003358805.1;

(o) ORF 16, encoding the amino acid sequence of SEQ ID NO: 42, corresponding to Protein ID Number YP 003358806.1;

(p) ORF 17, encoding the amino acid sequence of SEQ ID NO: 43, corresponding to Protein ID Number YP 003358807.1;

(q) ORF 18, encoding the amino acid sequence of SEQ ID NO: 44, corresponding to Protein ID Number YP 003358808.1;

(r) ORF 19, encoding the amino acid sequence of SEQ ID NO: 45, corresponding to Protein ID Number YP 003358809.1;

(s) ORF 20, encoding the amino acid sequence of SEQ ID NO: 46, corresponding to Protein ID Number YP 003358810.1;

(t) ORF 21, encoding the amino acid sequence of SEQ ID NO: 47, corresponding to Protein ID Number YP 003358811.1;

(u) ORF 22, encoding the amino acid sequence of SEQ ID NO: 48, corresponding to Protein ID Number YP 003358812.1;

(v) ORF 23, encoding the amino acid sequence of SEQ ID NO: 49, corresponding to Protein ID Number YP 003358813.1;

(w) ORF 24, encoding the amino acid sequence of SEQ ID NO: 50, corresponding to Protein ID Number YP 003358814.1;

(x) ORF 25, encoding the amino acid sequence of SEQ ID NO: 51, corresponding to Protein ID Number YP 003358815.1;

(y) ORF 26, encoding the amino acid sequence of SEQ ID NO: 52, corresponding to Protein ID Number YP 003358816.1;

(z) ORF 27, encoding the amino acid sequence of SEQ ID NO: 53, corresponding to Protein ID Number YP 003358817.1;

(aa) ORF 28, encoding the amino acid sequence of SEQ ID NO: 54, corresponding to Protein ID Number YP 003358818.1;

(bb) ORF 29, encoding the amino acid sequence of SEQ ID NO: 55, corresponding to Protein ID Number YP 003358819.1;

(cc) ORF 30, encoding the amino acid sequence of SEQ ID NO: 56, corresponding to Protein ID Number YP 003358820.1;

(dd) ORF 37, encoding the amino acid sequence of SEQ ID NO: 63, corresponding to Protein ID Number YP 003358827.1;

(ee) ORF 38, encoding the amino acid sequence of SEQ ID NO: 64, corresponding to Protein ID Number YP 003358828.1;

(ff) ORF 39, encoding the amino acid sequence of SEQ ID NO: 65, corresponding to Protein ID Number YP 003358829.1;

(gg) ORF 40, encoding the amino acid sequence of SEQ ID NO: 66, corresponding to Protein ID Number YP 003358830.1;

(hh) ORF 41, encoding the amino acid sequence of SEQ ID NO: 67, corresponding to Protein ID Number YP 003358831.1;

(ii) ORF 42, encoding the amino acid sequence of SEQ ID NO: 68, corresponding to Protein ID Number YP 003358832.1;

(jj) ORF 43, encoding the amino acid sequence of SEQ ID NO: 69, corresponding to Protein ID Number YP 003358833.1;

(kk) ORF 44, encoding the amino acid sequence of SEQ ID NO: 70, corresponding to Protein ID Number YP 003358834.1;

(ll) ORF 45, encoding the amino acid sequence of SEQ ID NO: 71, corresponding to Protein ID Number YP 003358835.1;

(mm) ORF 46, encoding the amino acid sequence of SEQ ID NO: 72, corresponding to Protein ID Number YP 003358836.1;

(nn) ORF 47, encoding the amino acid sequence of SEQ ID NO: 73, corresponding to Protein ID Number YP 003358837.1;

(oo) ORF 48, encoding the amino acid sequence of SEQ ID NO: 74, corresponding to Protein ID Number YP 003358838.1;

(pp) ORF 49, encoding the amino acid sequence of SEQ ID NO: 75, corresponding to Protein ID Number YP 003358839.1;

(qq) ORF 50, encoding the amino acid sequence of SEQ ID NO: 76, corresponding to Protein ID Number YP 003358840.1;

(rr) ORF 51, encoding the amino acid sequence of SEQ ID NO: 77, corresponding to Protein ID Number YP 003358841.1;

(ss) ORF 52, encoding the amino acid sequence of SEQ ID NO: 78, corresponding to Protein ID Number YP 003358842.1;

(tt) ORF 53, encoding the amino acid sequence of SEQ ID NO: 79, corresponding to Protein ID Number YP 003358843.1;

(uu) ORF 54, encoding the amino acid sequence of SEQ ID NO: 80, corresponding to Protein ID Number YP 003358844.1;

(vv) ORF 55, encoding the amino acid sequence of SEQ ID NO: 81, corresponding to Protein ID Number YP 003358845.1;

(ww) ORF 56, encoding the amino acid sequence of SEQ ID NO: 82, corresponding to Protein ID Number YP 003358846.1;

(xx) ORF 57, encoding the amino acid sequence of SEQ ID NO: 83, corresponding to Protein ID Number YP 003358847.1;

(yy) ORF 58, encoding the amino acid sequence of SEQ ID NO: 84 corresponding to Protein ID Number YP 003358848.1; and (zz) ORF 59, encoding the amino acid sequence of SEQ ID NO: 85, corresponding to Protein ID Number YP 003358849.1;

(aaa) ORF 60, encoding the amino acid sequence of SEQ ID NO: 86, corresponding to Protein ID Number YP 003358850.1;

(bbb) a portion of ORF 1, having the nucleic acid sequence of SEQ ID NO: 170;

(B) an inducible or constitutive promoter immediately upstream of ORF 37; and (C) the following ORFs from bacteriophage ΦFL1C:

(a) ORF 40 encoding the amino acid sequence of SEQ ID NO: 158;

(b) ORF 41 encoding the amino acid sequence of SEQ ID NO: 159;

(c) ORF 42 encoding the amino acid sequence of SEQ ID NO: 160;

(d) ORF 43 encoding the amino acid sequence of SEQ ID NO: 161;

(e) ORF 44 encoding the amino acid sequence of SEQ ID NO: 162.

In some embodiments, the bacteriophage has a genome comprising:

(A) the following ORFs having the corresponding Gene ID Numbers from Genbank Accession Number GQ452243.1, or having the following nucleic acid sequence:

(a) ORF 2, the nucleic acid sequence of SEQ ID NO: 94, corresponding to Gene ID Number 8683900;

(b) ORF 3, the nucleic acid sequence of SEQ ID NO: 95, corresponding to Gene ID Number 8683888;

(c) ORF 4, the nucleic acid sequence of SEQ ID NO: 96, corresponding to Gene ID Number 8683893;

(d) ORF 5, the nucleic acid sequence of SEQ ID NO: 97, corresponding to Gene ID Number 8683933;

(e) ORF 6, the nucleic acid sequence of SEQ ID NO: 98, corresponding to Gene ID Number 8683946;

(f) ORF 7, the nucleic acid sequence of SEQ ID NO: 99, corresponding to Gene ID Number 8683941;

(g) ORF 8, the nucleic acid sequence of SEQ ID NO: 100, corresponding to Gene ID Number 8683932;

(h) ORF 9, the nucleic acid sequence of SEQ ID NO: 101, corresponding to Gene ID Number 8683887;

(i) ORF 10, the nucleic acid sequence of SEQ ID NO: 102, corresponding to Gene ID Number 8683904;

(j) ORF 11, the nucleic acid sequence of SEQ ID NO: 103, corresponding to Gene ID Number 8683926;

(k) ORF 12, the nucleic acid sequence of SEQ ID NO: 104, corresponding to Gene ID Number 8683911;

(l) ORF 13, the nucleic acid sequence of SEQ ID NO: 105, corresponding to Gene ID Number 8683923;

(m) ORF 14, the nucleic acid sequence of SEQ ID NO: 106, corresponding to Gene ID Number 8683914;

(n) ORF 15, the nucleic acid sequence of SEQ ID NO: 107, corresponding to Gene ID Number 8683916;

(o) ORF 16, the nucleic acid sequence of SEQ ID NO: 108, corresponding to Gene ID Number 8683884;

(p) ORF 17, the nucleic acid sequence of SEQ ID NO: 109, corresponding to Gene ID Number 8683912;

(q) ORF 18, the nucleic acid sequence of SEQ ID NO: 110, corresponding to Gene ID Number 8683919;

(r) ORF 19, the nucleic acid sequence of SEQ ID NO: 111, corresponding to Gene ID Number 8683929;

(s) ORF 20, the nucleic acid sequence of SEQ ID NO: 112, corresponding to Gene ID Number 8683927;

(t) ORF 21, the nucleic acid sequence of SEQ ID NO: 113, corresponding to Gene ID Number 8683928;

(u) ORF 22, the nucleic acid sequence of SEQ ID NO: 114, corresponding to Gene ID Number 8683935;

(v) ORF 23, the nucleic acid sequence of SEQ ID NO: 115, corresponding to Gene ID Number 8683908;

(w) ORF 24, the nucleic acid sequence of SEQ ID NO: 116, corresponding to Gene ID Number 8683924;

(x) ORF 25, the nucleic acid sequence of SEQ ID NO: 117, corresponding to Gene ID Number 8683907;

(y) ORF 26, the nucleic acid sequence of SEQ ID NO: 118, corresponding to Gene ID Number 8683925;

(z) ORF 27, the nucleic acid sequence of SEQ ID NO: 119, corresponding to Gene ID Number 8683889;

(aa) ORF 28, the nucleic acid sequence of SEQ ID NO: 120, corresponding to Gene ID Number 8683944;

(bb) ORF 29, the nucleic acid sequence of SEQ ID NO: 121, corresponding to Gene ID Number 8683920;

(cc) ORF 30, the nucleic acid sequence of SEQ ID NO: 122, corresponding to Gene ID Number 8683896;

(dd) ORF 37, the nucleic acid sequence of SEQ ID NO: 129, corresponding to Gene ID Number 8683921;

(ee) ORF 38, the nucleic acid sequence of SEQ ID NO: 130, corresponding to Gene ID Number 8683898;

(ff) ORF 39, the nucleic acid sequence of SEQ ID NO: 131, corresponding to Gene ID Number 8683895;

(gg) ORF 40, the nucleic acid sequence of SEQ ID NO: 132, corresponding to Gene ID Number 8683940;

(hh) ORF 41, the nucleic acid sequence of SEQ ID NO: 133, corresponding to Gene ID Number 8683917;

(ii) ORF 42, the nucleic acid sequence of SEQ ID NO: 134, corresponding to Gene ID Number 8683897;

(jj) ORF 43 the nucleic acid sequence of SEQ ID NO: 135, corresponding to Gene ID Number 8683894;

(kk) ORF 44, the nucleic acid sequence of SEQ ID NO: 136, corresponding to Gene ID Number 8683883;

(ll) ORF 45, the nucleic acid sequence of SEQ ID NO: 137, corresponding to Gene ID Number 8683903;

(mm) ORF 46, the nucleic acid sequence of SEQ ID NO: 138, corresponding to Gene ID Number 8683943;

(nn) ORF 47, the nucleic acid sequence of SEQ ID NO: 139, corresponding to Gene ID Number 8683913;

(oo) ORF 48, the nucleic acid sequence of SEQ ID NO: 140, corresponding to Gene ID Number 8683910;

(pp) ORF 49, the nucleic acid sequence of SEQ ID NO: 141, corresponding to Gene ID Number 8683937;

(qq) ORF 50, the nucleic acid sequence of SEQ ID NO: 142, corresponding to Gene ID Number 8683915;

(rr) ORF 51, the nucleic acid sequence of SEQ ID NO: 143, corresponding to Gene ID Number 8683885;

(ss) ORF 52, the nucleic acid sequence of SEQ ID NO: 144, corresponding to Gene ID Number 8683890;

(tt) ORF 53, the nucleic acid sequence of SEQ ID NO: 145, corresponding to Gene ID Number 8683886;

(uu) ORF 54, the nucleic acid sequence of SEQ ID NO: 146, corresponding to Gene ID Number 8683909;

(vv) ORF 55, the nucleic acid sequence of SEQ ID NO: 147, corresponding to Gene ID Number 8683902;

(ww) ORF 56, the nucleic acid sequence of SEQ ID NO: 148, corresponding to Gene ID Number 8683931;

(xx) ORF 57, the nucleic acid sequence of SEQ ID NO: 149, corresponding to Gene ID Number 8683930;

(yy) ORF 58, the nucleic acid sequence of SEQ ID NO: 150 corresponding to Gene ID Number 8683899; and (zz) ORF 59, the nucleic acid sequence of SEQ ID NO: 151, corresponding to Gene ID Number 8683936;

(aaa) ORF 60, the nucleic acid sequence of SEQ ID NO: 152, corresponding to Gene ID Number 8683942;

(bbb) a portion of ORF 1, having the nucleic acid sequence of SEQ ID NO: 170;

(B) an inducible or constitutive promoter immediately upstream of ORF 37; and (C) the following ORFs from bacteriophage ΦFL1C:

(a) ORF 40 having the nucleic acid sequence of SEQ ID NO: 163;

(b) ORF 41 having the nucleic acid sequence of SEQ ID NO: 164;

(c) ORF 42 having the nucleic acid sequence of SEQ ID NO: 165;

(d) ORF 43 having the nucleic acid sequence of SEQ ID NO: 166;

(e) ORF 44 having the nucleic acid sequence of SEQ ID NO: 167.

In some embodiments the bacteriophage has the genome of the bacteriophage ΦEf11 from Genbank Accession Number GQ452243.1, corresponding to SEQ ID NO: 92:

(A) wherein the following ORFs have been deleted:

(a) a portion of ORF 1 having the nucleic acid sequence of SEQ ID NO: 169;

(b) ORF 31, encoding the amino acid sequence of SEQ ID NO: 57, corresponding to Protein ID Number YP 003358821.1;

(c) ORF 32, encoding the amino acid sequence of SEQ ID NO: 58, corresponding to Protein ID Number YP 003358822.1;

(d) ORF 33, encoding the amino acid sequence of SEQ ID NO: 59, corresponding to Protein ID Number YP 003358823.1;

(e) ORF 34, encoding the amino acid sequence of SEQ ID NO: 60, corresponding to Protein ID Number YP 003358824.1;

(f) ORF 35, encoding the amino acid sequence of SEQ ID NO: 61, corresponding to Protein ID Number YP 003358825.1;

(g) ORF 36, encoding the amino acid sequence of SEQ ID NO: 62, corresponding to Protein ID Number YP 003358826.1;

(h) ORF 61, encoding the amino acid sequence of SEQ ID NO: 87, corresponding to Protein ID Number YP 003358851.1;

(i) ORF 62, encoding the amino acid sequence of SEQ ID NO: 88, corresponding to Protein ID Number YP 003358852.1;

(j) ORF 63, encoding the amino acid sequence of SEQ ID NO: 89, corresponding to Protein ID Number YP 003358853.1;

(k) ORF 64, encoding the amino acid sequence of SEQ ID NO: 90, corresponding to Protein ID Number YP 003358854.1;

(l) ORF 65, encoding the amino acid sequence of SEQ ID NO: 91 corresponding to Protein ID Number YP 003358855.1;

(B) wherein the $P^{CRO}$ promoter between ORFs 36 and 37 has been replaced with an inducible promoter or a constitutive promoter; and (C) comprising the following ORFs from bacteriophage ΦFL1C:

(a) ORF 40 encoding the amino acid sequence of SEQ ID NO: 158;

(b) ORF 41 encoding the amino acid sequence of SEQ ID NO: 159;

(c) ORF 42 encoding the amino acid sequence of SEQ ID NO: 160;

(d) ORF 43 encoding the amino acid sequence of SEQ ID NO: 161;

(e) ORF 44encoding the amino acid sequence of SEQ ID NO: 162.

In yet further embodiments the bacteriophage has the genome of the ΦEf11bacteriophage that is comprised by *Enterococcus faecalis* NRRL Deposit Number NRRL B-50832, deposited on March 22, 2013:

(A) wherein the following ORFs have been deleted, which have the following nucleic acid sequence, or the following amino acid sequences, corresponding to the following Protein ID Numbers from Genbank Accession Number GQ452243.1:

(a) a portion of ORF 1 having the nucleic acid sequence of SEQ ID NO: 169;

(b) ORF 31, encoding the amino acid sequence of SEQ ID NO: 57, corresponding to Protein ID Number YP 003358821.1;

(c) ORF 32, encoding the amino acid sequence of SEQ ID NO: 58, corresponding to Protein ID Number YP 003358822.1;

(d) ORF 33, encoding the amino acid sequence of SEQ ID NO: 59, corresponding to Protein ID Number YP 003358823.1;

(e) ORF 34, encoding the amino acid sequence of SEQ ID NO: 60, corresponding to Protein ID Number YP 003358824.1;

(f) ORF 35, encoding the amino acid sequence of SEQ ID NO: 61, corresponding to Protein ID Number YP 003358825.1;

(g) ORF 36, encoding the amino acid sequence of SEQ ID NO: 62, corresponding to Protein ID Number YP 003358826.1;

(h) ORF 61, encoding the amino acid sequence of SEQ ID NO: 87, corresponding to Protein ID Number YP 003358851.1;

(i) ORF 62, encoding the amino acid sequence of SEQ ID NO: 88, corresponding to Protein ID Number YP 003358852.1;

(j) ORF 63, encoding the amino acid sequence of SEQ ID NO: 89, corresponding to Protein ID Number YP 003358853.1;

(k) ORF 64, encoding the amino acid sequence of SEQ ID NO: 90, corresponding to Protein ID Number YP 003358854.1;

(l) ORF 65, encoding the amino acid sequence of SEQ ID NO: 91, corresponding to Protein ID Number YP 003358855.1;

(B) wherein the $P^{CRO}$ promoter between ORFs 36 and 37 has been replaced with an inducible promoter or a constitutive promoter; and (C) comprising the following ORFs from bacteriophage ΦFL1C:

(a) ORF 40 encoding the amino acid sequence of SEQ ID NO: 158;

(b) ORF 41 encoding the amino acid sequence of SEQ ID NO: 159;

(c) ORF 42 encoding the amino acid sequence of SEQ ID NO: 160;

(d) ORF 43 encoding the amino acid sequence of SEQ ID NO: 161;

(e) ORF 44 encoding the amino acid sequence of SEQ ID NO: 162.

In some embodiments of the previous embodiment, for the following ORFs from bacteriophage ΦFL1C:

(a) ORF 40 has the nucleic acid sequence of SEQ ID NO: 163;

(b) ORF 41 has the nucleic acid sequence of SEQ ID NO: 164;

(c) ORF 42 has the nucleic acid sequence of SEQ ID NO: 165;

(d) ORF 43 has the nucleic acid sequence of SEQ ID NO: 166;

(e) ORF 44 has the nucleic acid sequence of SEQ ID NO: 167.

In further embodiments the bacteriophage comprises the genome of the bacteriophage ΦEf11 from Genbank Accession Number GQ452243.1 corresponding to SEQ ID NO: 92:

(A) wherein nucleotides 39671-42813 and nucleotides 1-336 have been deleted and replaced by nucleotides 14600-17836 from bacteriophage ΦFL1C; and (B) wherein the $P^{CRO}$ promoter between ORFs 36 and 37 of the genome of bacteriophage ΦEf11 have been replaced with an inducible promoter or a constitutive promoter.

In further embodiments the bacteriophage is ϕEf11 (vir)$^{PnisA}$ and is comprised by *Enterococcus faecalis* NRRL Deposit Number NRRL B-50833.

In further embodiments, the bacteriophage is a variant of the bacteriophage ϕEf11(vir)$^{PnisA}$ comprised by *Enterococcus faecalis* NRRL Deposit Number NRRL B-50833, wherein the nisin promoter present in said deposited bacteriophage is replaced by a constitutive promoter, and wherein the erythromycin resistance gene present in said deposited bacteriophage is deleted.

In some embodiments the promoter is a constitutive promoter. In further embodiments the constitutive promoter is the Tu promoter having the nucleic acid sequence of SEQ ID NO: 168.

In some embodiments the inducible promoter is the nisin promoter.

Also provided is a bacteria comprising the bacteriophage of any one of the preceding bacteriophage embodiments. In some bacteria embodiments, the bacteria is a strain of *Enterococcus faecalis*.

Provided is a composition for prevention and treatment of *Enterococcus faecalis* or *Enterococcus faecium* infection comprising the bacteriophage of any one of the preceding embodiments, provided that the inducible promoter is not a promoter that utilizes a toxic inducer (e.g., the promoter is not the nisin promoter); and a pharmaceutically acceptable carrier.

Also provided is a method for prevention or treatment of *Enterococcus faecalis* or *Enterococcus faecium* infection comprising administering to a subject in need of such treatment or prevention the composition of the preceding embodiment. In some embodiments the composition is administered orally, optically, subcutaneously, peritoneally, intravenously, topically, intradentally or parenterally. In further embodiments the composition is administered to a root canal. In yet further embodiments the infection is resistant to at least one antibiotic. In yet further embodiments the infection is in an immunocompromised patient.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

ABBREVIATIONS

AGE means agarose gel electrophoresis.
ORF means open reading frame.

Figure 3A:
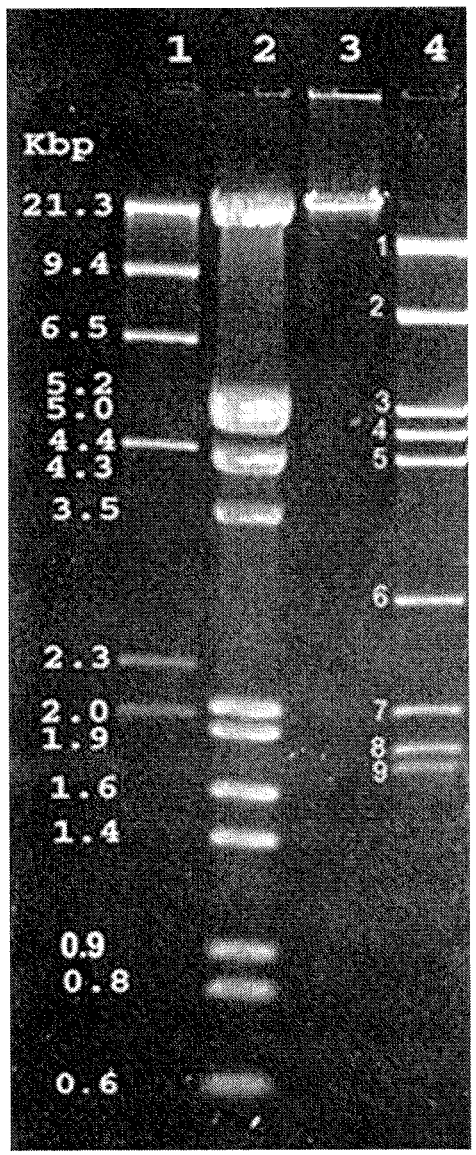
Figure 3B:
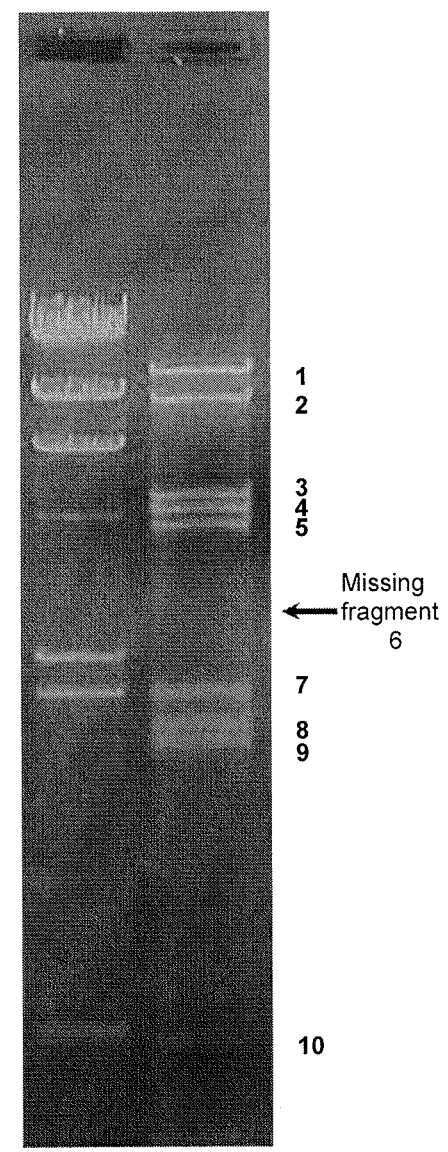
Figure 4:
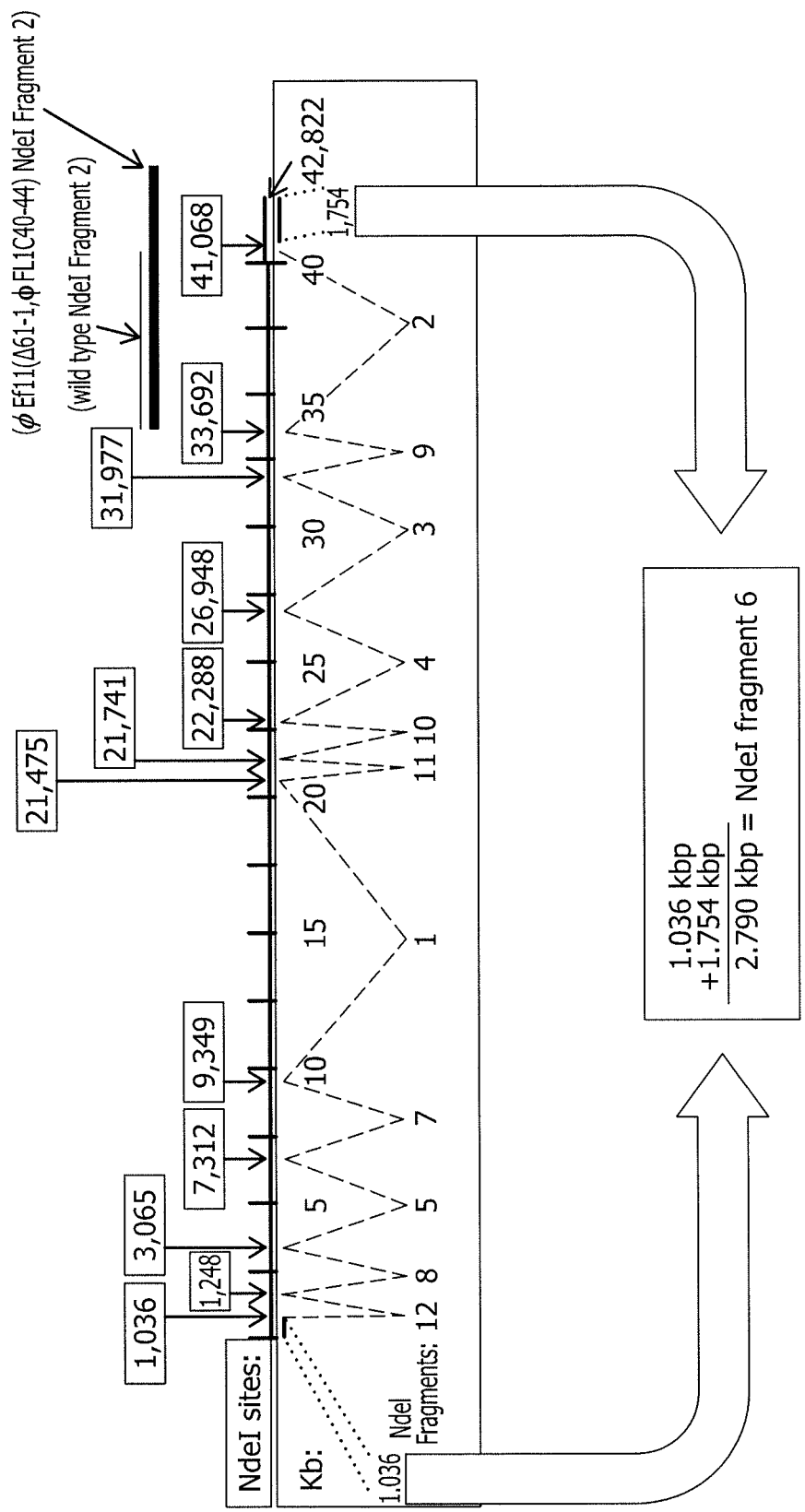

FIGS. 3A-3B show the results of an agarose gel electrophoresis analysis of ethidium bromide-stained NdeI restriction fragments of φEf11 and φEf11(φ61-1, φFL1C 40-44) DNA. (3A) Lanes 1 and 2: DNA molecular length standards (values on left are DNA lengths in kilobase pairs); 3: intact (undigested) φEf11 DNA; 4: NdeI-digested φEf11 DNA. (3B) Lane 1: DNA molecular length standards (values on left are DNA lengths in kilobase pairs); 2: NdeI-digested φEf11(φ61-1, φFL1C 40-44) DNA. Note that fragment 6, seen in gel containing NdeI fragments of φEf11 DNA, is missing in the gel containing the NdeI-digested φEf11(φ61-1, φFL1C FIG. 4 shows a NdeI restriction site analysis of the φEf11 DNA. The φEf11 DNA is 42,822 in length and is oriented as described in Stevens et al., 2011. supra), with the genes arranged with ORF 1 at the extreme left end and ORF 65 at the extreme right end. NdeI restriction sites (bp coordinates) are indicated the boxes. The NdeI restriction fragments, as visualized in agarose gel electrophoresis analysis AGE, are labeled 1-12. The first NdeI site is located 1.036 kbp from the left terminus of the DNA (coordinate 1036), and the NdeI site is located 1.754 kbp from the right terminus of the DNA (coordinate 41,068). The combined length of these two fragments (2,7980 kbp) is equal to the size estimated from NdeI fragment 6 observed in AGE analysis.

Figure 5:
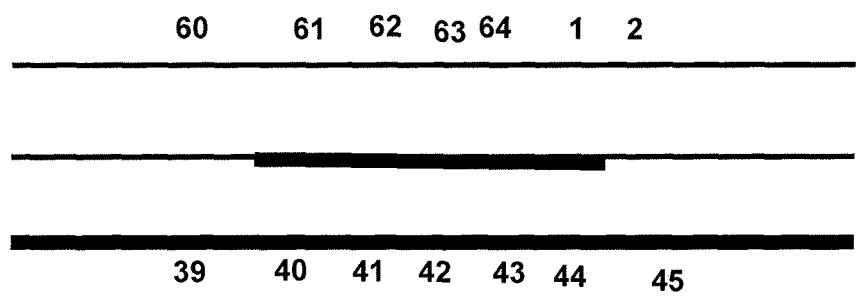

FIG. 5 presents an overview of the regions of φEf11 (top) and φFL1C (bottom) that recombined to yield recombinant φEf11(Δ61-1, φFL1C 40-44) (middle). Non-bolded line portions indicate φEf11 sequences, bolded lines indicate φFL1C sequences.

Figure 6:
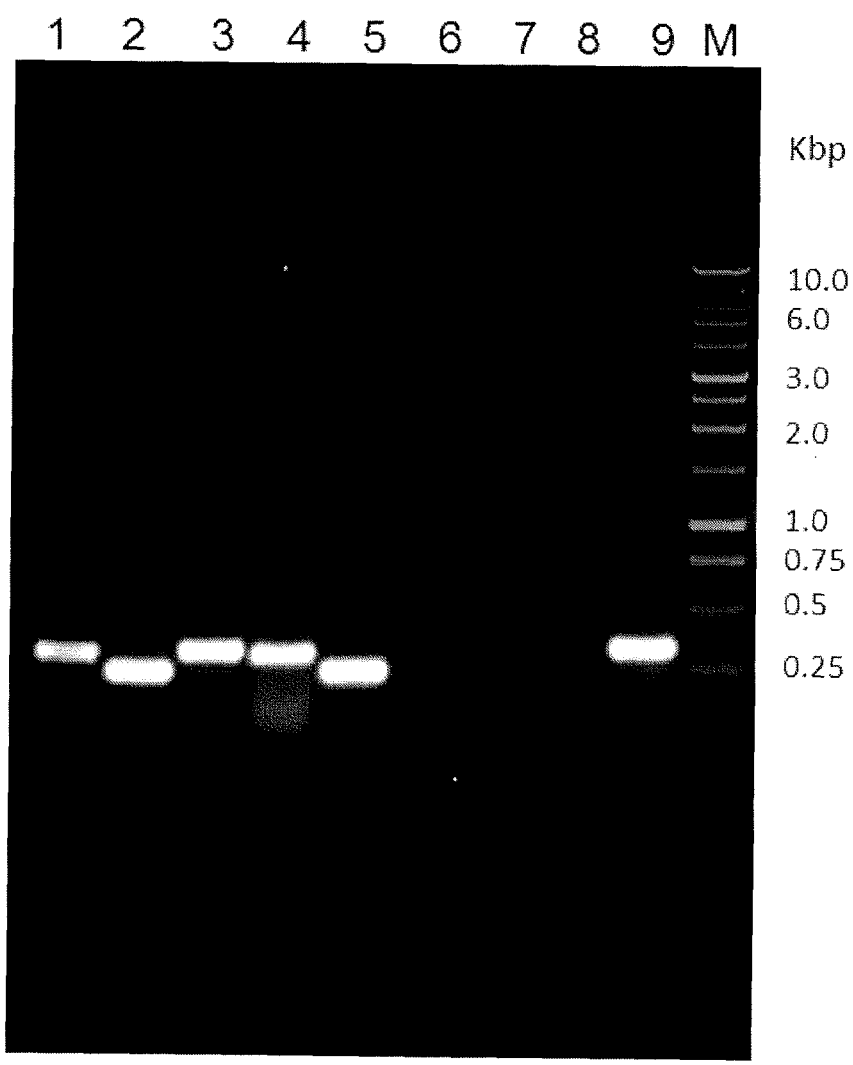

FIG. 6 shows the PCR detection of φFL1C genes in *E. faecalis* JH2-2. Template DNA, lanes: 1-3: φEf11(Δ61-1, φFL1C40-44); 4-6: *E. faecalis* JH2-2; 7-9: φEf11 wildtype. Primers, lanes: 1, 4, 7: φFL1C gp40 internal primers (FL1A35F/FL1A35R); 2, 5, 8: φFL1C gp44 internal primers (FL1A37F/FL1A38R); 3, 6, 9: φEf11 ORF44 internal primers (EF44F/EF44R); M: DNA marker.

Figure 7:
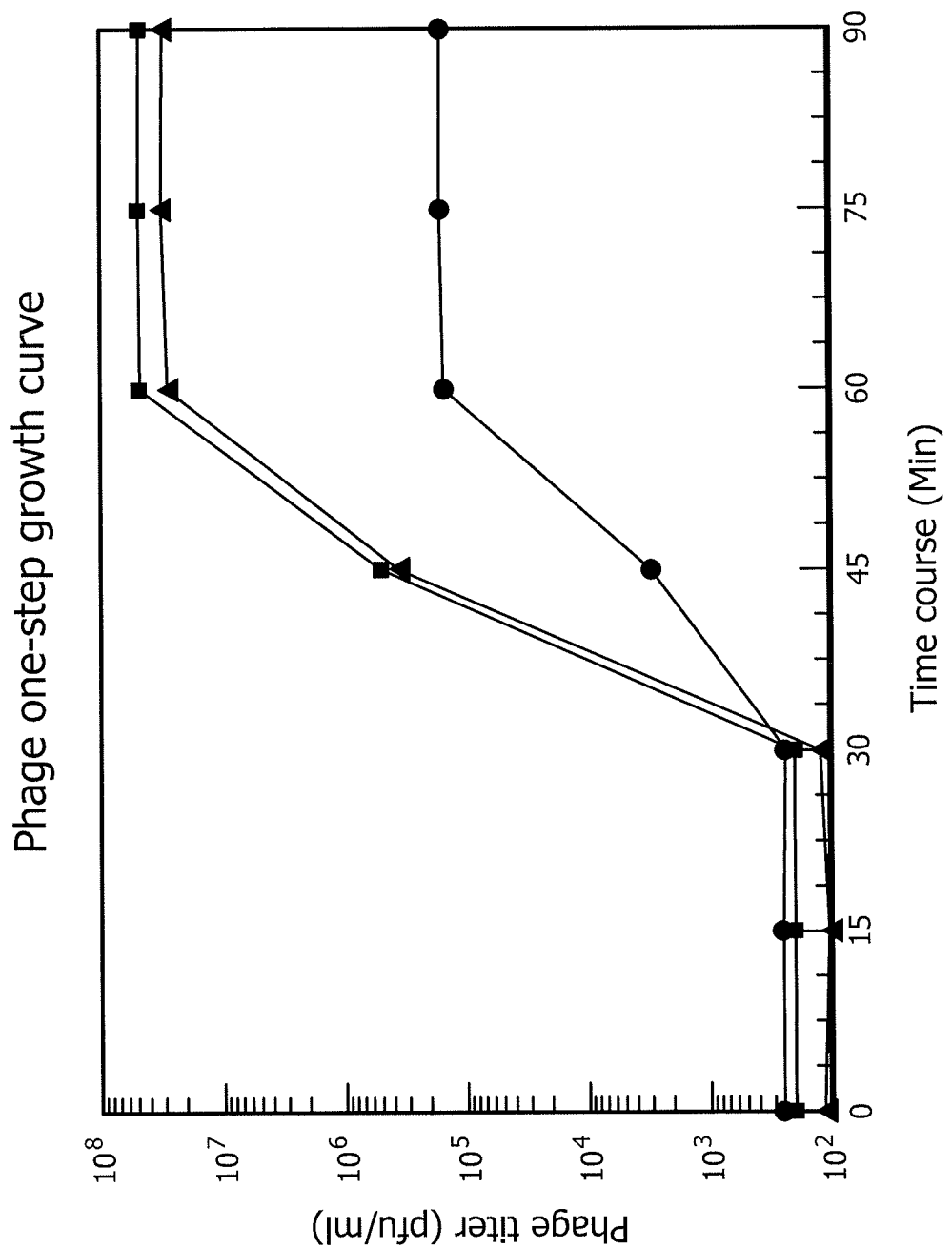

FIG. 7 shows a one-step growth curve for phage φEf11 (wild type), φEf11(Δ61-1, φFL1C40-44) (spontaneous recombinant), and φEf11(vir)$P^{nisA}$ (virulent variant). Log phase broth cultures of *E. faecalis* JH2-2 were infected with a phage stock. After adsorption for 30 minutes, the cells were collected by centrifugation, washed, and incubated at 37° C. At various time points aliquots of the suspension were centrifuged to remove the cells, and the supernatants were plaque assayed for phage titer (pfu/ml) using JH2-2 indicator cells. (-●- φEf11 titer (pfu/ml); -■- φEf11(Δ61-1, φFL1C40-44) titer (pfu/ml); -▲- φEf11 (vir)$P^{nisA}$ titer (pfu/ml).

Figure 8:
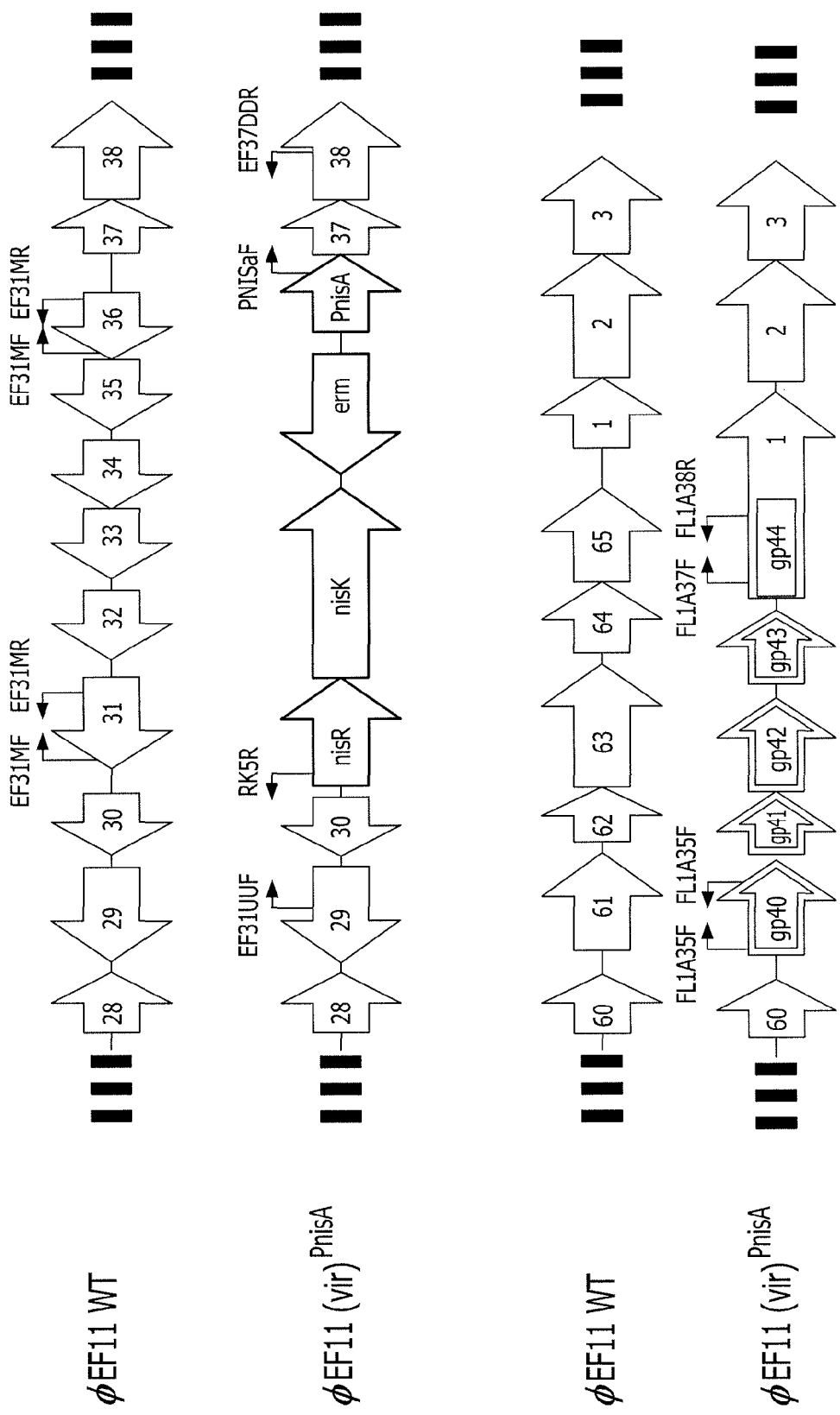

FIG. 8 represents a φEf11 (wild type) and φEf11(vir)$^{PnisA}$ sequence comparison. The virulent mutant, φEf11(vir)$^{PnisA}$, genes ORF30-ORF36 as well as the cro promoter were allelically exchanged for the Nisin promoter cassette, and OR61-ORF1 were allelically exchanged with gp40-gp44 of φFL1C.

Figure 9:
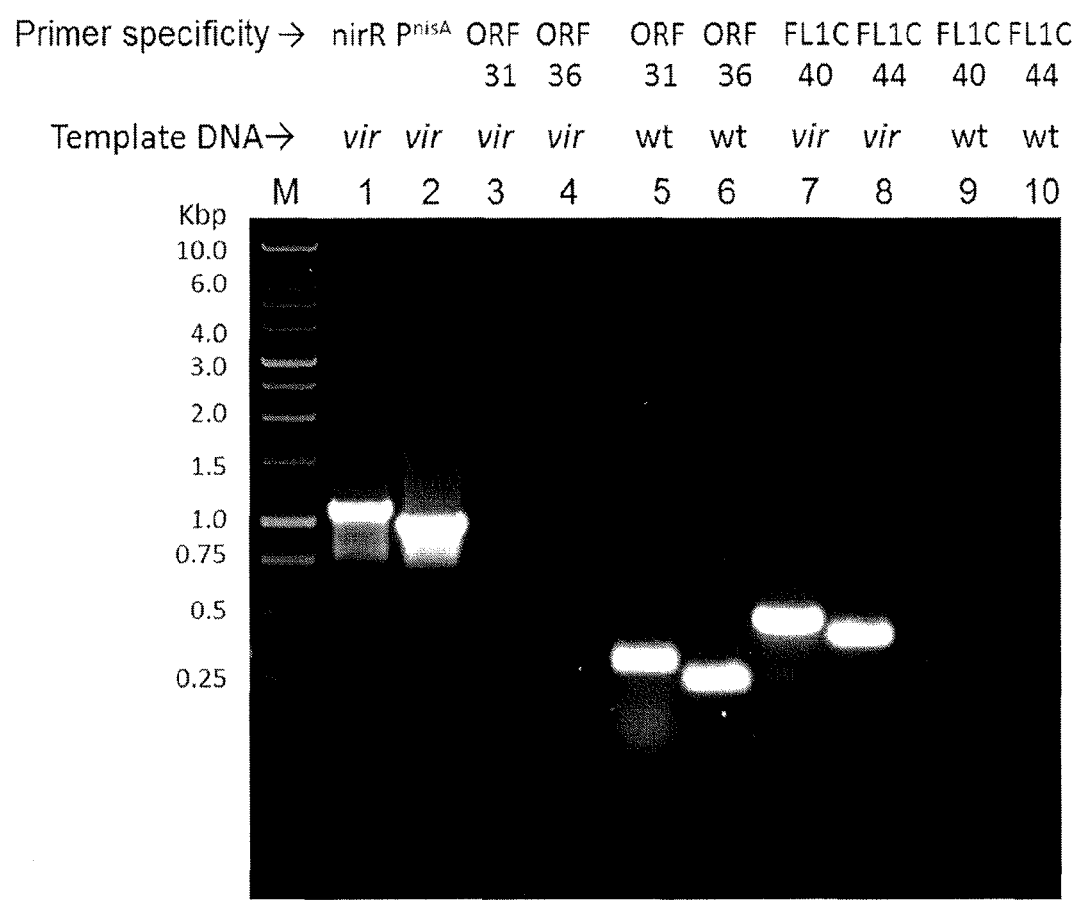

FIG. 9 shows a PCR analysis of the φEf11(vir)$^{PnisA}$ genome demonstrating absence of φEf11 ORFs 31 and 36, and the presence of nisR, $P^{nisA}$, φFL1C ORFs gp40 and gp44. PCR products were separated by electrophoresis in 2% agarose gels and detected by ethidium bromide staining. Numbers to the left of the gel indicate DNA fragment size (kbp). Template DNA for PCR reactions: φEf11(vir)$^{PnisA}$ (vir/lanes 1-4 and 7-8); φEf11 (wt/lanes 5-6 and 9-10). Primers used in the PCR reactions (see FIG. 8 for primer binding sites): Primer set EF31UUF/RK5R spanning ORF 29 to nisR (lane 1), primers PNISaF/37DDR spanning $P^{nisA}$ to ORF 38 (lane 2); primers EF31MF/EF31MR within ORF 31 (lanes 3 and 5); primers EF36MF/EF36MR within ORF 36 (lanes 4 and 6); primers FL1A35F/FL1A35R within φFL1C ORF gp40 (lanes 7 and 9), primers FL1A37F/FL1A38R within φFL1C ORF gp44 (lanes 8 and 10). Lane M: molecular weight markers (BenchTop 1 kb ladder, Promega).

Figures 10, 10A, 10B:
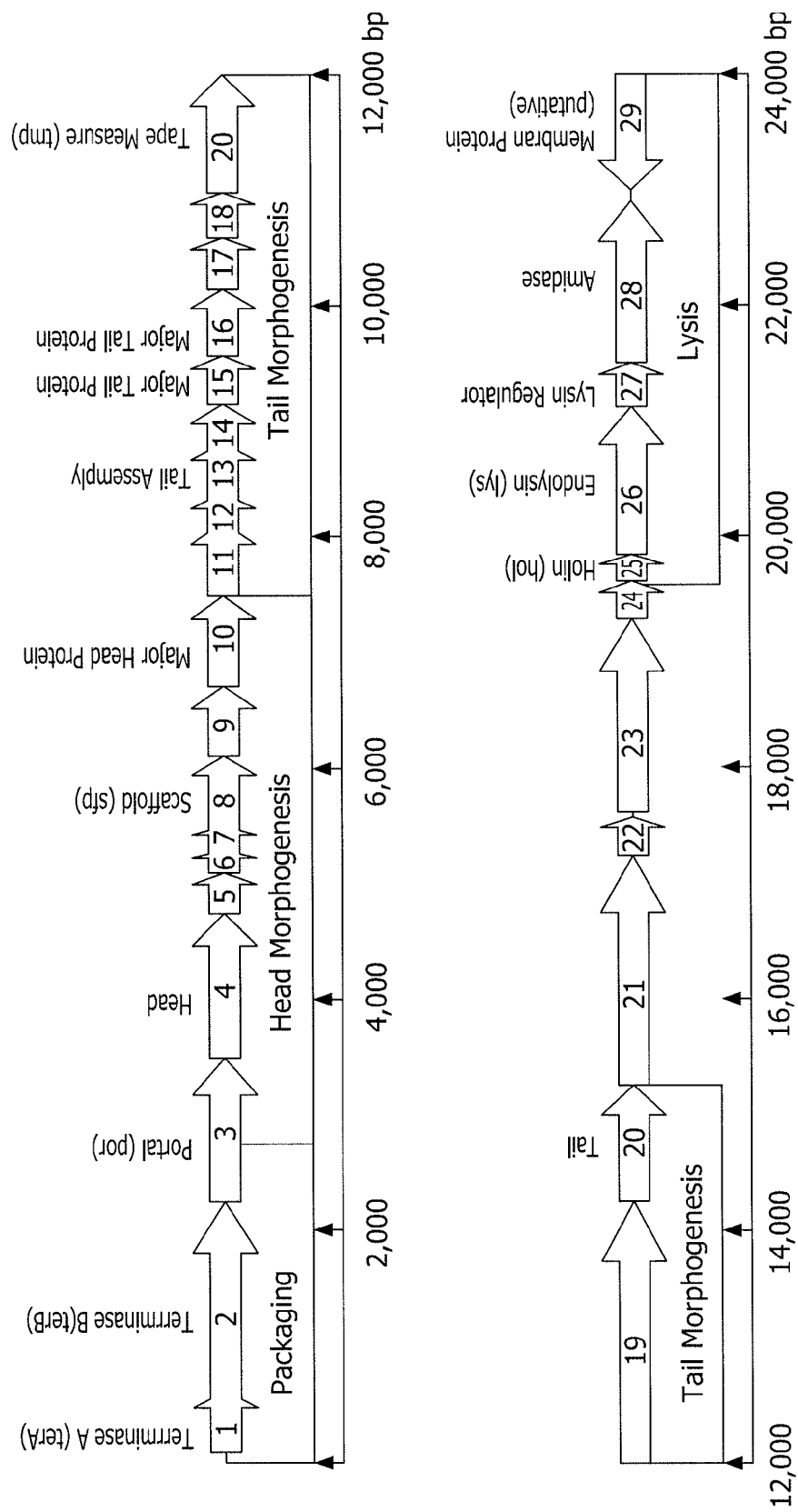
Figure 10B:
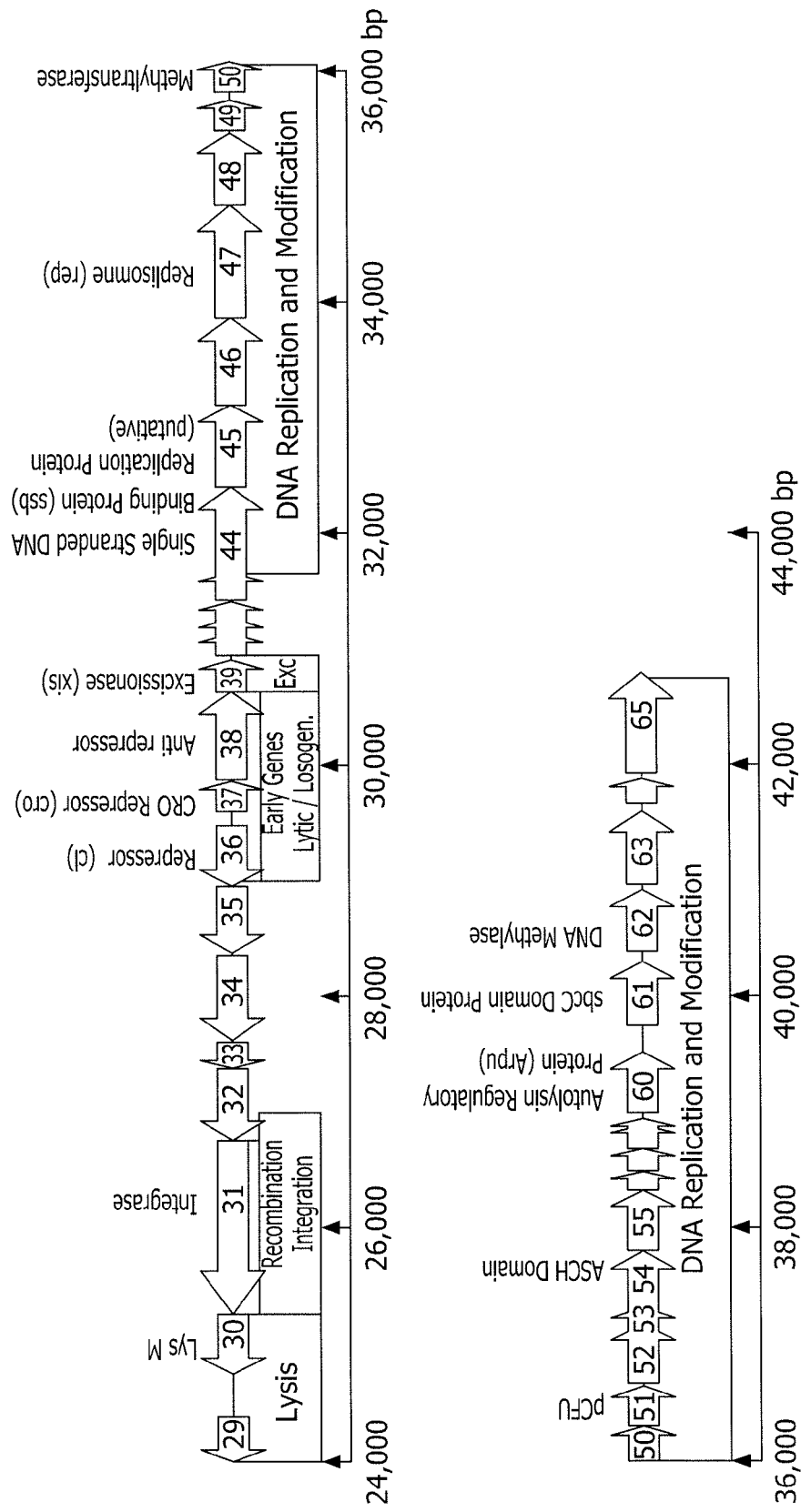

FIG. 10 shows the φEf11 genome. The numbered arrows indicate ORFs. The ORF numbering scheme in FIG. 10 corresponds to the numbering system contained in Stevens et al., 2011, supra. ORFs 25-29 are involved in host cell lysis.

FIGS. 11A-11E show a nucleotide sequence alignment of phages φEf11, φFL1C, and spontaneous recombinant phage [φEf11(Δ61-1, φFL1C 40-44)] in the region of recombination (φEf11 ORFs 60/61-1 and φFL1C ORFs 39/40-44). Non-bolded text indicates φEf11 sequences, boldface text indicates φFL1C sequences. Spontaneous recombinant is abbreviated as Sp. Genomic coordinates are indicated to right of each row of sequence. Sites of sequence identity between φEf11 and φEf11(Δ61-1, φFL1C 40-44) are indicated by *****. The figures show φEf11 sequence from 39307 to 41213 (SEQ ID NO: 171) (within ORF60) and from 1 through 451 (SEQ ID NO:172) (within ORF1), and φFL1C sequence from 14237 to 16206 (SEQ ID NO: 173) (within ORF39) and from 1672 to 17451 (SEQ ID NO: 174) (within ORF44). The segment of the φEf11 sequence that has been replaced by the φFL1C sequence to form the φEf11(Δ61-1, φFL1C 40-44) recombinant is indicated as enclosed by the hashed brackets. The figures shows the nucleotide sequence of the spontaneous recombinant phage [φEf11(Δ61-1, φFL1C 40-44)] from 1772 to 3740 (SEQ ID NO: 175) and from 4527 to 5006 (SEQ ID NO: 176). NdeI restriction site in φEf11 sequence is indicated.

DETAILED DESCRIPTION OF THE INVENTION

According to the present invention, engineered *Enterococcus faecalis* bacteriophages are provided that are virulent, highly lytic, incapable of lysogeny, insensitive to repressor, and capable of an extended host infectivity range. These characteristics make the recombinant phages useful as therapeutic agents in treatment and prevention of *Enterococcus faecalis* infections.

A recombinant bacteriophage, designated φEf11(vir)$^{PnisA}$, has been derived from φEf11. A lysogenic *Enterococcus faecalis* strain harboring phage φEf11(vir)$^{PnisA}$ was deposited in the Agricultural Research Service Culture Collection (NRRL), National Center for Agricultural Utilization Research Agricultural Research Service, USDA, 1815 North University Street Peoria, Illinois 61604-3999 on March 22, 2013 under accession number NRRL B-50833. The wild type phage φEf11 was deposited in the same depository on March 22, 2013 under accession number NRRL B-50832.

φEf11 is a temperate bacteriophage that was induced from a lysogenic root canal isolate of *Enterococcus faecalis* (Stevens et al., *Oral Microbiol. Immunol.*, 24: 278-284, 2009). Passage of φEf11 in *E. faecalis* JH2-2 has yielded the recombinant variant, φEf11(Δ61-1, φFL1C40-44), which provides elevated phage titers in broth cultures compared to the φEf11 wild type. The recombinant bacteriophage also produces much larger, clearer zones of lysis in lawns of *E. faecalis* cells, than does the wild type φEf11. Genetic analysis of the cloned virus producing the large plaques revealed that the variant was a recombinant between φEf11 and a defective φFL1C-like prophage located in the *E. faecalis* JH2-2 chromosome. The recombinant possessed 5 ORFs of the defective φFL1C-like prophage in place of 6 ORFs of the φEf11 genome. Deletion of ORFs 31-36 and replacement of the putative cro promoter from the recombinant phage genome with an exogenous regulatory element (inducible promoter) resulted in no loss of virus infectivity. Deletion of all lysogeny-related genes has resulted in a recombinant no longer having the capacity to form lysogens.

It was found that ORFs 31-36 are completely dispensable for lytic cycle function, since deletion of these genes did not prevent productive infection by the virus. Infection of lawns of host cells by the mutant virus lacking these genes produced clear plaques. Furthermore, surviving (presumptive lysogenic) cells from the plaques produced by the mutant virus lacking ORFs 31-36 could not be recovered. This confirms that deleting these genes from the viral genome, results in an φEf11 mutant that is incapable of lysogeny.

Regulatory elements in the φEf11 genome whose activation is required for the development of a productive/lytic infection within the cell, are inactivated by a protein (repressor) produced by ORF 36, one of the lysogeny-related genes. Lysogenic cells producing this repressor are thus immune to super infection by φEf11, and would consequently survive exposure to this virus.

Accordingly, a stem-loop structure surrounded by $P_L$ and $P_R$ promoter sequences in the φEf11 genome lying between a putative cI repressor gene and a putative cro gene was replaced with an exogenous regulatory element that is not susceptible to inactivation by the repressor. This $P^{CRO}$ region lies between ORFs 36 and 37. Specifically, the native promoter sequence was replaced with a nisin-inducible promoter, generating a virus that was capable of productively infecting *E. faecalis* (φEf11) lysogens, in the presence of the φEf11 cI repressor protein. Accordingly, replacement of the φEf11 wild type regulatory element with an exogenous regulatory element that is not susceptible to inactivation by the repressor, as provided herein, allows the variant bacteriophage to productively infect and lyse lysogenic cells that harbor a previously integrated φEf11 genome.

Surprisingly, spontaneous recombinational replacement of 5 genes (ORFs 61-65) of the DNA replication/modification module and 1 gene (ORF 1/terminase A) of the packaging module by 5 genes (ORFs 40-44) of *E. faecalis* phage φFL1C also had an effect on the virulence properties of the virus. While this genetic recombination had no effect upon host range, it did markedly alter the lytic properties observed during infection of either broth cultures or soft agar overlay lawns of susceptible host cells. Broth cultures rapidly and more thoroughly cleared, after infection by the recombinant phage φEf11(Δ61-1, φFL1C40-44), as compared to infection by the wild type φEf11 virus. Similarly, plaques produced by the recombinant phage φEf11(Δ61-1, φFL1C40-44) appeared as large, extensively spreading lytic zones with a clearer center, compared to those formed by the wild type φEf11 virus. Without wishing to be bound by any theory, the replacement (φFL1C) genes may contribute to a more robust, more productive lytic infection by increasing the efficiency of either phage DNA synthesis or packaging, or both. The results of one step growth experiments for wild type φEf11 and recombinant φEf11(Δ61-1, 95FL1C40-44) phages appear to bear out this hypothesis in that recombination of φEf11 with the φFL1C genes results in a greatly (>100 fold) enhanced production of progeny virus.

The recombination that occurred resulted in the deletion of a portion of ORF 1 of φEf11 corresponding to the nucleic acid sequence of SEQ ID NO: 169. The portion of ORF 1 of φEf11 corresponding to the nucleic acid sequence of SEQ ID NO: 170 was retained in the spontaneous recombinant phage φEf11 (Δ61-1, φFL1C40-44). The region upstream of the recombined ORF 1 sequence is an intergenic sequence between ORFs 65 and ORF 1.

In addition, the source of the φFL1C genes (i.e., the *E. faecalis* JH2-2chromosome) was unexpected, since previous studies reported that this *E. faecalis* strain was susceptible to φFL1C infection, and in fact, could form φFL1C lysogens following φFL1C infection, suggesting that this strain did not initially harbor a φFL1C prophage (Yasmin et al., *J. Bacteria* 192(4):1122-1130, 2010). PCR analysis failed to reveal other regions of the φFL1C genome that could be detected in JH2-2, suggesting that the φFL1C sequence that was detected was part of a defective (incomplete) prophage, or was the only φFL1C-like portion of a complete prophage.

A genetic construct incorporating all the afore-mentioned φEf11 genomic modifications has resulted in the generation of a variant, designated φEf11(vir)$^{PnisA}$, that is incapable of lysogeny and insensitive to repressor, rendering it virulent and highly lytic, with a notably extended host-range in comparison with the wild type virus φEf11. Compared to the wild type φEf11, the recombinant virus produces a more robust infection of *E. faecalis* cells and a greater degree of lysis of the host *E. faecalis* cells.

The φEf11(vir)$^{PnisA}$ virus has been constructed, in part, by replacing the repressor-sensitive cro promoter of the wild type φEf11 virus with the repressor-insensitive, nisin-inducible promoter system to drive phage lytic infection functions. This replacement has proved to be a very effective and useful strategy in making genetic modifications in the virus, and allows the φEf11(vir)$^{PnisA}$ virus to function as a useful intermediate in the preparation of derivative virus containing the desirable features discussed above. It may be appreciated, however, that to provide a therapeutic phage for managing Enterococcal infections would require replacement of the nisin-inducible promoter system of φEf11(vir)$^{PnisA}$ with an alternative inducible promoter responsive to a non-toxic inducer, or with a constitutive promoter.

One such promoter is the following constitutive promoter Tu derived from an *E. faecalis* strain:

```
                                         (SEQ ID NO: 168)
TCTAGATITTTCCTTGAGAATAAAAGGTTTGTTTTTAGAACTATCCTTT

TTTCAAGATTTCGTGTAAAATAGCTTATGATGATCAGACGATTTTTAGT

AACGTCTATCACATATAAAACAAACAATAAAATTTATATTTTTAGGAGG

AACATTCAAA
```

φEf11(vir)$^{PnisA}$ was engineered to include the property of antibiotic (erythromycin) resistance in order to assist in the selection of transformant lysogen clones containing prophages with the desired genotype. The skilled artisan would recognize that this feature would be omitted from a therapeutic phage, without prejudice to the desirable characteristics discussed above.

The bacteriophages of the present invention have been exemplified by preparation of φEf11 (vir)$^{PnisA}$ Further variants may be prepared by utilizing φEf11 as a template and carrying out the following genetic modifications as described in detail in the Example: (i) deletion of lysogeny ORFs 31-36; (i) replacement of the repressor-sensitive cro promoter of the wild type φEf11 virus with a repressor-insensitive inducible promoter system or constitutive promoter system to drive phage lytic infection functions; (iii)

replacement of 5 genes (ORFs 61-65) of the wild type DNA replication/modification module and 1 gene (ORF 1/terminase A) of the wild type packaging module by five genes (ORFs 40-44) of *E. faecalis* phage φFL1C. Utilization of the nisin-inducible promoter system as described in the Example, and provision for erythromycin resistance results in the φEf11(vir)$^{PnisA}$ phage, may be omitted.

Alternatively, variants of phage φEf11 (vir)$^{PnisA}$ may be prepared by utilizing φEf11(vir)$^{PnisA}$ phage as a starting material, and optionally removing the erythromycin resistance gene and optionally substituting the nisin-inducible promoter system of φEf11(vir)$^{PnisA}$ with either an inducible promoter system that does not rely on a toxic inducer, or with a constitutive promoter system, e.g., the constitutive Tu promoter of SEQ ID NO: 168.

Indications

The bacteriophages used in the methods and compositions of the present invention may be used to prevent and treat *Enterococcus faecalis* and *Enterococcus faecium* infections. Non-limiting sites of infection include, for example, the urinary tract, bloodstream, abdomen, biliary tract, burn wounds, indwelling catheters, infected root canals and the heart (e.g. endocardium).

The bacteriophages used in the methods and compositions of the present invention may be used to prevent and treat antibiotic-resistant *Enterococcus faecalis* and *Enterococcus faecium* infections, as well as infections that may be antibiotic-sensitive, to augment the antibiotic treatment regimen. The bacteriophages may also be used to treat immunocompromised patients and patients suffering from opportunistic hospital infections. Especially advantageous indications for the present invention may be as a treatment for root canal infections, infectious endocarditis, nosocomial infections, burn infections, urinary tract infections, meningitis and surgical wound infections.

Administration

The bacteriophages used in the methods and compositions of the present invention may be administered by any route, including orally, optically, subcutaneously, peritoneally, intravenously, topically, intradentally or parenterally. Also contemplated within the scope of the invention is the instillation of bacteriophage in the body of the patient in a controlled formulation, with systemic or local release of the drug to occur at a later time. For example, the bacteriophage may be localized in a depot for controlled release to the circulation, or for release to a local site of *Enterococcus* infection.

The bacteriophage may be placed on or imbedded within a wound dressing, e.g., a surgical wound dressing, to treat or prevent *Enterococcus* infection of the wound. The bacteriophage may be applied to the wound in this fashion alone or in combination with other antibacterial agents that do not interfere with antibacterial action of the bacteriophage. For example, the bacteriophage may be contained in a composition impregnated in a wound dressing, e.g. a cotton wool dressing, for topical administration to a wound site.

The specific dose of bacteriophage to obtain therapeutic benefit for treatment of an *Enterococcus* infection will, of course, be determined by the particular circumstances of the individual patient including, the size, weight, age and sex of the patient, the stage of the disease, the aggressiveness of the disease, and the route of administration of the bacteriophage.

The daily dose of the bacteriophage may be given in a single dose, or may be divided, for example into two, three, or four doses, equal or unequal, but preferably equal, that comprise the daily dose. When given intravenously, such doses may be given as a bolus dose injected over, for example, about 1 to about 4 hours.

The bacteriophages used in the methods of the present invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The bacteriophage is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

The compositions of the present invention can include pharmaceutically acceptable carriers such as lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The composition of the present invention can additionally include lubricants, wetting agents, sweetening agents, flavors, emulsifiers, suspensions and preservatives.

The composition of the present invention contains bacteriophage as an active ingredient. The bacteriophage may be included at the concentration of $1 \times 10^1$ pfu/ml-$1 \times 10^{15}$ pfu/ml or $1 \times 10^1$ pfu/g-$1 \times 10^{15}$ pfu/g, and more preferably at the concentration of $1 \times 10^4$ pfu/ml-$1 \times 10^9$ pfu/ml or $1 \times 10^4$ pfu/g-$1 \times 10^9$ pfu/g. Other concentrations may be envisioned by the skilled artisan.

For parenteral administration, the bacteriophage may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Preservatives may be included, but must be selected so as not to inactivate or otherwise impact the bacteriophage. The composition for parenteral administration may take the form of an aqueous or nonaqueous solution, dispersion, suspension or emulsion.

For oral administration, the bacteriophage may be combined with one or more solid inactive ingredients for the preparation of tablets, capsules, pills, powders, granules or other suitable oral dosage forms. For example, the bacteriophage may be combined with at least one excipient such as fillers, binders, humectants, disintegrating agents, solution retarders, absorption accelerators, wetting agents absorbents or lubricating agents. According to one tablet embodiment, the bacteriophage may be combined with carboxymethylcellulose calcium, magnesium stearate, mannitol and starch, and then formed into tablets by conventional tableting methods.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions of the present invention may be used for the prevention and treatment of *Enterococcus faecalis* and *Enterococcus faecium* infections.

The practice of the invention is illustrated by the following non-limiting example.

EXAMPLE

A. Materials and Methods
 1. Bacterial Strains and Growth Conditions
 TUSoD11 is a lysogenic *E. faecalis* strain, harboring a φEf11 prophage, which was previously isolated from an infected root canal (Stevens et al., *Oral Microbiol. Immunol.*, 24:278-284 (2009)). Following curing, the non-lysogenic variant of this strain was designated *E. faecalis* TUSoD11 (ΔφEf11).

JH2-2 is a Fus$^r$, Rif$^r$ mutant of a clinical *E. faecalis* isolate (Jacob & Hobbs, *J. Bacteriol.* 117(2):360-372, 1974) that was generously provided to us by Dr. Nathan Shankar. In the course of this study, it was found that this strain harbored a φFL1C-type prophage element (Yasmin et al., *J. Bacteriol.* 192(4):1122-1130, 2010), indicating that this strain was a lysogen with a defective prophage. Other *E. faecalis* strains used in this study are listed in Table 1.

All strains were grown in brain heart infusion (BHI) broth (or on brain heart infusion agar, with appropriate antibiotics). *Escherichia coli* one shot mach-T1® (Invitrogen) was used in cloning plasmids as describe below. The cells were grown in LB medium supplemented with the appropriate antibiotics. Additional bacterial species used as negative controls in PCR experiments are also listed in Table 1.

TABLE 1

| Bacterial strains | | |
|---|---|---|
| *E. faecalis* strain | Characteristics | Source |
| TUSoD11 | Lysogenic root canal isolate harboring φEfl1 prophage | 1 |
| JH2-2 | Rif$^r$, Fus$^r$, clinical isolate harboring defective φFL1C prophage | 2, 3 |
| OG1RF | Rif$^r$, Fus$^r$ | 3,4 |
| MMH594 | Gen$^r$ | 3 |
| OG1SSp | Str$^r$, Spc$^r$ | 5 |
| ER3/2s, ER5/1 | root canal isolates | 6, 7 |
| E1, E2, E3, E4, E5, E6, E7, E8, E10, E11 | oral isolates | 6, 8 |
| GS1, GS2, GS3, GS4, GS5, GS6, GS7, GS8, GS9, GS10, GS12, GS13, GS14, GS15, GS16, GS17, GS18, GS19, GS21, GS22, GS23, GS24, GS25, GS26, GS27, GS28, GS29, GS30, GS31, GS32, GS33 | root canal isolates | 9 |
| GS34 | tongue | 6, 7 |
| OS25 | oral isolate | 6, 10 |
| AA-OR3, AA-OR4, AA-OR26, AA-OR34 | oral isolates | 6, 11 |
| AA-T4, AA-T26 | tongue | 6, 11 |
| V583 | Van$^r$, clinical isolate | 6, 12 |
| OS16 | oral isolate | 6, 10 |
| TUSoD1, TUSoD2, TUSoD3 | Lysogenic root canal isolate | 1 |
| TUSoD9, TUSoD10, TUSoD12 TUSoD15, TUSoD17, TUSoD18 | root canal isolates | 1 |
| Non-Enterococcal spp: | | |
| *Streptococcus mutans* 10449 | grown in BHI broth | ATCC |
| *Streptococcus sanguis* 43055 | grown in BHI broth | ATCC |
| *Fingoldia (Peptostreptococcus) magna (magnus)* | grown in chopped meat broth | ATCC |
| *Clostridium perfringens* 13124 | grown in modified PY broth | ATCC |
| *Actinomyces israelii* 10049 | grown in BHI broth | ATCC |
| *Eubacterium lentum* 43033 | grown in chopped meat broth | ATCC |

[1] Stevens et al., *Oral Microbiol. Immunol.*, 24: 278-284 (2009);
[2] Jacobs and Hobbs, *J. Bacteriol.* 117(2): 360-372 (1974);
[3] Dr. Nathan Shankar;
[4] Dunny et al, *Plasmid*, 2: 454-465 (1979);
[5] Dunny, *Plasmid*, 2: 454-465 (1979);
[6] Dr. Christine Sedgley;
[7] Johnson et al., *J. Endod* 32: 946-950 (2006);
[8] Sedgley et al., *Oral Microbiol Immunol.* 19: 95-102(2004);
[9] Sedgely et al., *Oral Microbiol Immunol* 20: 10-19 (2005a);
[10] Sedgley et al., *Archs oral Biol.* 50(8): 575-583 (2005);
[11] Sedgley et al., *J. Endod* 32(2): 104-111 (2006);
[12] Sahm et al., *Antimicrob Agents Chemother* 33: 1588-1591 (1989).

2. Construction of Recombinant Plasmids

The allelic exchange plasmid pΔ31-36 P$^{nisA}$ was prepared as follows.

The Nisin promoter (P$^{nisA}$) cassette containing an erythromycin selection marker (erm) was PCR-amplified using the AccuPrime DNA Taq Polymerase High Fidelity kit (Invitrogen) with primer set PNISaF/PNISR (see Table 2 for primer specifications) from plasmid pMSP3535 (Bryan et al. *Plasmid*, 44:183-190, 2000), a kind gift from Dr. B. Buttaro. PCRs were performed in 30 µl reaction mixtures containing 2 µl template DNA, 2 µl (20 pmol) forward primer, 2 µl (20 pmol) reverse primer, 21.5 µl dH$_2$0, 2 µl buffer (provided by manufacturer), and 0.5 µl AccuPrime DNA Taq Polymerase. The PCR program used was: 95° C. for 2 min, followed by 35 cycles of (i) 95° C. for 45 sec, (ii) 55° C. for 45 sec, and (iii) 72° C. for 2 min. This was followed by an additional 5 min extension at 72° C. Following PCR, the amplicons were detected by agarose gel electrophoresis and ethidium bromide staining.

Figure 1:
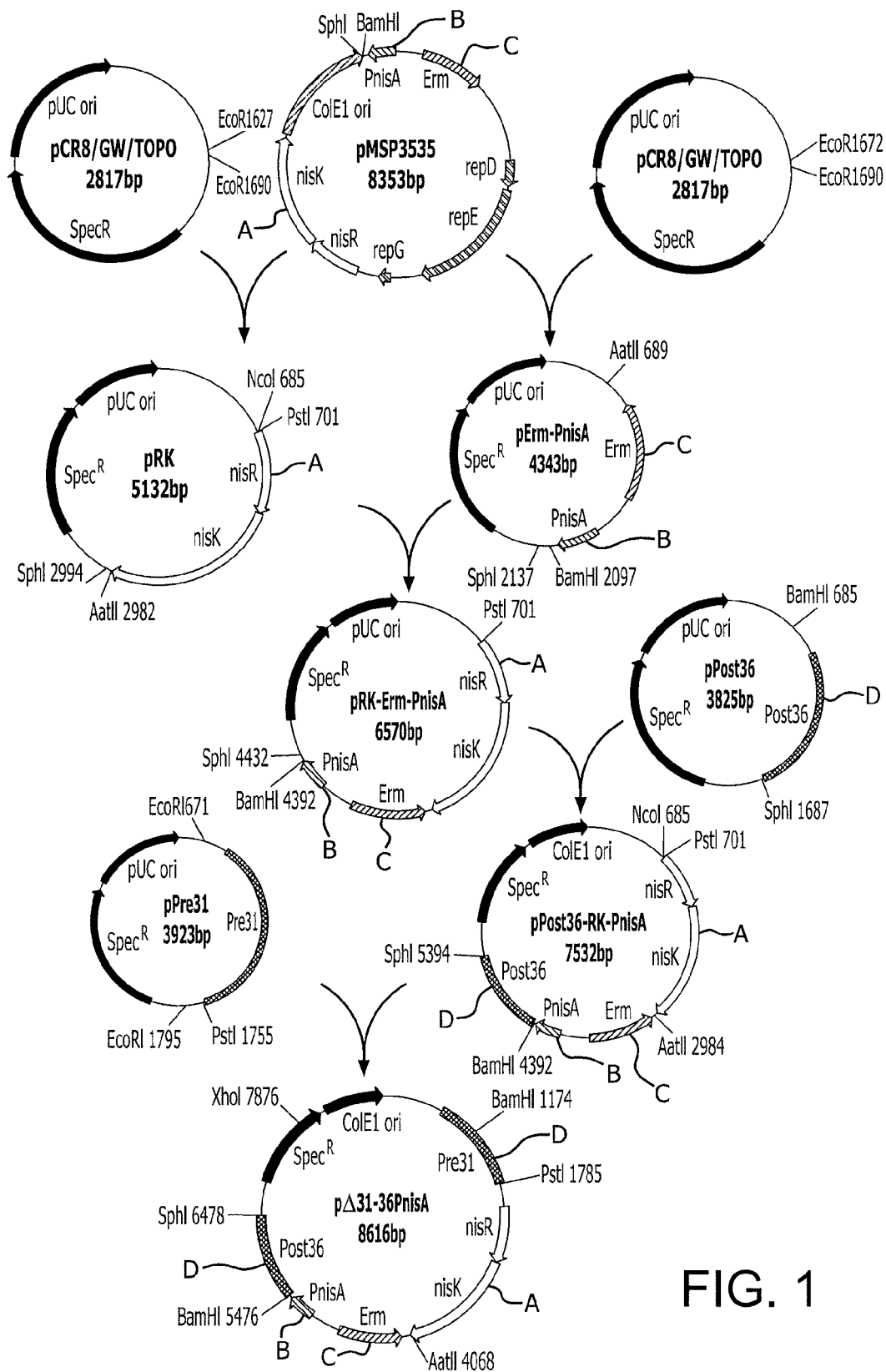
FIG. 1 is a schematic representation of the construction of plasmid pΔ31-36PnisA, the vector used to delete ORFs 31-36, and replace $P^{cro}$ with $P^{nisA}$ in the ϕEf11(Δ61-1, ϕFL1C40-44) prophage. The sequence comprising the two component nisin sensor system (nisR/nisK) is marked "A". The fragment representing the nisin promoter ($P^{nisA}$) is marked "B". The segment representing an erythromycin resistance marker (erm) is marked "C". Fragments immediately upstream (pre31) and downstream (post 36) of the ϕEf11 genomic region targeted for allelic exchange are marked "D".

The allelic exchange plasmid pΔ31-36 P$^{nisA}$ was then constructed as follows, as shown in FIG. 1. The amplicons generated by the above procedure were cloned into pCR8/GW/TOPO vector (Life Technologies) to create pErm-PnisA. The two-component Nisin sensor system (nisR/nisK) that controls the activation of P$^{nisA}$ by Nisin, was also amplified from pMSP3535 by PCR, using primer set RKnpF/RKaxR, and cloned into pCR8/GW/TOPO to create pRK. The P$^{nisA}$ fragment plus the erythromycin selection marker was digested from pErm-PnisA with AatII and SphI, and inserted into pRK to create pRK-Erm-PnisA. A fragment (pre31) of 1088 bp from nucleotide coordinates 24585 to 25672 of ϕEf11 (upstream of ORF31, the first gene of the putative lysogeny module) and a fragment (post36) of 1090 bp from 28588 to 29577 of ϕEf11 (immediately upstream of the putative cro gene, ORF37) were PCR-amplified using primer sets EF31UF/EF31UR and EF37DF/EF37DR, respectively, and cloned into pCR8/GW/TOPO to create pPre31 and pPost36. The post36 fragment was cut out from the pPost 36 with BamHI and SphI and inserted into pRK-Erm-PnisA, to create pPost36-RK-PnisA. The pPre31 was first digested with EcoRI and blunt-ended with the Klenow fragment of DNA polymerase I (Promega), then digested with PstI. Following this, the digested pre31 fragment was cloned into pPost36-RK-PnisA to create the allelic exchange plasmid pΔ31-36 P$^{nisA}$.

3. Isolation of Spontaneous Phage ϕEf11/ϕFL1C-Like Recombinant [ϕEf11(ϕ61-1, ϕFL1C40-44)] and the Creation of a Lysogen Harboring the Recombinant Prophage.

A log phase BHI broth culture of *E. faecalis* JH2-2 was inoculated with phage ϕEf11. After incubation at 37° C. for 1 hr, the culture was centrifuged (17,000×g for 3 min) and the supernatant was filtered (0.45 µm) before being plaque-assayed. After overnight incubation at 37° C., the plates were examined, and several large, extensively-spreading plaques were noticed among a background of small, turbid plaques. These large plaques were picked, and the virus in these large plaques was cloned by successive plaque purifications. The genomic DNA from the cloned virus was sequenced by Sanger di-deoxy sequencing reactions as described previously (Stevens et al., *FEMS Microbiol. Lett.*, 317: 9-26, 2011).

To create a lysogen harboring a ϕEf11(Δ61-1, ϕFL1C40-44) prophage, JH2-2 cells from surviving colonies in the center of the large plaques produced by this virus were cloned and screened for the presence of the recombinant phage genome. This was done by PCR using primers (EF60F/FL1A35R) that recognized ϕEf11 ORF 60 at the 5' end and ϕFL1C ORF 40 at the 3' end (see Table 2 for primer specifications). The lysogen harboring this recombinant prophage was designated *E. faecalis* JH2-2[ϕEf11(Δ61-1, ϕFL1C40-44)]. In addition, virus spontaneously released from this lysogen was detected by plaque assay, and also confirmed to be recombinant by PCR analysis.

TABLE 2

Primers

| Primer | Sequence (5'→3') | Use |
|---|---|---|
| EF31UF | GATAGTTCTTGTTTCGACAAATCAC (SEQ ID NO: 1) | Amplify upstream of ϕEf11 Orf31 |
| EF31UR | CTGTCGACGTTCCTGCAGAGCTCTAAATAAATATGG CAAGTA (SEQ ID NO: 2) | Amplify upstream of ϕEf11 Orf31 |
| EF37DF | CTGGATCCATGTGCTATGATTACTCAAAATTAGCAG (SEQ ID NO: 3) | Amplify downstream of ϕEf11 Orf36 |
| EF37DR | CTGCATGCCCTTTACCAGTAATTTTCGGCGT (SEQ ID NO: 4) | Amplify downstream of ϕEf11 Orf36 |
| RKnpF | CTCCATGGTCTCTCCTGCAGATAGAATTCTCATGTTT GACAGCTTATCA (SEQ ID NO: 5) | Amplify nisR and nisK |
| RKaxR | CTGCATGCTCTCTCGACGTCGCCAGTTAATAGTTTGC CGAA (SEQ ID NO: 6) | Amplify nisR and nisK |
| PNISaF | CTGACGTCACAAAAGCGACTCATAGAATTATTTCCTC C (SEQ ID NO: 7) | Amplify Erm-P$^{nisA}$ |
| PNISR | GCTTATCGAAATTAATACGACTCACTATAGG (SEQ ID NO: 8) | Amplify Erm-P$^{nisA}$ |
| EF31UUF | AAGAGCACCTCAAATTCCAGT (SEQ ID NO: 9) | Detection of ϕEf11 ΔOrf31-36 (upstream) |
| RK5R | TGATAAGCTGTCAAACATGAGAATTCT (SEQ ID NO: 10) | Detection of ϕEf11 ΔOrf31-36 (upstream) |

TABLE 2-continued

Primers

| Primer | Sequence (5'→3') | Use |
|---|---|---|
| 37DDR | TGTGATTTGCATGTAGACATCTCCT (SEQ ID NO: 11) | Detection of φEf11 ΔOr131-36 (downstream) |
| PNIS3F | TTGTAAAACAGGAGACTCTGCATG (SEQ ID NO: 12) | Detection of φEf11 ΔOrf31-36 (downstream) |
| EF31MF | AAGTTGTTTCCGTGTCAACGTGGC (SEQ ID NO: 13) | Detection of φEf11 Orf31 deletion |
| EF31MR | GTGTCCATCATGGTCGTTTAGCAG (SEQ ID NO: 14) | Detection of φEf11 Orf31 deletion |
| EF36MF | TTATCAGGGTCTGGTGAATGCG (SEQ ID NO: 15) | Detection of φEf11 Orf36 deletion |
| EF36MR | GCAACTTATGAGTGAGCGCAA (SEQ ID NO: 16) | Detection of φEf11 Orf36 deletion |
| φEF11F | GAGAGTGGAAGTGGA TTCAATG (SEQ ID NO: 17) | Detection of φEf11 Orf43 |
| φEf11R | GCACTTTCATCTAAACTCTCG (SEQ ID NO: 18) | Detection of φEf11 Orf43 |
| EF44F | ACCAAGATTTGACGCAGAAGTTGCC (SEQ ID NO: 19) | Detection of φEf11 Orf44 |
| EF44R | TGGCCATCGTCGTCTTTATCTGCT (SEQ ID NO: 20) | Detection of φEf11 Orf44 |
| EF60F | AGACGTTTGGACCGAATAGCTGGT (SEQ ID NO: 21) | Detection of φEf11 Orf60 |
| EF60R | TGCGGTAAGCTTCTGCGAATTCAA (SEQ ID NO: 22) | Detection of φEf11 Orf60 |
| F11A35F | GGGAACTAGCAGTTGAAGAATCGC (SEQ ID NO: 23) | Detection of φFL1C gp40 |
| F11A35R | TTCCTTTGTACTATCTTGATCTCCA (SEQ ID NO: 24) | Detection of φFL1C gp40 |
| F11A37F | GAGCGTTTAGATAAGTCGGATTGG (SEQ ID NO: 25) | Detection of φFL1C gp44 |
| F11A38R | CCAAGTTTCTTTAGCCTGGTCACG (SEQ ID NO: 26) | Detection of φFL1C gp44 |

4. Deletion of the Lysogeny Module and Replacement of Cro Promoter with $P^{nisA}$ by Allelic Exchange Cells of *E. faecalis* lysogen JH2-2[φEf11(Δ61-1, 4FL1C40-44)] were made competent using the procedures described by Shepard & Gilmore, *Methods Mol Biol.* 47:217-226 (1995). Briefly, the cells were grown in SGM17 medium (37.25 g/L M17, 0.5M sucrose and 8% glycine) for 48 hours at 37° C. The cells were then harvested by centrifugation, washed twice with EB buffer (0.5M sucrose and 10% glycerol), and finally resuspended in EB buffer. Plasmid pΔ31-36 $P^{nisA}$ was linearized with XhoI and then electroporated into the competent JH2-2 lysogens using the BioRad MicroPulser System. Following electroporation, 1 ml of SGM17MC medium (SGM17 plus 10 mM MgCl$_2$ and 10 mM CaCl$_2$) was added to the electroporation cuvette, which was then incubated for 2 hours. Transformants were selected on BHI agar containing erythromycin (30 µg/ml). Presumptive transformant colonies were screened for deletion of the lysogeny module genes (φEf11 ORFs 31-36) and replacement of $P^{cro}$ by $P^{nisA}$ by PCR using primers EF31UUF/RK5R, PNIS3F/37DDR, EF31MF/EF31MR and EF36MF/EF36MR. In addition, control of lytic functions in the prophage by the $P^{nisA}$ was demonstrated by measuring phage induction in the presence or absence of Nisin (40 ng/ml). The phage recovered from the induced lysogens lacking ORFs 31-36 and $P^{cro}$, but containing the $P^{nisA}$ promoter, was designated φEf11 (vir)$^{PnisA}$.

5. Screening for the Presence of φEf11 Prophages in *E. faecalis* Strains

Primers specific to φEf11 were designed from φEf11 ORF 43 (GenBank accession number GQ452243.1, Gene ID number 8683894). This sequence (ORF 43) of the φEf11 genome was chosen since searches of all available data bases failed to disclose any homologous sequences to this gene. The forward (φEf11F) and reverse (φEf11R) primers for amplification of a 165 bp amplicon of this gene are specified in Table 2, above. Template DNA was prepared as follows: 10 ml broth cultures of each strain to be screened were pelleted by centrifugation, washed in 4 ml of wash solution [20 mM Tris-HCl (pH 8.5), 0.85% NaCl], resuspended in 2 ml of lysis buffer [1% Triton X-100, 20 mM Tris-HCl (pH 8.5), 2 mM EDTA], and heated to 95°-100° C. for 10 min. The suspension was then centrifuged and the supernatants were collected and frozen away at −80° C. until being used in PCR assays (Goncharoff et al., 1993, *Oral Microbiol Immunol* 8:105-110). Extracts from *E. faecalis* TUSoD11 (lysogenic for φEf11) were used as positive controls, and extracts from *E. faecalis* JH2-2 (non-lysogenic for φEf11) and numerous unrelated species (see Table 1) were used as negative controls. Reaction mixtures (Σ=40 µl) for PCR contained 5 µl of template DNA, 5 µl (50 pmol) of forward primer, 5 µl (50 pmol) of reverse primer, 5 µl dH$_2$O, and 20 µl 2X Go Taq green PCR master mix (Promega). The PCR program used was 97° C. for 1 min, followed by 26 cycles of (i) 97° C. for 1 min, (ii) 50° C. for 45 sec, and (iii) 72° C. for 1 min. This was followed by an additional 4 min at 72° C. Following PCR, amplification products were detected by agarose (2%) gel electrophoresis and ethidium bromide staining.

6. Preparation of Cured *E. faecalis* TUSoD11

Cells of *E. faecalis* TUSoD11 were made competent for electroporation as described above. After electroporation with the allelic exchange vector pΔ31-36 PnisA, erythromycin-resistant colonies were screened for homologous recombination-mediated deletion of the lysogeny module genes (ORFs 31-36) in the genome of *E. faecalis* TUSoD11. Strains exhibiting deletion of ORFs 31-36 were further tested by PCR for the presence of φEf11 genes outside of the lysogeny module. In addition to clones containing φEf11 genes other than ORFs 31-36, a few rare clones were identified that lacked any of the φEf11 genes. Such clones could not be induced, but could now be infected by phage φEf11. These cured clones were designated *E. faecalis* TUSoD11(ΔφEf11).

7. Testing Adsorption of φEf11 and φEf11(Δ61-1, φFL1C40-44) to Lysogenic and Non-Lysogenic *E. faecalis* Strains

*E. faecalis* strains JH2-2, TUSoD11 and the cured strain, TUSoD11 (ΔφEf11) were grown in BHI medium to log phase. 100 μl of φEf11 or φEf11(Δ61-1, φFL1C40-44) preparations were added to 1 ml *E. faecalis* strains. After incubation at 37° C. for 10 minutes the mixtures were centrifuged at 17,000 g for 3 minutes, the supernatants were filtered through 0.45 μm filters, and filtrates containing any unabsorbed phage, were plaque-assayed, using JH2-2 indicator cells, to determine residual phage titers.

8. One Step Growth Curve

The cells of a log phase BHI broth culture (2 ml) of *E. faecalis* JH2-2 were collected by centrifugation, resuspended in 1 ml of BHI broth, and inoculated with 100 μl of a stock culture of either phage φEf11, φEf11(Δ61-1, φFL1C40-44) or φEf11(vir)$^{PnisA}$. After incubation for 30 minutes to allow phage adsorption, the cells were recovered by centrifugation, washed 3 times in BHI broth, and finally resuspended in 10 ml of BHI broth. Aliquots (500 μl) of the suspension were made, and each was incubated at 37° C. At various time points, an aliquot was centrifuged to remove the cells, and the supernatant was plaque-assayed, using fresh JH2-2 indicator cells, for phage titer.

9. Host range determination for φEf11, φEf11(Δ61-1, φFL1C40-44), and φEf11(Vir)$^{PnisA}$.

Plaque assays and spot tests were conducted with wild type phage φEf11 and recombinant phages φEf11(Δ61-1, φFL1C40-44) and φEf11(vir)$^{PnisA}$ using a panel of 66 *E. faecalis* strains as indicators. The *E. faecalis* panel included both lysogenic and non-lysogenic strains. Lytic infection by each phage was detected by plaque assay with each *E. faecalis* indicator strain.

B. Results and Discussion

1. Isolation of Spontaneous φEf11/φFL1C Recombinant

Figure 2A:
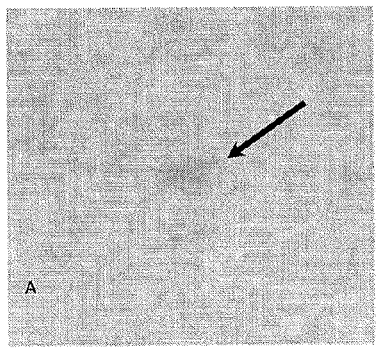
FIGS. 2A-2F show the results of a plaque assay of ϕEf11 wild type (WT), spontaneous recombinant [(ϕEf11(ϕ61-1, ϕFL1C40-44)], and virulent mutant [ϕEf11(vir)$^{PnisA}$]: (2A) WT after incubation for 1 day, (2B) WT after incubation for 2 days, (2C) spontaneous recombinant after incubation for 1 day, (2D) spontaneous recombinant after incubation for 4 days, (2E) virulent mutant after incubation for 1 day, (2F) virulent mutant after incubation for 4 days.
Figure 2B:
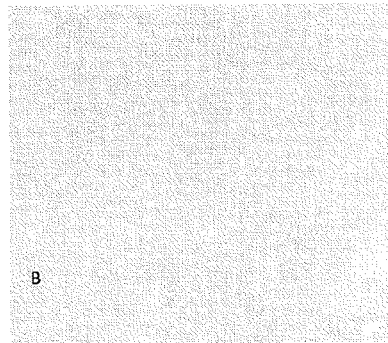
Figure 2C:
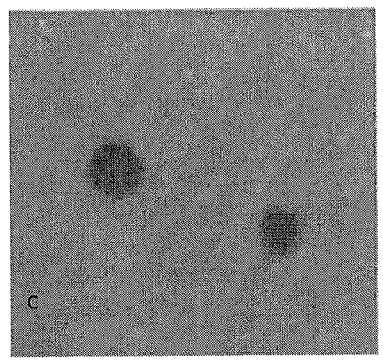
Figure 2D:
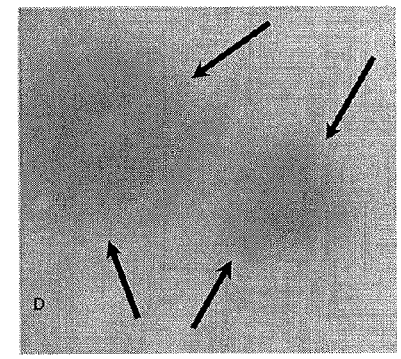

Repeated propagation and plaque assay of phage φEf11 on host strain *E. faecalis* JH2-2, revealed that variants of the wild type virus were being generated. Whereas wild type φEf11 produced small, turbid plaques in lawns of JH2-2 (FIG. 2A), approximately 0.02% of the plaques appeared as large, extensively spreading, somewhat clearer zones of lysis. Interestingly, incubation of plaque assays of clones obtained by plaque purification of the virus producing these larger plaques resulted in continued expansion of the plaques to the extent that virtually the entire JH2-2 lawn was lysed (FIGS. 2C-2D). In contrast, wild type plaques typically disappeared after extended incubation, presumably due to growth of surviving lysogens within the plaques (FIG. 2B).

AGE analysis of the NdeI restriction fragments of the DNA from the virus producing these large plaques revealed that it was missing one of the fragments (fragment 6, 2.79 kbp) that was present in the NdeI DNA digestion of the original φEf11 isolate (FIG. 3B). In addition, it was also noticed that another one of the NdeI fragments (fragment 2, approx. 9.4 kbp) from the DNA of the virus producing the large plaques, had increased in size (compared to the NdeI fragment 2 from the original φEf11 DNA) (FIG. 3A) by an amount approximately equal to the size of the missing NdeI fragment 6 (FIG. 3B).

FIG. 4 shows the NdeI restriction site analysis of the φEf11 DNA. The φEf11 DNA is 42,822 in length and is oriented as described in Stevens et al., *FEMS Microbiol. Lett.*, 317: 9-26 (2011), with the genes arranged with ORF 1 at the extreme left end and ORF 65 at the extreme right end. NdeI restriction sites (bp coordinates) are indicated the boxes. The NdeI restriction fragments, as visualized in agarose gel electrophoresis analysis AGE, are labeled 1-12.

Inspection of the φEf11 NdeI restriction map (FIG. 4) and the φEf11 NdeI restriction digest summary (Table 3), revealed that NdeI fragment 6 was composed of the two extreme ends of the genome (fragment coordinates 0-1,036 plus 41,068-42,822), and that in a circularly permuted genome, this fragment is immediately adjacent to NdeI fragment 2 (coordinates 33,692-41,068) (FIG. 4).

TABLE 3

NdeI restriction digest summary for φEf11 genome

| Fragment Number (as seen in gel) | Fragment Length | Fragment Coordinates |
|---|---|---|
| 1 | 12,126 | 9,349-21,475 |
| 2 | 7,376 | 33,692-41,068 |
| 3 | 5,029 | 26,948-31,977 |
| 4 | 4,660 | 22,288-26,948 |
| 5 | 4,247 | 3,065-7,312 |
| 6 | 2,790 | 0-1,036 + 41,068-42,822 |
| 7 | 2,037 | 7,312-9,349 |
| 8 | 1,818 | 1,248-3,065 |
| 9 | 1,715 | 31,977-33,682 |
| 10 | 547 | 21,741-22,288 |
| 11 | 266 | 21,475-21,741 |
| 12 | 212 | 1,036-1,248 |

FIGS. 5 and 11A-11E show the nucleotide sequence alignment of phages φEf11, φFL1C, and spontaneous recombinant phage [φEf11(Δ61-1, φFL1C 40-44)] in the region of recombination (φEf11 ORFs 60/61-1 and φFL1C ORFs 39/40-44). FIG. 5 presents an overview of the regions of φEf11 and φFL1C that recombined to yield recombinant φEf11(Δ61-1, φFL1C 40-44). FIGS. 11A-11E show φEf11 sequence from 39307 (within ORF60) through 451 (within ORF1), and φFL1C sequence from 14236 (within ORF39) to 17451 (within ORF44). Non-bolded text indicates φEf11 sequences, boldface text indicates φFL1C sequences. Spontaneous recombinant is abbreviated as Sp. Genomic coordinates are indicated to right of each row of sequence. Sites of sequence identity between φEf11 and φEf11(Δ61-1, φFL1C 40-44) are indicated by *****.

Figure 11E:
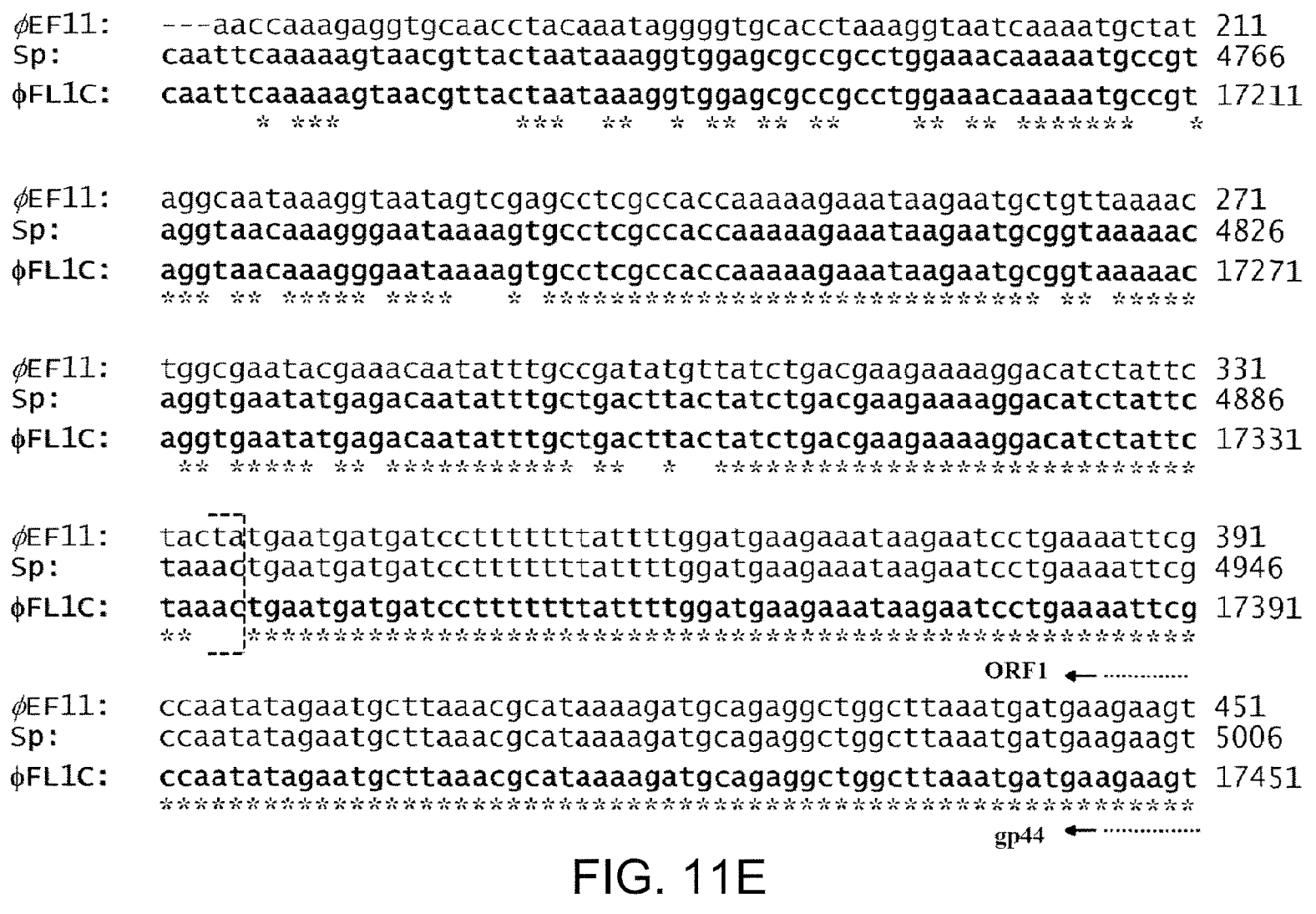

Sequencing this region of the genome thus disclosed that ORFs 60 through 65 and 1 of φEf11 (coordinates 39671-42822 and 1-336), were replaced by ORFs 40 through 44 (coordinates 14600-17336) of *E. faecalis* phage φFL1C (FIGS. 5 and 11). NdeI restriction site at coordinate 41,068 which divides NdeI fragment 2 from NdeI fragment 6 in the φEf11 DNA is absent in the φFL1C DNA and consequently in the DNA of the recombinant virus (FIGS. 11A-11E). No other modifications of the genome were detected. Consequently, this φEf11/φFL1C recombinant was designated phage φEf11(Δ61-1, φFL1C40-44).

Since the JH2-2 genome was the only possible source of the φFL1C genes, *E. faecalis* JH2-2 was screened for the φFL1C prophage. φFL1C (ORFs 40-44)-specific primers (Table 2) were used in PCR with JH2-2 extracts, prepared as described previously. As seen in FIG. 6, φFL1C-specific amplicons were generated from the JH2-2 templates and the φFL1C-specific primers, confirming the presence of (at least a portion of) a φFL1C prophage in the JH2-2 chromosome. PCR, using JH2-2 template DNA and primers specific for regions of the φFL1C genome other than ORFs 40-44, failed to produce any amplicons (data not shown).

2. Deletion of the Lysogeny Module and Replacement of Cro Promoter in φEf11(Δ61-1, φFL1C40-44) by Allelic Exchange A one-step growth curve was generated as follows for phage φEf11 (wild type), φEf11(Δ61-1, φFL1C40-44) (spontaneous recombinant), and φEf11(vir)$P^{nisA}$ (virulent variant). Log phase broth cultures of *E. faecalis* JH2-2 were infected with a phage stock. After adsorption for 30 minutes, the cells were collected by centrifugation, washed, and incubated at 37° C. At various time points aliquots of the suspension were centrifuged to remove the cells, and the supernatants were plaque assayed for phage titer using JH2-2 indicator cells. The results are shown in FIG. 7 (-●- φEf11 titer (pfu/ml); -■- φEf11 (Δ61-1, φFL1C40-44) titer; -▲- φEf11 (vir)$P^{nisA}$ titer. The φEf11(Δ61-1, φFL1C40-44) recombinant exhibited enhanced lytic activity (compared to wild type virus) as judged by the extensively enlarged plaques it forms in lawns of host cells (FIG. 2C), and the elevated titers it achieved in productive infection (FIG. 7). These variants of phage φEf11 could be subject to repression due to superinfection immunity, and be limited in lytic infection due to the possibility of entering into lysogeny, rather than generating a productive infection. Accordingly, all lysogeny-related genes were deleted and regulatory genetic elements were rendered insensitive to repressor control, as follows.

Clones of JH2-2[φEf11(Δ61-1, φFL1C40-44)] transformed with plasmid pΔ31-36 PnisA, were selected on erythromycin-containing media. PCR analysis and sequencing of these erythromycin-resistant JH2-2[φEf11(Δ31-36, ΔP$^{CRO}$, P$^{nisA}$, erm, nisR/K, Δ61-1, φFL1C40-44)] clones demonstrated that they lacked φEf11 ORFs 31-36, and the φEf11 cro promoter, but contained the nisin promoter (P$^{nisA}$) and nisR/nisK (FIG. 8 and FIG. 9). In the analysis, PCR products were separated by electrophoresis in 2% agarose gels and detected by ethidium bromide staining. Numbers in FIG. 9 to the left of the gel indicate DNA fragment size (kbp). Template DNA for PCR reactions: φEf11(vir)$^{PnisA}$ (vir/lanes 1-4 and 7-8); φEf11 (wt/lanes 5-6 and 9-10). For the primers used in the PCR reactions, see FIG. 8 for primer binding sites: Primer set EF31UUF/RK5R spanning ORF 29 to nisR (lane 1), primers PNISaF/37DDR spanning P$^{nisA}$ to ORF 38 (lane 2); primers EF31MF/EF31MR within ORF 31 (lanes 3 and 5); primers EF36MF/EF36MR within ORF 36 (lanes 4 and 6); primers FL1A35F/FL1A35R within φFL1C ORF gp40 (lanes 7 and 9), primers FL1A37F/FL1A38R within φFL1C ORF gp44 (lanes 8 and 10). In FIG. 9, lane M shows molecular weight markers (BenchTop 1 kb ladder, Promega).

Exposure of a population of this lysogenic clone, harboring a mutant prophage containing the nisin promoter (P$^{nisA}$) in place of the wild type cro promoter/operator (P$^{CRO}$), to nisin (40 ng/ml) resulted in the induction of phage, yielding a titer of 6.82×10$^7$ pfu/ml (±0.31×10$^7$). In the absence of nisin, a similar population of these lysogens spontaneously released phage, producing a titer of 5.57×10$^5$ pfu/ml (±0.31× 10$^5$). In contrast, phage induction from lysogens [JH2-2{φEf11(Δ61-1, φFL1C40-44)}] containing a prophage with the wild type cro promoter/operator did not appear to be affected by the presence of nisin: In the presence of nisin (40 ng/ml), these cells produced a phage titer of 3.36×10$^5$ pfu/ml (±0.25×10$^5$), whereas the same cells produced a titer of 3.31×10$^5$ pfu/ml (±0.38×10$^5$) in the absence of nisin. These data indicate that productive infection was now under control of the nisin-sensitive promoter (P$^{nisA}$), albeit somewhat leaky.

Figure 2E:
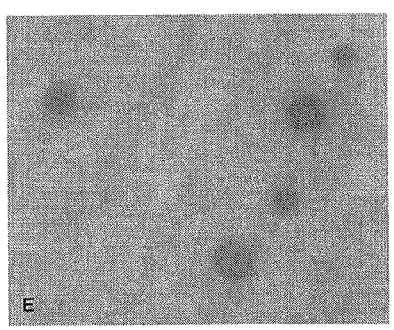
Figure 2F:
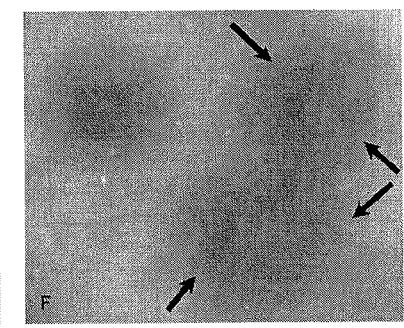

The virus obtained, phage [φEf11(Δ31-36, ΔP$^{CRO}$, P$^{nisA}$, erm, nisR/KΔ61-1, φFL1C40-44)], by Nisin induction of the JH2-2[φEf11(Δ31-36, ΔP$^{CRO}$, P$^{nisA}$, erm, nisR/KΔ61-1, φFL1C40-44)] lysogens produced large, clear plaques (FIG. 2E-2F), and was designated φEf11 (vir)$^{PnisA}$. As will be shown below, this derivative of temperate phage φEf11 had all the characteristics of a virulent virus.

3. Isolation of Cured *E. faecalis* TUSoD11

After electroporation of *E. faecalis* TUSoD11 with the gene exchange vector pΔ31-36 PnisA, erythromycin-resistant colonies were screened by PCR for deletion of ORF31-ORF36. Unexpectedly, a few colonies were found with deletions of not only the intended ORF31-ORF36 lysogeny module, but also all other phage genes outside this region. These clones may have been generated by the homologous recombination between the gene exchange vector and a permutated and terminally redundant prophage DNA that may have positioned the ORF30 and ORF37 regions at either end of the φEf11 prophage within the host *E. faecalis* TUSoD11 chromosome. These *E. faecalis* clones, lacking any detectable φEf11 genes, were designated TUSoD11 (φEf11), and were further tested for phage induction. No phage could be induced from these cells.

4. Restoration of Adsorption of φEf11 and φEf11(Δ61-1, φFL1C40-44) by a Cured *E. faecalis* Strain Phage suspensions were incubated with each of the *E. faecalis* strains indicated in Table 4 for 10 minutes, whereupon the cultures were centrifuged and filtered to remove the cells along with all adsorbed phage. The cell-free filtrates were then assayed for residual phage titer. The values shown in Table 4 represent the mean of triplicate assays ±standard deviation.

TABLE 4

Phage adsorption by lysogenic and non-lysogenic E. faecalis strains.

| Phage | Phage titer before adsorption | Residual phage titer after adsorption with: | | |
|---|---|---|---|---|
| | | Lysogen TUSoD11 | Non-lysogen JH2-2 | Non-lysogen Cured TUSoD11 |
| φEf11 | $1.2 \times 10^5$ | $1.17 \times 10^5 \pm 0.16 \times 10^5$ | $3.2 \times 10^2 \pm 0.25 \times 10^2$ | $2.74 \times 10^2 \pm 0.16 \times 10^2$ |
| φEf11(Δ61-1, ΦFL1C40-44) | $5.58 \times 10^7$ | $5.23 \times 10^7 \pm 3 \times 10^7$ | $0.24.79 \times 10^2 \pm 0.23 \times 10^2$ | $3.82 \times 10^2 \pm 0.17 \times 10^2$ |

As shown in Table 4, neither φEf11 nor φEf11(Δ61-1, φFL1C40-44) could produce a viable infection on the lysogenic TUSoD11 strain due to superinfection immunity. It was interesting that incubation of either φEf11 or φEf11 (Δ61-1, φFL1C40-44) with a cell suspension of lysogenic *E. faecalis* strain TUSoD11 failed to result in phage adsorption to the cells. In contrast, cell suspensions of either strain JH2-2 (non-lysogenic with respect to φEf11) or TUSoD11 (φEf11), a cured *E. faecalis* strain, effectively adsorbed both virus strains.

5. Host Range of φEf11(Vir)$^{PnisA}$

Plaque assays and spot tests were conducted with wild type phage φEf11 and recombinant phages φEf11(Δ61-1, φFL1C40-44) and φEf11 (vir)$^{PnisA}$ using a panel of 66 *E. faecalis* strains as indicators. The *E. faecalis* panel included both lysogenic and non-lysogenic strains. Lytic infection by each phage was detected by plaque assay with each *E. faecalis* indicator strain. The results are shown in Table 5. It can be seen that whereas wild type φEf11 productively infected only 4 (6%) of the 67 *E. faecalis* strains tested, productive infection occurred in 33 (49%) of these strains inoculated with phage φEf11(vir)$^{PnisA}$. The panel of *E. faecalis* strains was also screened by PCR for the presence of a prophage, using φEf11-specific primers. Among the strains tested, 14 were found to be φEf11 lysogens (data not shown). Of these 14 φEf11 lysogens, none were susceptible to wild type φEf11, however, 4 of these lysogenic strains (strains GS2, GS8, GS22 and GS25) could be productively infected by φEf11(vir)$^{PnisA}$. Furthermore, the presence of the φEf11 repressor gene (cI/ORF-36) was confirmed in these φEf11(vir)$^{PnisA}$-susceptible lysogenic strains by PCR (data not shown).

TABLE 5

Host range of *E. faecalis* phages

| E. faecalis strain | φEf11 (wild type) | φEf11 (Δ61-1, φFL1C39-44 (spontaneous recombinant) | φEf11(Δ31-36, ΔP$^{cro}$, P$^{nisA}$, Δ611, φFL1C39-44) (virulent mutant) |
|---|---|---|---|
| OG1RF | − | − | − |
| ER3/2s | − | − | − |
| ER5/1 | − | − | + |
| E1 | + | + | +* |
| E2# | − | − | − |
| E3# | − | − | − |
| E4# | − | − | − |
| E5# | − | − | − |
| E6 | − | − | − |
| E7# | − | − | − |
| E8 | − | − | + |
| E10 | − | − | + |
| E11 | − | − | + |
| GS1 | − | − | − |
| GS2# | − | − | + |
| GS3 | − | − | + |
| GS4 | − | − | − |
| GS5 | − | − | − |
| GS6 | − | − | + |
| GS7 | − | − | + |
| GS8# | − | − | + |
| GS9# | − | − | − |
| GS10 | − | − | − |
| GS12 | − | − | − |
| GS13 | − | − | + |
| GS14 | − | − | +* |
| GS15 | − | − | + |
| GS16 | − | − | + |
| GS17 | − | − | − |
| GS18 | − | − | − |
| GS19 | − | − | + |
| GS21 | − | − | − |
| GS22# | − | − | + |
| GS23# | − | − | − |
| GS24 | − | − | + |
| GS25# | − | − | + |
| GS26 | − | − | + |
| GS27 | − | − | + |
| GS28 | − | − | − |
| GS29# | − | − | − |
| GS30 | − | − | +* |
| GS31 | − | − | − |
| GS32 | − | − | − |
| GS33# | − | − | − |
| GS34 | − | − | − |
| OS25 | − | − | + |
| AA-OR3 | − | − | + |
| AA-OR4 | − | − | + |
| AA-OR26 | − | − | +* |
| AA-OR34# | − | − | − |
| AA-T4 | − | − | + |
| AA-26 | − | − | +* |
| V583 | − | − | + |
| OS16 | − | − | + |
| TUSoD1 | +* | +* | + |
| TUSoD2 | − | − | − |
| TUSoD3 | − | − | − |
| TUSoD9 | − | − | + |
| TUSoD10 | − | − | − |
| TUSoD12 | − | − | − |
| TUSoD15 | − | − | − |
| TUSoD17 | − | − | − |
| TUSoD18 | +* | − | − |
| MMH594 | − | − | − |
| OG1SSP | − | − | + |
| DG16 | − | − | − |

TABLE 5-continued

Host range of *E. faecalis* phages

| | Phage | | |
|---|---|---|---|
| E. faecalis strain | ɸEfl1 (wild type) | ɸEfl1 (Δ61-1, ɸFL1C39-44 (spontaneous recombinant) | ɸEfl1(Δ31-36, ΔP$^{cro}$, P$^{nisA}$, Δ611, ɸFL1C39-44) (virulent mutant) |
| JH2-2 | + | + | + |
| Cumulative | 6.0% | 4.5% | 49.3% |

+ = Sensitive to phage (plaque assay)
+* = Sensitive to phage (spot test)
− = Not sensitive to phage
\# = Lysogenic E. faecalis strain containing ɸEfl1 prophage The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A lytic bacteriophage capable of infecting and lysing an *Enterococcus faecalis* bacterium, said bacteriophage having a genome derived from the genome SEQ ID NO: 92, said lytic bacteriophage genome comprising:

(A) the following ORFs:
- an ORF 1, having the nucleic acid sequence of SEQ ID NO: 170;
- an ORF 2, encoding the amino acid sequence of SEQ ID NO: 28;
- an ORF 3, encoding the amino acid sequence of SEQ ID NO: 29;
- an ORF 4, encoding the amino acid sequence of SEQ ID NO: 30;
- an ORF 5, encoding the amino acid sequence of SEQ ID NO: 31;
- an ORF 6, encoding the amino acid sequence of SEQ ID NO: 32;
- an ORF 7, encoding the amino acid sequence of SEQ ID NO: 33;
- an ORF 8, encoding the amino acid sequence of SEQ ID NO: 34;
- an ORF 9, encoding the amino acid sequence of SEQ ID NO: 35;
- an ORF 10, encoding the amino acid sequence of SEQ ID NO: 36;
- an ORF 11, encoding the amino acid sequence of SEQ ID NO: 37;
- an ORF 12, encoding the amino acid sequence of SEQ ID NO: 38;
- an ORF 13, encoding the amino acid sequence of SEQ ID NO: 39;
- an ORF 14, encoding the amino acid sequence of SEQ ID NO: 40;
- an ORF 15, encoding the amino acid sequence of SEQ ID NO: 41;
- an ORF 16, encoding the amino acid sequence of SEQ ID NO: 42;
- an ORF 17, encoding the amino acid sequence of SEQ ID NO: 43;
- an ORF 18, encoding the amino acid sequence of SEQ ID NO: 44;
- an ORF 19, encoding the amino acid sequence of SEQ ID NO: 45;
- an ORF 20, encoding the amino acid sequence of SEQ ID NO: 46;
- an ORF 21, encoding the amino acid sequence of SEQ ID NO: 47;
- an ORF 22, encoding the amino acid sequence of SEQ ID NO: 48;
- an ORF 23, encoding the amino acid sequence of SEQ ID NO: 49;
- an ORF 24, encoding the amino acid sequence of SEQ ID NO: 50;
- (x)an ORF 25, encoding the amino acid sequence of SEQ ID NO: 51;
- an ORF 26, encoding the amino acid sequence of SEQ ID NO: 52;
- an ORF 27, encoding the amino acid sequence of SEQ ID NO: 53;
- an ORF 28, encoding the amino acid sequence of SEQ ID NO: 54;
- an ORF 29, encoding the amino acid sequence of SEQ ID NO: 55;
- an ORF 30, encoding the amino acid sequence of SEQ ID NO: 56;
- an ORF 37, encoding the amino acid sequence of SEQ ID NO: 63;
- an ORF 38, encoding the amino acid sequence of SEQ ID NO: 64;
- an ORF 39, encoding the amino acid sequence of SEQ ID NO: 65;
- an ORF 40, encoding the amino acid sequence of SEQ ID NO: 66;
- an ORF 41, encoding the amino acid sequence of SEQ ID NO: 67;
- an ORF 42, encoding the amino acid sequence of SEQ ID NO: 68;
- an ORF 43, encoding the amino acid sequence of SEQ ID NO: 69;
- an ORF 44, encoding the amino acid sequence of SEQ ID NO: 70;
- an ORF 45, encoding the amino acid sequence of SEQ ID NO: 71;
- an ORF 46, encoding the amino acid sequence of SEQ ID NO: 72;
- an ORF 47, encoding the amino acid sequence of SEQ ID NO: 73;
- an ORF 48, encoding the amino acid sequence of SEQ ID NO: 74;
- an ORF 49, encoding the amino acid sequence of SEQ ID NO: 75;
- an ORF 50, encoding the amino acid sequence of SEQ ID NO: 76;
- an ORF 51, encoding the amino acid sequence of SEQ ID NO: 77;
- an ORF 52, encoding the amino acid sequence of SEQ ID NO: 78;
- an ORF 53, encoding the amino acid sequence of SEQ ID NO: 79;
- an ORF 54, encoding the amino acid sequence of SEQ ID NO: 80;
- an ORF 55, encoding the amino acid sequence of SEQ ID NO: 81;
- an ORF 56, encoding the amino acid sequence of SEQ ID NO: 82;
- an ORF 57, encoding the amino acid sequence of SEQ ID NO: 83;
- an ORF 58, encoding the amino acid sequence of SEQ ID NO: 84;
- an ORF 59, encoding the amino acid sequence of SEQ ID NO: 85; and
- an ORF 60, encoding the amino acid sequence of SEQ ID NO: 86;

(B) immediately upstream of ORF 37, an inducible promoter responsive to a non-toxic inducer or constitutive promoter, which inducible promoter or constitutive promoter replaces the $P^{CRO}$ promoter between ORFs 36 and 37 of the genome SEQ ID NO: 92, which P$^{CRO}$ promoter is deleted in the genome of said lytic bacteriophage; and (C) immediately downstream of ORF 60, the following ORFs from bacteriophage ΦFL1C:
  (a) ΦFL1C ORF 40 encoding the amino acid sequence of SEQ ID NO: 158;
  (b) ΦFL1C ORF 41 encoding the amino acid sequence of SEQ ID NO: 159;
  (c) ΦFL1C ORF 42 encoding the amino acid sequence of SEQ ID NO: 160;
  (d) ΦFL1C ORF 43 encoding the amino acid sequence of SEQ ID NO: 161;
  (e) ΦFL1C ORF 44 encoding the amino acid sequence of SEQ ID NO: 162;

which ΦFL1C ORFs 40-44 replace the following ORFs 61-65 of the genome SEQ ID NO: 92, which ORFs 61-65 are deleted in the genome of the lytic bacteriophage:
  ORF 61, encoding the amino acid sequence of SEQ ID NO: 87;
  ORF 62, encoding the amino acid sequence of SEQ ID NO: 88;
  ORF 63, encoding the amino acid sequence of SEQ ID NO: 89;
  ORF 64, encoding the amino acid sequence of SEQ ID NO: 90; and
  ORF 65, encoding the amino acid sequence of SEQ ID NO: 91;

wherein the following segments of the genome SEQ ID NO: 92 are deleted in the genome of said lytic bacteriophage:
  (a) a portion of ORF 1 having the nucleic acid sequence of SEQ ID NO: 169;
  (b) ORF 31, encoding the amino acid sequence of SEQ ID NO: 57;
  (c) ORF 32, encoding the amino acid sequence of SEQ ID NO: 58;
  (d) ORF 33, encoding the amino acid sequence of SEQ ID NO: 59;
  (e) ORF 34, encoding the amino acid sequence of SEQ ID NO: 60;
  (f) ORF 35, encoding the amino acid sequence of SEQ ID NO: 61;and
  (g) ORF 36, encoding the amino acid sequence of SEQ ID NO: 62.

2. The bacteriophage of claim 1, wherein
(a) ORF 2 has the nucleic acid sequence of SEQ ID NO: 94;
(b) ORF 3 has the nucleic acid sequence of SEQ ID NO: 95;
(c) ORF 4 has the nucleic acid sequence of SEQ ID NO: 96;
(d) ORF 5 has the nucleic acid sequence of SEQ ID NO: 97;
(e) ORF 6 has the nucleic acid sequence of SEQ ID NO: 98;
(f) ORF 7 has the nucleic acid sequence of SEQ ID NO: 99;
(g) ORF 8 has the nucleic acid sequence of SEQ ID NO: 100;
(h) ORF 9 has the nucleic acid sequence of SEQ ID NO: 101;
(i) ORF 10 has the nucleic acid sequence of SEQ ID NO: 102;
(j) ORF 11 has the nucleic acid sequence of SEQ ID NO: 103;
(k) ORF 12 has the nucleic acid sequence of SEQ ID NO: 104;
(l) ORF 13 has the nucleic acid sequence of SEQ ID NO: 105;
(m) ORF 14 has the nucleic acid sequence of SEQ ID NO: 106;
(n) ORF 15 has the nucleic acid sequence of SEQ ID NO: 107;
(o) ORF 16 has the nucleic acid sequence of SEQ ID NO: 108;
(p) ORF 17 has the nucleic acid sequence of SEQ ID NO: 109;
(q) ORF 18 has the nucleic acid sequence of SEQ ID NO: 110;
(r) ORF 19 has the nucleic acid sequence of SEQ ID NO: 111;
(s) ORF 20 has the nucleic acid sequence of SEQ ID NO: 112;
(t) ORF 21 has the nucleic acid sequence of SEQ ID NO: 113;
(u) ORF 22 has the nucleic acid sequence of SEQ ID NO: 114,;
(v) ORF 23 has the nucleic acid sequence of SEQ ID NO: 115;
(w) ORF 24 has the nucleic acid sequence of SEQ ID NO: 116;
(x) ORF 25 has the nucleic acid sequence of SEQ ID NO: 117;
(y) ORF 26 has the nucleic acid sequence of SEQ ID NO: 118;
(z) ORF 27 has the nucleic acid sequence of SEQ ID NO: 119;
(aa) ORF 28 has the nucleic acid sequence of SEQ ID NO: 120;
(bb) ORF 29 has the nucleic acid sequence of SEQ ID NO: 121;
(cc) ORF 30 has the nucleic acid sequence of SEQ ID NO: 122;
(dd) ORF 37 has the nucleic acid sequence of SEQ ID NO: 129;
(ee) ORF 38 has the nucleic acid sequence of SEQ ID NO: 130;
(ff) ORF 39 has the nucleic acid sequence of SEQ ID NO: 131;
(gg) ORF 40 has the nucleic acid sequence of SEQ ID NO: 132;
(hh) ORF 41 has the nucleic acid sequence of SEQ ID NO: 133;
(ii) ORF 42 has the nucleic acid sequence of SEQ ID NO: 134;
(jj) ORF 43 has the nucleic acid sequence of SEQ ID NO: 135;
(kk) ORF 44 has the nucleic acid sequence of SEQ ID NO: 136;
(ll) ORF 45 has the nucleic acid sequence of SEQ ID NO: 137;
(mm) ORF 46 has the nucleic acid sequence of SEQ ID NO: 138;
(nn) ORF 47 has the nucleic acid sequence of SEQ ID NO: 139;
(oo) ORF 48 has the nucleic acid sequence of SEQ ID NO: 140;
(pp) ORF 49 has the nucleic acid sequence of SEQ ID NO: 141;
(qq) ORF 50 has the nucleic acid sequence of SEQ ID NO: 142;

(rr) ORF 51 has the nucleic acid sequence of SEQ ID NO: 143;
(ss) ORF 52 has the nucleic acid sequence of SEQ ID NO: 144;
(tt) ORF 53 has the nucleic acid sequence of SEQ ID NO: 145;
(uu) ORF 54 has the nucleic acid sequence of SEQ ID NO: 146;
(vv) ORF 55 has the nucleic acid sequence of SEQ ID NO: 147;
(ww) ORF 56 has the nucleic acid sequence of SEQ ID NO: 148;
(xx) ORF 57 has the nucleic acid sequence of SEQ ID NO: 149;
(yy) ORF 58 has the nucleic acid sequence of SEQ ID NO: 150;
(zz) ORF 59 has the nucleic acid sequence of SEQ ID NO: 151; and
(aaa) ORF 60 has the nucleic acid sequence of SEQ ID NO: 152.

3. The bacteriophage of claim 2 wherein:
(a) ΦFL1C ORF 40 has the nucleic acid sequence of SEQ ID NO: 163;
(b) ΦFL1C ORF 41 has the nucleic acid sequence of SEQ ID NO: 164;
(c) ΦFL1C ORF 42 has the nucleic acid sequence of SEQ ID NO: 165;
(d) ΦFL1C ORF 43 has the nucleic acid sequence of SEQ ID NO: 166;
(e) ΦFL1C ORF 44 has the nucleic acid sequence of SEQ ID NO: 167.

4. A bacteriophage having the genome of the ΦEf11 bacteriophage that is comprised by *Enterococcus faecalis* NRRL Deposit Number NRRL B-50832:
(A) wherein the following segments of the genome of bacteriophage ΦEf11 have been deleted:
(a) a portion of ORF 1 having the nucleic acid sequence of SEQ ID NO: 169;
(b) ORF 31, encoding the amino acid sequence of SEQ ID NO: 57;
(c) ORF 32, encoding the amino acid sequence of SEQ ID NO: 58;
(d) ORF 33, encoding the amino acid sequence of SEQ ID NO: 59;
(e) ORF 34, encoding the amino acid sequence of SEQ ID NO: 60;
(f) ORF 35, encoding the amino acid sequence of SEQ ID NO: 61;
(g) ORF 36, encoding the amino acid sequence of SEQ ID NO: 62;
(h) ORF 61, encoding the amino acid sequence of SEQ ID NO: 87;
(i) ORF 62, encoding the amino acid sequence of SEQ ID NO: 88;
(j) ORF 63, encoding the amino acid sequence of SEQ ID NO: 89;
(k) ORF 64, encoding the amino acid sequence of SEQ ID NO: 90;
(l) ORF65, encoding the amino acid sequence of SEQ ID NO: 91;
(B) wherein the $P^{CRO}$ promoter between ORFs 36 and 37 of the genome of bacteriophage ΦEf11 has been replaced with an inducible promoter responsive to a non-toxic inducer, or a constitutive promoter; and
(C) wherein immediately downstream of ORF 60 of the genome of bacteriophage ΦEf11 the following ORFs from bacteriophage ΦFL1C are inserted, which ΦFL1C ORFs replace ORFs 61-65 of the genome of bacteriophage ΦEf11:
(a) ΦFL1C ORF 40 encoding the amino acid sequence of SEQ ID NO: 158;
(b) ΦFL1C ORF 41 encoding the amino acid sequence of SEQ ID NO: 159;
(c) ΦFL1C ORF 42 encoding the amino acid sequence of SEQ ID NO: 160;
(d) ΦFL1C ORF 43 encoding the amino acid sequence of SEQ ID NO: 161; and
(e) ΦFL1C ORF 44 encoding the amino acid sequence of SEQ ID NO: 162.

5. The bacteriophage ϕEf11(vir)$^{PnisA}$, the genome of which is comprised by *Enterococcus faecalis* NRRL Deposit Number NRRL B-50833.

6. A bacteriophage which is a variant of the bacteriophage ϕEf11(vir)$^{PnisA}$, the genome of which bacteriophage 100 Ef11(vir)$^{PnisA}$ is comprised by *Enterococcus faecalis* NRRL Deposit Number NRRL B-50833, wherein the nisin promoter in said bacteriophage ϕEf11(vir)$^{PnisA}$ has been replaced by a constitutive promoter, and wherein the erythromycin resistance gene in said bacteriophage ϕEf11(vir)$^{PnisA}$ has been deleted.

7. The bacteriophage of claim 1, wherein said promoter is a constitutive promoter.

8. The bacteriophage of claim 6, wherein the constitutive promoter is the Tu promoter having the nucleic acid sequence of SEQ ID NO: 168.

9. The bacteriophage of claim 7, wherein the constitutive promoter is the Tu promoter having the nucleic acid sequence of SEQ ID NO: 168.

10. A bacteria comprising the bacteriophage of claim 1.

11. A bacteria comprising the bacteriophage of claim 6.

12. A bacteria comprising the bacteriophage of claim 7.

13. A composition comprising the bacteriophage of claim 1 and a pharmaceutically acceptable carrier.

14. A composition comprising the bacteriophage of claim 6 and a pharmaceutically acceptable carrier.

15. The composition of claim 13, wherein the promoter in said bacteriophage is a constitutive promoter.

16. The composition of claim 14, wherein the constitutive promoter in the bacteriophage is the Tu promoter having the nucleic acid sequence of SEQ ID NO: 168.

17. The composition of claim 15, wherein the constitutive promoter is the Tu promoter having the nucleic acid sequence of SEQ ID NO: 168.

18. A method for prevention or treatment of *Enterococcus faecalis* infection in a subject in need of such treatment or prevention comprising administering to the subject the composition of claim 13 or 14.

19. The method for prevention or treatment of claim 18 wherein the composition is administered orally, otically, subcutaneously, peritoneally, intravenously, intradentally or parenterally.

20. The method for prevention or treatment of claim 19 wherein said composition is administered to a root canal.

21. The method for prevention or treatment of claim 19 wherein said infection is resistant to at least one antibiotic.

22. The method for prevention or treatment of claim 19 wherein said infection is in an immunocompromised patient.

23. The method for prevention or treatment of claim 18 wherein the composition is administered topically.

24. The method for prevention or treatment of claim 23 wherein the composition is impregnated in a wound dressing.

* * * * *

```
                         SEQUENCE LISTING

<160> NUMBER OF SEQ ID NOS: 176

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatagttctt gtttcgacaa atcac                                             25

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgtcgacgt tcctgcagag ctctaaataa atatggcaag ta                          42

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctggatccat gtgctatgat tactcaaaat tagcag                                 36

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgcatgccc tttaccagta attttcggcg t                                      31

<210> SEQ ID NO 5
<211> LENGTH: 49
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
ctccatggtc tctcctgcag atagaattct catgtttgac agcttatca                49

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgcatgctc tctcgacgtc gccagttaat agtttgccga a                        41

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgacgtcac aaaagcgact catagaatta tttcctcc                            38

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcttatcgaa attaatacga ctcactatag g                                   31

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagagcacct caaattccag t                                              21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgataagctg tcaaacatga gaattct                                        27

<210> SEQ ID NO 11
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 11
tgtgatttgc atgtagacat ctcct                                           25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgtaaaaca ggagactctg catg                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagttgtttc cgtgtcaacg tggc                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgtccatca tggtcgttta gcag                                            24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttatcagggt ctggtgaatg cg                                              22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaacttatg agtgagcgca a                                               21

<210> SEQ ID NO 17
<211> LENGTH: 22
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 17
gagagtggaa gtggattcaa tg                                              22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcactttcat ctaaactctc g                                               21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
accaagattt gacgcagaag ttgcc                                           25

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggccatcgt cgtctttatc tgct                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agacgtttgg accgaatagc tggt                                            24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcggtaagc ttctgcgaat tcaa                                            24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gggaactagc agttgaagaa tcgc                                         24

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttcctttgta ctatcttgat ctcca                                        25

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagcgtttag ataagtcgga ttgg                                         24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaagtttct ttagcctggt cacg                                         24

<210> SEQ ID NO 27
<211> LENGTH: 264
<212> TYPE: PRT
<213> ORGANISM: Enterococcus phage

<400> SEQUENCE: 27

Met Asp Lys Lys Glu Gln Ala Lys Lys Tyr Tyr Glu Lys Gly Trp Lys
1               5                   10                  15

Tyr Lys Asp Ile Ser Glu Lys Leu Ser Val Pro Leu Asn Thr Leu Lys
            20                  25                  30

Ser Trp Arg Lys Arg Asp Lys Trp Glu Arg Gly Gly Ala Thr Lys Glu
        35                  40                  45

Val Gln Pro Thr Asn Arg Gly Ala Pro Lys Gly Asn Gln Asn Ala Ile
    50                  55                  60

Gly Asn Lys Gly Asn Ser Arg Ala Ser Pro Lys Arg Asn Lys Asn
65                  70                  75                  80

Ala Val Lys Thr Gly Glu Tyr Glu Thr Ile Phe Ala Asp Met Leu Ser
                85                  90                  95

Asp Glu Glu Lys Asp Ile Tyr Ser Thr Met Asn Asp Asp Pro Phe Phe
            100                 105                 110

Ile Leu Asp Glu Glu Ile Arg Ile Leu Lys Ile Arg Gln Tyr Arg Met
        115                 120                 125

Leu Lys Arg Ile Lys Asp Ala Glu Ala Gly Leu Asn Asp Glu Glu Val
    130                 135                 140

```
Glu Arg Leu Gln Gln Leu Arg Lys Val Lys Glu Pro Ser Val Ile Asp
145                 150                 155                 160

Gly Lys Met Val Thr Val Lys Arg Glu Val Leu Lys Asp Val Gln Val
                165                 170                 175

Thr Arg Lys Thr Phe Arg Lys Leu Asp Asp Ile Leu Ala Ile Glu Asp
            180                 185                 190

Ala Leu Thr Arg Val Ser Asn Gln Leu Ile Lys Ala Ile Lys Gln Gln
        195                 200                 205

Lys Glu Leu Leu Ser Thr Asp Lys Lys Ser Leu Leu Met Glu Ala Gln
    210                 215                 220

Ile Glu Lys Ile Lys Leu Glu Thr Asp Lys Leu Ser Gly Gly Ser Ser
225                 230                 235                 240

Asn Asp Glu Ala Asp Ser Trp Lys Gln Ala Val Ile Asn Ala Ala Asn
                245                 250                 255

Lys Arg Ala Val Glu Glu Asn Glu
                260

<210> SEQ ID NO 28
<211> LENGTH: 484
<212> TYPE: PRT
<213> ORGANISM: Enterococcus phage

<400> SEQUENCE: 28

Met Asn Lys Glu Phe Ile Pro Phe Ala Asp Ile Gly Ala Ala Ile Asp
1               5                   10                  15

Tyr Tyr Tyr Asp Lys Pro Val Ala Phe Cys Gln Asp Ile Leu His Leu
                20                  25                  30

Asp Pro Asp Glu Trp Gln Asp Lys Val Leu Asp Leu Ala Lys Phe
            35                  40                  45

Pro Lys Val Ser Val Arg Ser Gly Gln Gly Val Gly Lys Thr Ala Leu
        50                  55                  60

Glu Ala Gly Ala Ile Leu Trp Phe Leu Thr Cys Arg Pro Tyr Ala Lys
65                  70                  75                  80

Val Ile Ala Thr Ala Pro Thr Met Lys Gln Leu Tyr Asp Val Leu Trp
                85                  90                  95

Ala Glu Val Ala Lys Trp Leu Asn Asn Ser Leu Ile Lys Asp Leu Leu
                100                 105                 110

Lys Trp Thr Lys Thr Lys Ile Tyr Met Val Gly Asp Ser Glu Arg Trp
            115                 120                 125

Phe Ala Thr Ala Arg Thr Ala Thr Lys Pro Glu Asn Met Gln Gly Phe
        130                 135                 140

His Glu Asp His Met Leu Ile Val Val Asp Glu Ala Ser Gly Val Ala
145                 150                 155                 160

Asp Pro Ile Met Glu Ala Ile Leu Gly Thr Leu Ser Gly Phe Asp Asn
                165                 170                 175

Lys Leu Leu Met Cys Gly Asn Pro Asn Asn Ile Glu Gly Val Phe Tyr
            180                 185                 190

Asp Ser His Asn Thr Asp Arg Asp Lys Tyr Arg Thr His Lys Val Ser
        195                 200                 205

Ser Tyr Asp Ser Lys Arg Thr Asn Lys Glu Asn Ile Gln Met Leu Ile
    210                 215                 220

Asp Lys Tyr Gly Glu Asn Ser Asp Val Ala Arg Val Arg Ile Tyr Gly
225                 230                 235                 240

Glu Phe Pro Lys Gly Ala Leu Asp Ser Phe Ile Ser Leu Glu Ile Val
```

-continued

```
                    245                 250                 255
Glu Phe Ala Lys Asp Ile Asn Ile Ser Asp Ser Glu Leu Lys His Val
                260                 265                 270
Arg Glu Gly His Ile Gly Val Asp Val Ala Arg Phe Gly Asp Asp Ser
            275                 280                 285
Thr Ile Val Phe Pro Arg Ile Gly Ala Lys Ala Leu Pro Phe Glu Lys
        290                 295                 300
Tyr Ser Lys Gln Asp Thr Met Gln Thr Thr Gly Arg Val Leu Lys Ala
305                 310                 315                 320
Ala Lys Arg Met Met Asp Asp Tyr Pro Thr Ile Lys Lys Val Phe Ile
                325                 330                 335
Lys Val Asp Asp Thr Gly Val Gly Gly Val Thr Asp Arg Leu Lys
                340                 345                 350
Glu Val Ile Ser Asp Glu Lys Leu Pro Tyr Glu Val Ile Pro Val Asn
            355                 360                 365
Asn Gly Glu Ser Ser Thr Asp Asp Tyr Tyr Ala Asn Lys Gly Thr Gln
        370                 375                 380
Ile Trp Gly Asp Val Lys Glu Leu Leu Glu Gln Asn Ile Ser Asn Ser
385                 390                 395                 400
Ile Asn Gly Gln Gly Pro Thr Ile Glu Leu Pro Asp Asn Ala Asn Leu
                405                 410                 415
Ile Lys Glu Leu Ser Thr Arg Lys Phe Lys Met Thr Ser Asn Gly Lys
            420                 425                 430
Ile Arg Leu Glu Ser Lys Glu Asp Met Lys Lys Arg Asn Val Gly Ser
        435                 440                 445
Pro Asp Ile Ala Asp Ala Leu Thr Leu Ala Phe Tyr Glu Pro Phe Arg
450                 455                 460
Pro Glu Pro Ile Asn Val Lys Lys Ala Ile Asn Thr Phe Lys Lys Leu
465                 470                 475                 480
Gly Leu Ser Arg

<210> SEQ ID NO 29
<211> LENGTH: 537
<212> TYPE: PRT
<213> ORGANISM: Enterococcus phage

<400> SEQUENCE: 29

Met Asn Asn Lys Leu Leu Asn Gly Ser Arg Phe Asp Lys Glu Ala Asn
1               5                   10                  15
Leu Val Tyr Lys Val Pro Val Ser Lys Leu Pro Thr Arg Ile Met Gln
            20                  25                  30
Tyr Ser Asn Gly Glu Lys Glu Val Val Asp Phe Glu His Gln Asp
        35                  40                  45
Val Phe Asn Met Ile Val Lys Phe Val Arg His His Lys Glu Lys Gln
    50                  55                  60
Val Pro Arg Leu Lys Glu Leu Lys Arg Tyr Ser Leu Ala Gln Asn Asn
65                  70                  75                  80
Ile Lys Phe Thr Glu Asp Lys Ser Glu Asn Arg Ala Asp Asn Lys Ile
                85                  90                  95
Ala Asn Asp Trp Ala Arg Phe Ile Val Asn Phe Lys Lys Gly Val Leu
            100                 105                 110
Leu Gly Asn Pro Leu Lys Tyr Asn Gly Asp Lys Thr Ile Ala Asp Lys
        115                 120                 125
Ile Asn Asp Phe Ser Ser Lys Ser Asn Glu Asp Tyr His Asn Gln Leu
```

```
            130                 135                 140
Met Leu Asp Asp Leu Leu Val Tyr Gly Arg Ala Phe Glu Tyr Ile Gly
145                 150                 155                 160

Arg Asp Glu Tyr Gly Lys Glu Met Leu Ala Lys Phe Ser Ala Glu Glu
                165                 170                 175

Thr Phe Val Ile Tyr Asp Thr Thr Asn Lys Asn Ser Val Cys Ala
            180                 185                 190

Ile His Cys Tyr Asp Leu Glu Phe Asn Asp Glu Thr Phe Ser Tyr Ile
                195                 200                 205

Asp Ile Tyr Ala Asn Asp Gly Tyr Phe Tyr Gln His Glu Ser Lys Asn
            210                 215                 220

Gln Asp Tyr Glu Gln Ser Lys Leu Ile Asp Lys Tyr Gln Thr Phe Phe
225                 230                 235                 240

Asp Ser Ile Gln Val Asn Glu Trp Ile Asn Asn Glu Glu Arg Leu Gly
                245                 250                 255

Asp Phe Glu Thr Val Leu Asp Asn Ile Asp Ala Tyr Asp Leu Ser Gln
                260                 265                 270

Ser Ser Met Ala Asn Phe Gln Gln Asp Ser Ser Glu Ala Tyr Leu Val
            275                 280                 285

Ile Lys Gly Asn Pro Glu Thr Ala Ile Gly Asp Glu Glu Gly Asn Ser
            290                 295                 300

Ala Val Asp Val Leu Asn Asp Met Ile Lys Ala Arg Leu Leu Ile Leu
305                 310                 315                 320

Gly Asp Lys Lys Tyr Tyr Gly Asp Gly Gln Thr Gly Ser Asp Pro Asp
                325                 330                 335

Ala Tyr Tyr Leu Lys Lys Glu Tyr Asp Thr Gln Gly Thr Glu Ala Tyr
                340                 345                 350

Asn Asp Arg Leu Val Ser Asp Met Leu Arg Phe Thr Ser Leu Ile Asp
            355                 360                 365

Phe Thr Asp Glu Asn Ile Gly Ser Asn Gln Ser Gly Ile Gly Phe Arg
            370                 375                 380

Phe Lys Gly Trp Gly Ser Asp Asn Asp Arg Lys Asn Lys Glu Arg Met
385                 390                 395                 400

Val Lys Lys Ala Ile Met Arg Arg Leu Arg Leu Leu Thr Tyr Ser Trp
                405                 410                 415

Ser Leu Lys Asp Asn Leu Asn Lys Pro Thr Gly Leu Ala Glu Lys Val
            420                 425                 430

Lys Ser Phe Phe Val Ser Arg Asp Asn Asp Lys Glu Leu Leu Phe Glu
            435                 440                 445

Lys Val Asn Ala Ile Glu Ile Leu Phe Thr Pro Asn Val Pro Gln Ser
            450                 455                 460

Asp Lys Glu Ile Met Glu Val Ile Ala Gly Met Val Gly Ile Val Ser
465                 470                 475                 480

Asp Glu Thr Leu Cys Glu Met Ala Ala Lys Leu Thr Gly Val Pro Val
                485                 490                 495

Gln Thr Glu Leu Asn Arg Leu Lys Lys Glu Asn Gln Pro Asp Thr Leu
            500                 505                 510

Ser Asp Glu Glu Ala Ala Lys Leu Lys Glu Lys Gln Ala Glu Phe Leu
            515                 520                 525

Ala Asn Gln Ser Glu Thr Glu Glu Asp
            530                 535

<210> SEQ ID NO 30
```

```
<211> LENGTH: 312
<212> TYPE: PRT
<213> ORGANISM: Enterococcus phage

<400> SEQUENCE: 30

Met Ser Tyr Leu Lys Asp Arg Glu Asp Ala Trp Ile Lys Glu Gln Met
1               5                   10                  15

Lys Leu Asp Arg Asn Arg Glu Lys Glu Ile Val Lys Gln Leu Gln Asn
            20                  25                  30

Ala Ile Asp Ala Ile Gln Thr Glu Ile Glu Ala Asn Trp Asp Arg Phe
        35                  40                  45

Ser Asn Gly Gln Asn Ile Thr Ile Ser Glu Ala Arg Lys Met Ala Asn
    50                  55                  60

Lys Met Asp Val Lys Arg Phe Glu Arg Lys Ala Lys Glu Tyr Val Lys
65                  70                  75                  80

Asn Lys Asp Phe Ser Pro Gln Ala Asn Lys Glu Leu Lys Ile Tyr Asn
                85                  90                  95

Leu Val Met Arg Val Ser Arg Leu Glu Leu Leu Lys Ser Gln Ile Gly
            100                 105                 110

Leu Glu Leu Ile Thr Leu Phe Asp Glu Leu Asp Lys Trp Gly Tyr Ser
        115                 120                 125

Gln Leu Thr Glu Ala Ala Lys Glu Glu Tyr Leu Arg Gln Ala Gly Ile
    130                 135                 140

Leu Gly Glu Thr Val Gln Glu Asn Tyr Ser Ser Lys Val Arg Lys Ile
145                 150                 155                 160

Val Asn Ala Ser Phe Lys Ser Ser Asp Phe Pro Ser Phe Ser Asp Asn
                165                 170                 175

Ile Trp Gln Asn Phe Val Glu Met Lys Ala Asp Leu Glu Lys Ile Ile
            180                 185                 190

Thr Gln Ala Ile Thr Gln Gly Lys Asn Pro Arg Ala Val Ala Lys Glu
        195                 200                 205

Ile Ala Lys Phe Leu Lys Pro Asn Gln Leu Asn Ile Arg Tyr Lys Leu
    210                 215                 220

Asn Arg Leu Met Met Thr Glu Ile Ser Gly Ile Gln Thr Asp Ile Gln
225                 230                 235                 240

Lys Gln Ser Tyr Leu Asp Ala Asp Ile Glu Glu Tyr Asp Tyr Ile Ala
                245                 250                 255

Glu Pro Phe Ala Cys Glu Ile Cys Lys Lys Val Ala Lys Gly Ser Pro
            260                 265                 270

Tyr Arg Val Leu Lys Met Lys Lys Gly Ile Asn Ala Pro Tyr Met His
        275                 280                 285

Pro His Cys Lys Cys Ser Thr Val Pro Lys Val Ser Glu Asp Tyr Asp
    290                 295                 300

Lys Ser Leu Lys Glu Arg Cys Leu
305                 310

<210> SEQ ID NO 31
<211> LENGTH: 89
<212> TYPE: PRT
<213> ORGANISM: Enterococcus phage

<400> SEQUENCE: 31

Met Asp Asn Leu Tyr Lys Cys Asn Gln Cys His Lys Tyr Thr Pro Leu
1               5                   10                  15

Val Arg Lys Ser Glu Asn Ile Thr Lys Asp Ile Glu His His Tyr Ala
            20                  25                  30
```

```
Glu Cys Ala Asn Cys Gly Tyr Lys Ala Thr Ile Met Tyr Met Asn Thr
             35                  40                  45
Glu Ile Lys Leu Leu Met His Glu Gln Arg Lys Thr Asn Phe Gly Thr
 50                  55                  60
Lys Lys Lys Gly Lys Leu Thr Glu Lys Leu Asn Arg Leu Ile Ser Glu
 65                  70                  75                  80
Leu Arg Lys Glu Val Glu Glu Ser Leu
                 85

<210> SEQ ID NO 32
<211> LENGTH: 39
<212> TYPE: PRT
<213> ORGANISM: Enterococcus phage

<400> SEQUENCE: 32

Met Thr Glu Arg Arg Asp Ser Met Asn Asp Asp Pro Tyr Asp Tyr Leu
  1               5                  10                  15
Asp Ala Asp Tyr Glu Gly Tyr Leu Arg Lys Glu Glu Val Asn Glu Ser
             20                  25                  30
Thr Lys Glu Thr Ser Ser Asp
         35

<210> SEQ ID NO 33
<211> LENGTH: 92
<212> TYPE: PRT
<213> ORGANISM: Enterococcus phage

<400> SEQUENCE: 33

Met Lys Ala Arg Lys Lys Pro Val Val Ile Glu Thr Val Ile Phe Leu
  1               5                  10                  15
Gly Phe Tyr Gly Lys Asp Arg Asn Phe Ser Glu Arg Pro Lys Trp Leu
             20                  25                  30
Glu Arg Ala Ile Tyr Val Asp Lys Lys Ile Glu Phe Phe Asp Val Pro
             35                  40                  45
Glu Lys Leu Thr Ile His Thr Ile Glu Gly Pro Ile Tyr Ala Ile Pro
 50                  55                  60
Gly Asp Tyr Ile Ile Lys Gly Val Asn Gly Glu Leu Tyr Pro Cys Lys
 65                  70                  75                  80
Pro Asp Ile Phe Glu Lys Thr Tyr Glu Ile Ile Glu
                 85                  90

<210> SEQ ID NO 34
<211> LENGTH: 213
<212> TYPE: PRT
<213> ORGANISM: Enterococcus phage

<400> SEQUENCE: 34

Met Lys Thr Lys Lys Leu Leu Leu Pro Met His Leu Gln Phe Phe Ala
  1               5                  10                  15
Asp Asn Leu Asp Thr Gly Thr Gly Gly Thr Asp Gln Pro Ala Gly Gly
             20                  25                  30
Gln Glu Gln Thr Pro Pro Gly Asp Gly Lys Asp Lys Gly Asn Gly
             35                  40                  45
Lys Thr Phe Ser Arg Asp Glu Val Ala Lys Met Ile Ala Ala Glu Val
 50                  55                  60
Ser Lys Thr Lys Glu Ala Trp Glu Lys Glu Leu Gln Glu Lys Gln Glu
 65                  70                  75                  80
```

```
Glu Ala Asp Lys Leu Ala Lys Met Asn Asp Gln Glu Lys Asn Asp His
                85                  90                  95

Glu Lys Gln Lys Leu Leu Glu Lys Ile Lys Glu Leu Glu Ser Ala Gln
            100                 105                 110

Asn Leu Ala Glu Met Ser Lys Thr Ala Thr Lys Met Phe Ser Asp Lys
            115                 120                 125

Gly Ile Gln Ala Thr Glu Gly Leu Leu Ser Leu Val Lys Glu Thr
        130                 135                 140

Ala Glu Glu Thr Ser Glu Asn Val Lys Ala Val Val Lys Leu Ile Glu
145                 150                 155                 160

Thr Glu Arg Glu Thr Ile Lys Ala Asp Phe Glu Lys Arg Ile Gly Ser
                165                 170                 175

Lys Leu Pro Leu Asp Gly Asn Ala Asp Ala Ser Leu Ser Arg Gly Ala
            180                 185                 190

Gln Met Ala Lys Gln Ala Asn Asn Gln Asn Lys Ala Pro Glu Asn Asn
            195                 200                 205

Leu Trp Ala Thr Asn
        210

<210> SEQ ID NO 35
<211> LENGTH: 113
<212> TYPE: PRT
<213> ORGANISM: Enterococcus phage

<400> SEQUENCE: 35

Met Val Tyr Val Lys Lys Thr Gln Thr Tyr Gln Asp Ile Asn Phe Leu
1               5                   10                  15

Lys Ser Glu Lys Phe Ile Ser Phe Thr Lys Gln Val Asp Glu Thr Thr
            20                  25                  30

Glu Gly Val Val Lys Gly Val Leu Pro Ala Gly Ser Val Phe Pro Lys
        35                  40                  45

Asn Asp Ala Thr Ala Glu Gly Ile Thr Ile Asn Asp Val Asp Val Ser
    50                  55                  60

Asn Gly Pro Gln Pro Val Gly Val Ile Val Glu Gly His Val Leu Ile
65                  70                  75                  80

Lys Arg Leu Pro Ala Glu Pro Ser Ser Glu Ala Gln Lys Ala Met Arg
                85                  90                  95

Glu Leu Lys Phe Tyr Asp Ala Asn Gly Lys Met Leu Ala Val Pro Thr
            100                 105                 110

Ala

<210> SEQ ID NO 36
<211> LENGTH: 337
<212> TYPE: PRT
<213> ORGANISM: Enterococcus phage

<400> SEQUENCE: 36

Met Ala Asn Ile Ala Glu Leu Phe Ser Gln Lys Asn Val Leu Asp Tyr
1               5                   10                  15

Val Asn Asn Arg Gln Ala Pro Val Leu Leu Gly Glu Thr Leu Phe Pro
            20                  25                  30

Ala Arg Lys Val Gln Gly Leu Glu Phe Asp Val Leu Lys Ala Gly Ser
        35                  40                  45

Lys Ile Pro Thr Ile Ala Ser Val His Ala Phe Asp Thr Glu Ala Glu
    50                  55                  60

Ile Ala Ser Arg Val Gly Ser Lys Thr Ala Gln Glu Leu Ala Phe Ile
```

```
            65                  70                  75                  80
Lys Arg Lys Ile Gln Leu Lys Glu Lys Asp Leu Ile Ala Leu Arg Asn
                    85                  90                  95

Pro Arg Thr Ala Glu Glu Gln Arg Tyr Leu Glu Gln Glu Val Tyr Asn
                100                 105                 110

Asp Val Tyr Ser Met Val Ser Val Asn Ala Arg Val Glu Lys Met
                115                 120                 125

Arg Met Glu Val Leu Ala Asn Gly Lys Val Thr Leu Asp Glu Asn Gly
            130                 135                 140

Leu Asp Leu Val Val Asp Tyr Gly Val Pro Ala Asp His Lys Asp Thr
145                 150                 155                 160

Ala Asp Phe Ser Ala Pro Asp Thr Asp Ile Ile Gly Leu Leu Thr Glu
                165                 170                 175

Trp Ala Ser Lys Leu Asp Val Met Pro Thr Arg Ile Leu Thr Ser Thr
            180                 185                 190

Lys Val Arg Asn Ala Ile Leu Lys Asn Asp Gly Ile Lys Ala Phe Phe
                195                 200                 205

Lys Thr Ser Gly Leu Leu Pro Asn Ile Gly Ser Leu Asn Gln Met Leu
            210                 215                 220

Gln Gln Phe Asn Leu Pro Thr Ile Val Thr Tyr Asp Ala Lys Tyr Asn
225                 230                 235                 240

Lys Glu Asn Ala Glu Gly Val Leu Val Lys Glu Arg Tyr Phe Pro Glu
                245                 250                 255

Asn Lys Leu Val Met Phe Gly Asp Glu Asn Pro Gly Glu Ser Ile Phe
            260                 265                 270

Gly Val Thr Pro Glu Glu Ser Arg Leu Leu Ser Thr Gly Ser Asn Asn
            275                 280                 285

Tyr Thr Val Gly Asn Ile Phe Ala Met Val Tyr Glu Ser Asn Leu Asp
            290                 295                 300

Pro Val Gly Thr Trp Thr Lys Ala Ser Gly Thr Ala Leu Pro Ser Phe
305                 310                 315                 320

Pro Glu Ala Asp Asn Val Phe Gln Ala Thr Val Leu Pro Asp Ser Lys
                325                 330                 335

Lys

<210> SEQ ID NO 37
<211> LENGTH: 110
<212> TYPE: PRT
<213> ORGANISM: Enterococcus phage

<400> SEQUENCE: 37

Met Pro Ser Ile Thr Asp Asp Ile Thr Lys Leu Leu Asn Ser Pro Ala
1               5                   10                  15

Asn Glu Lys Leu Glu Val Ile Glu Arg Arg Thr Arg Glu Arg Leu Asn
                20                  25                  30

Ser Leu Leu Asn Val Ser Glu Thr Pro Ser Lys Phe Asp Ser Ile Ile
            35                  40                  45

Tyr Glu Val Val Leu Lys Arg Phe Asn Arg Ile Gly Gln Glu Gly Met
        50                  55                  60

Ile Ser Tyr Ser Gln Glu Gly Leu Thr Met Ala Phe Pro Asp Ser Asp
65                  70                  75                  80

Phe Ser Glu Tyr Glu Lys Gln Ile Asn Asp Tyr Leu Asn Glu Glu Lys
                85                  90                  95

Glu Val Gln Tyr Lys Lys Leu Arg Gly Lys Ala Arg Phe Val
```

<210> SEQ ID NO 38
<211> LENGTH: 111
<212> TYPE: PRT
<213> ORGANISM: Enterococcus phage

<400> SEQUENCE: 38

Met Arg Tyr Thr Asp Glu Ile Thr Phe Val Lys Lys Ser Ser Glu Ser
1               5                   10                  15

His Tyr Asp Pro Asn Ser Gly Glu Trp Ile Glu Glu Pro Phe Arg
            20                  25                  30

Lys Thr Thr Asp Val Asn Val Thr Asp Ile Gly Thr Asp Arg Ser Ile
        35                  40                  45

Thr Ile Phe Gly Ser Ile Lys Glu Gly Ala Lys Val Ile Arg Thr Gln
    50                  55                  60

Pro Leu Phe Val Ile Pro Glu Phe Asp Tyr Ile Glu Phe Glu Gly Lys
65                  70                  75                  80

Ala Trp Glu Val Ile Thr Ser Arg Val Pro Ala Leu Arg Asn Ser Leu
                85                  90                  95

Ile Ile Gln Glu Val Ile Asp Gly Asn Lys Ser Ser Lys Asn
            100                 105                 110

<210> SEQ ID NO 39
<211> LENGTH: 126
<212> TYPE: PRT
<213> ORGANISM: Enterococcus phage

<400> SEQUENCE: 39

Met Ala Ile Ser Gln Val Arg Ile Asn Gly Leu Ala Gly Ile Ser Lys
1               5                   10                  15

Lys Leu Lys Arg Asn Ala Gln Leu Asp Asp Val Lys Lys Val Val Arg
            20                  25                  30

Asn Asn Thr Ala Glu Leu Thr Ala Asn Met Gln Ala Glu Ala Gly Lys
        35                  40                  45

Val Leu Thr Gly His Arg Glu Gly Lys Lys Phe Val Lys Pro Thr Gly
    50                  55                  60

Ala Thr Lys Arg Ser Ile Val Met Arg Leu Ser Asn Asn Gly Phe Ser
65                  70                  75                  80

Gly His Thr Gly Pro Gly Thr Glu Tyr Ala Pro Tyr Leu Ile His Gly
                85                  90                  95

Thr Arg Phe Met Val Lys Arg Asp Phe Phe Leu Pro Pro Leu Lys Gln
            100                 105                 110

Gln Lys Val Lys Phe Arg Thr Asp Leu Glu Arg Leu Met Lys
        115                 120                 125

<210> SEQ ID NO 40
<211> LENGTH: 129
<212> TYPE: PRT
<213> ORGANISM: Enterococcus phage

<400> SEQUENCE: 40

Met Ile Lys Thr Arg Asp Gln Ser Ile Phe Asp Glu Val Tyr Lys Lys
1               5                   10                  15

Cys Gln Ser Leu Gly Tyr Glu Ile Tyr Asp Tyr Lys Pro Met Asn Asp
            20                  25                  30

Val Gly Tyr Pro Phe Val Glu Leu Glu Asp Thr Gln Thr Leu His Gln
        35                  40                  45

Ala Asn Lys Thr Asp Ile Lys Gly Ser Val Thr Leu Asn Leu Ser Val
    50                  55                  60

Trp Gly Leu Ala Lys Lys Arg Lys Gln Ile Ser Asp Met Ala Ser Ala
65                  70                  75                  80

Ile Phe Ala Glu Ala Leu Ser Ile Ser Glu Thr Glu Gly Tyr Tyr Trp
                85                  90                  95

Ser Leu Asn Ile Gln Ser Ser Gly Ile Arg Leu Val Asp Asp Ile Ser
                100                 105                 110

Thr Asn Thr Pro Leu Lys Arg Ala Met Ile Ser Leu Glu Phe Lys Ile
                115                 120                 125

Leu

<210> SEQ ID NO 41
<211> LENGTH: 197
<212> TYPE: PRT
<213> ORGANISM: Enterococcus phage

<400> SEQUENCE: 41

Met Ala Asn Glu Ala Lys Val Ala Ala Lys Gly Ile Asp Ile Ile Leu
1               5                   10                  15

Leu Phe Arg Leu Leu Lys Lys Ser Lys Glu Glu Ala Ala Trp Lys Leu
                20                  25                  30

Ala Phe Gln Thr Glu His Glu Asn Thr Lys Thr Lys Asp Ser Asp Ser
                35                  40                  45

Val Ala Thr Lys Asp Gly Pro Ile Arg Ile Pro Gly Ser Leu Glu Ile
    50                  55                  60

Asp Phe Ser Ala Thr Ser Ile Leu Ser Val Gly Asp Pro Tyr Val Asp
65                  70                  75                  80

Gln Leu Glu Glu Ala Leu Asp Asn Asp Ile Ile Glu Ile Trp Glu
                85                  90                  95

Ile Asn Lys Ala Glu Lys Gly Thr Gly Asp Asn Val Asp Lys Tyr Lys
                100                 105                 110

Ala Thr Tyr Tyr Gln Gly Tyr Val Thr Ser Phe Gly Lys Ser Pro Asn
                115                 120                 125

Ala Glu Asp Thr Val Glu Val Ser Leu Glu Phe Gly Ile Asn Gly Lys
                130                 135                 140

Gly Ala Lys Gly Phe Ala Thr Leu Thr Ala Asp Gln Glu Glu Val Val
145                 150                 155                 160

Gln Tyr Val Phe Lys Asp Thr Thr Ile Glu Lys Asp Asp Pro Glu Lys
                165                 170                 175

Val Asp Ser Pro Ser Val Glu Ser Val Thr Pro Thr Phe Asp Gly Ala
                180                 185                 190

Ser Thr Glu Leu Ser
        195

<210> SEQ ID NO 42
<211> LENGTH: 152
<212> TYPE: PRT
<213> ORGANISM: Enterococcus phage

<400> SEQUENCE: 42

Met Val Asp Thr Phe Lys Ile Tyr Lys Gly Gln Thr Glu Val Val Ser
1               5                   10                  15

Gly Thr Ser Pro Leu Thr Ile Thr Gly Met Glu Pro Asn Thr Ser Val
                20                  25                  30

Ser Ala Gly Glu Tyr Gln Val Thr Arg Val Val Asn Gly Lys Glu Ser
            35                  40                  45

Glu Arg Val Asp Ile Pro Ala Phe Lys Thr Leu Ser Ile Ala Val Thr
 50                  55                  60

Gly Leu Asp Phe Ser Pro Lys Thr Ser Thr Ala Asp Ala Gly Thr Ala
 65                  70                  75                  80

Gly Ser Arg Gln Ile Thr Ala Thr Val Leu Pro Glu Asn Ala Thr Thr
                85                  90                  95

Lys Lys Val Thr Tyr Asp Ile Ser Pro Val Thr Glu Gly Leu Ala Val
            100                 105                 110

Ser Glu Thr Gly Asn Ile Thr Trp Thr Glu Ser Val Pro Ala Gly Val
        115                 120                 125

Tyr Thr Thr Thr Gly Thr Thr Glu Asp Gly Lys Lys Thr Ala Gln His
    130                 135                 140

Thr Leu Thr Leu Asn Asn Gln Ala
145                 150

<210> SEQ ID NO 43
<211> LENGTH: 116
<212> TYPE: PRT
<213> ORGANISM: Enterococcus phage

<400> SEQUENCE: 43

Met Gln Ile Glu Ile Lys Gly Lys Lys Tyr Asn Cys Ile Phe Gly Val
 1               5                  10                  15

Lys Phe Ile Arg Glu Leu Asp Lys Gln His Gly Val Val Arg Asn Asp
            20                  25                  30

Val Asn Leu Gly Met Gly Leu Thr Thr Leu Pro Gln Leu Val Ser
        35                  40                  45

Gly Asn Ile Val Val Leu Ser Asp Val Leu Tyr Thr Ala Thr Ile Thr
 50                  55                  60

Glu Lys Ser Arg Pro Ser Lys Asp Glu Val Asp Glu Phe Val Glu Thr
 65                  70                  75                  80

Val Asp Asp Ile Glu Ala Leu Phe Asp Glu Thr Leu Lys Tyr Leu Glu
                85                  90                  95

Glu Ser Asn Ala Gly Lys Leu Thr Val Arg Asn Phe Lys Lys Ala Leu
            100                 105                 110

Met Glu Asn Lys
        115

<210> SEQ ID NO 44
<211> LENGTH: 85
<212> TYPE: PRT
<213> ORGANISM: Enterococcus phage

<400> SEQUENCE: 44

Met Thr Leu Tyr Glu Tyr Glu Val Arg Leu Leu Ala Phe Gln Leu Lys
 1               5                  10                  15

Arg Leu Asp His Glu Arg Asp Leu Tyr Leu Gln Ala Trp Leu Asn Asn
            20                  25                  30

Gln Ile Lys Ala Thr Lys Gly Lys Lys Ser Glu Pro Tyr Phe Lys Glu
        35                  40                  45

Phe Asn Lys Phe Phe Asn Tyr Glu Glu Gln Glu Lys Leu Ile Leu Gly
 50                  55                  60

Lys Ser Leu Ile Asp Glu Lys Ile Asp Ile Gly Ala Ile Asp Leu Leu
 65                  70                  75                  80

Arg Lys Ala Asn Lys
            85

<210> SEQ ID NO 45
<211> LENGTH: 1135
<212> TYPE: PRT
<213> ORGANISM: Enterococcus phage

<400> SEQUENCE: 45

Met Glu Ser Tyr Ser Val Glu Ala Ile Leu Thr Ala Thr Asp Arg Thr
1               5                   10                  15

Phe Ser Ser Thr Met Ser Ser Ala Glu Arg Ser Met Ala Gly Val Asn
            20                  25                  30

Lys Gln Ser Gly Glu Leu Gly Asp Gly Leu Asp Lys Ser Thr Thr Lys
        35                  40                  45

Gly Asn Gln Leu Gly Lys Ser Ile Leu Ser Ile Gly Ala Gly Val Gly
    50                  55                  60

Ala Val Lys Leu Val Ser Thr Ala Val Asn Met Val Lys Asp Ser Val
65                  70                  75                  80

Glu Gly Ala Ile Asn Arg Phe Asp Thr Leu Asn Lys Tyr Pro Val Val
                85                  90                  95

Met Lys Ala Leu Gly Tyr Ser Thr Glu Asp Val Asp Arg Ser Met Asn
            100                 105                 110

Lys Leu Ser Asp Gly Ile Asp Gly Leu Pro Thr Ser Leu Asp Glu Ile
        115                 120                 125

Val Ala Ser Thr Gln Gln Leu Ser Ile Ser Thr Gly Ser Leu Ser Lys
    130                 135                 140

Gly Thr Asp Thr Ala Ile Ala Leu Asn Asp Ala Phe Leu Ala Ser Gly
145                 150                 155                 160

Ala Ser Thr Ala Asp Ala Thr Arg Gly Met Gln Gln Tyr Ile Gln Met
                165                 170                 175

Leu Gly Lys Gly Glu Val Asp Met Gln Ser Trp Arg Thr Leu Gln Glu
            180                 185                 190

Thr Met Pro Ile Ala Met Asp Lys Val Ala Lys Ser Phe Lys Glu Gln
        195                 200                 205

Gly Val Asn Ser Val Asn Gln Leu Tyr Asp Ala Leu Lys Glu Gly Asp
    210                 215                 220

Ile Thr Phe Asn Glu Phe Asn Asn Arg Leu Ile Glu Leu Asp Lys Gly
225                 230                 235                 240

Val Gly Gly Phe Ala Asp Leu Ala Lys Lys Asn Ser Lys Gly Ile Lys
                245                 250                 255

Thr Ser Trp Ala Asn Ile Lys Thr Ala Thr Val Lys Gly Val Thr Thr
            260                 265                 270

Val Ile Lys Ser Phe Asp Glu Leu Ser Lys Ala Val Thr Gly Lys Asn
        275                 280                 285

Ile Ala Glu Asn Leu Asp Ser Leu Lys Asn Val Val Asn Ile Thr Phe
    290                 295                 300

Lys Ala Ile Asp Ala Ala Ile Gln Ser Thr Ile Pro Leu Met Lys Leu
305                 310                 315                 320

Phe Gly Lys Ala Ile Thr Ser Ile Gly Thr Ala Leu Thr Pro Leu Leu
                325                 330                 335

Pro Thr Ile Ala Ser Phe Ala Ala Thr Phe Thr Ala Leu Lys Val Ile
            340                 345                 350

Gln Gln Val Thr Gly Tyr Ile Lys Gln Ser Glu Leu Ala Ile Lys Ala
        355                 360                 365

```
Tyr Thr Thr Ala Ile Ser Leu Tyr Asn Gly Ile Ser Lys Leu Ala Thr
            370                 375                 380

Leu Ser Thr Thr Ala Leu Gly Arg Ala Trp Met Leu Asn Leu Ala Ala
385                 390                 395                 400

Asp Lys Ala Asn Ser Ala Ala Ile Ala Ile Lys Thr Gly Leu Leu Val
                    405                 410                 415

Ala Gln Asn Thr Ile Val Gly Val Leu Thr Gly Thr Ile Ser Leu Ala
                420                 425                 430

Thr Val Ala Thr Thr Val Phe Ser Thr Ala Met Lys Leu Leu Leu Gly
            435                 440                 445

Pro Ile Gly Trp Val Thr Ala Ala Ile Gly Gly Leu Val Ala Val Gly
450                 455                 460

Val Asn Leu Trp Lys Trp Leu Asn Lys Glu Thr Glu Ser Thr Lys Ala
465                 470                 475                 480

Val Lys Lys Glu Gln Glu Ser Leu Met Lys Thr Thr Asp Asp Leu Ile
                    485                 490                 495

Lys Lys Asn Gln Glu His Ala Gln Ser Arg Lys Asp Glu Ala Ile Glu
                500                 505                 510

Leu Asp Asn Thr Lys Glu Lys Phe Gln Ser Met Ile Ser Glu Met Glu
            515                 520                 525

Met Leu Ser Ala Lys Glu Lys Leu Ser Asn Ser Glu Lys Lys Arg Met
530                 535                 540

Val Glu Ile Val Glu Glu Leu Asn Gly Lys Met Thr Gly Leu Asn Leu
545                 550                 555                 560

Val Tyr Asp Asp Gln Lys Asn Ile Leu Ser Glu Met Pro Gly Thr Ile
                    565                 570                 575

Gln Gln Gln Val Asp Ala Tyr Asn Ala Leu Asp Glu Ala Ser Gln Ala
                580                 585                 590

Gln Glu Asn Ile Asn Gln Met Leu Lys Glu Arg Asn Asp Asn Glu Ala
            595                 600                 605

Lys Leu Met Glu Ile Asn Ala Ala Arg Glu Lys Trp Asn Gln Thr Leu
610                 615                 620

Lys Glu Ser Gly Gly Asn Thr Lys Glu Ala Arg Glu Asn Ile Glu Lys
625                 630                 635                 640

Leu Gly Glu Gln Glu Gln Val Leu Lys Gly Val Gln Gln Glu Leu Thr
                    645                 650                 655

Asn Glu Ile Ile Asn Thr Ala Asn Ala His Glu Gln Ser Met Gln Arg
                660                 665                 670

Ala Ser Gln Ala Val Glu Asn Gly Val Leu Asn Gln Thr Val Ser Tyr
            675                 680                 685

Asn Ala Leu Ser Gly Lys Thr Lys Glu Thr Met Asp Ala Met Arg Ser
690                 695                 700

Glu Tyr Ser Ser Leu Glu Glu Lys Val Gly Ser Ala Phe Asp Val Ile
705                 710                 715                 720

Glu Gln Lys Gln Ala Val Ser Val Asp Gln Met Ala Ala Asn Leu Gln
                    725                 730                 735

Lys Asn Gln Glu Ala Val Ala Gln Trp Gly Gln Asn Ile Ser Thr Leu
                740                 745                 750

Ala Glu Arg His Val Asp Gln Gly Leu Leu Glu Gln Leu Arg Lys Met
            755                 760                 765

Gly Pro Glu Gly Ala Ala Gln Ala Ala Glu Leu Val Asn Ala Ser Asp
770                 775                 780
```

Glu Gln Leu Gln Arg Leu Asn Asp Val Tyr Arg Asn Thr Gly Glu Thr
785                 790                 795                 800

Ser Met Asn Ala Met Lys Glu Gly Tyr Gln Leu Gly Lys Asn Gly Leu
                805                 810                 815

Asn Glu Glu Ile Gln Ala Leu Ile Pro Thr Gln Lys Glu Thr Leu Met
            820                 825                 830

Thr Gln Ile Lys Asn Thr Asp Phe Asn Ser Val Gly Leu Ser Val Thr
        835                 840                 845

Asp Asp Phe Lys Ala Gly Ile Glu Asn Gly Arg Thr Ala Val Glu Glu
    850                 855                 860

Met Thr Lys Gly Ile Val Pro Lys Val Gly Glu Asp Met Lys Gly Glu
865                 870                 875                 880

Val Gln Lys Ala Asp Phe Arg Gly Ile Gly Lys Ser Ile Pro Gln Gly
                885                 890                 895

Leu Glu Lys Gly Val Asp Asp Gly Lys Gly Val Pro Val Lys Thr Ser
            900                 905                 910

Asn Gln Met Ile Asp Asp Ile Val Ser Gly Ala Arg Lys Gly Leu Asp
        915                 920                 925

Ser His Ser Pro Ser Arg Val Phe His Ser Ile Gly Glu Asp Val Asp
    930                 935                 940

Ser Gly Leu Ser Asn Gly Ile Glu Gln Asn Ala Met Asn Pro Val Arg
945                 950                 955                 960

Ala Val Glu Ala Ile Val Asp Lys Ile Ile Ser Ala Met Asp Lys Leu
                965                 970                 975

Pro Ser Glu Met Asn Ser Ile Gly Ala Asn Ala Ile Asp Gly Leu Thr
            980                 985                 990

Asn Gly Ile Asn Ala Asn Ala Asn Ser Ala Leu Ala Ala Ala Arg Gly
        995                 1000                1005

Val Ala Asp Gln Ile Val Ser Thr Met Lys Ser Ala Met Asp Ile
    1010                1015                1020

His Ser Pro Ser Arg Val Met Arg Asp Glu Val Gly Lys Met Ile
    1025                1030                1035

Pro Ala Gly Val Ala Val Gly Ile Asp Lys Tyr Ser Asn Phe Val
    1040                1045                1050

Glu Lys Ser Met Gln Arg Leu Ser Lys Lys Val Ala Met Pro Ala
    1055                1060                1065

Leu Asp Asn Leu Asn Ser Asn Leu Ser Phe Ser Gly Gly Ser Gln
    1070                1075                1080

Ser Leu Ala Phe Ala Gly Asp Val Ser Ser Lys Phe Thr Val Glu
    1085                1090                1095

Val Pro Val Ile Phe Asp Ser Ser Glu Val Ala Arg Val Ile Ala
    1100                1105                1110

Lys Pro Met Ser Lys Glu Leu Gln Asn Gln Gln Asp Lys Lys Asn
    1115                1120                1125

Val Ser Leu Gly Arg Arg
    1130                1135

<210> SEQ ID NO 46
<211> LENGTH: 309
<212> TYPE: PRT
<213> ORGANISM: Enterococcus phage

<400> SEQUENCE: 46

Met Leu Tyr Asn Phe Ile Asp Val Asn Glu Gln Gln Thr Lys Ala Ser
1               5                   10                  15

```
Leu Pro Ser Glu Ala Met Asn Phe Asn Gly Ser Phe Leu Glu Asp Leu
             20                  25                  30

Val Pro Gly Tyr Arg Thr Leu Ser Val Val Gly Arg Glu Leu Ala Pro
         35                  40                  45

Thr Glu Ile Gln Ser Tyr Gln Leu Gly Ile Arg Asp Gly Met Arg His
 50                  55                  60

Val Tyr Ala Arg Ile Pro Glu Arg Glu Leu Thr Val Lys Phe Lys Val
 65                  70                  75                  80

Glu Ala Asn Ser Asn Glu Ala Phe Arg Asp Ser Phe Asn Arg Leu Asn
                 85                  90                  95

Val Ala Leu Phe Thr Glu Lys Asp Val Gln Ile Trp Phe Asn Asp Glu
            100                 105                 110

Pro Glu Met Leu Trp Ser Gly Ser Lys Ser Asp Ile Asp Ala Val Pro
        115                 120                 125

Glu Gly Leu Asn Arg Val Val Gly Thr Phe Thr Ile Leu Leu Asn Asn
130                 135                 140

Pro Tyr Lys Tyr Thr Arg Ser Asp Ala Thr Ser Val Met Trp Gly Ser
145                 150                 155                 160

Pro Thr Ile Thr Phe Gln Ala Asn Tyr Leu Met Gly Asn Thr Gly Ser
                165                 170                 175

Gly Ala Val Asp Leu Pro Ile Val Ile Glu Gly Gly Ala Tyr Trp Gly
            180                 185                 190

Ser Thr Met Ile Thr Phe Gln Asn Arg Ser Tyr Leu Met Gly Asp Asn
        195                 200                 205

Gly Gln Glu Val Lys Pro Ile Glu Ile Tyr Pro Thr Val Glu Gly Leu
210                 215                 220

Lys Val Lys Pro Ile Ile Thr Ile Glu Gly Thr Gly Arg Gly Val Trp
225                 230                 235                 240

Ile Lys Thr Arg Ser Asp Thr Ile Asp Ile Gly Asp Phe Asp Lys Ser
                245                 250                 255

Glu Ile Val Ile Asp Thr Glu Gln Phe Asn Ile Thr Lys Asn Gly Lys
            260                 265                 270

Pro Met Ile Arg Pro Met Asn Asp Phe Tyr Ile Tyr Pro Asn Glu Pro
        275                 280                 285

Leu Tyr Ile Gln Ala Lys Asp Ser Thr Phe Asn Leu Thr Ile Arg Tyr
290                 295                 300

Pro Asn Arg Phe Leu
305

<210> SEQ ID NO 47
<211> LENGTH: 671
<212> TYPE: PRT
<213> ORGANISM: Enterococcus phage

<400> SEQUENCE: 47

Met Leu Met Ala Met Asp Leu Lys Arg Glu Tyr Thr Ala Val Leu Asp
  1               5                  10                  15

Asn Ala Tyr Gln Val Ser Tyr Glu Lys Ile Glu Asn Gln Ile Gly Asn
             20                  25                  30

Leu Glu Phe Ser Met Pro Leu Asp Pro Lys Asn Glu Phe Leu Gln
         35                  40                  45

Glu Met Leu Trp Val Glu Leu Thr Asp Asn Glu Asn Glu Tyr Ile Gly
 50                  55                  60

Leu Tyr Arg Val Met Pro Ser Thr Val Arg Lys Asp Ala Ser Asn Asn
```

```
             65                  70                  75                  80
Ser Ile Thr Tyr Thr Ala Asn Glu Ala Leu Cys Thr Leu Leu Asp Thr
                     85                  90                  95
Val Leu Phe Gly Tyr His Glu Leu Val Asn Arg Lys Thr Val Asp Val
                    100                 105                 110
Ile Asn Tyr Leu Leu Asn Lys Gln Arg Thr Lys His Trp Val Leu Lys
                    115                 120                 125
Lys Cys Glu Phe Thr Arg Tyr Phe Ser Tyr Ala Trp Glu Asn Glu Asn
            130                 135                 140
Gly Leu Ala Asp Ala Leu Phe Ser Ile Pro Gln Ala Phe Asp Glu Asp
145                 150                 155                 160
Tyr Met Trp Gln Trp Asn Thr Lys Val Tyr Pro Phe Glu Leu Ser Leu
                    165                 170                 175
Val Lys Pro Pro Lys Glu Pro Ile Ala Arg Ile Gln Glu Gly Tyr Asn
                    180                 185                 190
Met Gln Gly Phe Glu Ile Glu Arg Asp Pro Asn Asn Leu Val Asn Arg
            195                 200                 205
Val Tyr Pro Leu Gly Ala Gly Glu Gly Val Asn Gln Ile Asn Ile Lys
        210                 215                 220
Ser Val Asn Lys Asn Ile Pro Tyr Val Glu Asp Ala Lys Ser Ile Lys
225                 230                 235                 240
Glu His Gly Leu Val Glu Tyr Val Trp Val Asp Gln Arg Phe Thr Val
                    245                 250                 255
Pro Gln Ala Leu Lys Asp Asn Ala Ile Asn Met Leu Lys Lys Trp Ala
                    260                 265                 270
Gln Pro Lys Ile Ser Trp Asp Val Thr Ala Ala Asp Leu Leu Lys Leu
            275                 280                 285
Thr Asp Glu Pro Leu Ser Ile Asp Lys Leu Arg Gln Gly Thr Val Ile
        290                 295                 300
Met Ile Asn Thr Asp Asp Phe Gly Ser Ile Asn Leu Arg Ile Lys Lys
305                 310                 315                 320
Glu Thr Lys Gln Asp Val Phe Gly Ala Pro Gln Asp Ile Gln Leu Glu
                    325                 330                 335
Leu Gly Asn Leu Ser Asp Asp Phe Thr Thr Met Ser Asp Leu Lys
                    340                 345                 350
Arg Lys Gln Glu Ile Asn Glu Thr Tyr Ser Gln Gly Ala Thr Asn Ile
            355                 360                 365
Leu Asn Tyr Ser Tyr Gln Asp Asn Cys Glu Lys Ala Tyr Pro Ala Glu
        370                 375                 380
Ile Glu Phe Phe Leu Asp Asp Val Phe His Val Asn Thr Val Glu
385                 390                 395                 400
Leu Thr Phe Lys Thr Lys Arg Tyr Arg Gly Tyr Thr Lys Ala Val Lys
                    405                 410                 415
Gly Gly Gly Ala Thr Val Lys Ser Thr Ser Ala Gly Ala Ser Thr
                    420                 425                 430
Gln Thr Ser Ser Ala Gly Gly Ser Val Val Ser Ser Ala Gly
            435                 440                 445
Gly Gly Gly Ser Thr Thr Ser Gly Ser Gly Gly Ser Tyr Gln Gly
        450                 455                 460
Gly Ser Thr Asn Thr Asp Gly Gly Ser Ala Gln Thr Ser Ser Ala Asn
465                 470                 475                 480
Gly Ser His Asp His Leu Met Phe Asn Val Ile Gln Gly Pro Pro Gln
                    485                 490                 495
```

```
Thr Leu Pro Lys Ile Thr Leu Arg Ala Gly Gly Gly Glu Ile Tyr
            500                 505                 510

Thr Glu Ala Arg Gly Gly Thr Phe Arg Thr Ala Ser Ala Ala Asp Asn
        515                 520                 525

His Thr His Thr Val Asn Val Pro Ser His Ser His Arg Phe Asn Ile
    530                 535                 540

Asp Ile Pro Ala His Ser His Val Val Ser Ile Pro Asn His Thr His
545                 550                 555                 560

Ser Ile Ser Val Pro Ser His Ser His Gln Val Arg Ile Pro Ala His
            565                 570                 575

Thr His Gln Ile Thr Leu Pro Asp His Ser His Pro Leu Glu Trp Gly
        580                 585                 590

Ile Tyr Glu Ala Pro Ser Ser Ala Thr Ser Val Asp Ile Val Val Asp
            595                 600                 605

Gly Thr Thr Ile Pro Val His Asp Thr Ser Gln Gln Arg Leu Asn Ile
        610                 615                 620

Val Asn Tyr Leu Arg Lys Thr Ser Gly Gly Lys Ile Ser Arg Gly Asn
625                 630                 635                 640

His Thr Ile Lys Ile Ile Pro Asn Lys Leu Ala Arg Ile Glu Ala Gln
            645                 650                 655

Val Ile Cys Arg Val Phe Ile Gln Ser Gln Leu Gly Gly Gln Phe
        660                 665                 670

<210> SEQ ID NO 48
<211> LENGTH: 57
<212> TYPE: PRT
<213> ORGANISM: Enterococcus phage

<400> SEQUENCE: 48

Met Arg Leu Thr Val Lys Leu Ile Ser Lys Gln Glu Glu Phe Ile Ile
1               5                   10                  15

Asn Asp Glu Ser Gly Lys Thr Leu Asp Asp Tyr Phe Ala Glu Leu Ile
            20                  25                  30

Asp Asn Ser Ser Pro Phe Ile Lys Ile Gly Asn Arg Ile Leu Gln Lys
        35                  40                  45

Ala Thr Ile Glu Tyr Ile Asn Ala Glu
    50                  55

<210> SEQ ID NO 49
<211> LENGTH: 587
<212> TYPE: PRT
<213> ORGANISM: Enterococcus phage

<400> SEQUENCE: 49

Met Ala Ile Glu Gln Ile Lys Glu Thr Asp Thr Leu Asn Gln Gly Arg
1               5                   10                  15

Ile Lys Ile Asn Ala Ile Leu Asp Gln Ser Asn Thr Ala Val Glu Lys
            20                  25                  30

Ile Asn Asp Tyr Gln Ser Gln Leu Thr Glu Gly Ile Asn Asp Ala Lys
        35                  40                  45

Lys Ile Ala Asp Asp Ala Gly Lys Glu Ala Val Gln Ile Ala Glu Gln
    50                  55                  60

Ala Gly Asn Gln Ala Asn Glu Thr Ala Asn Gln Ala Leu Thr Asn Ser
65                  70                  75                  80

Gln Thr Ala Ile Asn Thr Ser Asn Gln Ala Val Ser Thr Ala Asn Asn
            85                  90                  95
```

Asn Lys Gln Glu Phe Asp Ala Leu Arg Asn Asp Phe Glu Lys Leu Val
            100                 105                 110

Gly Glu Ala Gly Asp Ser Asn Pro Glu Ile Val Gln Ala Arg Thr Asp
            115                 120                 125

Thr Gln Gly Val Thr Gln Ser Thr Leu Ala Thr Arg Leu Gln Val Asp
            130                 135                 140

Phe Asn Asp Arg Met Thr Lys Ser Glu Gly Val Ser Leu Leu Ser Gly
145                 150                 155                 160

Thr Thr Asn Val Lys Ile Pro Met Asp Phe Thr Gly Lys Thr Ala Gly
            165                 170                 175

Asn Thr Ala Thr Asn Ala Asn Gln Tyr Phe Thr Asp Val Thr Ala Lys
            180                 185                 190

Val Leu Lys Lys Pro Lys Asp Thr Trp Asn Glu Ile Ser Gln Ser Asp
            195                 200                 205

Tyr Asn Lys Leu Val Ser Arg Asp Asp Ser Gly Val Ser Ser Gly Ser
            210                 215                 220

Thr Gln Asn Gly Val Ile Pro Gln Gln Leu Gly Val Phe Asn Ala Leu
225                 230                 235                 240

Glu Ala Ala Lys Lys Leu Ile Pro Gln Asn Phe Glu Gly Leu Ser Gln
            245                 250                 255

Glu Glu Ala Val Val Leu Leu Lys Asp Ser Phe Val Ala Phe Thr Ile
            260                 265                 270

Ser Glu Arg Val Lys Ala Thr Ser Pro Asn Asn Lys Thr Ile Lys Val
            275                 280                 285

Ser Thr Tyr Ile Glu Ser Thr Asp Ser Trp Thr Thr Gln Ile Gln Glu
            290                 295                 300

Asn Ala Gly Glu Tyr Lys Asp Leu Ser Val Gln Val Thr Asp Lys Asn
305                 310                 315                 320

Phe Ile Thr Ser Asp Gly Leu Ile Tyr Leu Ile Ser Tyr Thr Asp Pro
            325                 330                 335

Ser Asn Gly Val Thr Thr Ala Asn Leu Asp Val Asp Tyr Ser Ala Ile
            340                 345                 350

Gln Leu Glu Ile Ser Ile Asn Ala Gln Asp Val Leu Ala Lys Ser Gly
            355                 360                 365

Phe Val Arg Glu Glu Gln Leu Lys Glu His Thr Glu Ser Gln Asp Asn
            370                 375                 380

Pro His Lys Val Thr Ala Ser Gln Val Gly Leu Gly Asn Val Lys Asn
385                 390                 395                 400

Tyr Gly Phe Ala Thr Asp Ser Glu Ala Ser Ala Gly Thr Ser Thr Thr
            405                 410                 415

Lys Tyr Met Ser Pro Lys Asn Val Ala Asp Ala Ile Lys Gly Gln Ala
            420                 425                 430

Val Thr Gln Thr Gly Asp Gln Glu Ile Ala Gly Thr Lys Asp Phe Met
            435                 440                 445

Asn Pro Pro Lys Ile Ala Gly Gln Thr Val Ile Ser Glu Lys Val Ile
            450                 455                 460

Ala Phe Ser Ala Pro Asn Thr Val Ser Val Ser Gly Thr Gly Val Lys
465                 470                 475                 480

Val Ile Pro Ile Ser Gln Lys Val Ile Thr Asn Asn Glu Phe Phe Glu
            485                 490                 495

Leu Ser Ala Asn Lys Ile Lys Val Leu Lys Asp Gly Ile Ile Ser Val
            500                 505                 510

```
Val Thr Ser Tyr Thr Thr Asn Val Pro Ala Gly Trp Cys Asn Ile Glu
        515                 520                 525

Leu Thr Lys Asn Asn Ala Val Met Asn Arg Ser Asn Gln Gly Thr Gly
        530                 535                 540

Gly Leu His Ala Ala Gly Leu Thr Asp Val Phe Asp Val Lys Ala Gly
545                 550                 555                 560

Asp Thr Ile Ala Phe Gln Ser Asn Ser Asn Gln Ser Ser Tyr Thr Val
                565                 570                 575

Leu Tyr Leu Arg Gly Phe Leu Arg Tyr Leu Thr
            580                 585

<210> SEQ ID NO 50
<211> LENGTH: 73
<212> TYPE: PRT
<213> ORGANISM: Enterococcus phage

<400> SEQUENCE: 50

Met Ser Asn Glu Ile Val Ala Val Ile Gly Leu Ala Gly Ser Thr
1               5                   10                  15

Phe Gly Ala Phe Ile Gly Val Val Ala Ser Ala Asn Leu Thr Ala Tyr
                20                  25                  30

Arg Ile Glu Gln Leu Glu Lys Lys Val Glu Lys His Asn Gly Val Ile
            35                  40                  45

Glu Arg Thr Phe Lys Leu Glu Gly Arg Met Gln Glu Ala Glu His Asp
        50                  55                  60

Ile Ile Glu Leu Lys Gly Ala Lys Lys
65                  70

<210> SEQ ID NO 51
<211> LENGTH: 67
<212> TYPE: PRT
<213> ORGANISM: Enterococcus phage

<400> SEQUENCE: 51

Met Ile Leu Pro Asp Lys Tyr Tyr Lys Ile Ile Lys Trp Gly Val Leu
1               5                   10                  15

Thr Val Leu Pro Ala Ile Ser Val Leu Val Ala Thr Leu Gly Lys Gly
                20                  25                  30

Tyr Gly Trp Gln Gln Thr Asp Met Ala Val Leu Thr Ile Asn Ala Ile
            35                  40                  45

Ala Thr Phe Leu Gly Val Val Thr Gly Val Ser Ala Tyr Asn Leu Lys
        50                  55                  60

Asp Lys Glu
65

<210> SEQ ID NO 52
<211> LENGTH: 419
<212> TYPE: PRT
<213> ORGANISM: Enterococcus phage

<400> SEQUENCE: 52

Met Lys Lys Lys Ile Leu Val Gly Ala Leu Ile Ala Leu Phe Phe Met
1               5                   10                  15

Pro Leu Asn Val Phe Ala Ala Lys Gly Asp Gln Gly Val Asp Trp Ala
                20                  25                  30

Val Tyr Gln Gly Glu Gln Gly Arg Phe Gly Tyr Ala His Asp Lys Phe
            35                  40                  45

Ala Ile Ala Gln Ile Gly Gly Tyr Asn Ala Ser Gly Ile Tyr Glu Gln
```

```
            50                  55                  60
Tyr Thr Tyr Lys Thr Gln Val Ala Ser Ala Ile Ala Gln Gly Lys Arg
 65                  70                  75                  80
Ala His Thr Tyr Ile Trp Tyr Asp Thr Trp Gly Asn Met Asp Ile Ala
                     85                  90                  95
Lys Thr Thr Met Asp Tyr Phe Leu Leu Arg Ile Gln Thr Pro Lys Asn
                100                 105                 110
Ser Ile Val Ala Leu Asp Phe Glu His Gly Ala Ser Ser Asp Val Asn
                115                 120                 125
Ala Asn Thr Glu Thr Ile Leu Tyr Gly Met Arg Arg Ile Lys Gln Ala
130                 135                 140
Gly Tyr Thr Pro Met Tyr Ser Tyr Lys Pro Phe Thr Leu Gln Tyr
145                 150                 155                 160
Val Asp Tyr Gln Arg Ile Ile Lys Glu Phe Pro Asn Ser Leu Trp Ile
                165                 170                 175
Ala Ala Tyr Pro Ser Tyr Glu Val Thr Pro Glu Pro Leu Tyr Ala Tyr
                180                 185                 190
Phe Pro Ser Met Glu Gly Ile Gly Ile Trp Gln Phe Thr Ser Thr Tyr
                195                 200                 205
Ile Ala Gly Gly Leu Asp Gly Asn Val Asp Leu Thr Gly Ile Thr Asp
210                 215                 220
Ser Gly Tyr Thr Asp Asn Asn Lys Pro Glu Thr Asp Thr Pro Ala Thr
225                 230                 235                 240
Asp Ala Gly Glu Glu Ile Glu Lys Thr Pro Asn Ser Asp Val Lys Val
                245                 250                 255
Gly Asp Thr Val Lys Val Lys Phe Asn Val Asp Ala Trp Ala Thr Gly
                260                 265                 270
Glu Ala Ile Pro Asp Trp Val Lys Gly Asn Asn Tyr Lys Val Gln Glu
                275                 280                 285
Val Thr Gly Ser Arg Val Leu Leu Glu Gly Ile Leu Ser Trp Ile Ser
                290                 295                 300
Lys Gly Asp Ile Glu Leu Leu Pro Asp Ala Thr Ile Val Pro Asp Lys
305                 310                 315                 320
Gln Pro Glu Ser Ile His Val Val Gln Tyr Gly Glu Thr Leu Ser Ser
                325                 330                 335
Ile Ala Tyr Gln Tyr Gly Thr Asp Tyr Gln Thr Leu Ala Ser Leu Asn
                340                 345                 350
Gly Leu Ala Asn Pro Asn Leu Ile Tyr Pro Gly Gln Thr Leu Lys Val
                355                 360                 365
Asn Arg Ser Val Val Ser Asn Val Tyr Thr Val Gln Tyr Gly Asp Asn
                370                 375                 380
Leu Ser Ser Ile Ala Ser Lys Leu Gly Thr Thr Tyr Gln Ala Leu Ala
385                 390                 395                 400
Gln Arg Asn Arg Leu Thr Asn Leu Asn Leu Ile Tyr Pro Gly Gln Thr
                405                 410                 415
Leu Ile Tyr

<210> SEQ ID NO 53
<211> LENGTH: 126
<212> TYPE: PRT
<213> ORGANISM: Enterococcus phage

<400> SEQUENCE: 53

Met Lys Ser Glu Ile Lys Lys His Ile Arg Gln Leu Leu Cys Asp Tyr
```

```
1               5                    10                   15
Lys Lys Ile Glu Lys Gln Leu Lys Lys Tyr Glu Asp Ala Leu Val Tyr
                20                   25                  30

Pro Gln Ser Ser Phe Ser Leu Tyr Phe Glu Glu Lys Ser Asn Glu Lys
                35                   40                  45

Ile Ser Leu Asn Gln Ile Val Phe His Lys Phe Leu Asn Thr Val
     50                   55                  60

Glu Glu Val Leu Ser Asp Ala Thr Ser Asp Val Arg Asp Ile Phe Ile
65                   70                   75                  80

Ser Lys Tyr Lys Asn Gly Tyr Pro Arg Lys Lys Asn Glu Ile Val Ala
                85                   90                  95

Tyr Glu Thr Tyr Leu Ser Leu Ser Thr Ile Lys Arg Arg Asp Ser Glu
               100                  105                 110

Phe Leu Glu Glu Leu Ala Arg Gln Leu Gly Trp Leu Glu Val
               115                  120                 125
```

<210> SEQ ID NO 54
<211> LENGTH: 421
<212> TYPE: PRT
<213> ORGANISM: Enterococcus phage

<400> SEQUENCE: 54

```
Met Ala Asp Thr Trp Leu Ser Pro Leu Ala Val Ser Tyr Gln Ala Thr
1               5                    10                   15

Gln Glu Trp Asp Glu Pro Asp Tyr Leu Ser Gly Gln Ala Gly Ile
                20                   25                  30

His Gly Gly Ile Asp Leu Ala Pro Lys Ala Gly Thr Asn Pro Pro Val
                35                   40                  45

Tyr Ser Ala Lys Ser Gly Thr Val Glu Glu Val Pro Asn His Pro
     50                   55                  60

Ile Gly Gly Asn Tyr Ile Val Ile Arg His Met Asp Asn Tyr Trp Thr
65                   70                   75                  80

Tyr Tyr Gly His Leu Ala Thr Ile Asn Val Ser Val Gly Gln Gln Val
                85                   90                  95

Thr Asn Gln Thr Val Leu Gly Leu Cys Gly Ala Thr Gly Ala Thr
               100                  105                 110

Gly Ile His Leu His Phe Glu Val Trp Arg Gly Gly Lys Trp Gln Arg
               115                  120                 125

Ile Asn Pro Arg Glu Val Ile Asn Leu Asp Gly Ser Gly Arg Asp Ser
    130                  135                 140

Ser Asn Asn Gly Gly Asn Gly Gly Ile Tyr Thr Gly Gly Ala Leu Leu
145                  150                  155                 160

Asn Ala Gly Lys Ser Ile Ser Glu Ser Asn Ile Arg Leu Ile Ile Ser
                165                  170                 175

Ala Gly Lys Lys Tyr Asn Ile Lys Pro Ser Phe Met Ile Ala Gln Met
                180                  185                 190

Phe Ile Glu Ser His Trp Gly Asp Pro Ser Ile Ser Ile Val Gly Ser
                195                  200                 205

Lys Asp Asn Asn Trp Ala Gly Ile Ser Glu Pro Phe Ser Val Pro Ala
    210                  215                 220

Asp Leu Gly Ile Asn Met Ser Arg Gly Ser Ala Arg Pro Val Gly Glu
225                  230                  235                 240

Gly Gly Tyr Tyr Ile His Phe Ala Thr Met Asn Asp Phe Phe Lys Ala
                245                  250                 255
```

-continued

```
Tyr Ala Phe Val Leu Ser Lys Arg Asn Gly Leu Tyr Asn Val Gly
                260                 265                 270

Ala Asn Ser Ile Glu Glu Tyr Cys Lys Gly Leu Phe Arg Ile Gly Gly
                275                 280                 285

Ala Asn Ser Asp Tyr Ala Ala Thr Gly Tyr Gln Asn Tyr Phe Asn Met
                290                 295                 300

Leu Ile Pro Thr Tyr Asn Ser Ile Asn Lys Gln Asn Pro Gly Lys Leu
305                 310                 315                 320

Ala Gln Ile Asp Ala Ser Thr Glu Glu Ile Thr Asn Asn Gly Gly Leu
                325                 330                 335

Thr Thr Met Gln Cys Leu Tyr Glu Arg Pro Ile Asn Pro Asn Thr Gly
                340                 345                 350

Ala Leu Asp Ile Asn Gly Ser Ala Thr Thr Met Met Phe Cys Asn Gly
                355                 360                 365

Val Asn Thr Arg Arg Val Tyr His Asn Asp Glu Val Asn Ile Val Lys
                370                 375                 380

Glu Leu Tyr Arg Lys Asn Asn Gly Lys Glu Ile Pro Val Tyr Tyr Lys
385                 390                 395                 400

Lys Asp Trp Pro Lys Thr Ser Pro Trp Tyr Ile Arg Leu Glu Ala Met
                405                 410                 415

Phe Pro Val Val Lys
                420

<210> SEQ ID NO 55
<211> LENGTH: 500
<212> TYPE: PRT
<213> ORGANISM: Enterococcus phage

<400> SEQUENCE: 55

Met Lys Tyr Phe Phe Lys Glu Asn Lys Gly Leu Ala Ile Tyr Ser Phe
1               5                   10                  15

Leu Met Val Phe Ala Thr Tyr Gly Ile Lys Leu Phe Asn Asn Thr Tyr
                20                  25                  30

Ala Ile Asp Thr Met His Leu Met Thr Asn Tyr Arg Gly Tyr Leu Lys
                35                  40                  45

His Trp Val Ser Ile Gly Arg Pro Gly Leu Val Ala Leu Lys Leu Leu
            50                  55                  60

Thr Tyr Asn Tyr Val Asn Val Tyr Phe Leu Asn Leu Leu Ala Ile Ile
65                  70                  75                  80

Phe Phe Ala Ile Ala Thr Ile Leu Leu Cys Tyr Tyr Val Asp Leu Ser
                85                  90                  95

Thr Lys Gln Ile Tyr Asn Lys Lys Tyr Leu Tyr Val Ile Pro Ser Ile
                100                 105                 110

Phe Pro Thr Ser Gln Leu Phe Ser Glu Gln Phe Tyr Phe Val Leu Gln
                115                 120                 125

Asn Phe Glu Phe Ser Leu Gly Ile Cys Leu Val Ile Leu Ser Leu Ile
                130                 135                 140

Ala Ile Tyr His Ile Pro Asn Lys Ile Phe Lys Leu Phe Gly Phe Leu
145                 150                 155                 160

Leu Leu Thr Phe Thr Leu Thr Met Tyr Gln Ser Phe Phe Val Phe Ala
                165                 170                 175

Cys Thr Leu Ile Leu Phe Lys Ile Leu Met Ala Leu Tyr Phe Ala Gln
                180                 185                 190

Leu Asn Asp Leu Lys Ile Ser Phe Lys Asp Tyr Ala Phe Lys Ile Gly
                195                 200                 205
```

```
His Phe Ile Leu Leu Ala Ile Ser Ser Leu Val Leu Ser Gln Leu Met
    210                 215                 220
Ala Met Leu Ala Lys Lys Val Leu Asn Val Glu Ser Ser Tyr Leu Asp
225                 230                 235                 240
Asn Met Ile Leu Trp Gly Lys Arg Pro Leu Ile Asp Ser Ile Asn Asp
                245                 250                 255
Ile Lys Asp Tyr Ala Lys Glu Leu Phe Phe Pro Pro Val Gly Asp Thr
            260                 265                 270
Phe Phe Thr Pro Leu Phe Leu Ile Cys Val Leu Leu Val Ile Val
        275                 280                 285
Leu Ile Asn Met Ser Tyr Leu Lys Arg Lys Asn Val Phe Phe Ile Phe
    290                 295                 300
Ile Thr Leu Leu Gly Ile Leu Ile Thr Pro Leu Met Phe Thr Val Leu
305                 310                 315                 320
Gly Gly Lys Arg Pro Ala Ile Arg Gly Glu Val Pro Asn Phe Pro Ala
                325                 330                 335
Val Leu Ala Leu Leu Ile Phe Ile Met Ile Tyr Trp Gly Tyr Asn
            340                 345                 350
Phe Val Leu Lys His Leu Leu Val Gly Ile Val Ile Phe Thr Phe
        355                 360                 365
Ile Gln Val Arg Glu Thr Thr Asn Leu Glu Tyr Ser Glu Tyr Leu Thr
    370                 375                 380
Ala Glu Glu Asp Leu Arg Thr Ala Glu Met Ile Thr Asn Asn Ile Tyr
385                 390                 395                 400
Ser Met Glu Ile Glu Asn Pro Glu Ser Tyr Lys Leu Leu Met Tyr Gly
                405                 410                 415
Asn Arg Ser Pro Arg Asn Val Ser Asn Ile Lys Gly Glu Thr Asn Gly
            420                 425                 430
Val Ser Leu Phe Glu Phe Met Pro Asn Ser Val His Thr Ser Leu Asn
        435                 440                 445
Thr Leu Val Tyr Met Lys Thr Phe Gly Leu Asn Phe Asn Asp Pro Thr
    450                 455                 460
Pro Glu Asp Phe Glu Lys His Lys Ala Leu Gln Ala Glu Met Asn Val
465                 470                 475                 480
Trp Pro Ser Lys Asp Ser Ile Arg Val Val Asp Asp Cys Ile Ile Val
                485                 490                 495
Asn Leu Ser Lys
            500

<210> SEQ ID NO 56
<211> LENGTH: 193
<212> TYPE: PRT
<213> ORGANISM: Enterococcus phage

<400> SEQUENCE: 56

Met Lys Lys Ser Leu Ser Leu Val Phe Ala Leu Leu Leu Leu Thr Ala
1               5                   10                  15
Cys Thr Asn Glu Asn Thr Lys Thr Glu Asn Thr Lys Gly Ser Ser Thr
                20                  25                  30
Thr Val Thr Ser Thr Val Lys Glu Ser Ser Asn Asn Ser Ile Asn Glu
            35                  40                  45
Lys Asn Ile Leu Ser Thr Asn Thr Thr Thr Ser Thr Ala Asp Arg
    50                  55                  60
Lys Ser Ser Gln Thr Glu Glu Glu Gln Ser His Thr Glu Asp Pro Ala
```

```
                65                  70                  75                  80
Ser Leu Ser Ser Phe Val Gly Gly Trp Gly Ile Pro Gln Ser Gly Asn
                    85                  90                  95

Phe Phe Phe Ile Asn Pro Asp Gly Lys Met Ser Gly Ser Gly Gln Pro
                100                 105                 110

Asn Gly Val Ile Gln Ser Pro Asn Phe Leu Ser Asn Ala Asp Gly Ser
                115                 120                 125

Ile Thr Met Asn Phe Ile Ile Asn Asn Thr Ser Leu Ser Phe Thr Lys
    130                 135                 140

Asn Leu Asp Gly Thr Leu Ser Thr Glu Asn Gln Ile Tyr Ser Tyr Leu
145                 150                 155                 160

Gly Asn Ile Thr Leu Glu Gln Trp Leu Glu Leu Lys Asn Lys Gly Gln
                165                 170                 175

Met Ser Ser Glu Gln Gln Thr Gly Ile Leu Glu Ala Ser Ser Gln Thr
            180                 185                 190

Pro

<210> SEQ ID NO 57
<211> LENGTH: 378
<212> TYPE: PRT
<213> ORGANISM: Enterococcus phage

<400> SEQUENCE: 57

Met Trp Ile Glu Glu Leu Pro Asn Gly Lys Tyr Lys Tyr Phe Glu Arg
1               5                   10                  15

Tyr Lys Asp Pro Tyr Thr Glu Lys Tyr Arg Arg Val Ser Val Thr Leu
                20                  25                  30

Asn Ser Lys Ser Asn Gln Ala Lys Lys Gln Ala Met Met Glu Leu Gln
                35                  40                  45

Asp Lys Ile Asn Asn Arg Met Glu Lys Asp Gln Lys Lys Val Ser
    50                  55                  60

Leu Glu Asn Leu Leu Asn Ser Trp Trp Gln Gln His Gln Leu Ser Ile
65                  70                  75                  80

Arg Lys Thr Ser Val Lys Ala Tyr Gly Lys Ile Leu Lys Tyr Ile Phe
                85                  90                  95

Ser Asn Met Asn Val Asp Val Leu Ile Arg Asn Thr Asp Thr Lys Phe
                100                 105                 110

Phe Gln Asp Phe Ile Asn Asp Leu Pro His Ser Trp Glu Tyr Lys Lys
                115                 120                 125

Lys Phe Lys Ser Val Leu Asn Met Ser Phe Thr Tyr Ala Gln Asp Met
    130                 135                 140

Gly Met Ile Asp Glu Asn Pro Ile Asn Arg Val Lys Val Val Lys Pro
145                 150                 155                 160

Pro Leu Thr Lys Glu Asn Phe Glu Asn Ile Glu Ser Lys Tyr Leu Glu
                165                 170                 175

Glu Arg Glu Val Tyr Gln Leu Leu Ser Tyr Tyr Tyr Ser Thr Phe Gln
                180                 185                 190

Ser Val His His Gly Arg Leu Ala Glu Phe Met Tyr Leu Thr Gly Leu
                195                 200                 205

Arg Ala Gly Glu Ala Ile Ser Leu Thr Ile Asn Asp Tyr Val Lys Asn
                210                 215                 220

Glu His Ala Ile Leu Val Asn Gly Thr Leu Asp Tyr Ser Asn Gly Tyr
225                 230                 235                 240

Lys Asn Ala Thr Lys Glu Leu Pro Lys Thr Leu Ala Ser Phe Arg Lys
```

```
            245                 250                 255
Val Glu Leu Ser Asn Arg Ala Val Glu Ile Glu Leu Ile Leu
            260                 265                 270

Glu Arg Glu Ile Lys Phe Lys Glu Gln Thr Asn Tyr Leu Phe Val Gly
            275                 280                 285

Lys Thr Gly Asn Pro Ile Gln Val Asn Ser Phe Asn Ala Ser Leu Lys
            290                 295                 300

Lys Ala Asn Glu Ser Leu Gly Lys Asn Lys Ile Asn Lys Thr Ile Ser
305                 310                 315                 320

Ser His Ile Phe Arg His Ser His Ile Ser Leu Leu Ala Glu Leu Asn
            325                 330                 335

Val Pro Val Lys Ala Ile Met Glu Arg Val Gly His Val Asp Thr Glu
            340                 345                 350

Thr Thr Leu Lys Ile Tyr Thr His Val Thr Lys Lys Ala Lys Thr Asn
            355                 360                 365

Leu Val Glu Ala Leu Asn Lys Tyr Gly Lys
            370                 375

<210> SEQ ID NO 58
<211> LENGTH: 190
<212> TYPE: PRT
<213> ORGANISM: Enterococcus phage

<400> SEQUENCE: 58

Met Lys Lys Ile Thr Ile Ser Ile Leu Leu Leu Ser Ser Leu Thr Leu
1               5                   10                  15

Gly Ala Cys Asp Ser Ser Ser Thr Ala Pro Glu Lys Asn Lys Lys Glu
            20                  25                  30

Thr Ser Thr Thr Lys Ile Thr Glu Lys Thr Ser Ala Thr Lys Thr Ser
            35                  40                  45

Thr Ser Thr Glu Ser Thr Ser Asp Asn Lys Lys Thr Val Tyr Asn Leu
            50                  55                  60

Gly Glu Trp Trp Glu Val Pro Asn Gln Trp Lys Leu Lys Ile Asp Ser
65              70                  75                  80

Val Thr Ser Thr Asp Glu Arg Asn Pro Tyr Ser Asp Lys Ser Pro Gln
                85                  90                  95

Gln Val Val Ile Ile Ser Tyr Thr Tyr Glu Asn Leu Gly Tyr Glu Asp
            100                 105                 110

Asp Ile Gln Asp Leu Phe Ile Met Pro Glu Asn Val Val Asp Ser Ala
            115                 120                 125

Gly Ile Met Gly Glu Thr Tyr Pro Val Ser Thr Thr Gly Ala Lys Pro
            130                 135                 140

Thr Pro Val Gly Ala Thr Met Ser Gly Ala Gln Ala Ala Tyr Gly Val
145                 150                 155                 160

Gln Asn Pro Gly Gly Asn Ile Lys Ile Leu Phe Lys Lys Tyr Asp Ser
                165                 170                 175

Asn Arg Thr Gly Gln Ala Ala Thr Phe Glu Ile Pro Val Gln
            180                 185                 190

<210> SEQ ID NO 59
<211> LENGTH: 66
<212> TYPE: PRT
<213> ORGANISM: Enterococcus phage

<400> SEQUENCE: 59

Met Lys Val Gly Met Arg Lys Pro Ser Ile Lys Lys Ser Ile Ser Ala
```

```
                1               5                  10                 15
Arg Thr Thr Gly Lys Ala Lys Arg Lys Phe Lys Lys Ala Val Ile Pro
                20                      25                 30

Gly Tyr Gly Gln Lys Gly Thr Gly Phe Ile Lys Asn Pro Lys Lys Ala
            35                      40                 45

Met Tyr Asn Lys Val Tyr Asn Lys Thr Thr Phe Ser Phe Trp Asp Leu
    50                      55                 60

Phe Lys
65

<210> SEQ ID NO 60
<211> LENGTH: 184
<212> TYPE: PRT
<213> ORGANISM: Enterococcus phage

<400> SEQUENCE: 60

Met Lys Lys Ile Phe Ala Ser Met Ala Phe Leu Leu Phe Val Val Val
1               5                   10                  15

Ile Phe Val Gly Cys Ser Lys Asn Val Asn Pro Asp Ser Ser Lys Ser
            20                  25                  30

Ser Thr Gln Glu Ser Ser Lys Thr Tyr Lys Ile Leu Val Asp Gln Asp
        35                  40                  45

Ser Thr Glu Gln Lys Glu Lys Leu Glu Lys Ile Ser Glu Tyr Tyr Lys
    50                  55                  60

Thr Ala Asp Pro Lys Ser Tyr Asn Ser Asn Val Arg Val Asn Ser Met
65                  70                  75                  80

Leu Arg Asp Glu Lys Ala His Lys Gly Glu Lys Val Tyr Ser Leu Ala
                85                  90                  95

Lys Ile Ile Gln Ile Val Asp Glu Pro Ser Asp Glu Tyr Ile Tyr Tyr
            100                 105                 110

Met Gly Tyr Val Thr Tyr Ala Lys Asn Asp Arg Glu Tyr Val Met Leu
        115                 120                 125

Ala Val Leu Lys Asp Asn Val Tyr Ser Lys Val Leu Gln Asp Asp Glu
    130                 135                 140

Ile Leu Phe Trp Ala Ser Phe Ala Gly Ser Tyr Asp Tyr Thr Thr Asn
145                 150                 155                 160

Leu Gly Asp Asn Asn Thr Leu Pro Leu Leu Lys Val Asp Met Tyr Lys
                165                 170                 175

Asn Val Thr Ala Ser Glu Glu Lys
            180

<210> SEQ ID NO 61
<211> LENGTH: 157
<212> TYPE: PRT
<213> ORGANISM: Enterococcus phage

<400> SEQUENCE: 61

Met Asn Glu Tyr Glu Leu Leu Val Ser Glu Val Gln Lys Lys Ala Pro
1               5                   10                  15

Val Ile Glu Thr Asp Leu Phe Gln Asn Thr Gly Cys Tyr Gly Leu Tyr
            20                  25                  30

Arg Asp Gly Arg Ile Tyr Ile Glu Lys Ser Leu Ser Leu Ile Lys Lys
        35                  40                  45

Arg Asn Val Leu Ala Glu Glu Leu Gly His His Asp Thr Ser Phe Gly
    50                  55                  60

Asp Ile Leu Asn Gln Asp Cys Leu Glu Asn Arg Lys Gln Glu Leu Lys
```

```
            65                  70                  75                  80
Ala Arg Gln Tyr Ala Leu Glu Gln Leu Val Thr Leu Asp Asp Leu Ile
                85                  90                  95

Lys Cys Ser Glu Ser Gly Phe Ser Asn His Tyr Thr Cys Ala Glu Phe
               100                 105                 110

Leu Gly Val Asp Val Glu Thr Leu Lys Asn Val Leu Ala Tyr Tyr Arg
               115                 120                 125

Gln Lys Phe Gly Asp Thr His Phe Tyr Lys Gly Arg Ile Phe Glu Phe
       130                 135                 140

Asn Asp Leu Ser Val Met Ile Leu Asn Thr Asn Leu Gln
145                 150                 155

<210> SEQ ID NO 62
<211> LENGTH: 190
<212> TYPE: PRT
<213> ORGANISM: Enterococcus phage

<400> SEQUENCE: 62

Met Asp Arg Val Lys Thr Ser Ala Arg Leu Lys Gln Leu Met Ser Glu
1               5                  10                  15

Arg Asn Leu Lys Gln Val Asp Ile Leu Arg Leu Ser Glu Pro Tyr Gln
            20                  25                  30

Lys Glu Leu Asn Ile Lys Met Ser Lys Ser Thr Leu Ser Gln Tyr Val
        35                  40                  45

Thr Gly Lys Gln Ser Pro Asp Gln Asn Arg Ile Tyr Leu Leu Ser Lys
    50                  55                  60

Thr Leu Asp Val Asn Glu Ala Trp Leu Met Gly Phe Asp Val Ser Lys
65                  70                  75                  80

Lys Arg Ile Pro Asp Glu Gln Arg Ser Ser Glu Lys Asp Asp Phe Asp
                85                  90                  95

Ile Val Pro Ile Phe Asn Gln Leu Glu Pro Lys Leu Gln Gln Leu Ile
               100                 105                 110

Tyr Asn Glu Ala Lys Ser His Leu Glu Lys Gln Asn Lys Ala Ser Asn
           115                 120                 125

Asn Val Val Asn Ile Asn Lys Lys Tyr Asp Thr Leu Ala Ala His
       130                 135                 140

Ser Pro Asp Pro Asp Lys Val Phe Thr Asp Glu Glu Lys Leu Lys Ile
145                 150                 155                 160

Asn Gln Phe Leu Asp Lys Val Asp Ala Asp Tyr Asp Arg Lys Gln Lys
                165                 170                 175

Glu Cys Lys His Leu Phe Asp Asp Ser Asp Lys Glu
            180                 185                 190

<210> SEQ ID NO 63
<211> LENGTH: 77
<212> TYPE: PRT
<213> ORGANISM: Enterococcus phage

<400> SEQUENCE: 63

Met Cys Tyr Asp Tyr Ser Lys Leu Ala Gly Arg Ile Val Glu Lys Phe
1               5                  10                  15

Gly Thr Gln Tyr Asn Phe Ala Ile Ala Met Gly Leu Ser Glu Arg Thr
            20                  25                  30

Ile Ser Leu Lys Met Asn Gly Lys Val Ser Trp Lys Asp Thr Glu Ile
        35                  40                  45

Thr Lys Ala Cys Lys Leu Leu Asp Leu Glu Thr Asn Phe Ile His Leu
```

Tyr Phe Phe Lys Glu Lys Val His Val Cys Glu Gln Arg
65                  70                  75

<210> SEQ ID NO 64
<211> LENGTH: 239
<212> TYPE: PRT
<213> ORGANISM: Enterococcus phage

<400> SEQUENCE: 64

Met Asn Glu Leu Ile Lys Val Thr Thr Asn Glu Asn Asp Glu Gln Leu
1               5                   10                  15

Val Asn Gly Arg Glu Leu Tyr Glu Phe Leu Gly Val Lys Asp Asn Tyr
            20                  25                  30

Thr Asp Trp Phe Lys Arg Met Ile Lys Tyr Gly Phe Asp Glu Asn Val
        35                  40                  45

Asp Phe Ile Ser Phe Ser Glu Lys Ser Asp Lys Pro Phe Gly Gly Arg
    50                  55                  60

Pro Gln Val Asn His Tyr Val Lys Leu Asp Met Ala Lys Glu Ile Ser
65                  70                  75                  80

Met Leu Gln Arg Thr Glu Arg Gly Lys Gln Ala Arg Tyr Phe Ile
                85                  90                  95

Gln Leu Glu Lys Phe Trp Asn Ser Pro Glu Met Leu Thr Lys Arg Ala
            100                 105                 110

Leu Glu Phe Gln Gln Lys Lys Ile Glu Val Leu Gln Leu Glu Asn Glu
        115                 120                 125

Ser Leu Lys Pro Lys Ala Leu Phe Ala Asp Ala Val Asp Ala Ser Lys
    130                 135                 140

Thr Ser Ile Leu Ile Gly Asp Leu Ala Lys Leu Ile Lys Gln Asn Gly
145                 150                 155                 160

Ile Asp Ile Gly Gln Asn Arg Leu Phe Gln Trp Leu Arg Asp Asn Gly
                165                 170                 175

Tyr Leu Ile Ala Arg Lys Gly Glu Ser Tyr Asn Met Pro Thr Gln Arg
            180                 185                 190

Ser Leu Asp Leu Gly Ile Ala Glu Ile Lys Glu Arg Thr His Asn Asn
        195                 200                 205

Pro Asp Gly Ser Ile Arg Ile Ser Arg Thr Pro Lys Ile Thr Gly Lys
    210                 215                 220

Gly Gln Ile Tyr Phe Val Asn Lys Phe Leu His Asp Lys Thr Ala
225                 230                 235

<210> SEQ ID NO 65
<211> LENGTH: 82
<212> TYPE: PRT
<213> ORGANISM: Enterococcus phage

<400> SEQUENCE: 65

Met Gln Ile Thr Leu Ala Lys Thr Ile Asp Leu Gln Gln Ala Trp Met
1               5                   10                  15

Ala Lys Asp Glu Ala Ile Val Tyr Phe Gly Tyr Gln His His Lys Pro
            20                  25                  30

Thr Phe Gln Lys Leu Leu Arg Glu Phe Lys Glu His Lys Glu Phe Lys
        35                  40                  45

Asp Gly Tyr Arg Leu Val Thr Ser Cys Met Pro Ile Ile His Ile Gln
    50                  55                  60

Lys Phe Asp Glu Phe Leu Val Trp Arg Glu Lys Asn Lys Tyr Lys Arg 65                  70                  75                  80
Asn Lys

<210> SEQ ID NO 66
<211> LENGTH: 57
<212> TYPE: PRT
<213> ORGANISM: Enterococcus phage

<400> SEQUENCE: 66

Met Arg Lys Ile Tyr Asn Leu Arg Arg Ile Ala Val Leu Leu Ile Val
1               5                   10                  15

Phe Gly Leu Gly Leu Leu Val Gly Gly Asn Phe Asn Pro Ile Ile Gln
            20                  25                  30

Asn Val Tyr Ile Gly Leu Phe Ile Ile Trp Thr Leu Phe Tyr Asp Leu
        35                  40                  45

Ala Leu Glu Asp Arg Glu Val Asn Lys
    50                  55

<210> SEQ ID NO 67
<211> LENGTH: 41
<212> TYPE: PRT
<213> ORGANISM: Enterococcus phage

<400> SEQUENCE: 67

Met Thr Arg Lys Glu Lys Leu Gln Gln Thr Lys Leu Ala Asp Leu
1               5                   10                  15

Trp Tyr Gln Gln Gln Lys Asn Gln Ile Tyr Ile Met Gln Gln Lys Glu
            20                  25                  30

Arg Arg Glu Phe Arg Cys Leu Lys Gln
        35                  40

<210> SEQ ID NO 68
<211> LENGTH: 51
<212> TYPE: PRT
<213> ORGANISM: Enterococcus phage

<400> SEQUENCE: 68

Met Phe Lys Ala Val Gly Lys Asp Ser Leu Lys Ile Tyr Val Val Glu
1               5                   10                  15

Asp Thr Lys Ala Leu Val Phe Gln Lys Leu Lys Glu Lys Tyr Pro Asp
            20                  25                  30

Thr Ala Ile Asn Lys Ala Val Phe Pro Glu Ala Leu Phe Ile Gln Glu
        35                  40                  45

Thr Lys Lys
    50

<210> SEQ ID NO 69
<211> LENGTH: 78
<212> TYPE: PRT
<213> ORGANISM: Enterococcus phage

<400> SEQUENCE: 69

Met Arg Val Glu Val Asp Ser Met Gln Arg Ile Val Leu Ile Asp Asn
1               5                   10                  15

His Ser Pro Tyr Gly Ser Leu Ile Phe Glu Lys Asp Ala Ile Asn Asn
            20                  25                  30

His Val Ala Val Tyr Gln Asp Ser Gly Asp Glu Glu Val Arg Thr Val
        35                  40                  45

Phe Glu Ser Leu Asp Glu Ser Ala Tyr Phe Asn Gln Val Glu Leu Ile

```
                    50                  55                  60
Glu Gly Leu Gln Lys Val Ile Ser Leu Leu Lys Glu Gly Glu
 65                  70                  75

<210> SEQ ID NO 70
<211> LENGTH: 225
<212> TYPE: PRT
<213> ORGANISM: Enterococcus phage

<400> SEQUENCE: 70

Met Asn Glu Asn Ser Glu Asn Leu Lys Glu Leu Phe Asp Gly Met Tyr
  1               5                  10                  15

Lys Leu Lys Ser Lys Leu Ile Gln Pro Arg Phe Asp Ala Glu Val Ala
                 20                  25                  30

Tyr Thr Thr Lys Lys Gly Pro Met Asn Phe Gln Tyr Ala Thr Leu Lys
             35                  40                  45

Ala Ile Glu Glu Ala Ile Arg Lys Ala Ala Gln Glu Ser Glu Ser Gly
         50                  55                  60

Ile Asp Phe Gln Gln Asn Val Val Asn Glu Asn Asn Ala Leu Lys Val
 65                  70                  75                  80

Thr Thr Ile Ile Thr His Val Ser Gly Gln Tyr Ile Val His Gly Pro
                 85                  90                  95

Phe Glu Phe Pro Asn Ser Gly Thr Asn Pro Gln Gly Leu Gly Ser Leu
            100                 105                 110

Thr Thr Tyr Ala Arg Arg Tyr Ser Leu Ser Ala Ala Phe Gly Ile Ala
        115                 120                 125

Ala Asp Lys Asp Asp Asp Gly Gln Thr Ala Ala Glu Lys Asn Asn Asp
    130                 135                 140

Thr Ser Lys Val Asn Leu Ile Ser Gly Lys Gln Leu Ala Thr Leu Asn
145                 150                 155                 160

Asp His Ile Arg Gln Leu Ser Glu Leu Ser Asn Ser Glu Leu Asp Tyr
                165                 170                 175

Val Arg Asn Glu Leu Ser Lys Glu Leu Asn Val Asp Val Asn Glu Asn
            180                 185                 190

Met Pro Ser Ser Met Phe Asn Lys Ala Val Glu Val Leu Lys Gln Trp
        195                 200                 205

Ile Gln Gln Phe Gln Pro Gln Pro Glu Glu Asn Ile Thr Trp Gly Gln
    210                 215                 220

Ser
225

<210> SEQ ID NO 71
<211> LENGTH: 307
<212> TYPE: PRT
<213> ORGANISM: Enterococcus phage

<400> SEQUENCE: 71

Met Thr Asn Glu Leu Thr Thr Glu Leu Gln Phe Asn Val Asp Phe Lys
  1               5                  10                  15

Ala Ser Lys Ile Thr Ile Gln Asn Glu Ala Gln Leu Ala Glu Met Val
                 20                  25                  30

Glu Ser Ala Val Lys His Tyr Ser Thr Met Ile Phe Thr Asp Glu Asn
             35                  40                  45

Ile Pro Glu Ala Lys Lys Ala Arg Ala Asp Leu Asn Lys Val Val Thr
         50                  55                  60

Leu Leu Asp Asp Gln Arg Lys Glu Val Lys Asn Gln Tyr Asp Lys Pro
```

65                  70                  75                  80
Leu Lys Asp Phe Glu Glu Lys Ile Lys Lys Tyr Thr Glu Lys Ile Ser
                85                  90                  95

Glu Val Ser Ser Glu Ile Asn Glu Ser Ile Lys Ser Tyr Glu Glu Ala
            100                 105                 110

Glu Lys Gln Lys Arg Ser Lys Lys Leu Gln Lys Val Ile Ala Glu Met
        115                 120                 125

Ser Glu Asn Tyr Asn Val Ser Ile Asp Glu Ile Glu Ile Pro Ser Ser
    130                 135                 140

Trp Thr Asn Lys Thr Ala Phe Thr Val Lys Gly Glu Pro Asn Lys Lys
145                 150                 155                 160

Thr Ile Glu Glu Ile Ala Ala Ser Met Val Ala Val Ala Ser Glu Lys
                165                 170                 175

Glu Arg Ile Lys Asn Asp Lys Leu Ile Val Glu Asn Tyr Ala Lys Ala
            180                 185                 190

Val Gly Leu Asp Ser Phe Ser Trp Val Ala Leu Ile Asp Lys Gly Ser
        195                 200                 205

Thr Ala Pro Glu Leu Ile Lys Glu Ile Asp Ser Ala Val Ala Leu Lys
    210                 215                 220

Lys Glu Gln Glu Glu Arg Glu Arg Ala Lys Lys Glu His Asp Glu Ala
225                 230                 235                 240

Ile Ala Ala Leu Lys Thr Glu Thr Ile Asn Asn Lys Thr Val Asp Thr
                245                 250                 255

Ala Thr Gly Glu Ile Ile Thr Glu Glu Ala Pro Lys Thr Cys Lys Lys
            260                 265                 270

Gln Gln Glu Lys Thr Val Thr Leu Arg Leu Thr Ala Glu His Gln Lys
        275                 280                 285

Leu Val Ala Leu Asn Asn Phe Ile Ile Asn Asn Gly Ile Gln Val Glu
    290                 295                 300

Val Ile Glu
305

<210> SEQ ID NO 72
<211> LENGTH: 226
<212> TYPE: PRT
<213> ORGANISM: Enterococcus phage

<400> SEQUENCE: 72

Met Asn Leu Asn Asn Val Tyr Ser Ala Val Ile Lys Ser Leu Lys Asn
1               5                   10                  15

Asn Ser Ile Thr Ala Val Ile Asn Glu Ala Ile Asn Ile Glu Arg Leu
            20                  25                  30

Lys Thr Met Tyr Phe Asp Tyr Thr Gly Pro Arg Glu Val Glu Ile Arg
        35                  40                  45

Phe Ile Asp Pro Arg Lys Phe Ser Val Ala Gln Arg Arg Phe Ile Phe
    50                  55                  60

Ala Met Leu Glu Asp Ile Phe Ser Phe Thr Gly Gln Glu Thr Glu Val
65                  70                  75                  80

Leu Lys Glu Met Phe Tyr Leu Arg Phe Glu Ala Leu Gln Gly Tyr Glu
                85                  90                  95

Ile Ser Leu Arg Asn Asp Ser Glu Asn Thr Met Asp Asp Ala Thr Ile
            100                 105                 110

Leu Ala Asn Ile Ile Leu Asn Phe Ile Phe Glu Asn Asn Ile Pro Phe
        115                 120                 125

```
Arg Lys Gly Tyr Asp Ile Leu Pro Ala Asn Gln Glu Tyr Tyr Phe Tyr
    130                 135                 140

Lys Cys Ile Thr Lys Arg Val Cys Cys Ile Cys Gly Lys Thr Gly Ala
145                 150                 155                 160

Asp Ile Asp His Phe Asp Lys Ala Leu Gly Arg Arg Lys Arg Lys Ser
                165                 170                 175

Val Asp His Thr Glu Tyr Thr Tyr Ala Gly Leu Cys Arg Cys His His
            180                 185                 190

Thr Glu Lys His Asn Ile Gly Ile Thr Ala Phe Lys Lys Tyr His
        195                 200                 205

Val Lys Gly Ile Lys Leu Asn Gln Glu Thr Ile Lys Lys Leu His Ile
210                 215                 220

Gly Gly
225

<210> SEQ ID NO 73
<211> LENGTH: 318
<212> TYPE: PRT
<213> ORGANISM: Enterococcus phage

<400> SEQUENCE: 73

Met Ala Glu Ile Ser Trp Ile Lys Leu Ser Thr Ser Leu Pro Asp Asn
1               5                   10                  15

Lys Lys Ile Lys Arg Ile Arg Lys Leu Pro Asp Gly Asp Arg Val Ile
            20                  25                  30

Leu Phe Trp Val Phe Leu Leu Ala Arg Ala Gly Glu Ser Asn Gln Lys
        35                  40                  45

Gly Gly Leu Phe Leu Thr Asp Thr Leu Pro Tyr Ser Asp Glu Asp Leu
    50                  55                  60

Ala Ala Asp Phe Asp Phe Thr Val Glu Phe Val Lys Phe Ala Ile Leu
65                  70                  75                  80

Thr Leu Glu Lys Tyr Ser Met Val Thr Thr Tyr Glu Asp Val Ile Phe
                85                  90                  95

Ile Lys Asn Trp Glu Glu Tyr Gln Ala Ile Asp Gly Met Glu Lys Val
            100                 105                 110

Lys Glu Gln Asn Arg Ile Arg Gln Ala Lys Tyr Arg Glu Lys Gln Lys
        115                 120                 125

Gln Leu Ser Leu Ser Asn Val Thr Ser Asn Val Thr Arg Asn Ala Asp
    130                 135                 140

Val Thr Leu Ser Asn Gly Thr Asp Lys Asp Ile Asp Lys Glu Ile Asp
145                 150                 155                 160

Lys Glu Ile Asp Lys Asp Asn Lys Glu Glu Ser Lys Lys Pro Pro Cys
                165                 170                 175

Lys Tyr Ser Asp Glu His Leu Arg Leu Ala Gln Lys Leu Gln Asn Asn
            180                 185                 190

Leu Ile Asn Asp Phe Pro Ser Glu Met Lys Lys Val Lys Ile Glu Lys
        195                 200                 205

Trp Ala Asp Val Phe Arg Leu Ile Glu Glu Arg Asp Gln Gln Thr Ile
    210                 215                 220

Ala Ala Ile Asp Tyr Val Leu Asp Trp Leu Pro Thr Asn Ser Phe Trp
225                 230                 235                 240

Phe Gly Asn Ile Arg Ser Ala Ser Lys Leu Arg Thr Gln Phe Glu Lys
                245                 250                 255

Leu Lys Phe Glu Ile Lys Asn Glu Lys Glu Arg Gly Gln Gln Arg Thr
            260                 265                 270
```

```
Thr Tyr Gln Arg Gln Asn Val Arg Thr Glu Asn Leu Pro Glu Trp Ala
            275                 280                 285

Lys Glu Pro Asn Lys Gln Gln Glu Lys Leu Ser Pro Glu Glu Gln
    290                 295                 300

Leu Glu Leu Asp Arg Gln Ile Lys Glu Tyr Met Glu Gly Lys
305                 310                 315

<210> SEQ ID NO 74
<211> LENGTH: 174
<212> TYPE: PRT
<213> ORGANISM: Enterococcus phage

<400> SEQUENCE: 74

Met Thr Lys Tyr Pro Thr Gln Glu Leu Lys Asn Lys Arg Lys Ala His
1               5                   10                  15

Val Leu Phe Met Ser Thr Glu Val Met Lys Asn Ile Phe Glu Leu Gly
            20                  25                  30

Tyr Pro Phe Glu Phe Tyr Glu Ala Ser His Gln Phe Ala Ile His Ser
        35                  40                  45

Pro Leu Gly Val Ile Asp Tyr Phe Ala Ile Ser Gly Thr Trp Val Val
    50                  55                  60

Arg Lys Gly Gln Asp Arg Gly Lys Gly Ile Arg Lys Met Lys Gln Tyr
65                  70                  75                  80

Ile Lys Lys Arg Val Gly Asp Tyr Val Glu Lys Val Lys Val Val Lys
                85                  90                  95

Cys Ser Gly Tyr Leu Asp Lys Glu Gly Asn Ile Thr Asn Gln Ile Lys
            100                 105                 110

Gln Ala Met His Phe Thr Asp Asp Glu Leu Ala Asn Leu Ala Ala Glu
        115                 120                 125

Val Ala Gly Gly Lys Val Val Asn Val Val Ile Pro Pro Glu Lys Pro
    130                 135                 140

Lys Gln Leu Arg Glu Lys Ala Lys Glu Glu Ser Phe Gln Glu Lys Thr
145                 150                 155                 160

Lys Lys Lys Thr Lys Ser Asn Gln Ser Trp Met Asn Lys Lys
                165                 170

<210> SEQ ID NO 75
<211> LENGTH: 75
<212> TYPE: PRT
<213> ORGANISM: Enterococcus phage

<400> SEQUENCE: 75

Met Lys Leu Thr Ser Val Thr Phe Lys Pro Ser Ala Glu Arg Phe Pro
1               5                   10                  15

Pro Ile Val Ala Ile Asp Leu Asp Gln Leu Thr Pro Asp Glu Tyr Val
            20                  25                  30

Thr Leu Arg Asn Leu Gly Tyr Asp Thr Gln Leu Ser Lys Ile Thr Lys
        35                  40                  45

Arg Thr Phe Glu Glu Leu Glu Gly His Leu Gly Ile Arg Gly Asp Val
    50                  55                  60

Ala Lys Lys Asn Gly Phe Tyr Val Leu Val Lys
65                  70                  75

<210> SEQ ID NO 76
<211> LENGTH: 142
<212> TYPE: PRT
<213> ORGANISM: Enterococcus phage
```

<400> SEQUENCE: 76

Met Phe Trp Phe Asp Lys Gln Asn Glu Gln Val Leu Phe Met Asp Asn
1               5                   10                  15

Arg Glu His Tyr Glu Lys Leu Asp Ser Gly His Val Ile Asp Val Asn
            20                  25                  30

Pro Asn Leu Val Ala Asp Phe Arg Lys Met Pro Phe Glu Asp Asn Ser
        35                  40                  45

Phe Tyr His Val Val Phe Asp Pro Pro His Leu Leu Arg Cys Gly Asn
    50                  55                  60

Asn Ser Trp Leu Ala Lys Lys Tyr Gly Lys Leu Asn Glu Lys Thr Trp
65                  70                  75                  80

Lys Glu Asp Ile Gln Lys Gly Phe His Glu Cys Met Arg Val Leu Lys
                85                  90                  95

Pro Asn Gly Thr Leu Val Phe Lys Trp Asn Glu Glu Gln Ile Lys Leu
            100                 105                 110

Ser Glu Ile Leu Ser Thr Ile Asp Cys Glu Pro Leu Tyr Gly Asn Lys
        115                 120                 125

Arg Ala Lys Thr His Trp Leu Val Phe Met Lys Ala Gly Glu
    130                 135                 140

<210> SEQ ID NO 77
<211> LENGTH: 106
<212> TYPE: PRT
<213> ORGANISM: Enterococcus phage

<400> SEQUENCE: 77

Met Asn Glu Gln Ile Asn Leu Leu Glu Leu Asp Asn Asp Lys Leu Trp
1               5                   10                  15

Gln Phe Tyr Gly His Tyr Cys Asn Asp Asp Trp Ser Ala Lys Thr Glu
            20                  25                  30

Thr Val Asn Gly Val Thr Asp Ile Val Leu Gly Phe Arg Val Lys Leu
        35                  40                  45

Ser Lys Asn Glu Leu Arg Lys Ile Cys Arg Asp Ala Ile Glu Ile Ser
    50                  55                  60

Arg Ile Lys Tyr Gly Tyr Ser Val Arg Phe Leu Thr Asn Asn Val Lys
65                  70                  75                  80

Lys Glu Leu Phe Val Arg Phe Asp Asn Tyr Thr Thr Ser Lys Lys Arg
                85                  90                  95

Asp Val Phe Glu His Ile Asn Leu Tyr Phe
            100                 105

<210> SEQ ID NO 78
<211> LENGTH: 136
<212> TYPE: PRT
<213> ORGANISM: Enterococcus phage

<400> SEQUENCE: 78

Met Ile Pro Lys Phe Arg Ala Arg Asp Gln Arg Gly Asn Trp His Ile
1               5                   10                  15

Gly Leu Leu Thr Phe Met Phe Gly Gln Tyr Ala Ile Val Asn Glu Ser
            20                  25                  30

Asp Glu Asn Ser Val Tyr Leu Ile Asp Lys Glu Thr Val Gly Gln Ser
        35                  40                  45

Thr Gly Leu Lys Asp Lys Asn Gly Val Glu Ile Phe Glu Gly Asp Ile
    50                  55                  60

```
Leu Lys Ile Ile Glu Val Thr Asn Glu Gly Ile Ser Glu Tyr Ile Thr
 65                  70                  75                  80

Asp Val Ile Trp Glu Asp Cys Ser Phe Val Phe Lys Ser Glu Gly Val
                 85                  90                  95

Asp Tyr Tyr Asp Ser Phe Leu Gly Ala Phe Ser Gly Asp Pro Asn Lys
            100                 105                 110

Thr Tyr Pro Leu Phe Glu Leu Leu Val Ile Gly Asn Val Trp Asp Asn
        115                 120                 125

Leu Lys Leu Leu Glu Arg Thr Glu
        130                 135

<210> SEQ ID NO 79
<211> LENGTH: 55
<212> TYPE: PRT
<213> ORGANISM: Enterococcus phage

<400> SEQUENCE: 79

Met Lys Arg Leu Lys Ile Ser Tyr Ile Asp Leu Ala Val Ile Ile Glu
  1               5                  10                  15

Ser Ile Tyr Tyr Gly Glu Asp Glu Val Ser Asp Ile Asp Asp Leu
                 20                  25                  30

Leu Lys Tyr Leu Arg Asn Asn Gly His Leu Ser Thr Val Leu Thr Val
             35                  40                  45

Ser Arg Gly Ile Ser Asp Glu
         50                  55

<210> SEQ ID NO 80
<211> LENGTH: 201
<212> TYPE: PRT
<213> ORGANISM: Enterococcus phage

<400> SEQUENCE: 80

Met Asn Lys Gln Glu Phe Ile Glu Thr Leu Glu Glu Ile Arg Ala Asn
  1               5                  10                  15

Ile Asn Arg Asn Ala Glu Ile Ser Asp Tyr Thr Asp Phe Ser Arg Gly
             20                  25                  30

Lys Lys Asp Ala Tyr Asn Asn Ala Ile Gly Leu Ala Lys Gln Ile Asp
             35                  40                  45

Glu Pro Glu Lys Val Val Pro Lys Phe Val Ala Glu Trp Leu Asp
     50                  55                  60

Lys His Lys Tyr Ser Thr Asp Ile Ile Asp Leu Phe Leu Ser Val Glu
 65                  70                  75                  80

Tyr Ala Thr Asp Ser Asp Gly Phe Val Ala Glu Lys Trp Asp Tyr Ser
                 85                  90                  95

Gly Glu Phe Tyr Asp Trp Leu Ser Asn Ser Ala Asp Ile Gln Phe Thr
            100                 105                 110

Leu Cys Asp Ala Met Arg Tyr Gly Tyr Glu Val Glu Lys Glu Pro Thr
        115                 120                 125

Ile His Glu Leu Lys Ile Leu Pro Glu Tyr Phe Glu Ala Val Val Ser
        130                 135                 140

Gly Asn Lys Arg Phe Glu Ile Arg Lys Asn Asp Arg Asn Tyr Lys Lys
145                 150                 155                 160

Gly Asp Ile Leu Arg Leu Asn Glu Tyr Gln Glu Gly Gln Tyr Thr Gly
                165                 170                 175

Asp Val His Val Ser Glu Ile Thr Tyr Ile Thr Asp Tyr Ala Gln Gln
            180                 185                 190
```

```
Asp Gly Tyr Val Val Leu Gly Ile Lys
    195                 200
```

<210> SEQ ID NO 81
<211> LENGTH: 161
<212> TYPE: PRT
<213> ORGANISM: Enterococcus phage

<400> SEQUENCE: 81

```
Met Lys Thr Asp Leu Thr Arg Gln Ala Glu Lys Cys Leu Trp His Tyr
1               5                   10                  15

Thr Asn Lys Met Gly Val Phe Gly Cys Phe Glu Val Thr Ile Gly Trp
            20                  25                  30

Phe Gly Lys Glu Arg Val Asp Phe Met Thr Tyr Ser Thr Asp Asn Thr
        35                  40                  45

Ile Arg Cys Tyr Glu Ile Lys Val Thr Leu Ala Asp Leu Lys Ser Ser
    50                  55                  60

Ala Lys Gln Thr Phe Leu Gly Asp Tyr Asn Tyr Leu Val Val Thr Asn
65                  70                  75                  80

Glu Leu Trp Glu Lys Ile Gln Ala Asn Pro Asp Leu Lys Trp Lys Tyr
                85                  90                  95

Ser Asn Gln Gly Ile Leu Ile Phe Ser Glu Leu Arg His Asn Leu Gly
            100                 105                 110

Ile Thr Ser Val Lys Lys Ala Lys Lys Gln Asn Val Thr Leu Gly Thr
        115                 120                 125

Arg Ala Thr Val Leu Glu Ser Met Val Arg Ser Leu Asn Arg Glu Val
    130                 135                 140

Glu Lys Phe Tyr Lys Val Asn Pro Phe Trp Gly Leu Ser Glu Glu Val
145                 150                 155                 160

Lys
```

<210> SEQ ID NO 82
<211> LENGTH: 60
<212> TYPE: PRT
<213> ORGANISM: Enterococcus phage

<400> SEQUENCE: 82

```
Met Glu Gln Leu Leu Leu Thr Lys Thr Gly Glu Asn Glu Ile Gly Ile
1               5                   10                  15

Asn Ala Thr Gly Met Asp Asp Asn Glu Ile Val Phe Thr Leu Ala Ala
            20                  25                  30

Ala Leu Ile Gly Tyr Ser Lys Glu Leu Gly Leu Thr Glu Ala Ile Leu
        35                  40                  45

Asn Glu Ser Met Ser Val Leu Trp Lys Asp Gly Glu
    50                  55                  60
```

<210> SEQ ID NO 83
<211> LENGTH: 61
<212> TYPE: PRT
<213> ORGANISM: Enterococcus phage

<400> SEQUENCE: 83

```
Met Lys Arg Asn Trp Lys Arg Val Ile Asn Lys Val Ser Gly Ile Ala
1               5                   10                  15

Ile Met Ile Leu Val Ala Lys Val Ala Val Ser Tyr Phe Val Tyr Ser
            20                  25                  30

Asn Asp Ile Thr Ser Ser Asp Leu Val Tyr Phe Leu Ser Cys Ser Phe
        35                  40                  45
```

```
Ile Leu Gly Leu Gly Leu Tyr Leu Gly Gly Ser Ser Val
    50                  55                  60
```

<210> SEQ ID NO 84
<211> LENGTH: 66
<212> TYPE: PRT
<213> ORGANISM: Enterococcus phage

<400> SEQUENCE: 84

```
Met Ser Tyr Pro Glu Val Tyr Ile Leu Gly Arg Gln Val Asp Gly Val
1               5                   10                  15

Tyr Val Glu Tyr Ser Glu Pro Tyr Leu Ser Lys Ile Glu Ala Glu Leu
            20                  25                  30

Asp Lys His His Tyr Glu Ile Gly Gln Ser Met Ser His Asp Ala Gly
        35                  40                  45

Ser Trp Lys Ile Leu Lys Tyr Gly Arg Pro Ile Thr Leu Glu Val Gln
    50                  55                  60

His Gly
65
```

<210> SEQ ID NO 85
<211> LENGTH: 39
<212> TYPE: PRT
<213> ORGANISM: Enterococcus phage

<400> SEQUENCE: 85

```
Met Ala Asp Gln Leu His Trp Arg Cys Asn Met Gly Lys Lys Lys Ser
1               5                   10                  15

Lys Ile Lys Lys Lys Arg Arg Leu Gln Glu Lys Ala Ile Ala Asn
            20                  25                  30

Gly Thr Gln Asn Ser Lys Lys
            35
```

<210> SEQ ID NO 86
<211> LENGTH: 138
<212> TYPE: PRT
<213> ORGANISM: Enterococcus phage

<400> SEQUENCE: 86

```
Met Ile Gln Leu Leu Lys Glu Val Asp Phe Ser Gln Thr Arg Ala Asn
1               5                   10                  15

Ala Arg Ala Val Leu Lys Asn Phe Arg Arg Leu Asp Arg Ile Ala Gly
            20                  25                  30

Arg Ser Leu Val Asp Val Arg Ser Pro Ile Ile Thr Asp Met Pro Lys
        35                  40                  45

Gly Ile Lys His Gly Asn Lys Ala Glu Asp Ala Leu Ile Gln Met Met
    50                  55                  60

Asp Val Glu Ala Glu Arg Asp Ala Ile Leu Thr Ala Leu Met Ser Leu
65                  70                  75                  80

Ser Ile Ile Ser Arg Gln Ile Leu His Tyr Ser Phe Cys Val Gln Asp
                85                  90                  95

His Tyr Ser Asn Tyr Lys Ile Ala Arg Glu Val Gly Tyr Ser Glu Arg
            100                 105                 110

Ser Ile Gln Arg Met Lys Ser Glu Ala Leu Ile Glu Phe Ala Glu Ala
        115                 120                 125

Tyr Arg Asn Gly Lys Ile Ile Ala Tyr Lys
    130                 135
```

<210> SEQ ID NO 87
<211> LENGTH: 149
<212> TYPE: PRT
<213> ORGANISM: Enterococcus phage

<400> SEQUENCE: 87

```
Met Glu Thr Asn Asn Thr Phe Ser Asn Leu Leu Lys Asn Phe Asp Tyr
1               5                   10                  15

Pro Arg Ile Glu Pro Ser Met Lys Tyr Ala Glu Lys Leu Glu Thr Gly
            20                  25                  30

Ser Asn Trp Leu Gly Asp Ile Asn Arg Glu Lys Lys Gln Leu Gln Glu
        35                  40                  45

Leu Gln Lys Leu Ala Asn Glu Ser Thr Leu Lys Ser Glu Glu Leu Leu
    50                  55                  60

Lys Gln Ile Ala Glu Asn Thr Ser Tyr Ile Lys Asp Leu Val Met Ile
65                  70                  75                  80

Asn Arg Glu Thr Gln Leu Asn Thr Glu Glu Leu Thr Tyr Val Met Lys
                85                  90                  95

Ser Ile Tyr Lys Val Ser Lys Ala Glu Asn Lys Gln Glu Ala Asp Ser
            100                 105                 110

Leu Phe Ser Gln Ala Ile Gln Val Ile Asn Asp Ser Gly Glu Ala Ala
        115                 120                 125

Gly Asn Ile Ala Asn Leu Thr Ser Leu Leu Gly Ile Tyr Thr Phe
    130                 135                 140

Val Ser Thr Ile Ile
145
```

<210> SEQ ID NO 88
<211> LENGTH: 173
<212> TYPE: PRT
<213> ORGANISM: Enterococcus phage

<400> SEQUENCE: 88

```
Met His Ile Glu Lys Met Lys Leu Ser Asp Leu Arg Pro Ala Glu Tyr
1               5                   10                  15

Asn Pro Arg Val Lys Leu Asn Pro Gly Met Ala Glu Tyr Glu Lys Leu
            20                  25                  30

Lys Gln Ser Ile Leu Glu Phe Gly Phe Val Asp Pro Pro Ile Phe Asn
        35                  40                  45

Lys Asn Thr Gly Asn Leu Val Gly Gly His Gln Arg Val Thr Val Ala
    50                  55                  60

Lys Glu Leu Gly Leu Phe Asp Glu Ile Glu Val Ser Val Val Asp Leu
65                  70                  75                  80

Pro Leu Asp Lys Glu Lys Ala Leu Ser Ile Ala Leu Asn Lys Ile Ser
                85                  90                  95

Gly Asn Trp Asp Glu Asp Lys Leu Thr Glu Leu Leu Asn Glu Leu Thr
            100                 105                 110

Ala Asp Asn Leu Glu Leu Thr Gly Phe Asp Asn Glu Glu Leu Glu Ile
        115                 120                 125

Leu Ile Glu Asp Ala Asp Ile Pro Asn Phe Glu Pro Gly Ser Ile Asp
    130                 135                 140

Asp Gln Gly Asp Leu Thr Lys Leu Glu Pro Lys Phe Val Lys Cys Pro
145                 150                 155                 160

Cys Cys Gly Glu Glu Phe Asp Leu Arg Asp Val Glu Ser
                165                 170
```

-continued

<210> SEQ ID NO 89
<211> LENGTH: 202
<212> TYPE: PRT
<213> ORGANISM: Enterococcus phage

<400> SEQUENCE: 89

Met Leu Lys Val Asp Trp Ala Thr His Glu Ala Thr Lys Tyr Ala Cys
1               5                   10                  15

Thr His Phe His Tyr Ser Lys Ser Val Pro Val Gly Lys Leu Ile Lys
            20                  25                  30

Ile Gly Ala Trp Glu Asp Gly Gln Phe Ile Gly Val Val Ile Phe Ser
        35                  40                  45

Arg Gly Ala Asn Lys Ser Ile Gly Ser Pro Tyr Gly Leu Glu Gln Thr
    50                  55                  60

Glu Cys Cys Glu Leu Thr Arg Val Ala Leu Thr Asn His Lys Thr Phe
65                  70                  75                  80

Val Ser Glu Ile Leu Ala Lys Ala Ile Lys Phe Leu Lys Glu Phe Asn
                85                  90                  95

Pro Ser Met Gln Leu Ile Val Ser Tyr Ala Asp Thr Asp Gln Asn His
            100                 105                 110

His Gly Gly Ile Tyr Gln Ala Thr Asn Trp Ile Tyr Thr Gly Lys Thr
        115                 120                 125

Asp Gly Glu Arg Tyr Phe Ile Val Asn Gly Lys Lys Thr His Pro Lys
    130                 135                 140

Ser Ile His Ala Lys Tyr Gly Thr Gly Ser Gln Arg Leu Glu Phe Leu
145                 150                 155                 160

His Lys His Val Asp Pro Lys Ala Ser Ile Tyr Glu Ser Lys Gly Lys
                165                 170                 175

His Lys Tyr Leu Met Pro Leu Asn Lys Lys Ile Arg Lys Lys Ile Ile
            180                 185                 190

Lys Leu Ser Lys Pro Tyr Pro Lys Ala Lys
        195                 200

<210> SEQ ID NO 90
<211> LENGTH: 62
<212> TYPE: PRT
<213> ORGANISM: Enterococcus phage

<400> SEQUENCE: 90

Met Glu Thr Phe Asp Tyr Glu Val Gln Gln Ala Leu Glu Lys Gln Lys
1               5                   10                  15

Ile Ala Glu Glu Asn Asn Lys Ile Ile Arg Ala Ala Lys Ala Gln Trp
            20                  25                  30

Ile Ser Asn Phe Lys Ala Gly His Ile Lys Leu Asn Thr Val Lys Asp
        35                  40                  45

Leu Lys Asp Leu Ile Glu Ile Glu Ser His Leu Lys Glu Leu
    50                  55                  60

<210> SEQ ID NO 91
<211> LENGTH: 306
<212> TYPE: PRT
<213> ORGANISM: Enterococcus phage

<400> SEQUENCE: 91

Met Ala Lys Glu Lys Asn Glu Lys Lys Ala Asn Ser Asp Lys Gly Glu
1               5                   10                  15

Ile Lys Glu Thr Asn Leu Lys Lys Cys Phe Phe Ile Thr Pro Ile Gly

```
                   20                  25                  30
Glu Lys Asn Ser Asn Glu Phe Lys Lys Leu Lys Ala Ile Val Glu Asn
            35                  40                  45
Val Leu Asn Lys Val Leu Glu Lys Tyr Asp Tyr Glu Leu Ile Ile Ala
        50                  55                  60
His Glu Ile His Ser Met Gly Ser Ile Gly Asp Gln Val Phe Thr Asn
 65                  70                  75                  80
Ile Ile Gly Ala Asp Leu Val Ile Ser Asn Leu Ser Gly Trp Asn Ala
                85                  90                  95
Asn Val Met Tyr Glu Thr Ala Val Ala His Ser Phe Gly Lys Pro Thr
            100                 105                 110
Ile Met Ile Cys Glu Ser Gly Thr Glu Leu Pro Phe Asp Leu Ile Asn
        115                 120                 125
Asp Arg Thr Ile Phe Phe Glu Asp Thr Ile Glu Gly Thr Gly Ala Leu
130                 135                 140
Ile Glu Glu Leu Asp Lys Lys Ile Pro Lys Ile Ser Glu Asp Ser Thr
145                 150                 155                 160
Ala Asp Asn Pro Val Thr Arg Val Ile Arg Arg Lys Ala Leu Glu Asp
                165                 170                 175
Asp Leu Lys Gly Glu Thr Asp Asn Asp Ser Arg Ile Leu Gly Leu Leu
            180                 185                 190
Leu Asp Met Asp Lys Arg Leu Ser Met Tyr Glu Asp Ser Asn Ile Ile
        195                 200                 205
Glu Lys Lys Lys Ile Asn Thr Gly Asn Ile Glu Arg Ile Arg Ala Lys
    210                 215                 220
Ile Tyr Tyr Lys Asn Glu Gly Asn Ile Asn Val Ile Asp Glu Leu Glu
225                 230                 235                 240
Gly Tyr Leu Phe Glu Lys Tyr Arg Asp Thr Val Gln Ile Val Ser Val
                245                 250                 255
Thr Ser Gly Asn Arg Tyr Glu Asp Arg Asn Ser Glu Val Met Lys Val
            260                 265                 270
Ile Ile Val Asn Ser Leu Tyr Ser Pro Ala Lys Ile Phe Lys Asp Ile
        275                 280                 285
Glu Ile Thr Leu Gly Lys Leu Gly Met Val Asp Ile Ser Val Lys Val
    290                 295                 300
Phe Pro
305

<210> SEQ ID NO 92
<211> LENGTH: 42822
<212> TYPE: DNA
<213> ORGANISM: Enterococcus phage

<400> SEQUENCE: 92
gaggtggtgt tatatgtcag atggataaaa aggaacaagc aaagaaatat tatgaaaaag      60
gttggaaata caaggatatt tccgaaaagc tttctgtacc tctcaacaca ttgaagtcat     120
ggagaaaacg tgataaatgg gaaagagggg gtgcaaccaa agaggtgcaa cctacaaata     180
ggggtgcacc taaaggtaat caaaatgcta taggcaataa aggtaatagt cgagcctcgc     240
caccaaaaag aaataagaat gctgttaaaa ctggcgaata cgaaacaata tttgccgata     300
tgttatctga cgaagaaaag gacatctatt ctactatgaa tgatgatcct ttttttattt     360
tggatgaaga aataagaatc ctgaaaattc gccaatatag aatgcttaaa cgcataaaag     420
atgcagaggc tggcttaaat gatgaagaag ttgaacgttt gcagcagctt cgcaaagtta     480
```

```
aagagccatc ggtaattgat gggaaaatgg ttactgttaa gagagaagtt ttaaaagatg    540
tacaagtcac tcgtaaaaca tttagaaagt tagatgacat cctggctatt gaagatgcgt    600
tgactcgcgt tagcaatcaa ttaataaagg cgattaagca acaaaaagaa ttattgtcga    660
cagataaaaa atctctttta atggaggctc aaattgagaa gataaagctt gagacagaca    720
aattaagtgg cggatcatct aacgatgaag ctgactcttg gaaacaagca gttataaatg    780
cagcaaataa gcgggcggtg gaagaaaatg aataaagagt ttattccgtt tgccgatatt    840
ggtgcagcaa ttgattacta ctacgataaa ccagttgctt tttgtcagga tattttgcat    900
cttgatccag atgaatggca ggataaggtc ttggatgatt tggctaaatt cccaaaagtc    960
tcagttagat cagggcaggg tgttggaaaa acggcgttgg aggctggtgc tattctttgg   1020
tttctaacat gccggccata tgcaaaagta atagcaactg ctccgacgat gaaacaatta   1080
tacgatgttc tatgggcaga agtggctaag tggctgaata acagcttgat taaagactta   1140
cttaaatgga ccaagacgaa aatttatatg gttggcgatt cagaacgatg gtttgctaca   1200
gctcgaacag caactaaacc agaaaatatg caaggatttc acgaagacca tatgttaata   1260
gtggttgatg aagcatcagg tgttgctgat cccattatgg aagcaatatt aggtactctt   1320
tcaggatttg acaataaatt actaatgtgt gggaaccccca acaatattga aggggttttt   1380
tatgattcgc ataatacaga tagagacaag tatagaacgc acaaagtttc tagttacgat   1440
agcaaacgta ctaacaaaga aaatattcaa atgctcatcg ataagtatgg tgagaatagc   1500
gatgtagctc gtgttcgtat ttatggtgaa tttcccaaag gcgcacttga ttcatttatc   1560
agccttgaaa ttgttgagtt tgccaaagat attaatattt ctgattcaga attaaaacat   1620
gttagagaag gacacatagg tgtcgatgtg gctcgttttg gtgatgattc aacgatagta   1680
tttcctagaa tcggagctaa agcattgcca tttgaaaaat atagtaagca agataccatg   1740
cagaccactg gtcgagtttt aaaagcggcg aaaaggatga tggatgacta tcctacaata   1800
aaaaaagtgt tcatcaaagt agatgataca ggtgttggtg gaggtgttac tgatagactt   1860
aaagaagtaa ttagcgatga aaaacttccc tatgaagtaa ttccggtaaa taatggagaa   1920
tcttctacag acgattatta tgcaaataaa ggaacacaaa tatggggaga tgttaaagaa   1980
ctgttagaac aaaacatttc caattcgatt aatggtcaag ggccgacgat agaacttcct   2040
gataatgcaa atctaatcaa agaattgagc acacgtaaat ttaaaatgac tagcaatgga   2100
aaaatccgtt tagaaagtaa agaagatatg aaaaagcgta atgttggcag tccagatatt   2160
gctgatgcgt taacgttagc gttttacgag ccatttagac cagaacctat aaacgttaaa   2220
aaagctatta atacgttcaa aaaattagga ttaagtaggt gatagagtga ataataaatt   2280
attgaacggt tctagatttg ataaagaagc aaatctagtt tataaagtgc cagtaagcaa   2340
actgcctact cgaataatgc aatattcgaa cggagaaaaa gaagaagtcg tagattttga   2400
gcatcaagat gttttttaata tgattgtaaa atttgttcga caccataaag aaaaacaagt   2460
tcctcgcctt aaagaattaa agcgttattc tttagcgcaa aataatatta gtttactga    2520 agataaaagt gaaaatcgag cagacaacaa gattgcaaat gattgggcta gatttattgt   2580
caattttaaa aaaggcgtgt tattaggtaa tcctttgaag tacaatggcg ataaaactat   2640
agctgacaaa attaatgatt tttctagcaa atcaaatgaa gattatcata atcagttaat   2700
gttagacgac ttactcgttt atggaagagc gtttgaatat attggtagag atgaatacgg   2760
taaagaaatg ttagctaaat tcagtgcaga agagacgttc gttatttatg atacaacgac   2820
```

```
aaacaagaat tctgtatgtg ctattcactg ttatgatctg gagtttaacg atgaaacatt    2880
tagttatatc gatatttatg ccaatgatgg ctatttttat caacatgaat caaaaaatca    2940
agactatgaa caatctaaat taattgataa atatcaaact ttctttgatt ctattcaagt    3000
aaatgaatgg attaacaatg aagagcgttt aggagacttt gaaacagttt tagataatat    3060
agatgcatat gatttatcac aatcttcaat ggctaatttc caacaagatt catctgaagc    3120
ttatttagtt attaaaggaa accccgaaac tgctataggt gatgaagaag gtaattctgc    3180
agtagacgtt ttaaacgaca tgataaaagc tagattgtta atattagggg ataagaaata    3240
ttatggtgat ggtcaaacag gtagcgatcc tgatgcatac tatttgaaaa agagtatga    3300 tacacaagga acagaggcat ataatgaccg tttggtttct gacatgttgc gcttcacttc    3360
tttaattgat tttactgacg aaaacattgg tagtaatcag tctggtattg gatttagatt    3420
taaaggttgg ggaagtgaca atgatagaaa gaacaaagaa agaatggtca aaaaagcaat    3480
catgagaaga ctaagattat taacttattc ttggtcattg aaagataact taaataaacc    3540
aacagggctt gctgagaaag ttaagtcttt ttttgtatct agagataatg ataaagagct    3600 gcttttgaa aaggtgaatg ctatagagat attatttaca ccaaacgttc ctcaatcgga    3660
taaagaaatt atggaagtta ttgccggaat ggttggaatt gtttcagacg aaacactttg    3720
cgaaatggcg gctaaattga ctggtgttcc tgttcaaaca gaactaaata ggttgaaaaa    3780
ggaaaatcag ccagatacat tatccgatga agaagcagcg aagcttaaag aaaaacaggc    3840 agagttttg gcgaatcagt cggaaacaga ggaggactga tttagatgtc ctatttgaaa    3900
gatcgtgaag atgcttggat caaagagcag atgaagctag atcgtaatag agaaaaagaa    3960
attgttaaac agcttcaaaa tgctattgat gcgattcaaa ctgaaattga agctaactgg    4020
gatagatttt ccaatggtca aaatattacg attagcgaag caagaaaaat ggctaataag    4080
atggacgtaa aacgctttga gagaaagcg aaggaatatg taaaaaataa ggactttagc    4140
ccgcaagcca ataagaatt gaaaatctat aacttagtaa tgcgagtgtc tagattagag    4200
ctattaaagt ctcagattgg tttagaatta atcacgttgt ttgatgagct agataagtgg    4260
ggatattctc agttaactga agcggcaaaa gaggaatatt taagacaggc gggaatacta    4320
ggcgaaaccg ttcaagaaaa ttattcgtct aaggttagaa aaattgttaa tgcctcattc    4380
aaatcaagtg acttcccttc gtttagtgat aacatttggc aaaattttgt tgaaatgaaa    4440
gctgatttag aaaaaataat cactcaggca atcactcaag gtaaaaatcc aagagccgta    4500
gcaaaagaga tagctaaatt tttaaagcct aaccaattaa atataagata caagctaaat    4560
aggctaatga tgactgaaat atctggtatt caaacagata ttcaaaagca agttacttg    4620 gatgcagata tcgaagaata tgattacatt gcagaaccgt ttgcctgtga atatgtaaa    4680 aaagtggcta aggaagccc ttatagagta ttaaagatga aaaaaggtat taatgctcct    4740
tatatgcatc ctcattgtaa atgctctact gtccctaaag ttagtgagga ttatgataag    4800
tcgctgaaag aaagatgttt gtaaatggat aatctatata aatgcaatca atgtcataaa    4860
tacactccgt tagttagaaa atctgaaaat atcacgaagg atattgaaca ccattatgct    4920
gaatgtgcca actgtgggta taaagcgaca attatgtata tgaataccga aattaagtta    4980
ttaatgcatg aacaagaaa aacaaacttt ggcacaaaaa agaaaggtaa attgacggaa    5040
aagctaaaca gattaatttc tgaattaaga aaagaagttg aggaatcact ttgaaaacat    5100
gacagaaagg cgtgattcta tgaacgacga tccatacgat tacctagatg ctgattatga    5160
agaatattta agaaaggaag aagtaaatga aagcacgaaa gaaaccagta gtgattgaaa    5220
```

```
ctgtaatttt tttaggtttt tatgggaagg atcgcaattt cagtgaaaga cctaagtggc    5280
tggagagagc aatctatgtt gataaaaaaa ttgaattttt tgatgttcct gaaaaattaa    5340
ctatccatac tattgaagga ccaatttatg caattcctgg tgattacatc ataaaaggcg    5400
ttaatggcga actttatccg tgcaagccgg acatatttga aaaaacttat gagattattg    5460
agtagagtct aacaaacgtt agactttta tattgccttc ttactgcttg caggcattaa     5520
agagaaagct gtttcgattg ataggcgtaa cttatcaaat atatcgggta gcggcgtaac    5580
cgtggaggat aatcatgaaa acaaaaaaac tattattgcc aatgcattta caattctttg    5640
ctgataatct agatactggc actgggggta cggaccaacc ggccggaggt caagagcaaa    5700
caccgccagg agatggcggc aaagataaag gtaatggaaa aacgttttct cgtgatgaag    5760
tagcaaaaat gattgctgct gaagtatcaa aaacaaaaga agcttgggaa aaagagcttc    5820
aagagaaaca agaagaagct gataaattag ccaaaatgaa tgatcaggag aaaaatgatc    5880
atgaaaagca gaagttacttt gaaaaaatca aagagctgga aagtgcgcaa aacttagctg    5940
aaatgtctaa gactgctact aaaatgtttt ctgataaagg tattcaagcg actgagggat    6000
tactttcgtt agtagtaaag gaaacagcag aggagacatc tgaaaatgtt aaagctgttg    6060
taaaacttat cgaaactgaa cgtgaaacga ttaaagcaga ttttgagaaa cgaattggtt    6120
ctaaactccc acttgatgga aatgctgatg ctagcttatc tcgtggtgca caaatggcta    6180
aacaagcaaa taatcaaaat aaagcgcctg aaaataatct ttgggcgaca aattaggagg    6240
aattttgaat ggtttatgta agaaaaactc aaacatatca agatattaat tttttaaaga    6300
gcgaaaaatt tatttcattt acaaagcaag ttgatgaaac aactgaaggg gtagtaaaag    6360
gagtattacc cgcagggtca gtgttcccta aaaatgatgc tacagcagaa ggtattacaa    6420
ttaacgatgt tgatgtgtcg aatggaccac aaccggtagg agtaattgtt gaagggcatg    6480
ttcttattaa acgattacca gctgagccat catcggaagc tcaaaaagca atgcgtgaac    6540 ttaaattta tgatgcaaac ggtaaaatgc tagcagttcc aactgcttaa ttaataatta    6600
ggaggatttc aaatggcaaa tattgcagaa ttattttcac agaaaaatgt attagattat    6660
gtaaataatc gtcaagcacc agttttatta ggagaaacat tgtttccagc acgtaaggta    6720
caggggttag agtttgatgt tttaaaagcg ggatctaaaa tcccaacaat tgcaagcgtt    6780
catgcattcg atacagaagc tgagattgct tcacgtgttg gatcaaagac agctcaagag    6840
ctagcgttca tcaaacgtaa gattcaatta aagaaaaag atttaattgc tttgcgtaat    6900
cctcgtacgg ctgaagaaca gcgttattta gaacaagaag tatataatga tgtttactca    6960
atggtatctt ccgttaacgc tcgtgttgaa aaaatgcgta tggaagttct agcaaatggt    7020
aaagtaacgt tagatgaaaa tgggttagat ttagtagttg attatggcgt gccagcagat    7080
cataaagata ctgctgattt ttctgctcct gatacagaca tcattgggtt attaacagaa    7140
tgggcaagca agttggatgt aatgccaaca cgcattttga catctactaa agtacgtaac    7200
gcaatcttga aaacgacgg aatcaaggca ttctttaaaa cttctggttt gttaccaaat    7260
attggctcgt taaccaaat gttacaacaa tttaatttac cgacaattgt gacatatgat    7320
gcaaaatata taaagaaaa cgctgaaggt gtactagtaa agaacgtta tttcccagaa    7380 aacaagctag tcatgtttgg ggatgaaaac ccaggagagt ctattttcgg tgtaacacca    7440
gaagaatctc gtttgttatc aactggatca aataactaca cagtaggcaa tattttcgca    7500
atggtatacg aatctaattt agacccagtt ggaacatgga ctaaagcatc aggaacagct    7560
```

```
ctaccaagtt tcccagaagc tgacaatgta ttccaagcta ctgtcttacc tgattcaaaa    7620
aaatagaagc cccgaaagtt gaaagtgtaa taccaacaac tgacggggcc tcaattgtat    7680
taagttaggt ggtgttttaaa tgcctagcat tacagatgac ataacaaaac tgttaaatag    7740
tccagctaat gaaaagttag aagtgattga gcgacgaact agagaacgtc tcaatagttt    7800
gttaaatgta tcggaaacgc caagcaaatt tgattcgatt atatacgagg tcgttttaaa    7860
aagatttaac cggattggtc aagagggtat gatttcatat tctcaagaag gtttaacaat    7920
ggcctttcct gattctgatt tctctgaata tgaaaaacaa attaacgatt atttgaatga    7980
agaaaaagaa gtgcaatata aaaaacttcg tggaaaggcc cgattcgtat gagatataca    8040
gatgaaatta cctttgtaaa aaaatcttca gaatcgcatt atgatccaaa ctcagggaa     8100 tggattgaag aagaaccgtt tagaaaaact actgatgtca atgtaactga tattggtaca    8160
gatcgttcta ttactatttt cggaagcatt aaagaagggg ctaaagtcat taggacacag    8220
cccctttttg ttattccaga atttgattac attgagtttg agggtaaagc ttgggaagtt    8280
attacaagta gagttcctgc attaagaaat agcttgatta ttcaggaagt gattattgat    8340
ggcaataagt caagtaagaa ttaatggatt agctggaatt tctaaaaaac taaagagaaa    8400
tgctcaactt gatgatgtga aaaaagttgt tagaaataac acagcagaat taaccgccaa    8460
tatgcaagct gaagcaggaa aggtgttaac tggacatcgg gaaggtaaaa agtttgttaa    8520
accaactggg gcaacaaaaa gaagtatcgt tatgaggctt tcgaacaatg gtttttctgg    8580
gcatacagga ccaggaacag aatacgcacc atacttaata cacggaacaa gattcatggt    8640
gaaacgtgat ttcttttttac caccgctgaa acaacaaaaa gtgaaattta gaacggactt    8700
ggaaaggttg atgaaatgat taaaacaaga gatcaatcaa tcttcgatga agtgtataag    8760
aagtgtcaat cactgggtta tgaaatttac gattataaac ctatgaatga tgtaggttat    8820
ccatttgtcg aattagaaga tactcagaca ctgcaccaag ccaacaaaac tgatattaaa    8880
ggttcggtta cattgaatct atctgtatgg ggattggcaa aaaaacgtaa acaaatatcg    8940
gatatggctt cagcaatttt tgctgaggct ctatctattt ctgaaacgga aggttattat    9000
tggtcgctaa atatccaatc aagcggtatt cggttagtag atgacatttc gactaacaca    9060
ccattgaagc gggcaatgat atctttagaa ttcaaaatac tatagagaga aggaatataa    9120
atggctaatg aagcaaaagt agcggctaaa ggtattgata ttattttact tttccgtttg    9180
ttaaaaaaat caaaagagga agcagcatgg aaattagctt tccagacaga acatgaaaat    9240
acaaaaacaa aagatagtga ctccgtggcc actaaagatg gtccgattcg tatcccagga    9300
tcattggaaa ttgattttc ggcaacatct attttatcag tcggtgatcc atatgttgac    9360
cagctagaag aagctttaga caatgacgat attattgaaa tctgggaaat caacaaagca    9420
gaaaaaggca caggagataa tgttgacaaa tacaaggcaa cctactacca agggtacgta    9480
acatcatttg gtaaatcacc taatgctgaa gataccgtag aggtttcatt agaatttggt    9540
atcaatggta aaggcgcaaa aggatttgca acattaactg ctgatcaaga agaagtagtt    9600
caatatgtat tcaaagatac gactattgag aaagatgatc cagaaaaagt agatagccct    9660
tctgtggaaa gtgtaactcc tacattcgat ggggcatcta ctgaattaag ttaagaaagg    9720
aaaattataa tggtggatac ttttaagatt tataaaggcc aaaccgaagt tgtttctggc    9780
acatcacctt taactatcac aggaatggaa cctaacacat cagtgtcggc tggtgaatat    9840
caagtaactc gtgttgttaa tggaaaagaa tcagagcgag tagatattcc agcttttaaa    9900
acattgtcta ttgctgtaac tggcttagat ttttctccta aaacgtccac agcagatgct    9960
```

```
ggtactgcag gtagccgaca aatcacagca actgtcttgc ctgaaaatgc aaccaccaaa   10020
aaagtaacct atgatatttc acctgtaaca gaaggtcttg ctgtctctga aacaggaaat   10080
attacttgga cagaatcggt accagctggt gtttatacca caacaggaac aacagaggat   10140
ggtaaaaaaa cagctcaaca caccttaaca ttgaataatc aagcttaaaa taaaatttag   10200
agggcagctt agcggctgtc cttttcttat ggaggaaaag acatgcaaat cgaattaaa    10260 gggaaaaaat ataactgtat ttttggagtc aagtttattc gtgaattgga taagcagcat   10320
ggggtagtgc gtaatgatgt gaatcttggg atgggactaa caacattatt accgcagcta   10380
gtaagtggaa atatcgttgt tctatctgat gtactttaca cagctactat tacagaaaaa   10440
agtagacctt ctaaggatga agtggatgag tttgttgaaa ctgttgatga tattgaggcg   10500
ttatttgatg aaacgttgaa atacttagaa gaaagcaatg cgggaaagtt aacggtcaga   10560
aatttcaaga aagctctgat ggagaacaag taagagagga actaagctca gctgaagctt   10620
atgaaaatat tcttattaat tgttttcgtt acctagaaat tactgattta tcagaaattg   10680
aacgaatgac tttgtatgaa tatgaagtta ggctattggc gttccagtta aaaagacttg   10740
accatgaaag agacctctat ctccaagctt ggctaaataa ccaaattaag gcgactaaag   10800
gtaaaaaatc tgaaccttat ttcaaggaat tcaataagtt ttttaattat gaagaacaag   10860
aaaagttaat tttgggtaag tcattaattg atgaaaagat tgatataggg gcaattgatt   10920
tattaagaaa agcaaataag taggaaagga ggaaaatgat ggaatcatat tcagtcgaag   10980
caatacttac tgctactgat agaacgttta gtagcacaat gagtagcgct gaacgctcta   11040
tggctggtgt aaataagcaa tctggcgaac taggtgatgg attggataaa agcaccacta   11100
aagggaatca attgggtaag tcaattctta gcattgggc aggcgtgggc gctgtaaaat    11160
tagtatctac ggccgtaaat atggttaagg actctgttga aggagcgatt aaccgttttg   11220
atacgttgaa taagtatcct gtagttatga aggctctagg ttactcaaca gaagatgttg   11280
atcggtccat gaataaacta tctgatggga ttgatggatt acctacatcc ctcgatgaaa   11340
ttgtagctag tacgcaacaa ctatcaattt caactggtag cttgagtaaa ggtactgaca   11400
cagctattgc attaaatgat gcctttcttg cttctggagc ttcaactgct gatgcaactc   11460
gtggtatgca acaatatatt caaatgcttg gtaagggtga agttgatatg caatcttggc   11520
gaactttaca agaaacaatg ccaatagcta tggataaagt tgctaagtct ttcaaagaac   11580
aaggtgtaaa ctcagttaac caattatatg atgccttaaa agaaggagat attacattta   11640
atgagttcaa taatcgtttg attgagttgg acaaaggcgt aggtggtttt gcggatttag   11700
ccaagaaaaa ctcaaaggt atcaaaacct catgggcaaa tattaaaaca gccaccgtta    11760 aagtgtgac tacagttatt aaatcatttg atgaattatc caaagcagtg acaggaaaaa   11820
atattgccga aaacttagac tctttaaaaa atgtagttaa tataactttt aaggcaattg   11880
atgcagcgat tcaatcaact attccgttga tgaaactatt cggaaaagct attacgtcga   11940
taggtacagc cttaacacca ttactaccaa caattgccag ttttgctgcc acttttacag   12000
cattgaaagt aattcagcaa gtgacaggtt atataaaaca atctgaattg gcaatcaaag   12060
cttatacaac cgcaataagt ttatacaatg gaatatcaaa actggcaacg ttgtctacca   12120
cagcactcgg aagagcatgg atgttaaact tagcagccga taaagccaat tctgcagcaa   12180
tagcaataaa aactggtctt ttagtggcgc aaaatacaat cgttggtgtt ttgacggaa    12240 caattagttt agctacagta gctacaactg ttttagtac cgctatgaaa ttgttattgg    12300
```

```
gccctattgg ttgggtaaca gccgcaatag gaggactagt agctgtaggg gtaaacttgt   12360
ggaaatggtt aaataaggaa actgaatcaa ctaaggcagt aaaaaaagaa caagaaagcc   12420
ttatgaaaac cacagatgat ttgattaaaa agaatcaaga acatgcacaa tcacgaaaag   12480
atgaagctat tgaattggat aatactaaag aaaaattcca atctatgatt tctgaaatgg   12540
aaatgctctc tgctaaagaa aaattaagca acagcgagaa aaaacgtatg gtggaaattg   12600
ttgaggaatt gaacggtaaa atgacaggtt taaacttagt ttatgacgat caaaaaaata   12660
ttttatctga aatgcctgga acaattcaac aacaagttga tgcctataat gctttagatg   12720
aagcttctca agctcaagaa aacattaatc aaatgttaaa agaacgaaat gataatgaag   12780
cgaagctgat ggaaatcaat gccgctagag aaaaatggaa tcagacatta aaagaatctg   12840
gcgggaatac aaaagaagct cgtgaaaata ttgaaaagtt gggcgagcaa gagcaagtgt   12900
taaagggcgt tcaacaggaa ttaacgaatg aaattataaa tacagctaat gcccatgaac   12960
aatcaatgca gcgtgcaagc caagctgtgg aaaatggtgt gttaaatcaa acagtttcat   13020
acaatgcttt aagtggtaag acgaaagaaa caatggatgc aatgcgttca gaatattcat   13080
cacttgaaga aaaagtaggg agtgcctttg atgttattga acaaaagcaa gctgtttcgg   13140
ttgatcagat ggctgctaac ttacagaaaa atcaagaagc tgtcgcacag tggggacaaa   13200
atatttcaac acttgcagaa cgacatgttg accaagggtt attggaacaa ctaagaaaaa   13260
tggggccaga gggtgcagca caagcagcag agcttgttaa tgcatcagac gaacaattac   13320
aacgcttaaa tgatgtctat cgtaacactg gtgaaacttc tatgaatgca atgaagaag   13380 gttatcaatt aggcaaaaat ggtttgaacg aggaaattca agctcttata ccaactcaaa   13440
aagaaacttt gatgactcaa attaagaata cagactttaa cagcgtgggc ctaagtgtaa   13500
ctgatgattt taaagcaggt attgaaaacg ggcgtacagc agtcgaagaa atgaccaagg   13560
gaattgttcc taaagtcggg gaagacatga aaggcgaagt tcaaaaagct gattttagag   13620
gtataggtaa gtccattcct caaggcttag aaaaaggtgt tgacgacggc aaaggagttc   13680
ctgtaaaaac atcaatcaa atgattgatg atattgtttc tggtgccaga aaaggtttag   13740
attctcactc tccttctcgt gtatttcact caattggcga agatgttgat tctggattat   13800
caaacggtat cgaacaaaac gcaatgaatc cagtaagagc tgtggaggcg attgttgata   13860
aaataatttc tgcaatggat aaattgccat cagaaatgaa ttctattggt gcaaatgcaa   13920
ttgatggatt gactaatggc attaatgcta atgctaatag tgctttagct gcagcaagag   13980
gtgtggcaga tcaaattgta agtacaatga aaagtgctat ggatattcat tctccctcac   14040
gtgtaatgcg tgatgaagta ggtaaaatga ttccagcagg agtagcggtt ggtattgata   14100
aatattcaaa ctttgtagaa aaatctatgc aacgactaag taaaaggta gccatgccag   14160 cgctggataa tttaaattca aatctgtcat ttagtggagg atcacaaagc ttagcatttg   14220
ccggagatgt atcttcaaaa ttcactgtag aggtacctgt tattttcgat agttcagagg   14280
ttgcaagggt tattgctaaa ccaatgagta aagaattgca gaatcaacaa gataaaaaga   14340
atgtttcttt aggaaggagg cgctaaatgt tatacaactt tattgatgta aatgaacaac   14400
aaacaaaagc ctctttgcct tcggaagcca tgaattttaa tggttccttt ttagaagatt   14460
tagttccagg ttatagaaca ttatctgttg ttggaagaga gttagctcct actgagatac   14520
aaagctacca gttgggaatt cgtgatggaa tgcgacatgt ttatgctcgt attccggaaa   14580
gagaattaac agttaaattc aaagttgagg ctaactctaa cgaagcgttt agggattctt   14640
ttaatagact aaacgttgcc ttgtttacag aaaaagatgt acagatttgg tttaatgatg   14700
```

```
aaccagaaat gctttggtcg ggtagtaaat cagacattga tgcagttcct gagggattga   14760
atcgagtcgt tggtacattt acaattttgt tgaacaatcc atataaatat actcgaagcg   14820
atgctactag tgttatgtgg ggttcgccaa ccattacatt tcaagcaaat tacttaatgg   14880
ggaatacagg ctcaggtgca gttgacttac ctattgttat cgaaggtggg gcttattggg   14940
gttctaccat gattactttt caaaatcgtt cctatttaat gggagataac ggtcaagaag   15000
tgaaaccaat tgaaatatat ccaactgtcg aagggttaaa agtaaaaccg attattacta   15060
tagaaggtac tggtagaggc gtgtggataa aaactagaag cgatactatt gatattggtg   15120
attttgataa gtcagaaata gtaatcgata cagaacagtt taatattacg aaaaatggga   15180
agccaatgat tcgtcctatg aacgattttt atatttatcc aaatgagcca ctatacatcc   15240
aagcgaaaga tagtactttt aatctaacta ttcgatatcc aaatcgtttt ttataggagg   15300
tgttgctaaa atatgttgat ggcaatggat ttaaaaaggg aatatacggc agttttggac   15360
aatgcctatc aagtcagtta tgaaaaaatt gaaaaccaaa tagggaatct tgaattttca   15420
atgccgttgg atgatcctaa aaatgaattt ttgcaagaaa tgttatgggt tgaactaaca   15480
gataatgaga atgaatatat aggggttatac cgtgttatgc cttcaacggt tcgcaaagat   15540
gctagtaaca attcaattac gtatacggca aatgaagccc tgtgtacttt gctagacacg   15600
gttctttttg gttatcatga actagtgaat cgaaaaacgg ttgatgttat taactatctt   15660
ttgaataaac aaaggacaaa acactgggtt ttaaaaaaat gtgaattcac tcgatatttt   15720
agttatgcat gggaaaatga aaatggtctc gctgatgctt tgtttagtat tcctcaagca   15780
tttgatgaag actatatgtg gcaatggaat accaaagttt atccattcga attatcttta   15840
gtgaagccac caaagaaacc tattgctcgt attcaagaag gatataacat gcaaggcttt   15900
gagattgaaa gagatcctaa caatttagtt aatcgagttt atcctttagg tgctggtgaa   15960
ggcgtcaatc agataaaatat taaatcggta aataaaaata ttccttatgt agaagatgca   16020
aagtctataa aagaacatgg tttagttgaa tatgtttggg tcgaccaacg attcacagtt   16080
ccacaagctt taaagacaa tgcaatcaac atgttaaaaa aatgggcgca acctaaaatt   16140
tcttgggatg tgactgcggc tgacttattg aaattaacag atgaaccttt aagcattgat   16200
aagttaagac aaggaactgt aattatgatt aacacagatg actttggaag tataaatttg   16260
cgtattaaaa aagagacaaa acaggatgta ttcggcgcac cacaagatat tcagctagag   16320
cttggtaatt tatctgacga ttttactacg acaatgtctg atttgaaacg taaacaggaa   16380
ataaatgaga cgtattcgca aggcgcaacg aatattttga actatagtta tcaagataac   16440
tgtgaaaagg catcccagc agaaattgaa ttcttcttag atgatgatgt atttcatgta   16500
aatactgtgg aactgacttt taaaactaag cgctatcgtg gttatacaaa agccgtaaaa   16560
ggcggaggag ctacagtaaa aagtacgtca gctggtggag cttcaacaca aacgagctct   16620
gctggtggcg gaagtgtcgt ttcaagttca gctggcggag gaggttctac aacttctgga   16680
tcaggaggag gatcttatca agggggatct acaaacactg atggaggaag tgcacagaca   16740
agtagtgcta atggcagtca tgaccatttta atgtttaatg taattcaagg gccacctcaa   16800
acccttccta aaataacatt aagagccggt ggcggtggag aaatatatac ggaagcacgt   16860
ggcggaacgt tcagaacagc aagtgctgca gataatcata cgcatacagt caatgtgcct   16920
agtcactcac atagattcaa tattgatata cccgcacatt ctcatgtcgt tagcatacca   16980
aaccatacac acagcatatc ggttcctagc catagccacc aagtaagaat accagcacat   17040
```

```
acacaccaaa ttactttacc tgatcatagc catccattag aatgggggat ttatgaggca   17100
ccaagtagcg caactagtgt tgatatagtt gtagatggta ccaccattcc agtcacgat   17160 actagccaac aaagattaaa cattgttaat tatcttagga aaactagtgg aggtaaaatc   17220
tctagaggta atcatacaat caagataata cctaacaaac ttgcacgaat cgaagcgcaa   17280
gttatttgtc gtgtttttat acaatcacaa ctaggaggac aattttaaat gagattaaca   17340
gtaaaactaa ttagcaaaca agaagaattt ataattaatg atgaatcagg taaaacgtta   17400
gatgattatt ttgcagagct gattgataat agttcgccat tcatcaaaat aggaaatcgt   17460
attttacaaa aagctacaat tgaatacatt aatgcagagt aggagtgaga aaatggctat   17520
cgagcaaatt aaagaaaccg acacgctgaa tcaaggtcga attaaaatta atgcaatttt   17580
ggatcaatct aatactgctg ttgaaaaaat aaatgattat caaagtcagt tgacagaagg   17640
aattaatgat gccaaaaaaa ttgctgacga cgccggaaaa gaagccgtac aaattgcaga   17700
acaagcaggg aatcaagcga atgaaacagc aaaccaagct ttaactaatt ctcaaactgc   17760
tattaatact tcaaatcaag cagtatctac agcaaacaac aataaacaag aatttgatgc   17820
tttgcgtaat gactttgaaa aacttgttgg agaagctggt gacagtaacc ccgaaatcgt   17880
acaggcgaga acagataccc aaggagtaac acaatcaaca ttagctactc gcttacaggt   17940
tgactttaat gaccgcatga caaaatctga aggtgtatcg ttactttctg gaacaacaaa   18000
cgtaaaaata cctatggatt tcactggaaa acagcgggt aatacggcaa caaatgcaaa   18060
tcaatatttt accgatgtaa cagctaaagt actaaaaaaa ccaaaagata catggaatga   18120
gatttctcaa tctgattaca acaaattagt aagtcgtgat gattctggag taagtagtgg   18180
ttcgacgcaa aacggagtta taccacaaca gttaggagtg ttcaatgctt tagaagctgc   18240
caaaaaatta attcctcaaa attttgaagg attaagtcaa gaagaagcgg tggttttatt   18300
aaaagatagc tttgtcgctt ttactattag tgaacgtgtt aaagcaactt cgcctaacaa   18360
caaaacaatt aaagtttcca cttatattga gtcaactgac tcgtggacta ctcaaattca   18420
agaaaatgct ggcgaataca aagatttatc agtccaagta actgataaaa atttcattac   18480
tagcgatggt cttatctatc taattagcta tacagatcca tcaaatggag tgacaactgc   18540
taatttggat gttgactatt cagctattca attagaaatt agtattaatg cacaagatgt   18600
attagcaaaa agtggctttg taagagagga acaactaaag gagcatacgg aaagtcaaga   18660
caatccacat aaagtgaccg caagtcaagt tggattggga aatgttaaaa attatggatt   18720
tgctactgat agcgaagcat ctgctggaac atcaacgacc aaatatatga gcccctaaaaa   18780 tgttgcagat gctattaaag ggcaagcggt gactcaaact ggagatcaag aaatagcagg   18840
aacaaaagat tttatgaatc ctccgaaaat cgctggacaa actgttattt ctgaaaaagt   18900
aatagccttt tctgccccta atacagtatc agttagtggt acaggggtta aggtcattcc   18960
aatttctcaa aaggtcatca ctaataatga attttttgag ttatcagcaa acaaaatcaa   19020
agtgttgaaa gatggaataa ttagtgtcgt tactagctat acaaccaacg ttccagcagg   19080
ttggtgtaat attgagctta ctaagaataa tgcggttatg aacaggagca atcaaggtac   19140
aggaggatta cacgctgctg gtttgacaga tgtatttgat gtaaaagctg gcgatactat   19200
tgcatttcaa agtaattcta atcaatcttc atatacggtt ttatatttga gaggattttt   19260
aagatactta acgtgataat gattttttata aatttattta atgaaataa ccgtttagca   19320 aaaagctaag cggcttttaa attggaggaa tgattttgtc aaatgaaata gttgttgctg   19380
taataggatt agcgggcagt acatttggtg cgtttattgg agtggtagct agtgccaatt   19440
```

```
tgacagctta cagaatagaa cagttagaaa aaaaagtaga aaaacataat ggtgtaattg    19500
aaagaacctt taaattagaa ggtcgaatgc aagaagcgga acacgacata atagaattga    19560
aaggagcaaa aaaatgattc taccagataa gtactacaaa attatcaaat ggggagtact    19620
tactgtgctt ccagccatat ctgttttagt agcaacgtta ggcaaaggtt atggatggca    19680
gcaaacagat atggctgttt taactatcaa tgccattgca acttttttag gagtagtaac    19740
aggtgtgtca gcatataatt taaaagacaa ggagtaaacg aatgaaaaag aaaattttag    19800
tcggagcgtt aatcgctcta tttttatgc ctttaaatgt atttgctgct aaaggcgatc    19860
aaggtgttga ttgggccgtt tatcaaggtg aacaaggtcg ttttggttat gcgcatgata    19920
aattcgctat tgctcaaatt ggcggctaca atgccagtgg tatttacgag cagtatacct    19980
ataaaacgca agtagcaagt gccattgctc aaggaaaacg agcacacacc tatatttggt    20040
atgacacttg gggaaacatg acattgcga aaacaacgat ggattacttc ttattacgta    20100
ttcaaacgcc taaaaattcc attgttgctt tagactttga gcatggcgct agttctgatg    20160
taaacgcaaa tacagaaacg attttgtatg gtatgcgtcg catcaaacaa gcaggttaca    20220
cgccaatgta ttatagctac aagccttta cgttacaata cgtggactat cagagaatta    20280
ttaaagagtt tcctaactct ttatggattg ctgcctatcc tagctatgag gtaacgccag    20340
aaccactata tgcttatttc ccaagtatgg agggcattgg aatttggcaa tttacgtcca    20400
cttatattgc aggcggctta gatggtaacg tagatttaac aggaattacg gatagtggtt    20460
atacagataa caataaacca gaaacggaca ctccagcaac agatgcaggt gaagaaattg    20520
aaaaaacacc gaattctgat gttaaagtcg gcgacacagt taaagtgaaa tttaatgtag    20580
atgcatgggc aactggtgaa gctattccag attgggtaaa aggaaacaac tacaaagtgc    20640
aagaagtaac tggaagcaga gtattgttag aaggtatcct gtcatggatt agcaaaggcg    20700
atattgaatt attgccagat gcaacaattg ttcccgataa gcaaccagaa tctattcacg    20760
tagttcaata tggtgaaaca ttatccagca ttgcttacca atacggtact gactatcaaa    20820
ccttagcttc gctaaatgga ttggctaatc caaatcttat ttaccctgga caaactttga    20880
aagtaaatcg atcagtagta agcaatgttt acacagttca atacggtgat aatttatcaa    20940
gtattgcatc taagcttggt acgacatacc aagctttagc acaacgaaac aggttaacta    21000
atcttaactt gatttatcca gggcaaacat taatttatta ggagagtggc agtatgaat    21060 cagaaataaa aaaacatatt cgtcaattat tatgtgatta taaaaaaata gaaaaacaat    21120
tgaaaaagta tgaagatgca ttagtttatc cccaatcttc ttttctta tactttgaag    21180 aaaagtcaaa tgaaaaaata agtttgaacc aaatagtttt tcataagttt ttttaaata    21240 cagttgaaga ggttttatca gatgcaacat cggatgtacg tgatatttt atttctaagt    21300 ataaaaatgg ctatccacgt aaaaagaatg aaattgtggc ctatgaaact tatttaagtt    21360
tatcaacgat taaagaagg gatagtgaat tcttagagga attagcacga caattaggtt    21420
ggctagaagt ttgagcaaaa aaaagtgta tttagttgta gactttagat aaggacatat    21480
gttctccatg gacgcatgga cagaatatta aggaggggaa ttatggcaga cacatggtta    21540
agtcctcttg ctgtttctta tcaagcaact caagaatggg atgaacctga ttatttgagc    21600
ggagggcaag caggaattca cggaggcatt gacttagctc caaaagcagg tactaatcca    21660
cctgtttatt cagctaaatc tgggacagta gaagaggtag taccaaatca tccaattggt    21720
ggtaattaca ttgttatcag acatatggat aactactgga cctattatgg gcatttagca    21780
```

```
actataaatg tatcagtagg acaacaagta acaaatcaaa cggttcttgg attatgtgga   21840
gcaactgggg gtgccacagg tatccatctt cattttgaag tatggcgtgg tggtaaatgg   21900
cagagaatca atccacgaga agtaattaat ttagatggat ctggcagaga ctctagtaat   21960
aacggtggca atggtggaat ttatacaggc ggagctttat taaatgcagg aaaaagcatt   22020
tcagaatcaa atattcgtct aatcatttct gctggaaaaa aatataatat caagccaagt   22080
tttatgattg cacaaatgtt tattgaaagt cattggggag atccaagcat ttcaattgtt   22140
ggaagtaaag acaataattg ggcaggaatt tcagaacctt ttagcgttcc agctgattta   22200
ggaattaata tgagtcgtgg atcagcaaga ccagttggtg aaggtggtta ttatattcat   22260
tttgcaacca tgaacgattt ttttaaagca tatgcatttg tattatcaaa aagaaatggc   22320
ttatataatg ttgaaggtgc aaattcaatt gaagaatact gtaaaggctt atttcgcata   22380
ggtggagcaa attcagacta tgccgcgaca ggctatcaaa attattttaa tatgttaata   22440
ccaacttata attcaataaa caaacaaaat cctggtaaac ttgcacaaat tgatgcaagt   22500
actgaagaaa ttactaataa tggaggactg acaactatgc aatgtttata tgaacgacca   22560
attaatccga atactggagc tttagatata aatggctcag caactacaat gatgttttgt   22620 aatgggtca atacacgaag agtatatcat aatgatgaag ttaatattgt taaagagcta   22680
tatcgtaaaa acaatggaaa agaaatcccg gtatattata aaaagattg gcctaaaact   22740 tcgccatggt atattcgact agaggcaatg tttccagtag tgaaatgatt ttatgtaaat   22800
aaccctattc ctaatagaat agggttattt ttattaacag aagtttgaaa tttattttga   22860
taaattaaca attatacaat catctaccac tctgatggaa tctttactag ccagacgtt   22920 catttccgct tgtaaagctt tgtgtttttc aaaatcttct ggtgtaggat cattaaaatt   22980
taatccaaat gttttcatat aaactagagt atttaaacta gtgtgcaccg agttaggcat   23040
gaattcaaat aatgaaacac cgtttgtttc accttttata ttcgaaacat tccgaggaga   23100
acgatttcca tacattaaaa gtttatagga ttctggattc tcaatttcca ttgaataaat   23160
attatttgta atcatttccg cagtacgtaa atcttcttcc gctgttagat actcagaata   23220
ttctaggttg gttgttcccc gaacttgaat aaaagtaaag ataattacta tgccaactaa   23280
taaatgttta agcacaaagt tgtatcccca gtaaatcata ataaagatga gtaataacgc   23340
taaaacagca gggaagttag gtacttcacc tctaattgcc ggacgttttc cacctaaaac   23400
tgtaaacatg agtggagtga ttagaatacc taacaaggta ataaagatga aaaaaacatt   23460
tttgcgtttc agataggaca tattaattaa tacaatgacc agtaaaagaa cacatatcaa   23520
aaacagcggt gtaaaaaaag tgtctccgac tggagggaag aatagttctt tggcgtaatc   23580
tttaatatcg ttgatagaat ctatcaaggg gcgtttaccc caaagaatca tattatctag   23640
ataggagctt tcaacgttta aactttttt cgctaacatc gccattagtt gagatagaac   23700
gagagatgaa atagctagta gaataaaatg gccgattttg aaggcatagt ctttaaagaa   23760
aattttaaga tcatttaact gagcaaaata caatgccatt aaaatcttga ataaaattaa   23820
ggtacacgca aatacaaaga atgattgata catagtaagt gtaaacgtca gtaacaaaaa   23880
gccaaataat ttaaaaattt tattgggaat atggtaaata gcaatgagag aaagtataac   23940
caaacagata cctaatgaaa attcaaaatt ttgtaggacg aagtaaaatt gttcgctaaa   24000
taattgactg gttggaaaaa tacttgggat aacatataaa tacttttgt tataaatctg    24060 cttagttgaa agatcaacat aatagcataa caagatagtg gcgatagcaa agaaaataat   24120
agctaacaaa tttaaaaaat aaacatttac atagttgtat gttaaaagct ttaaagctac   24180
```

```
taatcctggt ctaccaattg aaacccaatg ttttaagtag cctctgtagt tagtcattaa    24240
gtgcatagta tcaatagcgt aagtattgtt aaatagttta ataccataag tagcaaagac    24300
catcaaaaag ctgtagatgg ctaagccttt gttttcttta aaaaaatatt tcattttttt    24360
ctcctatcgt tttatttctt aaccatataa atttacttag ttttgaattt ttcataaatc    24420
atactaacaa acacatattt gctaaataga aaaaacttt tttgaaaaaa gtcttactag    24480
ttaaataaaa taacctataa attaccaaaa atatatttat acagtacatt aattataaaa    24540
taagagcacc tcaaattcca gttttaatta aaacaagta attagatagt tcttgtttcg    24600
acaaatcact tattaatatc aacagctagt tgtatgaaaa aactatatat actatatata    24660
attataaaaa tagatagagt cagctaagat gacttaaaaa attaacatga tggatatttt    24720
taaggtgtct gagaagatgc ttctaggatt ccagtttgtt gttcagatga catttgtcct    24780 ttattttta gttcaagcca ttgctctagc gtaatgtttc caagataact atagatttga    24840
ttttcagtag ataaagtgcc atctaagttt tttgtaaatg agagagaggt attattaatt    24900
ataaaattca ttgtaatgct tccgtcagca ttacttagaa aattaggact ctgaatgact    24960
ccgtttggct ggccagatcc agacattttt ccatcaggat taatgaaaaa gaaattacca    25020
ctttgcggaa taccccagcc accaacaaaa gaagacaaac tagctggatc ctcagtatgt    25080
gattgttctt cttcagtttg ggatgatttt ctgtcagcag ttgaagtagt tgttgtgtta    25140
gtggacagta tgttttttc atttatacta ttattagatg attcctttac tgtagaggtg    25200
acagtagtag atgacccttt tgtattttct gttttcgtat tttcattagt acaagctgtt    25260
agtaataata atgcaaagac cagcgaaaga gatttcttca tttgtaatca ttcctttcaa    25320
tctattcata aatttagtaa tgtaaataac tgctgtaaaa aactataccca tactataaaa    25380 atataataaa aaaaaagagt caaaaagcta aggctattaa taagggcca aaaaagggc    25440 aaaaattgta aaaggttgta aaaaaatata tagtattaaa ttataatatt cttgatttaa    25500
cagtgttttt acaaggctat aaatagtcgt aaaatacgct tgaaagacta agcaagtgcc    25560
gccatgtgtc tgaattatag ttgatatcaa aggcttaag ccttttttta tttgttttga    25620
attaaaaaag gggcacgaaa ggggcaatta cttgccatat ttatttagag cttctaccag    25680
atttgtttta gcttttttg taacatgagt ataaattttt aaagttgttt ccgtgtcaac    25740
gtggcctaca cgttccatta ttgcttttac tggtacattt aattctgcaa gtagtgaaat    25800
atgagaatgt ctaaaaatat gacttgatat agttttgttt attttatttt tacctagact    25860
ttcattagct ttctttagag aggcattgaa tgaattaact tgaattgggt tgcccgtttt    25920
gccaacaaat agataaatttg tttgctcttt gaattttatt tctctttcta aaattaactc    25980
ttcgattatt tctacagctc tatttgataa ttctactttc ctgaatgatg ctagagtttt    26040
aggtaattct tttgtagcgt tttataacc gttagaataa tccaaagtcc cattaactaa    26100
aatagcatgt tcatttttta cataatcatt tatagtaaga ctaattgctt caccagctct    26160
taatccagtt aaatacataa actctgctaa acgaccatga tggacacttt gaaatgtaga    26220
ataataatag cttaataatt gataaacctc tctctcttcg aggtatttac tttctatatt    26280
ttcaaaattt tcttttgtta gtggggggttt aacaactttc actctattga taggattttc    26340
atcaatcatt cccatgtctt gtgcataagt gaaggacatg ttaagcacac ttttgaattt    26400
tttcttatac tcccacgaat gcggtaaatc attaataaag tcttggaaaa attttgtatc    26460
tgtgtttctt atgagtacat caacattcat attggaaaat atatattta aaatttttcc    26520
```

```
gtaagcttta actgatgttt tcctaataga taattgatgt tgttgccacc agctatttaa    26580
gagattctct aatgatactt ttttttgatc tttttctcc attcgattat taatcttatc     26640
ctgtaactcc atcatcgctt gttttttcgc ttggttagac ttcgaattaa gtgtaactga    26700
aacacgtcga tattttcctg tgtacggatc tttatatcgc tcaaagtatt tatattttcc    26760
attaggaagt tcctcaatcc acaattttaa aactcctttc gaatgtatgt tcttaatttt    26820
tgaaaaagaa aagccctaag gctatttctt ttattgtaca ggtatttcaa atgtagcagc    26880
ttgaccagta cgatttgaat catatttttt gaataatatt ttgatgtttc caccaggatt    26940
ttgaacgcca tatgcggcct gagcccact cattgttgct ccaacaggtg ttggctttgc     27000
tcctgtggta gagacgggat aagtttcacc cattattccg gcactatcta ccacattttc    27060
tggcataata aataaatctt gaatgtcatc ttcatatcct agattttcat aagtataaga    27120
aattataact acttgctgtg gtgatttatc tgaataggg tttctttcat ctgtagaagt     27180
cacgctgtca attttgagtt tccattgatt gggaacttcc caccattcac ctaaattata    27240
aactgtcttt ttattatcgc tagttgattc agtactggta ctggttttg tagcagatgt     27300 tttttcagtt atttttgttg tgctagtttc ttttttgttt ttttcaggtg cagtactaga    27360
agaatcgcaa gcacctaaag tcaatgaaga tagtagtaaa atactgatag ttatttttt     27420 cattttaag actccattca attatttta taaactaaat taaaactgta aaatttaggg      27480
tgattatttg aacaaatccc aaaagctaaa agttgtttta ttatatactt tattatacat    27540
agctttcttg gggttcttaa tgaaaccagt tccttttgc ccataaccag gaattactgc     27600 tttttaaac ttacgtttag ctttccagt agtacgagca cttattgatt ttttatact      27660 tggtttacgc attcctactt tcatggttgt atccttcctt taaataacaa aactacgcat    27720
ttttattatt tttcttctga ggcagttaca tttttataca tatctacttt aagcaaagga    27780
agtgtattgt tatcacctaa gtttgtagta tagtcataag aaccagcaaa tgaagcccaa    27840
aataaaattt catcatcttg taaaactttg gaataaacat tatcttttaa taccgctaac    27900
ataacatact ctctatcgtt ttttgcataa gtaacatagc ccatgtaata aatatattca    27960
tcacttggtt catctacaat ttgaattatt ttagctaatg aatataccttc tcgcccttta    28020 tgtgcctttt catctcttaa catcgaatta actctaacgt tagaattata gcttttgga    28080 tctgcggttt tataatactc agatatcttt tctaatttt cctttgttc agtgaatct     28140 tgatcaacta aaattttata ggtctttgaa gattcttgtg tagaagattt cgaagaatca    28200
gggttcacat ttttagaaca accaacaaat attactacga caaataataa aaaagccata    28260
gatgcaaata ttttttcat ttttaaagct ccccatttct gatataatgt atttattgaa     28320
taattctcat aatgaggaaa gagttccgtg ttgtagcacg ggcttttta ttgtaaattt     28380 gtatttaaaa tcatgactga taaatcatta aactcgaaaa ttcttccttt ataaaaatgg    28440
gtatcaccaa attttgtcg ataataggcg agtacatttt tgagcgtttc aacgtctacc     28500
cctaaaaatt cagcacacgt gtaatgatta ctgaatcctg attctgaaca cttaattaga    28560
tcatccaaag tgactaattg ttctaaagca tattgtctag cttttagttc ttgtttacga    28620
ttttctaaac aatcttggtt taatatgtca ccaaacgatg tatcgtggtg gccaagttcc    28680
tcagctagca cattccttt ttttattaga ctcaacgatt tttcaatata aattctacca     28740
tcacggtaca aaccatagca tccagtattt tgaaacaaat ctgtttcaat aactggtgct    28800
tttttctgta cctctgacac caacagctca tattcgttca taaatactc ctgaaaatta     28860 ttctttatca tctgaatcat catcaaaaag atgtttacat tcttttttgct tcctatcata   28920
```

```
atcagcatcc actttatcta gaaattgatt aattttaagt ttctcttcat cagtaaatac   28980
tttatcaggg tctggtgaat gcgcagctaa agtatcatat tttttcttgt taatgttaac   29040
cacgttatta gaagctttgt tttgtttttc taaatgagac ttagcttcgt tatatataag   29100
ctgttggagc ttgggttcta actggttgaa tataggtact atgtcgaagt catctttttc   29160
actagatctt tgttcgtcag ggattctttt tttagagaca tcaaacccca ttagccacgc   29220
ttcgttaaca tctaaagttt ttgacaaaag ataaattcta ttttggtcag gtgattgctt   29280
tccagttaca tattgtgaca aagtactttt actcatttt atatttaatt cttttgata   29340 tggttctgac aaacgcagaa tatcaacttg ttttaaattg cgctcactca taagttgctt   29400
tagacgagca gatgttttaa ctctatccat tggtacacct ccttatagat ttaagtatac   29460
aagatattga atatatcttc aacgaaaaaa ttcatgaatc atgaactttt tcgttgacaa   29520
taagaaatga acaatgtatt atatggttat aaagttcatg ttcatgaact tgaaggaggt   29580
gtttataaat gtgctatgat tactcaaaat tagcaggaag aattgttgaa aagttttggaa   29640 ctcaatataa ttttgctatc gcaatgggat tgtcggagag aacaatatca ttgaaaatga   29700
acgggaaagt ctcttggaaa gacactgaaa ttacgaaagc ttgcaaattg ctagacttgg   29760
aaacaaattt tattcatta tatttttta aagagaaagt tcatgtttgt gaacaaaggt   29820
agttttggaa gtatacaaat gaaaaaggaa aagtgttcca ttaatggaac gaaagacaac   29880
cagaatagaa gggatgaaac cgtatgaacg aactaattaa agttacaaca aatgaaaatg   29940
atgaacagtt agttaacggt agagagttat atgaatttct gggagttaaa gataattata   30000
ctgattggtt taaacgaatg attaaatacg ggtttgatga aaacgttgat tttatcagtt   30060
tctcggaaaa atccgataaa ccttttggtg gtcgcccaca agtaaatcat tatgtgaaac   30120
tagacatggc taaggaaatt tcaatgctac aacgtaccga aagaggaaag caagctcgta   30180
gatattttat tcaactagaa aagttttgga atagcccaga aatgctgact aaacgagctc   30240
ttgaatttca acagaaaaaa atagaagtat tacaactaga aaatgaatca ttaaaaccta   30300
aagcattatt tgcagatgcc gttgatgcaa gtaagacttc cattttaatc ggtgacctag   30360
ctaagctaat caagcaaaac ggcatcgaca ttgggcagaa tcgtttattc caatggctgc   30420
gagacaatgg gtatctaatt gctcgaaaag gtgaaagcta caatatgcca acccagcggt   30480
cacttgattt gggaattgcg gaaatcaagg aacgaaccca taacaatcca gatggaagta   30540
ttcgaattag tcgaacgccg aaaattactg gtaaagggca aatatatttt gttaacaagt   30600
tcttacatga caagacagca tagaaaggag atgtctacat gcaaatcaca ctagcaaaga   30660
ctatcgattt acagcaagct tggatggcaa aagatgaagc aattgtttat tttggctatc   30720
agcatcacaa accaacattt caaaaacttc tgagagagtt taaggaacat aaagaattta   30780
aagatggata tagactcgtt acatcatgca tgccaattat ccacattcag aaatttgatg   30840 aattttggt ttggcgggaa aaaacaagt ataagcgaaa taaatagacg ttataggagg   30900
taaataatat gagaaaaatt tataacttaa gaagaattgc agtactgctt attgttttcg   30960
gattgggtct gctagtgggt ggaaacttta atccaatcat ccaaaatgtg tatattggat   31020
tgttcattat ttggacatta ttttatgact tagctcttga agatagagag gtaaataaat   31080
gacaaggaaa gaaaaactac agcaaacgaa aaaacttgct gatttatggt accagcaaca   31140
aaaaaatcaa atatacatta tgcaacaaaa agagagaagg gaatttagat gtttaaagca   31200
gtaggaaaag atagtttgaa aatttacgtg gttgaggata cgaaagccct ggtatttcaa   31260
```

```
aagcttaaag aaaaatatcc agacactgcg ataaataagg ctgtatttcc agaagcgtta   31320
tttatccaag aaacaaaaaa gtgacttccg ccggcaagca aaaagtcaca aacaaaatta   31380
attgatagga gaattatagc atgagagtgg aagtggattc aatgcaaaga attgtcttaa   31440
ttgataatca ttcaccttat ggatcactga tttttgaaaa ggatgctatt aataatcatg   31500
ttgctgttta ccaagatagc gaagatgaag aagttagaac agtattcgag agtttagatg   31560
aaagtgctta ttttaatcaa gttgaattaa tcgaaggact tcaaaaagtt atttcattac   31620
tgaaagaagg ggaataaatg aacgagaaca gcgaaaattt aaaagaattg tttgatggga   31680
tgtataagct aaaaagcaaa ttaattcaac caagatttga cgcagaagtt gcctatacaa   31740
cgaaaaaagg tccaatgaat tccaatatg caactctaaa agcgattgaa gaagcaatta   31800
gaaaagctgc acaagaatca gaaagcggaa ttgatttcca acaaaatgtc gtcaatgaga   31860
ataatgcttt aaaagtcaca acaattatta ctcatgttag tggtcaatat atagttcatg   31920
gaccttttga atttccaaac agcgggacaa atcctcaagg attaggaagt ttaacgacat   31980
atgcaagacg ttactcgctt tcggcagcgt ttggaattgc agcagataaa gacgacgatg   32040
gccaaacggc agctgaaaag aacaatgata catcgaaagt taatttgatt agcggtaaac   32100
agttagccac gttaaacgat catatcagac aactttctga gttatcgaat tctgaacttg   32160
actatgtgcg gaatgaacta agtaaagaat tgaatgttga tgtcaatgaa acatgccgt   32220 ctagtatgtt caataaagct gttgaagttc tgaaacaatg gatacaacaa ttccagccac   32280
aaccagaaga aaacattaca tgggggcaaa gctaatgaca aacgaattaa caacagaatt   32340
gcagtttaat gttgattta aagctagtaa aatcactatc caaatgaag cacagttggc   32400 tgagatggtt gagagcgcag ttaagcacta ttcaacaatg attttcacag atgaaaacat   32460
tcctgaagct aaaaaagcaa gagcagactt aaataaagtt gtaacgttgc tagatgatca   32520
acgtaaagaa gttaaaaatc aatatgataa gccgttaaaa gattttgagg aaaaaataaa   32580
aaaatatact gaaaaaataa gtgaagttag ttcagaaatt aacgaaagca tcaaatcata   32640
cgaagaagca gagaagcaga aacgaagcaa aaagcttcaa aaagtgattg ctgaaatgtc   32700
tgaaaactac aatgtatcca ttgacgaaat tgaaattcct agttcgtgga ctaataaaac   32760
agctttcaca gttaaaggtg aaccaaataa tgaaactatt gaggaaatag cggcatcgat   32820
ggtagcagtt gcatctgaaa aagaacgtat aaaaaacgat aagctcattg ttgaaaatta   32880
tgctaaggca gttggccttg actcgttttc ttgggtcgca ttaattgata aagggtctac   32940
tgcaccagct ctgataaaag aaattgattc cgccgttgct ttaaaaaaag aacaagaaga   33000
acgtgaaaga gcaaaaaaag aacacgacga agccattgct gctttgaaaa ctgaaacaat   33060
caacaataaa acagttgaca ctgctacagg cgaaatcatc acagaagaag cgccaaaaac   33120
ctgcaaaaaa caacaagaga aaacagttac gttaagacta acagcagaac atcaaaagtt   33180
agttgctcta aacaatttta ttattaataa cgggattcaa gtggaagtga ttgaatgaac   33240
ctaaacaatg tttattctgc tgttattaag agtttgaaaa acaactcaat aacagcagta   33300
ataaacgaag caataaatat tgaacgatta aaaaccatgt attttgatta tacagggcca   33360
agagaagttg aaataagatt tattgatccg agaaaattta gtgttgccca acgtcgattt   33420
atctttgcaa tgctagagga tatattctct ttcacagggc aagaaacgga agtgttaaag   33480
gaaatgttct atctccgttt tgaagcgctc cagggctatg aaattagcct caggaacgat   33540
tcagaaaaca caatggacga cgcaacaatt ttagcgaaca ttatttaaa tttcatcttt   33600 gaaaataaca ttccatttag aaaaggctat gacattttgc cagcaaatca agagtattac   33660
```

```
ttttacaaat gtatcactaa acgagtttgt tgcatatgtg gaaaaactgg tgcagatatt   33720
gaccatttcg ataaagctct aggtcgtcgc aaaagaaaaa gcgtagacca tacagaatac   33780
acttacgctg gtttgtgtcg atgccatcac accgaaaaac ataacattgg tattacagca   33840
tttaagaaaa aatatcatgt taaaggtatc aaattgaacc aagaaactat caaaaaatta   33900
cacataggag gctagataag tggctgaaat tagctggata aaattaagta ctagtttacc   33960
tgataataag aaaatcaaac gaatacgcaa attgccagat ggcgatcgag taattttgtt   34020
ttgggtattt ttactagctc gtgctggtga aagcaaccaa aaaggcggat tgttttttaac  34080
tgatactttg ccctattcag atgaagattt agcagctgat tttgatttca cagttgagtt   34140
tgtaaaattt gccatttaa ctttagaaaa atacagcatg gtaacaacct atgaagatgt    34200
aattttcatt aagaattggg aagaatacca ggccattgat ggtatggaaa aagtcaaaga   34260
gcaaaatcgc attagacaag cgaaataccg agaaaaacaa aagcaactgt cattaagtaa   34320
cgttactagt aacgttacac gtaacgctga tgtaacgctg agtaacggaa cagataaaga   34380
tatagataaa gaaatagata aagaaataga taaagataat aaagaagagt caaagaaacc   34440
tccttgtaaa tattctgacg aacatttacg tcttgctcaa aaattacaaa ataatttaat   34500
caatgatttt ccaagtgaaa tgaaaaaagt gaagattgaa aaatgggcag atgttttcag   34560
attaatcgaa gaacgagatc aacaaactat tgcagcaatt gactatgttc ttgattggtt   34620
accgacaaat tcattttggt ttggaaacat tagaagtgct tctaagctaa gaacgcagtt   34680
tgaaaaacta aaatttgaaa tcaagaatga aaaagaacgt ggccaacaac gaacgactta   34740
ccaacgtcaa aatgttagga ctgaaaattt accagaatgg gcaaagaac caaataaaca   34800
gcaagaagaa aagctatcgc cagaagaaca attggaactt gatagacaaa taaaagtaga   34860
catggagggg aaatagtgaa tgacaaagta cccaacacaa gaattaaaaa acaaaagaaa   34920
agctcatgtc ttatttatga gtacagaggt aatgaagaat attttgtgaac ttggttatcc  34980
tttcgaattt tatgaagcaa gtcaccagtt tgcgattcac tcaccgttag gggttattga   35040
ttatttcgct atctcaggca cttgggttgt tcgcaaagga caagatagag gtaagggtat   35100
acgaaaaatg aagcagtaca ttaaaaaaag agtaggtgat tacgtggaaa aagtaaaagt   35160
agtgaaatgt agtgggtatc ttgataaaga gggtaatatc actaatcaaa ttaagcaggc   35220
gatgcatttt acagacgatg aattagcgaa tcttgctgca gaagtggcag gtggaaaggt   35280
cgtaaacgtt gtaattccac cagaaaagcc aaaacaatta cgtgaaaaag cgaaagaaga   35340
atcatttcaa gaaaaaacta agaagaaaac aaaaagtaat cagtcgtgga tgaataagaa   35400
ataatttgtt gttttttacgg cgtaatttaa cgacagttaa attcaataat tagtttaggg   35460
taattaatca taaatgattt aaaacgcctt aaatcgaaaa ataaagcggt aaaattgtga   35520
ggtaaaaaaa tatgaaatta actagtgtga catttaaacc gtctgctgaa cggtttccac   35580
caattgtggc aatagattta gaccaattaa caccagatga atacgtgaca cttagaaatt   35640
tgggtgatga cacgcaactt tctaaaatta caaaaaggac ctttgaagag ttggaaggcc   35700
atttgggaat tcgaggagac gttgcaaaga aaaatggatt ttatgtatta gttaaataat   35760
cagaaaggag cggagatttg cggccgcatt aaaaagcttt ttctcctttg aaattatgaa   35820
aagaatactt gatgcttgct gtggtagcag aatgttttgg tttgataagc aaaacgaaca   35880
agttttgttt atggacaaca gagaacatta cgaaaaatta gacagtgggc atgttatcga   35940
tgttaatcct aatctagttg cagattttag aaagatgcct tttgaagata actcgttta   36000
```

```
tcatgttgta tttgatcctc cgcatttatt gaggtgtggt aataacagct ggttggctaa    36060
aaaatatggc aagctaaacg agaaaacttg gaaagaagat atacaaaaag gttttcatga    36120
gtgtatgagg gttttgaagc ccaatgggac gttagttttt aaatggaacg aggaacaaat    36180
caagttatct gaaatattaa gcacaattga ttgtgagcca ttgtacggca ataaaagagc    36240
aaaaacacat tggttagtat ttatgaaagc gggtgaataa gatgaatgag caaataaatt    36300
tgcttgagtt agataatgat aaactttggc aattttatgg gcattattgt aatgacgatt    36360
ggtccgctaa gacagagacc gtgaatggtg ttactgacat agtgctaggt tttagagtta    36420
aactatcgaa aaatgagctg agaaaaatat gcagagatgc cattgaaata agcagaatta    36480
agtatggata ttctgtcagg tttttaacaa ataatgtaaa gaaagagctg ttcgttcgtt    36540
ttgacaacta caccactagt aaaaaaagag atgtctttga acatataaat ttatattttt    36600
aagcggaaag agagtaaaga agatgatccc aaaatttaga gcaagagatc aaagaggtaa    36660
ctggcatatt ggacttctaa ctttttatgtt tggccagtat gccatcgtaa atgaatcaga    36720
tgaaaattcg gtttatctga ttgataagga aacagtcgga caatcaacag ggttgaaaga    36780
caagaacggc gttgaaattt tgagggtga tattttgaaa ataatagaag taacaaatga    36840
aggtatttca gaatacatca ctgatgttat ttgggaagac tgttcattcg tgtttaaaag    36900
tgagggtgta gattactatg actctttttt aggggcattt tcaggagatc caaataagac    36960
atatccactt tttgaactat tagtcatcgg aaatgtatgg gataacttaa aactattgga    37020
gagaacagaa tgaaacgatt aaaaataagc tatatagatt tagctgtaat aattgaaagc    37080
atctattacg gagaagatga agatgtatct gatattgatg acttattgaa atatttgcgt    37140
aataacggac atctgtctac tgttttaaca gtttcaaggg ggattagcga tgaataaaca    37200
agaatttatt gaaacgttag aagaaattag agcaaatata aatcgcaacg cagaaattag    37260
tgattatact gattttcgc gaggtaaaaa agacgcatat aacaacgcga ttggcttagc    37320
aaaacagata gacgaaccag aaaaagtcgt ggtaccgaag tttgttgcgg aatggccttga   37380 taaacataag tattccactg atataattga tctctttta agcgttgagt acgcaactga    37440
ttcagatggg tttgttgctg aaaaatggga ttacagcgga gaattttatg attggttgag    37500
taatagtgca gatatacagt ttacgttgtg cgacgctatg aggtatggct acgaagtcga    37560
gaaagagcca accattcacg agcttaaaat tttaccagaa tactttgaag cggttgtttc    37620
agggaataaa cgttttgaaa tccgtaaaaa tgaccgtaac tataaaaaag gtgatatctt    37680
acgcttaaac gaatatcaag agggacaata taccggtgat gtccatgtct cagaaataac    37740
gtacattaca gattatgccc aacaagatgg ttatgtcgtc ttaggaatta agtgaaagtg    37800
ggtaactaat gaaaactgat ttaaccagac aagctgagaa atgcttgtgg cactatacca    37860
acaaaatggg agtattcggc tgttttgagg taaccattgg ctggtttggc aaggaaagag    37920
tcgactttat gacttattct actgacaaca ctattagatg ttatgaaata aaagtaacgt    37980
tggcagactt aaaaagttcc gcaaaacaaa cgttttagg tgattataac tatttagttg    38040
tcactaacga attatgggaa aagattcaag ccaatccaga tttaaaatgg aaatatagta    38100
atcagggaat actaattttt tctgaattaa gacacaactt aggcattaca agtgtcaaaa    38160
aagcgaaaaa gcaaaatgtc acattaggaa cgcgagcaac agttttagaa agtatggtgc    38220
gatctttgaa tcgagaagtt gagaaatttt acaaggtaaa tccttttggg ggattaagtg    38280
aggaggtcaa ataaatggaa caactcttat taacaaaaac tggtgaaaac gaaatcgtaa    38340
taaatgctac aggaatggat gataatgaaa ttgtcttcac gttagctgct gctttaattg    38400
```

```
gatacagcaa ggaattggga ctaacagaag caatactaaa cgaaagtatg tccgtgctgt   38460
ggaaagatgg tgaataaatg aaacgcaatt ggaaaagagt aataaataaa gttagtggca   38520
ttgcaataat gattcttgta gcaaaagtag ccgtgagtta tttcgtgtat agcaatgaca   38580
taacaagcag tgacctcgtt tatttccttt catgctcgtt tattttgggg ttagggctat   38640
atttaggggg ttcaagtgta tgagttatcc agaagtttat atcttaggaa ggcaagttga   38700
tggagtgtac gttgagtatt cagagccata tctttcaaaa atagaagctg aacttgataa   38760
gcatcactat gaaattggcc aatcaatgtc acatgatgct ggctcttgga aaattttaaa   38820
gtatggcaga ccaattacac tggaggtgca acatgggtaa gaaaaaatca aaaattaaaa   38880
agaaaaagcg tcgcttgcaa gaaaaggcga ttgcaaacgg cactcaaaat tctaaaaaat   38940
aaaaaaagtc ggaatcgctc cgaccaacca cattgatatt ataacataaa aggagcgatt   39000
taacttgatt caattgttaa agaagttgat tttcagtcag actagagcca atgcgagagc   39060
cgtgttgaaa aattttagac gtttggaccg aatagctggt cgttccttag tagatgttcg   39120
atcaccaatc attacagaca tgcccaaagg tataaagcat gggaacaaag cagaggatgc   39180
gttgatccag atgatggatg ttgaagcaga acgtgatgca attttaacag ctttgatgtc   39240
cttaagcata ataagtcgtc aaattcttca ctacagtttc tgtgtgcagg accattactc   39300
taattataaa atcgcaagag aagttggcta ttctgaaaga agtattcaaa gaatgaaatc   39360
agaagctttg attgaattcg cagaagctta ccgcaatggc aaaataattg catataaata   39420 attttttggcg gttttttggc ggaaagttgg cggttttttat acgaatttga gtgctaatat   39480
agtaatatcg aaagtcaaag aaatggacac attacacaac actttctggt ttagtcaccg   39540
tttgatttga ctttcgatgg tcacttgcag acatacgttc tcaataaaat gaagtgaggt   39600
gaataacctc ctctttttc tacaagtttg caagtgacac gttaatggaa tatagctcag   39660
ttggtagagc atacgactgt taatcgtagg gtcatgagtt cgagtctcgt tattccagta   39720
agtggcataa gctgcttaaa taaaaatatc gtcaataatt cagtgtaact acctttacga   39780
tcgaatgacg gttaagattt ccctcctatc tgagactaca caaaagtgt agtcttcctt   39840 ttatttaata aaattgatat tatgaatgta aaggaggtt tattatggag actaacaata   39900
cattttcgaa tctattaaaa aatttcgact atcctagaat cgaaccatct atgaaatatg   39960
cggaaaaact agagactggt agtaattggc ttggagacat taatagagaa aagaagcagc   40020
tacaagaact gcagaagtta gcaaatgaat ctacattaaa aagtgaagaa cttttaaaac   40080
agattgctga aaatacatct tatattaaag acttagtcat gataaataga gaaacgcaat   40140
taaatacaga agaattaact tacgttatga aatcaattta caaagtttct aaggctgaga   40200
ataagcaaga ggctgatagt ttgttttctc aagcaattca agtcataaat gattctggag   40260
aagctgctgg aaatatagct aatttaactt ctttattgct tggcatatat acatttgttt   40320
ctacaataat ataacttgga cctcaaatta tgaggtcttt ttttatacat aagtaaagga   40380
gtaaaataat gcatattgaa aaaatgaaat tatcagattt aaggccggcg gaatataatc   40440
caagagtaaa attgaatcca ggtatggcag aatatgaaaa acttaaacaa tcaatttttag   40500 aatttggctt tgttgatcct cccattttta ataaaaatac aggaaacttg gttggtggac   40560
atcaacgcgt tactgttgca aaagaattgg ggctatttga tgagatagag gtttctgtgg   40620
ttgatttacc attggataaa gagaaagctc taagcatagc tttaaataag atttctggaa   40680
attgggatga agataaacta acagaattac ttaatgaact aactgcagat aatttggagt   40740
```

| | |
|---|---|
| taacagggtt tgacaacgaa gaattagaaa ttttaattga agatgctgac attccaaatt | 40800 |
| ttgaaccagg tagtattgat gaccaaggag atttgacgaa acttgaaccg aaatttgtta | 40860 |
| aatgcccatg ttgtggagag gagttcgatt taagagatgt tgaaagttga ttgggctact | 40920 |
| catgaagcta caaagtatgc ttgcacgcac tttcattaca gcaaaagtgt gcctgtcgga | 40980 |
| aagctcatta aaataggagc atgggaagat ggccaattta taggagtagt aatttttagt | 41040 |
| agaggtgcaa ataagagcat aggaagccca tatggattgg aacaaacaga atgctgtgaa | 41100 |
| ctaactaggg ttgctttaac caatcacaag acgtttgtat ctgaaatttt ggccaaagca | 41160 |
| attaagttcc taaaagaatt taatccaagc atgcaattaa tagtaagcta tgcagatacg | 41220 |
| gaccaaaacc atcatggagg tatctatcaa gcaacaaact ggatatatac tggaaagaca | 41280 |
| gatggggaac gctatttcat tgttaatgga aaaaagacac atcctaagtc tatccatgct | 41340 |
| aagtatggga caggatctca aaggttagaa tttttgcata acatgtgga tccaaaagct | 41400 |
| tccatttatg aatcaaaagg taaacataag tatttaatgc cactaaataa aaagatacgt | 41460 |
| aaaaaaatca ttaaattatc aaaaccttat ccaaaagcta ataaaaaga acaagtgcg | 41520 |
| ctaacacttg cctcaattca acgagatacg aataccccga agacacagag aattcccacg | 41580 |
| cgtggatttt cgacaccctc cgtgtctttt agcattatat aatagtgcga ggtattctac | 41640 |
| aatggaaaca tttgattatg aagttcagca agctttagaa aagcaaaaga ttgcggaaga | 41700 |
| aaacaacaag attatcaggg ctgcaaaggc tcaatggata agtaacttta aagcaggtca | 41760 |
| tatcaaattg aatacagtta aggacctaaa agacttaatt gaaattgaaa gtcatttgaa | 41820 |
| agagctatag gttttgtcgt atactttaat aaaaatgtat taaggagat taatatggca | 41880 |
| aaagaaaaga atgaaaagaa agctaattcc gataagggtg aaatcaaaga aacgaattta | 41940 |
| aaaaaatgtt tttttataac gccaattgga gaaaagaatt ctaatgaatt taagaagcta | 42000 |
| aaagctatag tagaaaatgt attaaataaa gtgttggaaa aatatgatta cgagttaata | 42060 |
| atagcccatg aaatacattc tatgggttcg attggagatc aagtattcac aaatataatt | 42120 |
| ggagctgatt tagttatatc taacttatct gggtggaacg ctaatgtaat gtatgaaacg | 42180 |
| gcagtagctc attcttttgg gaaacctact ataatgattt gcgagagtgg aacagaactt | 42240 |
| ccatttgatt taataaatga tagaacaata ttttcgagg atactatcga aggaactgga | 42300 |
| gccttaatag aagagttgga taaaaagatt cctaaaatta gtgaagactc tacggctgat | 42360 |
| aatccagtta cgagagtaat tcgcagaaag gctctcgaag atgatttgaa gggtgaaaca | 42420 |
| gacaatgatt caaggattct gggactactt cttgatatgg ataaacgatt aagcatgtac | 42480 |
| gaagatagta acataataga aaagaaaaaa ataaatactg gaaatattga aaggattcgt | 42540 |
| gcaaaaatat attacaaaaa tgaaggaaat atcaatgtta ttgatgaact tgaaggctat | 42600 |
| ttatttgaaa aatatagaga cactgtacaa atcgtttcgg taacatcagg aaataggtat | 42660 |
| gaagatagaa atagtgaagt gatgaaagtc ataatagtaa attctttgta ttctccagca | 42720 |
| aagatattca aagatattga gattacacta ggaaaactag gaatggttga tatttctgtc | 42780 |
| aaagttttc cgtaaaacaa aactcaattc aacaagtatt gt | 42822 |

<210> SEQ ID NO 93
<211> LENGTH: 795
<212> TYPE: DNA
<213> ORGANISM: Enterococcus phage

<400> SEQUENCE: 93

| | |
|---|---|
| atggataaaa aggaacaagc aaagaaatat tatgaaaaag gttggaaata caaggatatt | 60 |

```
tccgaaaagc tttctgtacc tctcaacaca ttgaagtcat ggagaaaacg tgataaatgg      120
gaaagagggg gtgcaaccaa agaggtgcaa cctacaaata ggggtgcacc taaaggtaat      180
caaaatgcta taggcaataa aggtaatagt cgagcctcgc caccaaaaag aaataagaat      240
gctgttaaaa ctggcgaata cgaaacaata tttgccgata tgttatctga cgaagaaaag      300
gacatctatt ctactatgaa tgatgatcct ttttttattt tggatgaaga aataagaatc      360
ctgaaaattc gccaatatag aatgcttaaa cgcataaaag atgcagaggc tggcttaaat      420
gatgaagaag ttgaacgttt gcagcagctt cgcaaagtta agagccatc  ggtaattgat      480 gggaaaatgg ttactgttaa gagagaagtt ttaaaagatg tacaagtcac tcgtaaaaca      540
tttagaaagt tagatgacat cctggctatt gaagatgcgt tgactcgcgt tagcaatcaa      600
ttaataaagg cgattaagca acaaaaagaa ttattgtcga cagataaaaa atctctttta      660
atggaggctc aaattgagaa gataaagctt gagacagaca aattaagtgg cggatcatct      720
aacgatgaag ctgactcttg gaaacaagca gttataaatg cagcaaataa gcgggcggtg      780
gaagaaaatg aataa                                                      795

<210> SEQ ID NO 94
<211> LENGTH: 1455
<212> TYPE: DNA
<213> ORGANISM: Enterococcus phage

<400> SEQUENCE: 94
atgaataaag agtttattcc gtttgccgat attggtgcag caattgatta ctactacgat       60
aaaccagttg cttttttgtca ggatattttg catcttgatc cagatgaatg gcaggataag     120
gtcttggatg atttggctaa attcccaaaa gtctcagtta gatcagggca gggtgttgga      180
aaaacggcgt tggaggctgg tgctattctt tggtttctaa catgccggcc atatgcaaaa      240
gtaatagcaa ctgctccgac gatgaaacaa ttatacgatg ttctatgggc agaagtggct      300
aagtggctga ataacagctt gattaaagac ttacttaaat ggaccaagac gaaaatttat      360
atggttggcg attcagaacg atggtttgct acagctcgaa cagcaactaa accagaaaat      420
atgcaaggat ttcacgaaga ccatatgtta atagtggttg atgaagcatc aggtgttgct      480
gatcccatta tggaagcaat attaggtact cttttcaggat ttgacaataa attactaatg     540
tgtgggaacc ccaacaatat tgaagggggtt ttttatgatt cgcataatac agatagagac     600
aagtatagaa cgcacaaagt ttctagttac gatagcaaac gtactaacaa agaaaatatt      660
caaatgctca tcgataagta tggtgagaat agcgatgtag ctcgtgttcg tatttatggt      720
gaatttccca aggcgcact  tgattcattt atcagccttg aaattgttga gtttgccaaa      780
gatattaata tttctgattc agaattaaaa catgttagag aaggacacat aggtgtcgat      840
gtggctcgtt ttggtgatga ttcaacgata gtatttccta aatcggagc  taaagcattg      900 ccatttgaaa atatagtaa  gcaagatacc atgcagacca ctggtcgagt tttaaaagcg      960
gcgaaaagga tgatggatga ctatcctaca ataaaaaaag tgttcatcaa agtagatgat     1020
acaggtgttg gtggaggtgt tactgataga cttaaagaag taattagcga tgaaaaactt     1080
ccctatgaag taattccggt aaataatgga gaatcttcta cagacgatta ttatgcaaat     1140 aaggaacac  aaatatgggg agatgttaaa gaactgttag aacaaaacat ttccaattcg     1200
attaatggtc aagggccgac gatagaactt cctgataatg caaatctaat caaagaattg     1260
agcacacgta aatttaaaat gactagcaat ggaaaaatcc gttagaaaag taagaagat      1320
```

```
atgaaaaagc gtaatgttgg cagtccagat attgctgatg cgttaacgtt agcgttttac   1380
gagccattta gaccagaacc tataaacgtt aaaaaagcta ttaatacgtt caaaaaatta   1440
ggattaagta ggtga                                                    1455

<210> SEQ ID NO 95
<211> LENGTH: 1614
<212> TYPE: DNA
<213> ORGANISM: Enterococcus phage

<400> SEQUENCE: 95
gtgaataata aattattgaa cggttctaga tttgataaag aagcaaatct agtttataaa     60
gtgccagtaa gcaaactgcc tactcgaata atgcaatatt cgaacggaga aaagaagaa    120 gtcgtagatt ttgagcatca agatgttttt aatatgattg taaaatttgt tcgacaccat    180
aaagaaaaac aagttcctcg ccttaaagaa ttaaagcgtt attctttagc gcaaataat    240 attaagttta ctgaagataa agtgaaaat cgagcagaca acaagattgc aaatgattgg    300
gctagattta ttgtcaattt taaaaaaggc gtgttattag gtaatccttt gaagtacaat    360
ggcgataaaa ctatagctga caaaattaat gattttcta gcaaatcaaa tgaagattat    420
cataatcagt taatgttaga cgacttactc gtttatggaa gagcgtttga atatattggt    480
agagatgaat acggtaaaga aatgttagct aaattcagtg cagaagagac gttcgttatt    540
tatgatacaa cgacaaacaa gaattctgta tgtgctattc actgttatga tctggagttt    600
aacgatgaaa catttagtta tatcgatatt tatgccaatg atggctattt ttatcaacat    660
gaatcaaaaa atcaagacta tgaacaatct aaattaattg ataaatatca aactttctt    720 gattctattc aagtaaatga atggattaac aatgaagagc gtttaggaga ctttgaaaca    780
gttttagata atatagatgc atatgattta tcacaatctt caatggctaa tttccaacaa    840
gattcatctg aagcttattt agttattaaa ggaaaccccg aaactgctat aggtgatgaa    900
gaaggtaatt ctgcagtaga cgttttaaac gacatgataa agctagatt gttaatatta    960 ggggataaga atattatgg tgatggtcaa acaggtagcg atcctgatgc atactatttg   1020
aaaaaagagt atgatacaca aggaacagag gcatataatg accgtttggt ttctgacatg   1080
ttgcgcttca cttctttaat tgattttact gacgaaaaca ttggtagtaa tcagtctggt   1140
attggattta gatttaaagg ttggggaagt gacaatgata gaaagaacaa agaaagaatg   1200
gtcaaaaaag caatcatgag aagactaaga ttattaactt attcttggtc attgaaagat   1260
aacttaaata aaccaacagg gcttgctgag aaagttaagt cttttttgt atctagagat   1320 aatgataaag agctgctttt tgaaaaggtg aatgctatag agatattatt tacaccaaac   1380
gttcctcaat cggataaaga aattatgaa gttattgccg aatggttgg aattgtttca   1440 gacgaaacac tttgcgaaat ggcggctaaa ttgactggtg ttcctgttca aacagaacta   1500
aataggttga aaaggaaaa tcagccagat acattatccg atgaagaagc agcgaagctt   1560
aaagaaaaac aggcagagtt tttggcgaat cagtcggaaa cagaggagga ctga         1614

<210> SEQ ID NO 96
<211> LENGTH: 939
<212> TYPE: DNA
<213> ORGANISM: Enterococcus phage

<400> SEQUENCE: 96
atgtcctatt tgaagatcg tgaagatgct tggatcaaag agcagatgaa gctagatcgt    60
aatagagaaa agaaattgt taaacagctt caaaatgcta ttgatgcgat tcaaactgaa   120
```

```
attgaagcta actgggatag attttccaat ggtcaaaata ttacgattag cgaagcaaga      180
aaaatggcta ataagatgga cgtaaaacgc tttgagagaa aagcgaagga atatgtaaaa      240
aataaggact ttagcccgca agccaataaa gaattgaaaa tctataactt agtaatgcga      300
gtgtctagat tagagctatt aaagtctcag attggtttag aattaatcac gttgtttgat      360
gagctagata agtggggata ttctcagtta actgaagcgg caaagagga atatttaaga      420 caggcgggaa tactaggcga aaccgttcaa gaaaattatt cgtctaaggt tagaaaaatt      480
gttaatgcct cattcaaatc aagtgacttc ccttcgttta gtgataacat ttggcaaaat      540
tttgttgaaa tgaaagctga tttagaaaaa ataatcactc aggcaatcac tcaaggtaaa      600
aatccaagag ccgtagcaaa agagatagct aaattttttaa agcctaacca attaaatata      660
agatacaagc taataggct aatgatgact gaaatatctg gtattcaaac agatattcaa      720
aagcaaagtt acttggatgc agatatcgaa gaatatgatt acattgcaga accgtttgcc      780
tgtgaaatat gtaaaaaagt ggctaaagga agcccttata gagtattaaa gatgaaaaaa      840
ggtattaatg ctccttatat gcatcctcat tgtaaatgct ctactgtccc taaagttagt      900
gaggattatg ataagtcgct gaaagaaaga tgtttgtaa                             939

<210> SEQ ID NO 97
<211> LENGTH: 270
<212> TYPE: DNA
<213> ORGANISM: Enterococcus phage

<400> SEQUENCE: 97
atggataatc tatataaatg caatcaatgt cataaataca ctccgttagt tagaaaatct      60
gaaaatatca cgaaggatat tgaacaccat tatgctgaat gtgccaactg tgggtataaa     120
gcgacaatta tgtatatgaa taccgaaatt aagttattaa tgcatgaaca agaaaaaaca     180
aactttggca caaaaagaa aggtaaattg acggaaaagc taaacagatt aatttctgaa     240
ttaagaaaag aagttgagga atcactttga                                       270

<210> SEQ ID NO 98
<211> LENGTH: 120
<212> TYPE: DNA
<213> ORGANISM: Enterococcus phage

<400> SEQUENCE: 98
atgacagaaa ggcgtgattc tatgaacgac gatccatacg attacctaga tgctgattat      60
gaagaatatt taagaaagga agaagtaaat gaaagcacga agaaaccag tagtgattga     120

<210> SEQ ID NO 99
<211> LENGTH: 279
<212> TYPE: DNA
<213> ORGANISM: Enterococcus phage

<400> SEQUENCE: 99
atgaaagcac gaaagaaacc agtagtgatt gaaactgtaa ttttttttagg tttttatggg      60 aaggatcgca atttcagtga aagacctaag tggctggaga gagcaatcta tgttgataaa     120
aaaattgaat tttttgatgt tcctgaaaaa ttaactatcc atactattga aggaccaatt     180
tatgcaattc ctggtgatta catcataaaa ggcgttaatg gcgaacttta tccgtgcaag     240
ccggacatat ttgaaaaaac ttatgagatt attgagtag                             279

<210> SEQ ID NO 100
```

<211> LENGTH: 642
<212> TYPE: DNA
<213> ORGANISM: Enterococcus phage

<400> SEQUENCE: 100

| | |
|---|---|
| atgaaaacaa aaaactatt attgccaatg catttacaat tctttgctga taatctagat | 60 |
| actggcactg ggggtacgga ccaaccggcc ggaggtcaag agcaaacacc gccaggagat | 120 |
| ggcggcaaag ataaaggtaa tggaaaaacg ttttctcgtg atgaagtagc aaaaatgatt | 180 |
| gctgctgaag tatcaaaaac aaaagaagct tgggaaaaag agcttcaaga gaaacaagaa | 240 |
| gaagctgata aattagccaa atgaatgat caggagaaaa atgatcatga aaagcagaag | 300 |
| ttacttgaaa aaatcaaaga gctggaaagt gcgcaaaact agctgaaat gtctaagact | 360 |
| gctactaaaa tgttttctga taaggtatt caagcgactg agggattact ttcgttagta | 420 |
| gtaaaggaaa cagcagagga gacatctgaa atgttaaag ctgttgtaaa acttatcgaa | 480 |
| actgaacgtg aaacgattaa agcagatttt gagaaacgaa ttggttctaa actcccactt | 540 |
| gatggaaatg ctgatgctag cttatctcgt ggtgcacaaa tggctaaaca agcaaataat | 600 |
| caaaataaag cgcctgaaaa taatctttgg gcgacaaatt ag | 642 |

<210> SEQ ID NO 101
<211> LENGTH: 342
<212> TYPE: DNA
<213> ORGANISM: Enterococcus phage

<400> SEQUENCE: 101

| | |
|---|---|
| atggtttatg taaagaaaac tcaaacatat caagatatta attttttaaa gagcgaaaaa | 60 |
| tttatttcat ttacaaagca agttgatgaa acaactgaag gggtagtaaa aggagtatta | 120 |
| cccgcagggt cagtgttccc taaaaatgat gctacagcag aagtattac aattaacgat | 180 |
| gttgatgtgt cgaatggacc acaaccggta ggagtaattg ttgaagggca tgttcttatt | 240 |
| aaacgattac cagctgagcc atcatcggaa gctcaaaaag caatgcgtga acttaaattt | 300 |
| tatgatgcaa acgtaaaat gctagcagtt ccaactgctt aa | 342 |

<210> SEQ ID NO 102
<211> LENGTH: 1014
<212> TYPE: DNA
<213> ORGANISM: Enterococcus phage

<400> SEQUENCE: 102

| | |
|---|---|
| atggcaaata ttgcagaatt attttcacag aaaaatgtat tagattatgt aaataatcgt | 60 |
| caagcaccag ttttattagg agaaacattg tttccagcac gtaaggtaca ggggttagag | 120 |
| tttgatgttt taaagcgggg atctaaaatc ccaacaattg caagcgttca tgcattcgat | 180 |
| acagaagctg agattgcttc acgtgttgga tcaaagacag ctcaagagct agcgttcatc | 240 |
| aaacgtaaga ttcaattaaa agaaaaagat ttaattgctt tgcgtaatcc tcgtacggct | 300 |
| gaagaacagc gttatttaga acaagaagta tataatgatg tttactcaat ggtatcttcc | 360 |
| gttaacgctc gtgttgaaaa aatgcgtatg gaagttctag caaatggtaa agtaacgtta | 420 |
| gatgaaaatg ggttagattt agtagttgat tatggcgtgc cagcagatca taagatact | 480 |
| gctgattttt ctgctcctga tacagacatc attgggttat aacagaatg ggcaagcaag | 540 |
| ttggatgtaa tgccaacacg cattttgaca tctactaaag tacgtaacgc aatcttgaaa | 600 |
| aacgacggaa tcaggcatt ctttaaaact tctggttttgt taccaaatat tggctcgtta | 660 |
| aaccaaatgt tacaacaatt taatttaccg acaattgtga catatgatgc aaaatataat | 720 |

```
aaagaaaacg ctgaaggtgt actagtaaaa gaacgttatt tcccagaaaa caagctagtc      780
atgtttgggg atgaaaaccc aggagagtct attttcggtg taacaccaga agaatctcgt      840
ttgttatcaa ctggatcaaa taactacaca gtaggcaata ttttcgcaat ggtatacgaa      900
tctaatttag acccgttggg aacatggact aaagcatcag gaacagctct accaagtttc      960
ccagaagctg acaatgtatt ccaagctact gtcttacctg attcaaaaaa atag           1014

<210> SEQ ID NO 103
<211> LENGTH: 333
<212> TYPE: DNA
<213> ORGANISM: Enterococcus phage

<400> SEQUENCE: 103
atgcctagca ttacagatga cataacaaaa ctgttaaata gtccagctaa tgaaaagtta       60
gaagtgattg agcgacgaac tagagaacgt ctcaatagtt tgttaaatgt atcggaaacg      120
ccaagcaaat ttgattcgat tatatacgag gtcgttttaa aaagatttaa ccggattggt      180
caagagggta tgatttcata ttctcaagaa ggtttaacaa tggcctttcc tgattctgat      240
ttctctgaat atgaaaaaca aattaacgat tatttgaatg aagaaaaaga agtgcaatat      300
aaaaaacttc gtggaaaggc ccgattcgta tga                                   333

<210> SEQ ID NO 104
<211> LENGTH: 336
<212> TYPE: DNA
<213> ORGANISM: Enterococcus phage

<400> SEQUENCE: 104
atgagatata cagatgaaat tacctttgta aaaaaatctt cagaatcgca ttatgatcca       60
aactcagggg aatggattga agaagaaccg tttagaaaaa ctactgatgt caatgtaact      120
gatattggta cagatcgttc tattactatt ttcggaagca ttaaagaagg ggctaaagtc      180
attaggacac agccccttt tgttattcca gaatttgatt acattgagtt tgagggtaaa      240
gcttgggaag ttattacaag tagagttcct gcattaagaa atagcttgat tattcaggaa      300
gtgattattg atggcaataa gtcaagtaag aattaa                                336

<210> SEQ ID NO 105
<211> LENGTH: 381
<212> TYPE: DNA
<213> ORGANISM: Enterococcus phage

<400> SEQUENCE: 105
atggcaataa gtcaagtaag aattaatgga ttagctggaa tttctaaaaa actaaagaga       60
aatgctcaac ttgatgatgt gaaaaaagtt gttagaaata cacagcaga attaaccgcc       120 aatatgcaag ctgaagcagg aaaggtgtta actggacatc gggaaggtaa aaagtttgtt      180
aaaccaactg ggcaacaaa agaagtatc gttatgaggc tttcgaacaa tggttttttct      240 gggcatacag gaccaggaac agaatacgca ccatacttaa tacacggaac aagattcatg      300
gtgaaacgtg atttcttttt accaccgctg aaacaacaaa aagtgaaatt tagaacggac      360
ttggaaaggt tgatgaaatg a                                                381

<210> SEQ ID NO 106
<211> LENGTH: 390
<212> TYPE: DNA
<213> ORGANISM: Enterococcus phage
```

<400> SEQUENCE: 106

```
atgattaaaa caagagatca atcaatcttc gatgaagtgt ataagaagtg tcaatcactg    60
ggttatgaaa tttacgatta taaacctatg aatgatgtag gttatccatt tgtcgaatta   120
gaagatactc agacactgca ccaagccaac aaaactgata ttaaaggttc ggttacattg   180
aatctatctg tatggggatt ggcaaaaaaa cgtaaacaaa tatcggatat ggcttcagca   240
attttttgctg aggctctatc tatttctgaa acggaaggtt attattggtc gctaaatatc   300
caatcaagcg gtattcggtt agtagatgac atttcgacta cacaccatt gaagcgggca    360
atgatatctt tagaattcaa aatactatag                                    390
```

<210> SEQ ID NO 107
<211> LENGTH: 594
<212> TYPE: DNA
<213> ORGANISM: Enterococcus phage

<400> SEQUENCE: 107

```
atggctaatg aagcaaaagt agcggctaaa ggtattgata ttattttact tttccgtttg    60
ttaaaaaaat caaagagga agcagcatgg aaattagctt tccagacaga acatgaaaat   120
acaaaaacaa agatagtga ctccgtggcc actaaagatg gtccgattcg tatcccagga    180
tcattggaaa ttgatttttc ggcaacatct attttatcag tcggtgatcc atatgttgac   240
cagctagaag aagctttaga caatgacgat attattgaaa tctgggaaat caacaaagca   300
gaaaaaggca caggagataa tgttgacaaa tacaaggcaa cctactacca agggtacgta   360
acatcatttg gtaaatcacc taatgctgaa gataccgtag aggtttcatt agaatttggt   420
atcaatggta aaggcgcaaa aggatttgca acattaactg ctgatcaaga agaagtagtt   480
caatatgtat tcaaagatac gactattgag aaagatgatc agaaaaagt agatagccct   540
tctgtggaaa gtgtaactcc tacattcgat ggggcatcta ctgaattaag ttaa           594
```

<210> SEQ ID NO 108
<211> LENGTH: 459
<212> TYPE: DNA
<213> ORGANISM: Enterococcus phage

<400> SEQUENCE: 108

```
atggtggata cttttaagat ttataaaggc caaaccgaag ttgtttctgg cacatcacct    60
ttaactatca caggaatgga acctaacaca tcagtgtcgg ctggtgaata tcaagtaact   120
cgtgttgtta atggaaaaga atcagagcga gtagatattc cagcttttaa acattgtct    180
attgctgtaa ctggcttaga ttttctcct aaaacgtcca cagcagatgc tggtactgca    240
ggtagccgac aaatcacagc aactgtcttg cctgaaaatg caaccaccaa aaagtaacc   300
tatgatattt cacctgtaac agaaggtctt gctgtctctg aaacaggaaa tattacttgg   360
acagaatcgg taccagctgg tgtttatacc acaacaggaa caacagagga tggtaaaaa   420
acagctcaac acaccttaac attgaataat caagcttaa                          459
```

<210> SEQ ID NO 109
<211> LENGTH: 351
<212> TYPE: DNA
<213> ORGANISM: Enterococcus phage

<400> SEQUENCE: 109

```
atgcaaatcg aaattaaagg gaaaaaatat aactgtattt ttggagtcaa gtttattcgt    60
gaattggata agcagcatgg ggtagtgcgt aatgatgtga atcttgggat gggactaaca   120
```

```
acattattac cgcagctagt aagtggaaat atcgttgttc tatctgatgt actttacaca    180
gctactatta cagaaaaaag tagaccttct aaggatgaag tggatgagtt tgttgaaact    240
gttgatgata ttgaggcgtt atttgatgaa acgttgaaat acttagaaga aagcaatgcg    300
ggaaagttaa cggtcagaaa tttcaagaaa gctctgatgg agaacaagta a             351

<210> SEQ ID NO 110
<211> LENGTH: 258
<212> TYPE: DNA
<213> ORGANISM: Enterococcus phage

<400> SEQUENCE: 110
atgactttgt atgaatatga agttaggcta ttggcgttcc agttaaaaag acttgaccat     60
gaaagagacc tctatctcca agcttggcta ataaccaaa ttaaggcgac taaaggtaaa    120
aaatctgaac cttatttcaa ggaattcaat aagtttttta attatgaaga acaagaaaag    180
ttaattttgg gtaagtcatt aattgatgaa aagattgata tagggcaat tgatttatta    240 agaaaagcaa ataagtag                                                  258

<210> SEQ ID NO 111
<211> LENGTH: 3408
<212> TYPE: DNA
<213> ORGANISM: Enterococcus phage

<400> SEQUENCE: 111
atggaatcat attcagtcga agcaatactt actgctactg atagaacgtt tagtagcaca     60
atgagtagcg ctgaacgctc tatggctggt gtaaataagc aatctggcga actaggtgat    120
ggattggata aaagcaccac taaagggaat caattgggta agtcaattct tagcattggg    180
gcaggcgtgg gcgctgtaaa attagtatct acggccgtaa atatggttaa ggactctgtt    240
gaaggagcga ttaaccgttt tgatacgttg aataagtatc ctgtagttat gaaggctcta    300
ggttactcaa cagaagatgt tgatcggtcc atgaataaac tatctgatgg gattgatgga    360
ttacctacat ccctcgatga aattgtagct agtacgcaac aactatcaat ttcaactggt    420
agcttgagta aaggtactga cacagctatt gcattaaatg atgcctttct tgcttctgga    480
gcttcaactg ctgatgcaac tcgtggtatg caacaatata ttcaaatgct tggtaagggt    540
gaagttgata tgcaatcttg gcgaacttta caagaaacaa tgccaatagc tatggataaa    600
gttgctaagt ctttcaaaga acaaggtgta aactcagtta accaattata tgatgcctta    660
aaagaaggag atattacatt taatgagttc aataatcgtt tgattgagtt ggacaaaggc    720
gtaggtggtt ttgcggattt agccaagaaa aactcaaaag gtatcaaaac ctcatgggca    780
aatattaaaa cagccaccgt taaagtgtg actacagtta ttaaatcatt tgatgaatta    840
tccaaagcag tgacaggaaa aaatattgcc gaaaacttag actctttaaa aaatgtagtt    900
aatataactt ttaaggcaat tgatgcagcg attcaatcaa ctattccgtt gatgaaacta    960
ttcggaaaag ctattacgtc gataggtaca gccttaacac cattactacc aacaattgcc   1020
agttttgctg ccactttac agcattgaaa gtaattcagc aagtgacagg ttatataaaa   1080
caatctgaat tggcaatcaa agcttataca accgcaataa gttatacaa tggaatatca   1140 aaactggcaa cgttgtctac cacagcactc ggaagagcat ggatgttaaa cttagcagcc   1200
gataaagcca attctgcagc aatagcaata aaaactggtc ttttagtggc gcaaaataca   1260
atcgttggtg ttttgacggg aacaattagt ttagctacag tagctacaac tgttttagt   1320
```

```
accgctatga aattgttatt gggccctatt ggttgggtaa cagccgcaat aggaggacta      1380
gtagctgtag gggtaaactt gtggaaatgg ttaaataagg aaactgaatc aactaaggca      1440
gtaaaaaaag aacaagaaag ccttatgaaa accacagatg atttgattaa aaagaatcaa      1500
gaacatgcac aatcacgaaa agatgaagct attgaattgg ataatactaa agaaaaattc      1560
caatctatga tttctgaaat ggaaatgctc tctgctaaag aaaaattaag caacagcgag      1620
aaaaaacgta tggtggaaat tgttgaggaa ttgaacggta aatgacagg ttttaaactta      1680 gtttatgacg atcaaaaaaa tattttatct gaaatgcctg aacaattca caacaagtt       1740 gatgcctata atgctttaga tgaagcttct caagctcaag aaaacattaa tcaaatgtta      1800
aaagaacgaa atgataatga agcgaagctg atggaaatca atgccgctag agaaaaatgg      1860
aatcagacat taaagaatc tggcgggaat acaaagaag ctcgtgaaaa tattgaaaag        1920
ttgggcgagc aagagcaagt gttaaagggc gttcaacagg aattaacgaa tgaaattata      1980
aatacagcta atgcccatga acaatcaatg cagcgtgcaa gccaagctgt ggaaaatggt      2040
gtgttaaatc aaacagtttc atacaatgct ttaagtggta agacgaaaga aacaatggat      2100
gcaatgcgtt cagaatattc atcacttgaa gaaaaagtag ggagtgcctt tgatgttatt      2160
gaacaaaagc aagctgtttc ggttgatcag atggctgcta acttacagaa aaatcaagaa      2220
gctgtcgcac agtggggaca aaatatttca acacttgcag aacgacatgt tgaccaaggg      2280
ttattggaac aactaagaaa atggggggca gagggtgcag cacaagcagc agagcttgtt       2340
aatgcatcag acgaacaatt acaacgctta aatgatgtct atcgtaacac tggtgaaact      2400
tctatgaatg caatgaaaga aggttatcaa ttaggcaaaa atggtttgaa cgaggaaatt      2460
caagctctta taccaactca aaaagaaact ttgatgactc aaattaagaa tacagactt       2520 aacagcgtgg gcctaagtgt aactgatgat tttaaagcag gtattgaaaa cgggcgtaca      2580
gcagtcgaag aaatgaccaa gggaattgtt cctaaagtcg gggaagacat gaaaggcgaa      2640
gttcaaaaag ctgattttag aggtataggt aagtccattc ctcaaggctt agaaaaaggt      2700
gttgacgacg gcaaggagt tcctgtaaaa acatctaatc aaatgattga tgatattgtt       2760
tctggtgcca gaaaaggttt agattctcac tctccttctc gtgtatttca ctcaattggc      2820
gaagatgttg attctggatt atcaaacggt atcgaacaaa acgcaatgaa tccagtaaga      2880
gctgtggagc gattgttga taaaataatt tctgcaatgg ataaattgcc atcagaaatg       2940
aattctattg gtgcaaatgc aattgatgga ttgactaatg gcattaatgc taatgctaat      3000
agtgctttag ctgcagcaag aggtgtggca gatcaaattg taagtacaat gaaaagtgct      3060
atggatattc attctccctc acgtgtaatg cgtgatgaag taggtaaaat gattccagca      3120
ggagtagcgg ttggtattga taaatattca aactttgtag aaaaatctat gcaacgacta      3180
agtaaaaagg tagccatgcc agcgctggat aatttaaatt caaatctgtc atttagtgga      3240
ggatcacaaa gcttagcatt tgccggagat gtatcttcaa aattcactgt agaggtacct      3300
gttattttcg atagttcaga ggttgcaagg gttattgcta aaccaatgag taagaaattg      3360
cagaatcaac aagataaaaa gaatgtttct ttaggaagga ggcgctaa                  3408
```

<210> SEQ ID NO 112
<211> LENGTH: 930
<212> TYPE: DNA
<213> ORGANISM: Enterococcus phage

<400> SEQUENCE: 112

```
atgttataca actttattga tgtaaatgaa caacaaacaa aagcctcttt gccttcggaa        60
```

-continued

```
gccatgaatt ttaatggttc cttttagaa gatttagttc caggttatag aacattatct      120
gttgttggaa gagagttagc tcctactgag atacaaagct accagttggg aattcgtgat      180
ggaatgcgac atgtttatgc tcgtattccg gaaagagaat taacagttaa attcaaagtt      240
gaggctaact ctaacgaagc gtttagggat tctttaata gactaaacgt tgccttgttt       300
acagaaaaag atgtacagat ttggtttaat gatgaaccag aaatgctttg gtcgggtagt      360
aaatcagaca ttgatgcagt tcctgaggga ttgaatcgag tcgttggtac atttacaatt      420
ttgttgaaca atccatataa atatactcga agcgatgcta ctagtgttat gtggggttcg      480
ccaaccatta catttcaagc aaattactta atggggaata caggctcagg tgcagttgac      540
ttacctattg ttatcgaagg tggggcttat tggggttcta ccatgattac ttttcaaaat      600
cgttcctatt taatgggaga taacggtcaa gaagtgaaac caattgaaat atatccaact      660
gtcgaagggt taaagtaaa accgattatt actatagaag gtactggtag aggcgtgtgg       720
ataaaaacta gaagcgatac tattgatatt ggtgattttg ataagtcaga aatagtaatc      780
gatacagaac agtttaatat tacgaaaaat gggaagccaa tgattcgtcc tatgaacgat      840
ttttatattt atccaaatga gccactatac atccaagcga agatagtac ttttaatcta       900 actattcgat atccaaatcg tttttatag                                         930
```

<210> SEQ ID NO 113
<211> LENGTH: 2016
<212> TYPE: DNA
<213> ORGANISM: Enterococcus phage

<400> SEQUENCE: 113

```
atgttgatgg caatggattt aaaagggaa tatacggcag ttttggacaa tgcctatcaa        60
gtcagttatg aaaaattga aaccaaata gggaatcttg aattttcaat gccgttggat       120
gatcctaaaa atgaattttt gcaagaaatg ttatggttg aactaacaga taatgagaat       180
gaatatatag ggttataccg tgttatgcct tcaacggttc gcaaagatgc tagtaacaat      240
tcaattacgt atacggcaaa tgaagccctg tgtactttgc tagacacggt tcttttggt      300 tatcatgaac tagtgaatcg aaaaacggtt gatgttatta ctatcttttt gaataaacaa      360
aggacaaaac actgggtttt aaaaaaatgt gaattcactc gatatttag ttatgcatgg       420 gaaaatgaaa atggtctcgc tgatgctttg tttagtattc ctcaagcatt tgatgaagac      480
tatatgtggc aatggaatac caaagtttat ccattcgaat tatctttagt gaagccacca      540
aaagaaccta ttgctcgtat tcaagaagga taacatgc aaggctttga gattgaaaga        600
gatcctaaca atttagttaa tcgagtttat cctttaggtg ctggtgaagg cgtcaatcag      660
ataaatatta atcggtaaa taaaatatt cctatgtag aagatgcaaa gtctataaaa         720
gaacatggtt tagttgaata tgtttgggtc gaccaacgat tcacagttcc acaagcttta      780
aaagacaatg caatcaacat gttaaaaaaa tgggcgcaac ctaaaatttc ttgggatgtg      840
actgcggctg acttattgaa attaacagat gaacctttaa gcattgataa gttaagacaa      900
ggaactgtaa ttatgattaa cacagatgac tttggaagta taaatttgcg tattaaaaaa      960
gagacaaaac aggatgtatt cggcgcacca caagatattc agctagagct tggtaattta     1020
tctgacgatt ttactacgac aatgtctgat ttgaaacgta acaggaaat aaatgagacg      1080 tattcgcaag gcgcaacgaa tattttgaac tatagttatc aagataactg tgaaaaggca     1140
tacccagcag aaattgaatt cttcttagat gatgatgtat ttcatgtaaa tactgtggaa     1200
```

| | |
|---|---|
| ctgactttta aaactaagcg ctatcgtggt tatacaaaag ccgtaaaagg cggaggagct | 1260 |
| acagtaaaaa gtacgtcagc tggtggagct tcaacacaaa cgagctctgc tggtggcgga | 1320 |
| agtgtcgttt caagttcagc tggcggagga ggttctacaa cttctggatc aggaggagga | 1380 |
| tcttatcaag ggggatctac aaacactgat ggaggaagtg cacagacaag tagtgctaat | 1440 |
| ggcagtcatg accatttaat gtttaatgta attcaagggc cacctcaaac ccttcctaaa | 1500 |
| ataacattaa gagccggtgg cggtggagaa atatatacgg aagcacgtgg cggaacgttc | 1560 |
| agaacagcaa gtgctgcaga taatcatacg catacagtca atgtgcctag tcactcacat | 1620 |
| agattcaata ttgatatacc cgcacattct catgtcgtta gcataccaaa ccatacacac | 1680 |
| agcatatcgg ttcctagcca tagccaccaa gtaagaatac cagcacatac acaccaaatt | 1740 |
| actttacctg atcatagcca tccattagaa tgggggattt atgaggcacc aagtagcgca | 1800 |
| actagtgttg atatagttgt agatggtacc accattccag tacacgatac tagccaacaa | 1860 |
| agattaaaca ttgttaatta tcttaggaaa actagtggag gtaaaatctc tagaggtaat | 1920 |
| catacaatca agataatacc taacaaactt gcacgaatcg aagcgcaagt tatttgtcgt | 1980 |
| gtttttatac aatcacaact aggaggacaa ttttaa | 2016 |

<210> SEQ ID NO 114
<211> LENGTH: 174
<212> TYPE: DNA
<213> ORGANISM: Enterococcus phage

<400> SEQUENCE: 114

| | |
|---|---|
| atgagattaa cagtaaaact aattagcaaa caagaagaat ttataattaa tgatgaatca | 60 |
| ggtaaaacgt tagatgatta ttttgcagag ctgattgata atagttcgcc attcatcaaa | 120 |
| ataggaaatc gtattttaca aaaagctaca attgaataca ttaatgcaga gtag | 174 |

<210> SEQ ID NO 115
<211> LENGTH: 1764
<212> TYPE: DNA
<213> ORGANISM: Enterococcus phage

<400> SEQUENCE: 115

| | |
|---|---|
| atggctatcg agcaaattaa agaaaccgac acgctgaatc aaggtcgaat taaaattaat | 60 |
| gcaattttgg atcaatctaa tactgctgtt gaaaaaataa atgattatca aagtcagttg | 120 |
| acagaaggaa ttaatgatgc caaaaaaatt gctgacgacg ccggaaaaga agccgtacaa | 180 |
| attgcagaac aagcagggaa tcaagcgaat gaaacagcaa accaagcttt aactaattct | 240 |
| caaactgcta ttaatacttc aaatcaagca gtatctacag caaacaacaa taaacaagaa | 300 |
| tttgatgctt tgcgtaatga ctttgaaaaa cttgttggag aagctggtga cagtaacccc | 360 |
| gaaatcgtac aggcgagaac agatacccaa ggagtaacac aatcaacatt agctactcgc | 420 |
| ttacaggttg actttaatga ccgcatgaca aaatctgaag gtgtatcgtt actttctgga | 480 |
| acaacaaacg taaaaatacc tatggatttc actggaaaaa cagcgggtaa tacggcaaca | 540 |
| aatgcaaatc aatatttttac cgatgtaaca gctaaagtac taaaaaaacc aaaagataca | 600 |
| tggaatgaga tttctcaatc tgattacaac aaattagtaa gtcgtgatga ttctggagta | 660 |
| agtagtggtt cgacgcaaaa cggagttata ccacaacagt taggagtgtt caatgcttta | 720 |
| gaagctgcca aaaaattaat tcctcaaaat tttgaaggat taagtcaaga agaagcggtg | 780 |
| gttttattaa aagatagctt tgtcgctttt actattagtg aacgtgttaa agcaacttcg | 840 |
| cctaacaaca aaacaattaa agtttccact tatattgagt caactgactc gtggactact | 900 |

```
caaattcaag aaaatgctgg cgaatacaaa gatttatcag tccaagtaac tgataaaaat    960
ttcattacta gcgatggtct tatctatcta attagctata cagatccatc aaatggagtg   1020
acaactgcta atttggatgt tgactattca gctattcaat agaaattag tattaatgca   1080 caagatgtat tagcaaaaag tggctttgta agagaggaac aactaaagga gcatacggaa   1140
agtcaagaca atccacataa agtgaccgca agtcaagttg gattgggaaa tgttaaaaat   1200
tatggatttg ctactgatag cgaagcatct gctggaacat caacgaccaa atatatgagc   1260
cctaaaaatg ttgcagatgc tattaaaggg caagcggtga ctcaaactgg agatcaagaa   1320
atagcaggaa caaagatttt tatgaatcct ccgaaaatcg ctggacaaac tgttatttct   1380
gaaaaagtaa tagccttttc tgcccctaat acagtatcag ttagtggtac aggggttaag   1440
gtcattccaa tttctcaaaa ggtcatcact aataatgaat tttttgagtt atcagcaaac   1500
aaaatcaaag tgttgaaaga tggaataatt agtgtcgtta ctagctatac aaccaacgtt   1560
ccagcaggtt ggtgtaatat tgagcttact aagaataatg cggttatgaa caggagcaat   1620
caaggtacag gaggattaca cgctgctggt ttgacagatg tatttgatgt aaaagctggc   1680
gatactattg catttcaaag taattctaat caatcttcat atacggtttt atatttgaga   1740
ggatttttaa gatacttaac gtga                                          1764

<210> SEQ ID NO 116
<211> LENGTH: 222
<212> TYPE: DNA
<213> ORGANISM: Enterococcus phage

<400> SEQUENCE: 116
ttgtcaaatg aaatagttgt tgctgtaata ggattagcgg gcagtacatt tggtgcgttt     60
attggagtgg tagctagtgc caatttgaca gcttacagaa tagaacagtt agaaaaaaaa    120
gtagaaaaac ataatggtgt aattgaaaga acctttaaat tagaaggtcg aatgcaagaa    180
gcggaacacg acataataga attgaaagga gcaaaaaaat ga                      222

<210> SEQ ID NO 117
<211> LENGTH: 204
<212> TYPE: DNA
<213> ORGANISM: Enterococcus phage

<400> SEQUENCE: 117
atgattctac cagataagta ctacaaaatt atcaaatggg gagtacttac tgtgcttcca     60
gccatatctg ttttagtagc aacgttaggc aaaggttatg gatggcagca acagatatg    120 gctgttttaa ctatcaatgc cattgcaact tttttaggag tagtaacagg tgtgtcagca    180
tataatttaa aagacaagga gtaa                                          204

<210> SEQ ID NO 118
<211> LENGTH: 1260
<212> TYPE: DNA
<213> ORGANISM: Enterococcus phage

<400> SEQUENCE: 118
atgaaaaaga aaatttagt cggagcgtta atcgctctat tttttatgcc tttaaatgta     60
tttgctgcta aaggcgatca aggtgttgat tgggccgttt atcaaggtga acaaggtcgt    120
tttggttatg cgcatgataa attcgctatt gctcaaattg gcggctacaa tgccagtggt    180
atttacgagc agtataccta taaaacgcaa gtagcaagtg ccattgctca aggaaaacga    240
```

| | |
|---|---|
| gcacacacct atatttggta tgacacttgg ggaaacatgg acattgcgaa acaacgatg | 300 |
| gattacttct tattacgtat tcaaacgcct aaaaattcca ttgttgcttt agactttgag | 360 |
| catggcgcta gttctgatgt aaacgcaaat acagaaacga ttttgtatgg tatgcgtcgc | 420 |
| atcaaacaag caggttacac gccaatgtat tatagctaca agccttttac gttacaatac | 480 |
| gtggactatc agagaattat taaagagttt cctaactctt tatggattgc tgcctatcct | 540 |
| agctatgagg taacgccaga accactatat gcttatttcc caagtatgga gggcattgga | 600 |
| atttggcaat ttacgtccac ttatattgca ggcggcttag atggtaacgt agatttaaca | 660 |
| ggaattacgg atagtggtta tacagataac aataaaccag aaacggacac tccagcaaca | 720 |
| gatgcaggtg aagaaattga aaaaacaccg aattctgatg ttaaagtcgg cgacacagtt | 780 |
| aaagtgaaat ttaatgtaga tgcatgggca actggtgaag ctattccaga ttgggtaaaa | 840 |
| ggaaacaact acaaagtgca agaagtaact ggaagcagag tattgttaga aggtatcctg | 900 |
| tcatggatta gcaaaggcga tattgaatta ttgccagatg caacaattgt tcccgataag | 960 |
| caaccagaat ctattcacgt agttcaatat ggtgaaacat tatccagcat tgcttaccaa | 1020 |
| tacggtactg actatcaaac cttagcttcg ctaaatggat tggctaatcc aaatcttatt | 1080 |
| taccctggac aaactttgaa agtaaatcga tcagtagtaa gcaatgttta cacagttcaa | 1140 |
| tacggtgata atttatcaag tattgcatct aagcttggta cgacatacca agctttagca | 1200 |
| caacgaaaca ggttaactaa tcttaacttg atttatccag ggcaaacatt aatttattag | 1260 |

<210> SEQ ID NO 119
<211> LENGTH: 381
<212> TYPE: DNA
<213> ORGANISM: Enterococcus phage

<400> SEQUENCE: 119

| | |
|---|---|
| atgaaatcag aaataaaaaa acatattcgt caattattat gtgattataa aaaaatagaa | 60 |
| aaacaattga aaaagtatga agatgcatta gtttatcccc aatcttcttt ttctttatac | 120 |
| tttgaagaaa agtcaaatga aaaaataagt ttgaaccaaa tagttttca taagtttttt | 180 |
| ttaaatacag ttgaagaggt tttatcagat gcaacatcgg atgtacgtga tattttatt | 240 |
| tctaagtata aaaatggcta tccacgtaaa aagaatgaaa ttgtggccta tgaaacttat | 300 |
| ttaagtttat caacgattaa agaagggat agtgaattct tagaggaatt agcacgacaa | 360 |
| ttaggttggc tagaagtttg a | 381 |

<210> SEQ ID NO 120
<211> LENGTH: 1266
<212> TYPE: DNA
<213> ORGANISM: Enterococcus phage

<400> SEQUENCE: 120

| | |
|---|---|
| atggcagaca catggttaag tcctcttgct gtttcttatc aagcaactca agaatgggat | 60 |
| gaacctgatt atttgagcgg agggcaagca ggaattcacg gaggcattga cttagctcca | 120 |
| aaagcaggta ctaatccacc tgtttattca gctaaatctg gacagtaga agaggtagta | 180 |
| ccaaatcatc caattggtgg taattacatt gttatcagac atatggataa ctactggacc | 240 |
| tattatgggc atttagcaac tataaatgta tcagtaggac aacaagtaac aaatcaaacg | 300 |
| gttcttggat tatgtggagc aactgggggt gccacaggta tccatcttca ttttgaagta | 360 |
| tggcgtggtg gtaaatggca gagaatcaat ccacgagaag taattaattt agatggatct | 420 |
| ggcagagact ctagtaataa cggtggcaat ggtggaattt atacaggcgg agctttatta | 480 |

| | |
|---|---|
| aatgcaggaa aaagcatttc agaatcaaat attcgtctaa tcatttctgc tggaaaaaaa | 540 |
| tataatatca agccaagttt tatgattgca caaatgttta ttgaaagtca ttggggagat | 600 |
| ccaagcattt caattgttgg aagtaaagac aataattggg caggaatttc agaacctttt | 660 |
| agcgttccag ctgatttagg aattaatatg agtcgtggat cagcaagacc agttggtgaa | 720 |
| ggtggttatt atattcattt tgcaaccatg aacgattttt ttaaagcata tgcatttgta | 780 |
| ttatcaaaaa gaaatggctt atataatgtt gaaggtgcaa attcaattga agaatactgt | 840 |
| aaaggcttat ttcgcatagg tggagcaaat tcagactatg ccgcgacagg ctatcaaaat | 900 |
| tattttaata tgttaatacc aacttataat tcaataaaca aacaaaatcc tggtaaactt | 960 |
| gcacaaattg atgcaagtac tgaagaaatt actaataatg gaggactgac aactatgcaa | 1020 |
| tgtttatatg aacgaccaat taatccgaat actggagctt tagatataaa tggctcagca | 1080 |
| actacaatga tgttttgtaa tggggtcaat acacgaagag tatatcataa tgatgaagtt | 1140 |
| aatattgtta aagagctata tcgtaaaaac aatggaaaag aaatcccggt atattataaa | 1200 |
| aaagattggc ctaaaacttc gccatggtat attcgactag aggcaatgtt tccagtagtg | 1260 |
| aaatga | 1266 |

<210> SEQ ID NO 121
<211> LENGTH: 1503
<212> TYPE: DNA
<213> ORGANISM: Enterococcus phage

<400> SEQUENCE: 121

| | |
|---|---|
| ttattttgat aaattaacaa ttatacaatc atctaccact ctgatggaat ctttactagg | 60 |
| ccagacgttc atttccgctt gtaaagcttt gtgtttttca aaatcttctg gtgtaggatc | 120 |
| attaaaattt aatccaaatg ttttcatata aactagagta tttaaactag tgtgcaccga | 180 |
| gttaggcatg aattcaaata tgaaacacc gtttgtttca cctttttatat tcgaaacatt | 240 |
| ccgaggagaa cgatttccat acattaaaag tttataggat tctggattct caatttccat | 300 |
| tgaataaata ttatttgtaa tcatttccgc agtacgtaaa tcttcttccg ctgttagata | 360 |
| ctcagaatat tctaggttgg ttgtttcccg aacttgaata aagtaaaga taattactat | 420 |
| gccaactaat aaatgtttaa gcacaaagtt gtatccccag taaatcataa taaagatgag | 480 |
| taataacgct aaaacagcag ggaagttagg tacttcacct ctaattgccg gacgttttcc | 540 |
| acctaaaact gtaaacatga gtggagtgat tagaatacct aacaaggtaa taagatgaa | 600 |
| aaaaacattt ttgcgtttca gataggacat attaattaat acaatgacca gtaaaagaac | 660 |
| acatatcaaa acagcggtg taaaaaagt gtctccgact ggagggaaga atagttcttt | 720 |
| ggcgtaatct ttaatatcgt tgatagaatc tatcaagggg cgtttacccc aaagaatcat | 780 |
| attatctaga taggagcttt caacgtttaa aactttttc gctaacatcg ccattagttg | 840 |
| agatagaacg agagatgaaa tagctagtag aataaaatgg ccgattttga aggcatagtc | 900 |
| tttaaaagaa atttaagat catttaactg agcaaaatac aatgccatta aatcttgaa | 960 |
| taaaattaag gtacacgcaa atacaaagaa tgattgatac atagtaagtg taaacgtcag | 1020 |
| taacaaaaag ccaaataatt taaaattttt attgggaata tggtaaatag caatgagaga | 1080 |
| aagtataacc aaaacagatac ctaatgaaaa ttcaaaattt tgtaggacga agtaaaattg | 1140 |
| ttcgctaaat aattgactgg ttggaaaaat acttgggata acatataaat acttttgtt | 1200 |
| ataaatctgc ttagttgaaa gatcaacata atagcataac aagatagtgg cgatagcaaa | 1260 |

-continued

| | |
|---|---|
| gaaaataata gctaacaaat ttaaaaaata aacatttaca tagttgtatg ttaaaagctt | 1320 |
| taaagctact aatcctggtc taccaattga aacccaatgt tttaagtagc ctctgtagtt | 1380 |
| agtcattaag tgcatagtat caatagcgta agtattgtta aatagtttaa taccataagt | 1440 |
| agcaaagacc atcaaaaagc tgtagatggc taagcctttg ttttctttaa aaaaatattt | 1500 |
| cat | 1503 |

<210> SEQ ID NO 122
<211> LENGTH: 582
<212> TYPE: DNA
<213> ORGANISM: Enterococcus phage

<400> SEQUENCE: 122

| | |
|---|---|
| ttaaggtgtc tgagaagatg cttctaggat tccagtttgt tgttcagatg acatttgtcc | 60 |
| tttattttta agttcaagcc attgctctag cgtaatgttt ccaagataac tatagatttg | 120 |
| attttcagta gataaagtgc catctaagtt ttttgtaaat gagagagagg tattattaat | 180 |
| tataaaattc attgtaatgc ttccgtcagc attacttaga aaattaggac tctgaatgac | 240 |
| tccgtttggc tggccagatc cagacatttt tccatcagga ttaatgaaaa agaaattacc | 300 |
| actttgcgga ataccccagc caccaacaaa agaagacaaa ctagctggat cctcagtatg | 360 |
| tgattgttct tcttcagttt gggatgattt tctgtcagca gttgaagtag ttgttgtgtt | 420 |
| agtggacagt atgttttttt catttatact attattgat gattcccttta ctgtagaggt | 480 |
| gacagtagta gatgacccctt ttgtatttc tgttttcgta ttttcattag tacaagctgt | 540 |
| tagtaataat aatgcaaaga ccagcgaaag agatttcttc at | 582 |

<210> SEQ ID NO 123
<211> LENGTH: 1137
<212> TYPE: DNA
<213> ORGANISM: Enterococcus phage

<400> SEQUENCE: 123

| | |
|---|---|
| ttacttgcca tatttatttta gagcttctac cagatttgtt ttagcttttt ttgtaacatg | 60 |
| agtataaatt tttaaagttg tttccgtgtc aacgtggcct acacgttcca ttattgcttt | 120 |
| tactggtaca tttaattctg caagtagtga aatatgagaa tgtctaaaaa tatgacttga | 180 |
| tatagttttg tttattttat ttttacctag actttcatta gctttcttta gagaggcatt | 240 |
| gaatgaatta acttgaattg ggttgcccgt tttgccaaca aatagataat ttgtttgctc | 300 |
| tttgaatttt attctctttt ctaaaattaa ctcttcgatt attttctacag ctctatttga | 360 |
| taattctact ttcctgaatg atgctagagt tttaggtaat tcttttgtag cgttttttata | 420 |
| accgttagaa taatccaaag tcccattaac taaaatagca tgttcatttt ttacataatc | 480 |
| atttatagta agactaattg cttcaccagc tcttaatcca gttaaataca taactctgc | 540 |
| taaacgacca tgatggacac tttgaaatgt agaataataa tagcttaata attgataaac | 600 |
| ctctctctct tcgaggtatt tactttctat attttcaaaa ttttctttttg ttagtggggg | 660 |
| tttaacaact ttcactctat tgataggatt ttcatcaatc attcccatgt cttgtgcata | 720 |
| agtgaaggac atgttaagca cactttttgaa tttttttctta tactcccacg aatgcggtaa | 780 |
| atcattaata aagtcttgga aaattttgt atctgtgttt cttatgagta catcaacatt | 840 |
| catattggaa aatatatatt ttaaaatttt tccgtaagct ttaactgatg ttttcctaat | 900 |
| agataattga tgttgttgcc accagctatt taagagattc tctaatgata cttttttttg | 960 |
| atcttttttc tccattcgat tattaatctt atcctgtaac tccatcatcg cttgtttttt | 1020 |

```
cgcttggtta gacttcgaat taagtgtaac tgaaacacgt cgatattttt ctgtgtacgg   1080
atctttatat cgctcaaagt atttatattt tccattagga agttcctcaa tccacaa     1137

<210> SEQ ID NO 124
<211> LENGTH: 573
<212> TYPE: DNA
<213> ORGANISM: Enterococcus phage

<400> SEQUENCE: 124
ttattgtaca ggtatttcaa atgtagcagc ttgaccagta cgatttgaat catatttttt    60
gaataatatt ttgatgtttc caccaggatt ttgaacgcca tatgcggcct gagccccact   120
cattgttgct ccaacaggtg ttggctttgc tcctgtggta gagacgggat aagtttcacc   180
cattattccg gcactatcta ccacattttc tggcataata aataaatctt gaatgtcatc   240
ttcatatcct agattttcat aagtataaga aattataact acttgctgtg gtgatttatc   300 tgaataggggg tttctttcat ctgtagaagt cacgctgtca attttgagtt tccattgatt   360
gggaacttcc caccattcac ctaaattata aactgtcttt ttattatcgc tagttgattc   420
agtactggta ctggtttttg tagcagatgt ttttcagtt attttgttg tgctagtttc     480 ttttttgttt tttcaggtg cagtactaga agaatcgcaa gcacctaaag tcaatgaaga    540
tagtagtaaa atactgatag ttattttttt cat                                573

<210> SEQ ID NO 125
<211> LENGTH: 201
<212> TYPE: DNA
<213> ORGANISM: Enterococcus phage

<400> SEQUENCE: 125
ttatttgaac aaatcccaaa agctaaaagt tgttttatta tatactttat tatacatagc    60
tttcttgggg ttcttaatga aaccagttcc tttttgccca taaccaggaa ttactgcttt   120
tttaaactta cgtttagctt ttccagtagt acgagcactt attgattttt ttatacttgg   180
tttacgcatt cctactttca t                                              201

<210> SEQ ID NO 126
<211> LENGTH: 555
<212> TYPE: DNA
<213> ORGANISM: Enterococcus phage

<400> SEQUENCE: 126
ttatttttct tctgaggcag ttacatttt atacatatct actttaagca aaggaagtgt    60
attgttatca cctaagtttg tagtatagtc ataagaacca gcaaatgaag cccaaaataa   120
aatttcatca tcttgtaaaa ctttggaata aacattatct tttaataccg ctaacataac   180
atactctcta tcgttttttg cataagtaac atagcccatg taataaatat attcatcact   240
tggttcatct acaatttgaa ttattttagc taatgaatat accttctcgc ctttatgtgc   300
cttttcatct cttaacatcg aattaactct aacgttagaa ttatagcttt ttggatctgc   360
ggttttataa tactcagata tcttttctaa ttttttcctt tgttcagtgg aatcttgatc   420
aactaaaatt ttataggtct ttgaagattc ttgtgtagaa gatttcgaag aatcaggctt   480 cacatttta gaacaaccaa caaatattac tacgacaaat aataaaaaag ccatagatgc    540
aaatattttt ttcat                                                    555

<210> SEQ ID NO 127
```

<211> LENGTH: 474
<212> TYPE: DNA
<213> ORGANISM: Enterococcus phage

<400> SEQUENCE: 127

```
ttattgtaaa tttgtattta aaatcatgac tgataaatca ttaaactcga aaattcttcc      60
tttataaaaa tgggtatcac caaattttg tcgataatag gcgagtacat ttttgagcgt      120
ttcaacgtct accctaaaa attcagcaca cgtgtaatga ttactgaatc ctgattctga      180
acacttaatt agatcatcca aagtgactaa ttgttctaaa gcatattgtc tagcttttag      240
ttcttgttta cgattttcta acaatcttg gtttaatatg tcaccaaacg atgtatcgtg      300
gtggccaagt tcctcagcta gcacattcct ttttttatt agactcaacg attttcaat      360
ataaattcta ccatcacggt acaaaccata gcatccagta ttttgaaaca aatctgtttc      420
aataactggt gctttttct gtacctctga caccaacagc tcatattcgt tcat           474
```

<210> SEQ ID NO 128
<211> LENGTH: 573
<212> TYPE: DNA
<213> ORGANISM: Enterococcus phage

<400> SEQUENCE: 128

```
ttattcttta tcatctgaat catcatcaaa aagatgttta cattctttt gcttcctatc      60
ataatcagca tccactttat ctagaaattg attaatttta agtttctctt catcagtaaa      120
tactttatca gggtctggtg aatgcgcagc taaagtatca tatttttct tgttaatgtt      180
aaccacgtta ttagaagctt tgttttgttt ttctaaatga gacttagctt cgttatatat      240
aagctgttgg agcttgggtt ctaactggtt gaatataggt actatgtcga agtcatcttt      300
ttcactagat ctttgttcgt cagggattct ttttttagag acatcaaacc ccattagcca      360
cgcttcgtta acatctaaag ttttgacaa aagataaatt ctattttggt caggtgattg      420
ctttccagtt acatattgtg acaaagtact tttactcatt tttatattta attctttttg      480
atatggttct gacaaacgca gaatatcaac ttgttttaaa ttgcgctcac tcataagttg      540
ctttagacga gcagatgttt taactctatc cat                                   573
```

<210> SEQ ID NO 129
<211> LENGTH: 234
<212> TYPE: DNA
<213> ORGANISM: Enterococcus phage

<400> SEQUENCE: 129

```
atgtgctatg attactcaaa attagcagga agaattgttg aaaagtttgg aactcaatat      60
aattttgcta tcgcaatggg attgtcggag agaacaatat cattgaaaat gaacgggaaa      120
gtctcttgga aagacactga aattacgaaa gcttgcaaat tgctagactt ggaaacaaat      180
tttattcatt tatattttt taaagagaaa gttcatgttt gtgaacaaag gtag            234
```

<210> SEQ ID NO 130
<211> LENGTH: 720
<212> TYPE: DNA
<213> ORGANISM: Enterococcus phage

<400> SEQUENCE: 130

```
atgaacgaac taattaaagt tacaacaaat gaaaatgatg aacagttagt taacggtaga      60
gagttatatg aatttctggg agttaaagat aattatactg attggtttaa acgaatgatt      120
aaatacgggt ttgatgaaaa cgttgatttt atcagtttct cggaaaaatc cgataaacct      180
```

```
tttggtggtc gcccacaagt aaatcattat gtgaaactag acatggctaa ggaaatttca    240
atgctacaac gtaccgaaag aggaaagcaa gctcgtagat atttattca  actagaaaag    300 ttttggaata gcccagaaat gctgactaaa cgagctcttg aatttcaaca gaaaaaata     360 gaagtattac aactagaaaa tgaatcatta aaacctaaag cattatttgc agatgccgtt    420
gatgcaagta agacttccat tttaatcggt gacctagcta agctaatcaa gcaaaacggc    480
atcgacattg gcagaatcg  tttattccaa tggctgcgag acaatgggta tctaattgct    540
cgaaaaggtg aaagctacaa tatgccaacc cagcggtcac ttgatttggg aattgcggaa    600
atcaaggaac gaacccataa caatccagat ggaagtattc gaattagtcg aacgccgaaa    660
attactggta aagggcaaat atattttgtt aacaagttct tacatgacaa gacagcatag    720
```

```
<210> SEQ ID NO 131
<211> LENGTH: 249
<212> TYPE: DNA
<213> ORGANISM: Enterococcus phage

<400> SEQUENCE: 131
atgcaaatca cactagcaaa gactatcgat ttacagcaag cttggatggc aaaagatgaa     60
gcaattgttt attttggcta tcagcatcac aaaccaacat ttcaaaaact tctgagagag    120
tttaaggaac ataagaatt  taaagatgga tatagactcg ttacatcatg catgccaatt    180
atccacattc agaaatttga tgaatttttg gtttggcggg aaaaaaacaa gtataagcga    240
aataaatag                                                            249
```

```
<210> SEQ ID NO 132
<211> LENGTH: 174
<212> TYPE: DNA
<213> ORGANISM: Enterococcus phage

<400> SEQUENCE: 132
atgagaaaaa tttataactt aagaagaatt gcagtactgc ttattgtttt cggattgggt     60
ctgctagtgg gtggaaactt taatccaatc atccaaaatg tgtatattgg attgttcatt    120
atttggacat tattttatga cttagctctt gaagatagag aggtaaataa atga          174
```

```
<210> SEQ ID NO 133
<211> LENGTH: 126
<212> TYPE: DNA
<213> ORGANISM: Enterococcus phage

<400> SEQUENCE: 133
atgacaagga aagaaaaact acagcaaacg aaaaaacttg ctgatttatg gtaccagcaa     60
caaaaaaatc aaatatacat tatgcaacaa aaagagagaa gggaatttag atgtttaaag    120
cagtag                                                                126
```

```
<210> SEQ ID NO 134
<211> LENGTH: 156
<212> TYPE: DNA
<213> ORGANISM: Enterococcus phage

<400> SEQUENCE: 134
atgtttaaag cagtaggaaa agatagtttg aaaatttacg tggttgagga tacgaaagcc     60
ctggtatttc aaaagcttaa agaaaaatat ccagacactg cgataaataa ggctgtattt    120
ccagaagcgt tatttatcca agaaacaaaa aagtga                               156
```

<210> SEQ ID NO 135
<211> LENGTH: 237
<212> TYPE: DNA
<213> ORGANISM: Enterococcus phage

<400> SEQUENCE: 135

```
atgagagtgg aagtggattc aatgcaaaga attgtcttaa ttgataatca ttcaccttat      60
ggatcactga tttttgaaaa ggatgctatt aataatcatg ttgctgttta ccaagatagc     120
gaagatgaag aagttagaac agtattcgag agtttagatg aaagtgctta tttttaatcaa    180
gttgaattaa tcgaaggact tcaaaaagtt atttcattac tgaaagaagg ggaataa        237
```

<210> SEQ ID NO 136
<211> LENGTH: 678
<212> TYPE: DNA
<213> ORGANISM: Enterococcus phage

<400> SEQUENCE: 136

```
atgaacgaga acagcgaaaa tttaaaagaa ttgtttgatg ggatgtataa gctaaaaagc      60
aaattaattc aaccaagatt tgacgcagaa gttgcctata caacgaaaaa aggtccaatg    120
aatttccaat atgcaactct aaaagcgatt gaagaagcaa ttagaaaagc tgcacaagaa    180
tcagaaagcg gaattgattt ccaacaaaat gtcgtcaatg agaataatgc tttaaaagtc    240
acaacaatta ttactcatgt tagtggtcaa tatatagttc atggaccttt tgaatttcca    300
aacagcggga caaatcctca aggattagga agtttaacga catatgcaag acgttactcg    360
ctttcggcag cgtttggaat tgcagcagat aaagacgacg atggccaaac ggcagctgaa    420
aagaacaatg atacatcgaa agttaatttg attagcggta acagttagc cacgttaaac     480
gatcatatca gacaactttc tgagttatcg aattctgaac ttgactatgt gcggaatgaa    540
ctaagtaaag aattgaatgt tgatgtcaat gaaaacatgc cgtctagtat gttcaataaa    600
gctgttgaag ttctgaaaca atggatacaa caattccagc cacaaccaga gaaaacatt     660
acatggggc aaagctaa                                                    678
```

<210> SEQ ID NO 137
<211> LENGTH: 924
<212> TYPE: DNA
<213> ORGANISM: Enterococcus phage

<400> SEQUENCE: 137

```
atgacaaacg aattaacaac agaattgcag tttaatgttg attttaaagc tagtaaaatc      60
actatccaaa atgaagcaca gttggctgag atggttgaga gcgcagttaa gcactattca    120
acaatgattt tcacagatga aacattcct gaagctaaaa aagcaagagc agacttaaat      180
aaagttgtaa cgttgctaga tgatcaacgt aaagaagtta aaaatcaata tgataagccg    240
ttaaaagatt ttgaggaaaa aataaaaaaa tatactgaaa aataagtga agttagttca     300
gaaattaacg aaaagcatca aatcatacgaa gaagcagaga agcagaaacg aagcaaaaag   360
cttcaaaaag tgattgctga atgtctgaa aactacaatg tatccattga cgaaattgaa     420
attcctagtt cgtggactaa taaacagct ttcacagtta aaggtgaacc aaataagaaa      480
actattgagg aaatagcggc atcgatggta gcagttgcat ctgaaaaaga acgtataaaa    540
aacgataagc tcattgttga aaattatgct aaggcagttg ccttgactc gttttcttgg     600
gtcgcattaa ttgataaagg gtctactgca ccagagctga taaagaaat tgattccgcc     660
gttgctttaa aaaagaaca agaagaacgt gaaagagcaa aaaagaaaca cgacgaagcc    720
```

```
attgctgctt tgaaaactga aacaatcaac aataaaacag ttgacactgc tacaggcgaa      780
atcatcacag aagaagcgcc aaaaacctgc aaaaaacaac aagagaaaac agttacgtta      840
agactaacag cagaacatca aaagttagtt gctctaaaca attttattat taataacggg      900
attcaagtgg aagtgattga atga                                             924

<210> SEQ ID NO 138
<211> LENGTH: 681
<212> TYPE: DNA
<213> ORGANISM: Enterococcus phage

<400> SEQUENCE: 138
atgaacctaa acaatgttta ttctgctgtt attaagagtt tgaaaaacaa ctcaataaca       60
gcagtaataa acgaagcaat aaatattgaa cgattaaaaa ccatgtattt tgattataca      120
gggccaagag aagttgaaat aagatttatt gatccgagaa aatttagtgt tgcccaacgt      180
cgatttatct ttgcaatgct agaggatata ttctctttca cagggcaaga aacggaagtg      240
ttaaaggaaa tgttctatct ccgttttgaa gcgctccagg gctatgaaat tagcctcagg      300
aacgattcag aaaacacaat ggacgacgca acaattttag cgaacattat tttaaatttc      360
atctttgaaa ataacattcc atttagaaaa ggctatgaca ttttgccagc aaatcaagag      420
tattactttt acaaatgtat cactaaacga gtttgttgca tatgtggaaa aactggtgca      480
gatattgacc atttcgataa agctctaggt cgtcgcaaaa gaaaaagcgt agaccataca      540
gaatacactt acgctggttt tgtcgatgc catcacaccg aaaaacataa cattggtatt       600
acagcattta agaaaaaata tcatgttaaa ggtatcaaat tgaaccaaga aactatcaaa      660
aaattacaca taggaggcta g                                                681

<210> SEQ ID NO 139
<211> LENGTH: 957
<212> TYPE: DNA
<213> ORGANISM: Enterococcus phage

<400> SEQUENCE: 139
gtggctgaaa ttagctggat aaaattaagt actagtttac ctgataataa gaaaatcaaa       60
cgaatacgca aattgccaga tggcgatcga gtaattttgt tttgggtatt tttactagct      120
cgtgctggtg aaagcaacca aaaaggcgga ttgttttaa ctgatacttt gcccatttca       180
gatgaagatt tagcagctga ttttgatttc acagttgagt ttgtaaaatt tgccattta      240 actttagaaa aatacagcat ggtaacaacc tatgaagatg taattttcat taagaattgg      300
gaagaatacc aggccattga tggtatggaa aaagtcaaag agcaaaatcg cattagacaa      360
gcgaaatacc gagaaaaaca aaagcaactg tcattaagta acgttactag taacgttaca      420
cgtaacgctg atgtaacgct gagtaacgga acagataaag atatagataa agaaatagat      480
aaagaaatag ataagataa taagaagag tcaaagaaac ctccttgtaa atattctgac       540
gaacatttac gtcttgctca aaattacaa aataattaa tcaatgattt tccaagtgaa       600
atgaaaaaag tgaagattga aaatgggca gatgttttca gattaatcga agaacgagat       660
caacaaacta ttgcagcaat tgactatgtt cttgattggt taccgacaaa ttcatttttgg     720 tttggaaaca ttagaagtgc ttctaagcta agaacgcagt ttgaaaaact aaaatttgaa      780
atcaagaatg aaaagaacg tggccaacaa cgaacgactt accaacgtca aatgttaagg      840
actgaaaatt taccagaatg ggcaaaagaa ccaaataaac agcaagaaga aaagctatcg      900
```

```
ccagaagaac aattggaact tgatagacaa ataaagagt acatggaggg gaaatag        957

<210> SEQ ID NO 140
<211> LENGTH: 525
<212> TYPE: DNA
<213> ORGANISM: Enterococcus phage

<400> SEQUENCE: 140
atgacaaagt acccaacaca agaattaaaa aacaaaagaa aagctcatgt cttatttatg     60
agtacagagg taatgaagaa tattttttgaa cttggttatc ctttcgaatt ttatgaagca   120
agtcaccagt ttgcgattca ctcaccgtta gggttattg attatttcgc tatctcaggc    180
acttgggttg ttcgcaaagg acaagataga ggtaagggta tacgaaaaat gaagcagtac   240
attaaaaaaa gagtaggtga ttacgtggaa aaagtaaaag tagtgaaatg tagtgggtat   300
cttgataaag agggtaatat cactaatcaa attaagcagg cgatgcattt tacagacgat   360
gaattagcga atcttgctgc agaagtggca ggtggaaagg tcgtaaacgt tgtaattcca   420
ccagaaaagc caaacaatt acgtgaaaaa gcgaagaag aatcatttca agaaaaaact    480
aagaagaaaa caaaaagtaa tcagtcgtgg atgaataaga aataa                   525

<210> SEQ ID NO 141
<211> LENGTH: 228
<212> TYPE: DNA
<213> ORGANISM: Enterococcus phage

<400> SEQUENCE: 141
atgaaattaa ctagtgtgac atttaaaccg tctgctgaac ggtttccacc aattgtggca     60
atagatttag accaattaac accagatgaa tacgtgacac ttagaaattt ggggtatgac   120
acgcaacttt ctaaaattac aaaaaggacc tttgaagagt tggaaggcca tttgggaatt   180
cgaggagacg ttgcaaagaa aaatggattt tatgtattag ttaaataa                228

<210> SEQ ID NO 142
<211> LENGTH: 429
<212> TYPE: DNA
<213> ORGANISM: Enterococcus phage

<400> SEQUENCE: 142
atgttttggt ttgataagca aaacgaacaa gttttgttta tggacaacag agaacattac     60
gaaaaattag acagtgggca tgttatcgat gttaatccta atctagttgc agattttaga   120
aagatgcctt ttgaagataa ctcgttttat catgttgtat ttgatcctcc gcatttattg   180
aggtgtggta ataacagctg gttggctaaa aaatatggca agctaaacga gaaaacttgg   240
aaagaagata tacaaaaagg ttttcatgag tgtatgaggg ttttgaagcc caatgggacg   300 ttagtttttta aatggaacga ggaacaaatc aagttatctg aaatattaag cacaattgat   360
tgtgagccat tgtacggcaa taaaagagca aaaacacatt ggttagtatt tatgaaagcg   420
ggtgaataa                                                           429

<210> SEQ ID NO 143
<211> LENGTH: 321
<212> TYPE: DNA
<213> ORGANISM: Enterococcus phage

<400> SEQUENCE: 143
atgaatgagc aaataaattt gcttgagtta gataatgata aactttggca attttatggg     60
cattattgta atgacgattg gtccgctaag acagagaccg tgaatggtgt tactgacata   120
```

```
gtgctaggtt ttagagttaa actatcgaaa aatgagctga gaaaaatatg cagagatgcc    180
attgaaataa gcagaattaa gtatggatat tctgtcaggt ttttaacaaa taatgtaaag    240
aaagagctgt tcgttcgttt tgacaactac accactagta aaaaaagaga tgtctttgaa    300
catataaatt tatatttta a                                               321

<210> SEQ ID NO 144
<211> LENGTH: 411
<212> TYPE: DNA
<213> ORGANISM: Enterococcus phage

<400> SEQUENCE: 144
atgatcccaa aatttagagc aagagatcaa agaggtaact ggcatattgg acttctaact     60
tttatgtttg gccagtatgc catcgtaaat gaatcagatg aaaattcggt ttatctgatt    120
gataaggaaa cagtcggaca atcaacaggg ttgaaagaca agaacggcgt tgaaattttt    180
gagggtgata ttttgaaaat aatagaagta acaaatgaag gtatttcaga atacatcact    240
gatgttattt gggaagactg ttcattcgtg tttaaaagtg agggtgtaga ttactatgac    300
tcttttttag gggcattttc aggagatcca aataagacat atccactttt tgaactatta    360
gtcatcggaa atgtatggga taacttaaaa ctattggaga gaacagaatg a             411

<210> SEQ ID NO 145
<211> LENGTH: 168
<212> TYPE: DNA
<213> ORGANISM: Enterococcus phage

<400> SEQUENCE: 145
atgaaacgat taaaaataag ctatatagat ttagctgtaa taattgaaag catctattac     60
ggagaagatg aagatgtatc tgatattgat gacttattga aatatttgcg taataacgga    120
catctgtcta ctgttttaac agtttcaagg gggattagcg atgaataa                 168

<210> SEQ ID NO 146
<211> LENGTH: 606
<212> TYPE: DNA
<213> ORGANISM: Enterococcus phage

<400> SEQUENCE: 146
atgaataaac aagaatttat tgaaacgtta gaagaaatta gagcaaatat aaatcgcaac     60
gcagaaatta gtgattatac tgattttcg cgaggtaaaa agacgcata taacaacgcg    120 attggcttag caaacagat agacgaacca gaaaaagtcg tggtaccgaa gtttgttgcg    180
gaatggcttg ataaacataa gtattccact gatataattg atctcttttt aagcgttgag    240
tacgcaactg attcagatgg gtttgttgct gaaaaatggg attacagcgg agaatttat    300 gattggttga gtaatagtgc agatatacag tttacgttgt gcgacgctat gaggtatggc    360
tacgaagtcg agaaagagcc aaccattcac gagcttaaaa ttttaccaga atactttgaa    420
gcggttgttt cagggaataa acgttttgaa atccgtaaaa atgaccgtaa ctataaaaaa    480
ggtgatatct tacgcttaaa cgaatatcaa gagggacaat atacaggtga tgtccatgtc    540
tcagaaataa cgtacattac agattatgcc caacaagatg gttatgtcgt cttaggaatt    600
aagtga                                                               606

<210> SEQ ID NO 147
<211> LENGTH: 486
<212> TYPE: DNA
```

<213> ORGANISM: Enterococcus phage

<400> SEQUENCE: 147

| | |
|---|---|
| atgaaaactg atttaaccag acaagctgag aaatgcttgt ggcactatac caacaaaatg | 60 |
| ggagtattcg gctgttttga ggtaaccatt ggctggtttg gcaaggaaag agtcgacttt | 120 |
| atgacttatt ctactgacaa cactattaga tgttatgaaa taaagtaac gttggcagac | 180 |
| ttaaaaagtt ccgcaaaaca aacgttttta ggtgattata actatttagt tgtcactaac | 240 |
| gaattatggg aaaagattca agccaatcca gatttaaaat ggaaatatag taatcaggga | 300 |
| atactaattt tttctgaatt aagacacaac ttaggcatta caagtgtcaa aaaagcgaaa | 360 |
| aagcaaaatg tcacattagg aacgcgagca acagttttag aaagtatggt gcgatctttg | 420 |
| aatcgagaag ttgagaaatt ttacaaggta aatccttttt ggggattaag tgaggaggtc | 480 |
| aaataa | 486 |

<210> SEQ ID NO 148
<211> LENGTH: 183
<212> TYPE: DNA
<213> ORGANISM: Enterococcus phage

<400> SEQUENCE: 148

| | |
|---|---|
| atggaacaac tcttattaac aaaaactggt gaaaacgaaa tcggtataaa tgctacagga | 60 |
| atggatgata tgaaattgt cttcacgtta gctgctgctt taattggata cagcaaggaa | 120 |
| ttgggactaa cagaagcaat actaaacgaa agtatgtccg tgctgtggaa agatggtgaa | 180 |
| taa | 183 |

<210> SEQ ID NO 149
<211> LENGTH: 186
<212> TYPE: DNA
<213> ORGANISM: Enterococcus phage

<400> SEQUENCE: 149

| | |
|---|---|
| atgaaacgca attggaaaag agtaataaat aaagttagtg gcattgcaat aatgattctt | 60 |
| gtagcaaaag tagccgtgag ttatttcgtg tatagcaatg acataacaag cagtgacctc | 120 |
| gtttatttcc tttcatgctc gtttattttg gggttagggc tatatttagg gggttcaagt | 180 |
| gtatga | 186 |

<210> SEQ ID NO 150
<211> LENGTH: 201
<212> TYPE: DNA
<213> ORGANISM: Enterococcus phage

<400> SEQUENCE: 150

| | |
|---|---|
| atgagttatc cagaagttta tatcttagga aggcaagttg atggagtgta cgttgagtat | 60 |
| tcagagccat atctttcaaa aatagaagct gaacttgata agcatcacta tgaaattggc | 120 |
| caatcaatgt cacatgatgc tggctcttgg aaaattttaa agtatggcag accaattaca | 180 |
| ctggaggtgc aacatgggta a | 201 |

<210> SEQ ID NO 151
<211> LENGTH: 120
<212> TYPE: DNA
<213> ORGANISM: Enterococcus phage

<400> SEQUENCE: 151

| | |
|---|---|
| atggcagacc aattacactg gaggtgcaac atgggtaaga aaaaatcaaa aattaaaaag | 60 | aaaaagcgtc gcttgcaaga aaaggcgatt gcaaacggca ctcaaaattc taaaaaataa    120

<210> SEQ ID NO 152
<211> LENGTH: 417
<212> TYPE: DNA
<213> ORGANISM: Enterococcus phage

<400> SEQUENCE: 152
ttgattcaat tgttaaaaga agttgatttc agtcagacta gagccaatgc gagagccgtg     60
ttgaaaaatt ttagacgttt ggaccgaata gctggtcgtt ccttagtaga tgttcgatca    120
ccaatcatta cagacatgcc caaaggtata aagcatggga acaaagcaga ggatgcgttg    180
atccagatga tggatgttga agcagaacgt gatgcaattt aacagctttt gatgtcctta    240
agcataataa gtcgtcaaat tcttcactac agtttctgtg tgcaggacca ttactctaat    300
tataaaatcg caagagaagt tggctattct gaaagaagta ttcaaagaat gaaatcagaa    360
gctttgattg aattcgcaga agcttaccgc aatggcaaaa taattgcata taaataa       417

<210> SEQ ID NO 153
<211> LENGTH: 450
<212> TYPE: DNA
<213> ORGANISM: Enterococcus phage

<400> SEQUENCE: 153
atggagacta acaatacatt ttcgaatcta ttaaaaaatt tcgactatcc tagaatcgaa     60
ccatctatga aatatgcgga aaaactagag actggtagta attggcttgg agacattaat    120
agagaaaaga agcagctaca agaactgcag aagttagcaa atgaatctac attaaaaagt    180
gaagaacttt taaacagat tgctgaaaat acatcttata ttaaagactt agtcatgata    240
aatagagaaa cgcaattaaa tacagaagaa ttaacttacg ttatgaaatc aatttacaaa    300
gtttctaagg ctgagaataa gcaagaggct gatagtttgt tttctcaagc aattcaagtc    360
ataaatgatt ctggagaagc tgctggaaat atagctaatt taacttcttt attgcttggc    420
atatatacat ttgtttctac aataatataa                                     450

<210> SEQ ID NO 154
<211> LENGTH: 522
<212> TYPE: DNA
<213> ORGANISM: Enterococcus phage

<400> SEQUENCE: 154
atgcatattg aaaaaatgaa attatcagat ttaaggccgg cggaatataa tccaagagta     60
aaattgaatc caggtatggc agaatatgaa aaacttaaac aatcaatttt agaatttggc    120
tttgttgatc ctcccatttt taataaaaat acaggaaact tggttggtgg acatcaacgc    180
gttactgttg caaaagaatt ggggctattt gatgagatag aggtttctgt ggttgattta    240
ccattggata aagagaaagc tctaagcata gctttaaata agatttctgg aaattgggat    300
gaagataaac taacagaatt acttaatgaa ctaactgcag ataatttgga gttaacaggg    360
tttgacaacg aagaattaga aattttaatt gaagatgctg acattccaaa ttttgaacca    420
ggtagtattg atgaccaagg agatttgacg aaacttgaac cgaaatttgt taaatgccca    480
tgttgtggag aggagttcga tttaagagat gttgaaagtt ga                       522

<210> SEQ ID NO 155
<211> LENGTH: 609
<212> TYPE: DNA

<213> ORGANISM: Enterococcus phage

<400> SEQUENCE: 155

| | |
|---|---|
| atgttgaaag ttgattgggc tactcatgaa gctacaaagt atgcttgcac gcactttcat | 60 |
| tacagcaaaa gtgtgcctgt cggaaagctc attaaaatag gagcatggga agatggccaa | 120 |
| tttataggag tagtaatttt tagtagaggt gcaaataaga gcataggaag cccatatgga | 180 |
| ttggaacaaa cagaatgctg tgaactaact agggttgctt taaccaatca caagacgttt | 240 |
| gtatctgaaa ttttggccaa agcaattaag ttcctaaaag aatttaatcc aagcatgcaa | 300 |
| ttaatagtaa gctatgcaga tacgaccaa aaccatcatg gaggtatcta tcaagcaaca | 360 |
| aactggatat atactggaaa gacagatggg gaacgctatt tcattgttaa tggaaaaaag | 420 |
| acacatccta gtctatcca tgctaagtat gggacaggat ctcaaaggtt agaattttg | 480 |
| cataaacatg tggatccaaa agcttccatt tatgaatcaa aggtaaaca taagtattta | 540 |
| atgccactaa ataaaagat acgtaaaaaa atcattaaat tatcaaaacc ttatccaaaa | 600 |
| gctaaataa | 609 |

<210> SEQ ID NO 156
<211> LENGTH: 189
<212> TYPE: DNA
<213> ORGANISM: Enterococcus phage

<400> SEQUENCE: 156

| | |
|---|---|
| atggaaacat ttgattatga agttcagcaa gctttagaaa agcaaaagat tgcggaagaa | 60 |
| aacaacaaga ttatcagggc tgcaaaggct caatggataa gtaactttaa agcaggtcat | 120 |
| atcaaattga atacagttaa ggacctaaaa gacttaattg aaattgaaag tcatttgaaa | 180 |
| gagctatag | 189 |

<210> SEQ ID NO 157
<211> LENGTH: 921
<212> TYPE: DNA
<213> ORGANISM: Enterococcus phage

<400> SEQUENCE: 157

| | |
|---|---|
| atggcaaaag aaaagaatga aaagaaagct aattccgata agggtgaaat caagaaaacg | 60 |
| aatttaaaaa aatgtttttt tataacgcca attggagaaa agaattctaa tgaatttaag | 120 |
| aagctaaaag ctatagtaga aaatgtatta aataaagtgt tggaaaaata tgattacgag | 180 |
| ttaataatag cccatgaaat acattctatg ggttcgattg gagatcaagt attcacaaat | 240 |
| ataattggag ctgatttagt tatatctaac ttatctgggt ggaacgctaa tgtaatgtat | 300 |
| gaaacggcag tagctcattc ttttgggaaa cctactataa tgatttgcga gagtggaaca | 360 |
| gaacttccat ttgatttaat aaatgataga acaatatttt tcgaggatac tatcgaagga | 420 |
| actggagcct aatagaaga gttggataaa aagattccta aaattagtga agactctacg | 480 |
| gctgataatc cagttacgag agtaattcgc agaaaggctc tcgaagatga tttgaagggt | 540 |
| gaaacagaca tgattcaag gattctggga ctacttcttg atatggataa acgattaagc | 600 |
| atgtacgaag atagtaacat aatagaaaag aaaaaaataa atactggaaa tattgaaagg | 660 |
| attcgtgcaa aaatatatta caaaaatgaa ggaaatatca atgttattga tgaacttgaa | 720 |
| ggctatttat ttgaaaaata tagagacact gtacaaatcg tttcggtaac atcaggaaat | 780 |
| aggtatgaag atagaaatag tgaagtgatg aaagtcataa tagtaaattc tttgtattct | 840 |
| ccagcaaaga tattcaaaga tattgagatt acactaggaa aactaggaat ggttgatatt | 900 | tctgtcaaag tttttccgta a                                              921

<210> SEQ ID NO 158
<211> LENGTH: 204
<212> TYPE: PRT
<213> ORGANISM: Enterococcus phage

<400> SEQUENCE: 158

Met Ser Leu Asn Ser Leu Leu Leu Leu Ile Phe Gly Gly Ile Ala
1               5                   10                  15

Ile Ile Gly Tyr Phe Val Lys Asp Leu Pro Asn Leu Phe Arg Glu Leu
            20                  25                  30

Ala Val Glu Glu Ser Arg Gly Lys Asn Glu Arg Glu Ile Gln Lys Glu
        35                  40                  45

Ala Phe Phe Arg Gln Ile Lys Gly Ser Asp Ile Asp Glu Ala Phe Asn
    50                  55                  60

Tyr Trp Thr Ser Leu Met Val Asp Met Asp Asn Lys Ile Asn Gln Ile
65                  70                  75                  80

Gly Thr Ala Ser Gly Lys Lys Glu Phe Val Lys Met Gln Gln Lys Val
                85                  90                  95

Leu Met Tyr Gly Ser Asn Gly Thr Val Thr Ile Leu Ser Ser Met Met
            100                 105                 110

Gln His Val Tyr Arg Arg Gly Glu Leu Lys Asn Thr Val Lys Val Ser
        115                 120                 125

Phe Gly Asp Gln Asp Ser Thr Lys Glu Asn Ile Gln Asn Tyr Met Leu
    130                 135                 140

Met Phe Tyr Ile Ala Tyr Leu Ile Ser Ser Leu Lys Lys Asp Phe Thr
145                 150                 155                 160

Gly Tyr Ser Ile Asp Pro Ile Glu Ile Leu Leu Ile Lys Ile Asn Asp
                165                 170                 175

Ile Asp Ser His Lys Asn Lys Pro Leu Phe Glu Gln Ala Glu Lys Asn
            180                 185                 190

Val Arg Lys Glu Leu Lys Lys Leu Gly Val Thr Ile
        195                 200

<210> SEQ ID NO 159
<211> LENGTH: 52
<212> TYPE: PRT
<213> ORGANISM: Enterococcus phage

<400> SEQUENCE: 159

Met Leu Leu Val Ile Ala Phe Ala Phe Ile Leu Leu Lys Ile Ala Gly
1               5                   10                  15

Phe Val Gln Leu Thr Trp Asn Glu Val Ile Leu Cys Glu Leu Ile Leu
            20                  25                  30

Leu Met Cys Ser Ile Leu Glu Leu Ile Leu Ile Tyr Lys Lys Ile Asn
        35                  40                  45

Asn Arg Phe Lys
    50

<210> SEQ ID NO 160
<211> LENGTH: 112
<212> TYPE: PRT
<213> ORGANISM: Enterococcus phage

<400> SEQUENCE: 160

Leu Glu Asn Asn Ser Lys Ser Ala Asp Asp Lys Val Ile Lys Asn Tyr

```
1               5                   10                  15
Glu Glu Thr Leu Ser Ile Ile Phe Lys Lys Ile Pro Asp Ser Asn Glu
                20                  25                  30
Pro Leu Ile Tyr Met Val Ala Ser Glu Ile Gly Phe Glu Ile Leu Asp
                35                  40                  45
Leu Lys Leu Ser Ile Asn Ala Leu Leu Glu Ser Ala Cys Tyr Ala Gly
 50                  55                  60
Ile Leu Ala Leu Ser Arg Thr Met Val Glu Asn Tyr Ile Tyr Leu Met
 65                  70                  75                  80
Tyr Ile Leu Glu Gln Asp Ser Phe Lys Arg Ser Lys Ala Tyr Gln Leu
                85                  90                  95
Asn Met Tyr Arg Asp Ile Lys Lys Gln Tyr Glu Ala Gln Lys Lys Glu
                100                 105                 110
```

<210> SEQ ID NO 161
<211> LENGTH: 104
<212> TYPE: PRT
<213> ORGANISM: Enterococcus phage

<400> SEQUENCE: 161

```
Met Ser Glu Gln Asp Gln Ser Phe Asn Glu Gln Ile Val Leu Tyr Glu
 1               5                   10                  15
Gln Asn Glu Pro Lys Ile Ile Glu Tyr Leu Glu Glu Leu Asp Ser Leu
                20                  25                  30
Tyr Gly His Arg Leu Val Pro Trp Tyr Asn Asp Asp Glu Glu Thr Lys
                35                  40                  45
Gly Ile Tyr Lys Leu Phe Glu Arg Leu Asp Lys Ser Asp Trp Tyr Asp
 50                  55                  60
Gly Ile Tyr Arg Tyr Leu Cys Met Glu Ser His Gly Asn Asn Gly Leu
 65                  70                  75                  80
Lys His Phe Glu Met Leu Glu Asp Gly Thr Ala Lys Leu Lys Pro Thr
                85                  90                  95
Thr Leu Asp Glu Lys Thr Asn Gln
                100
```

<210> SEQ ID NO 162
<211> LENGTH: 269
<212> TYPE: PRT
<213> ORGANISM: Enterococcus phage

<400> SEQUENCE: 162

```
Met Ala Arg Lys Arg Asp Pro Arg Arg Asp Gln Ala Lys Glu Thr Trp
 1               5                   10                  15
Leu Lys Ser Asn Gly Lys Lys Val Leu Lys Glu Leu Ala Asn Glu Leu
                20                  25                  30
Asn Val Ser Asp Ser Gln Ile Arg Lys Trp Lys Ser Ile Asp Lys Trp
                35                  40                  45
Ala Asp Glu Leu Lys Gly Asn Val Thr Asn Ser Lys Ser Asn Val Thr
 50                  55                  60
Asn Lys Gly Gly Ala Pro Pro Gly Asn Lys Asn Ala Val Gly Asn Lys
 65                  70                  75                  80
Gly Asn Lys Ser Ala Ser Pro Lys Arg Asn Lys Asn Ala Val Lys
                85                  90                  95
Thr Gly Glu Tyr Glu Thr Ile Phe Ala Asp Leu Leu Ser Asp Glu Glu
                100                 105                 110
Lys Asp Ile Tyr Ser Lys Leu Asn Asp Asp Pro Phe Phe Ile Leu Asp
```

```
              115                 120                 125
Glu Glu Ile Arg Ile Leu Lys Ile Arg Gln Tyr Arg Met Leu Lys Arg
        130                 135                 140

Ile Lys Asp Ala Glu Ala Gly Leu Asn Asp Glu Val Glu Arg Leu
145                 150                 155                 160

Gln Gln Leu Arg Lys Val Lys Glu Pro Ser Val Ile Asp Gly Lys Met
                165                 170                 175

Val Thr Val Lys Arg Glu Val Leu Lys Asp Val Gln Ile Thr Arg Lys
            180                 185                 190

Thr Phe Arg Lys Leu Asp Asp Ile Leu Ala Ile Glu Asp Ala Leu Thr
        195                 200                 205

Arg Val Ser Asn Gln Leu Val Lys Ala Ile Lys Gln Gln Lys Glu Leu
    210                 215                 220

Ala Met Ser Asp Ser Arg Ile Ser Leu Leu Asn Ala Gln Val Ala Lys
225                 230                 235                 240

Ile Arg Gln Asn Thr Asp Glu Thr Glu Ser Thr Glu Ser Lys Leu Asp
                245                 250                 255

Glu Leu Met Ser Met Ile Ser Gly Glu Leu Asn Glu Ser
            260                 265

<210> SEQ ID NO 163
<211> LENGTH: 615
<212> TYPE: DNA
<213> ORGANISM: Enterococcus phage

<400> SEQUENCE: 163
atgagtttaa atagtctatt gttgttattg attttggtg gtattgcaat tattggttat      60
tttgtaaaag atttaccaaa tttgtttagg gaactagcag ttgaagaatc gcgaggaaaa    120
aacgaaagag aaattcaaaa agaggctttc tttcgtcaaa tcaagggttc agatatagat    180 gaagcttta actattggac tagcttgatg gttgatatgg ataataagat aaatcagatt    240
ggaacggcat ctggtaaaaa agagttcgta aaaatgcaac aaaaggtttt gatgtacggt    300
tcgaatggca cagtcactat cctttcttct atgatgcagc atgtttatag acggggagaa    360
ttgaagaata cagtaaaagt ttcatttgga gatcaagata gtacaaagga aaatatacaa    420
aactatatgt taatgtttta cattgcgtat ctaataagtt cattaaaaaa agactttaca    480
ggatacagta ttgatcctat agaaattcta ttaattaaaa taaatgatat agatagtcat    540
aagaataaac cactttttga caagctgaa aaaatgttc gaaagaatt aagaagcta    600 ggggtgacta tctag                                                     615

<210> SEQ ID NO 164
<211> LENGTH: 159
<212> TYPE: DNA
<213> ORGANISM: Enterococcus phage

<400> SEQUENCE: 164
atgctacttg taatagcttt tgcttttata ttattaaaga tagcaggttt tgtacaattg      60
acttggaatg aagtgatact atgtgaatta attctactga tgtgttctat tttagaactc    120
atattaattt acaagaaaat aaataataga tttaaatag                            159

<210> SEQ ID NO 165
<211> LENGTH: 339
<212> TYPE: DNA
<213> ORGANISM: Enterococcus phage
```

<400> SEQUENCE: 165

```
ttggaaaata attcaaagag tgctgatgac aaagtaatca aaaactatga agagacgttg      60
agtattattt ttaaaaaaat accggactca aatgagcccc tgatctatat ggtcgcaagt     120
gaaataggtt tcgagattct agatttaaaa ctgtcaataa atgctttatt agaaagtgct    180
tgttatgctg gtattttagc tttatccaga acaatggtgg aaaattatat ttatttaatg    240
tatatactcg aacaagattc ttttaaaaga agcaaagcgt atcaattgaa catgtataga    300
gatataaaaa aacaatatga ggcgcaaaaa aaagaataa                           339
```

<210> SEQ ID NO 166
<211> LENGTH: 315
<212> TYPE: DNA
<213> ORGANISM: Enterococcus phage

<400> SEQUENCE: 166

```
atgtctgaac aagatcaaag ctttaatgaa caaattgttt tatatgaaca aaatgagcct     60
aaaattatag aatatttaga agaacttgat tcactctatg ggcatagatt agtaccatgg    120
tacaatgatg acgaagaaac aaaaggaata tataagctat ttgagcgttt agataagtcg    180
gattggtatg atggtatata tagatactta tgtatggaat cccatggtaa taacggatta    240
aaacattttg aaatgttaga agatggtact gcaaaattaa aaccaactac gttggatgaa    300
aaaacaaatc agtag                                                     315
```

<210> SEQ ID NO 167
<211> LENGTH: 810
<212> TYPE: DNA
<213> ORGANISM: Enterococcus phage

<400> SEQUENCE: 167

```
atggctagaa aaagagatcc acgtcgtgac caggctaaag aaacttggtt aaagtcaaac     60
ggtaaaaagg ttcttaaaga attagctaat gaattaaatg tttcagattc ccaaataaga    120
aaatggaaat cgatagataa atgggctgat gaattaaaag gtaatgttac caattcaaaa    180
agtaacgtta ctaataaagg tggagcgccg cctggaaaca aaaatgccgt aggtaacaaa    240
gggaataaaa gtgcctcgcc accaaaaaga ataagaatg cggtaaaaac aggtgaatat    300
gagacaatat ttgctgactt actatctgac gaagaaaagg acatctattc taaactgaat    360
gatgatcctt ttttatttt ggatgaagaa ataagaatcc tgaaaattcg ccaatataga    420
atgcttaaac gcataaaaga tgcagaggct ggcttaaatg atgaagaagt tgaacgtttg    480
cagcagcttc ggaaagttaa agagccatcg gtaattgatg ggaaaatggt tactgtcaaa    540
agagaagttt tgaaagatgt acaaataact cgtaaaacat ttagaaagtt agatgacatt    600
ttagctatag aagatgcgtt gactcgcgtt agcaatcaac tagtcaaagc gattaagcaa    660
caaaaagaac ttgctatgag tgatagtcgt atttcgctac taaatgcaca ggtcgcaaaa    720
ataagacaga atactgatga gacagaatct acagagtcta gcttgatga attgatgtct    780
atgattagtg gtgaattaaa tgagtcttaa                                     810
```

<210> SEQ ID NO 168
<211> LENGTH: 157
<212> TYPE: DNA
<213> ORGANISM: Enterococcus

<400> SEQUENCE: 168

```
tctagatttt tccttgagaa taaaaggttt gttttttagaa ctatcctttt ttcaagattt     60
```

```
cgtgtaaaat agcttatgat gatcagacga tttttagtaa cgtctatcac atataaaaca    120
aacaataaaa tttatatttt taggaggaac attcaaa                             157
```

<210> SEQ ID NO 169
<211> LENGTH: 316
<212> TYPE: DNA
<213> ORGANISM: Enterococcus phage

<400> SEQUENCE: 169

```
atggataaaa aggaacaagc aaagaaatat tatgaaaaag gttggaaata caaggatatt     60
tccgaaaagc tttctgtacc tctcaacaca ttgaagtcat ggagaaaacg tgataaatgg    120
gaaagagggg gtgcaaccaa agaggtgcaa cctacaaata ggggtgcacc taaaggtaat    180
caaaatgcta taggcaataa aggtaatagt cgagcctcgc caccaaaaag aaataagaat    240
gctgttaaaa ctggcgaata cgaaacaata tttgccgata tgttatctga cgaagaaaag    300
gacatctatt ctacta                                                    316
```

<210> SEQ ID NO 170
<211> LENGTH: 479
<212> TYPE: DNA
<213> ORGANISM: Enterococcus phage

<400> SEQUENCE: 170

```
tgaatgatga tccttttttt attttggatg aagaaataag aatcctgaaa attcgccaat     60
atagaatgct taaacgcata aaagatgcag aggctggctt aaatgatgaa gaagttgaac    120
gtttgcagca gcttcgcaaa gttaaagagc catcggtaat tgatgggaaa atggttactg    180
ttaagagaga agtttttaaa gatgtacaag tcactcgtaa acatttagaa agttagatg    240 acatcctggc tattgaagat gcgttgactc gcgttagcaa tcaattaata aaggcgatta    300
agcaacaaaa agaattattg tcgacagata aaaaatctct tttaatggag gctcaaattg    360
agaagataaa gcttgagaca gacaaattaa gtggcggatc atctaacgat gaagctgact    420
cttggaaaca agcagttata aatgcagcaa ataagcgggc ggtggaagaa atgaataa      479
```

<210> SEQ ID NO 171
<211> LENGTH: 907
<212> TYPE: DNA
<213> ORGANISM: Enterococcus phage

<400> SEQUENCE: 171

```
aaaatcgcaa gagaagttgg ctattctgaa agaagtattc aaagaatgaa atcagaagct     60
ttgattgaat tcgcagaagc ttaccgcaat ggcaaaataa ttgcatataa ataatttttg    120
gcggtttttt ggcggaaagt tggcggtttt tatacgaatt tgagtgctaa tatagtaata    180
tcgaaagtca agaaatggac cattacac aacactttct ggtttagtca ccgtttgatt    240
tgactttcga tggtcacttg cagacatacg ttctcaataa aatgaagtga ggtgaataac    300
ctcctctttt ttctacaagt ttgcaagtga cacgttaatg aatatagct cagttggtga    360 gcatacgact gttaatcgta gggtcatgag ttcgagtctc gttattccag taagtggcat    420
aagctgctta aataaaaata tcgtcaataa ttcagtgtaa ctacctttac gatcgaatga    480
cggttaagat ttccctccta tctgagacta cacaaaaagt gtagtcttcc ttttatttaa    540
taaaattgat attatgaatg taaaaggagg tttattatgg agactaacaa tacattttcg    600
aatctattaa aaaatttcga ctatcctaga atcgaaccat ctatgaaata tgcggaaaaa    660
```

| | |
|---|---|
| ctagagactg gtagtaattg gcttggagag gagcatggga agatggccaa tttataggag | 720 |
| tagtaatttt tagtagaggt gcaaataaga gcataggaag cccatatgga ttggaacaaa | 780 |
| cagaatgctg tgaactaact agggttgctt taaccaatca caagacgttt gtatctgaaa | 840 |
| ttttggccaa agcaattaag ttcctaaaag aatttaatcc aagcatgcaa ttaatagtaa | 900 |
| gctatgc | 907 |

<210> SEQ ID NO 172
<211> LENGTH: 451
<212> TYPE: DNA
<213> ORGANISM: Enterococcus phage

<400> SEQUENCE: 172

| | |
|---|---|
| gaggtggtgt tatatgtcag atggataaaa aggaacaagc aaagaaatat tatgaaaaag | 60 |
| gttggaaata caaggatatt tccgaaaagc tttctgtacc tctcaacaca ttgaagtcat | 120 |
| ggagaaaacg tgataaatgg aaagaggggg gtgcaaccaa agaggtgcaa cctacaaata | 180 |
| ggggtgcacc taaaggtaat caaaatgcta taggcaataa aggtaatagt cgagcctcgc | 240 |
| caccaaaaag aaataagaat gctgttaaaa ctggcgaata cgaaacaata tttgccgata | 300 |
| tgttatctga cgaagaaaag gacatctatt ctactatgaa tgatgatcct tttttttatt | 360 |
| tggatgaaga aataagaatc ctgaaaattc gccaatatag aatgcttaaa cgcataaaag | 420 |
| atgcagaggc tggcttaaat gatgaagaag t | 451 |

<210> SEQ ID NO 173
<211> LENGTH: 918
<212> TYPE: DNA
<213> ORGANISM: Enterococcus phage

<400> SEQUENCE: 173

| | |
|---|---|
| aagattgcta gagaagttgg atattctgaa agaagtattc aacgcatgaa atcagaagct | 60 |
| ttgattgaat cgcggaagc ttaccgaaat ggcaaaataa ttgcatataa ataattttg | 120 |
| gcggttttt ggcggaaagt tggcggtttt tatacgaatt tgagtgctaa tatagtaata | 180 |
| tcgaaagtca agaaatagaa cacattacac aacactttct cgtttagtca ccgttcactt | 240 |
| tgtctttcga tggtcacttg cagacttacg ttctcaataa aatgaagtga ggtgaataac | 300 |
| ctcctctttt ttctacaagt ttgcaaggga cactttaatg gaatatagct cagttggtga | 360 |
| gcgtacgact gttaatcgta gggtcatgag ttcgagtctc gttattccag taagtagcta | 420 |
| tgctacttaa ataaaaaaat cgtcaataag tcaaatgtaa ctacctttac gatcagatga | 480 |
| cggttaagat tttccctcct atctgagact gcacttctga gtgtggtctt ttttcttaa | 540 |
| aaattcatag ctaatcaaat ttcactttt acattcttt tatattagct tatagtatta | 600 |
| tgtagtaagt aaaaaatatg aaaataagtg gagtgaaaat ttaatgagtt taaatagtct | 660 |
| attgttgtta ttgattttg gtggtagaag cgtttgtctt acaataaaca aatatacata | 720 |
| aaaacaatta ggagagagaa catgaaaagc tattggtatg tatcgttaac acatgaatat | 780 |
| ccacagccga accgctcaac tgattcagta cgtgtctaaa ggccgcacaa taaaagtgta | 840 |
| gccttttatt ttattcctcg tgttgaaaga aattagtaat tagtagataa ttaattcaaa | 900 |
| agacagatgg aggtataa | 918 |

<210> SEQ ID NO 174
<211> LENGTH: 480
<212> TYPE: DNA
<213> ORGANISM: Enterococcus phage

<400> SEQUENCE: 174

| gtgttaatgg atggctagaa aaagagatcc acgtcgtgac caggctaaag aaacttggtt | 60 |
| aaagtcaaac ggtaaaaagg ttcttaaaga attagctaat gaattaaatg tttcagattc | 120 |
| ccaaataaga aaatggaaat cgatagataa atgggctgat gaattaaaag gtaatgttac | 180 |
| caattcaaaa agtaacgtta ctaataaagg tggagcgccg cctggaaaca aaaatgccgt | 240 |
| aggtaacaaa gggaataaaa gtgcctcgcc accaaaaaga aataagaatg cggtaaaaac | 300 |
| aggtgaatat gagacaatat ttgctgactt actatctgac gaagaaaagg acatctattc | 360 |
| taaactgaat gatgatcctt ttttattttt ggatgaagaa ataagaatcc tgaaaattcg | 420 |
| ccaatataga atgcttaaac gcataaaaga tgcagaggct ggcttaaatg atgaagaagt | 480 |

<210> SEQ ID NO 175
<211> LENGTH: 918
<212> TYPE: DNA
<213> ORGANISM: Enterococcus phage

<400> SEQUENCE: 175

| aaaatcgcaa gagaagttgg ctattctgaa agaagtattc aaagaatgaa atcagaagct | 60 |
| ttgattgaat tcgcagaagc ttaccgcaat ggcaaaataa ttgcatataa ataattttg | 120 |
| gcggttttt ggcggaaagt tggcggtttt tatacgaatt tgagtgctaa tatagtaata | 180 |
| tcgaaagtca agaaatgga cacattacac aacactttct ggtttagtca ccgtttgatt | 240 |
| tgactttcga tggtcacttg cagacatacg ttctcaataa aatgaagtga ggtgaataac | 300 |
| ctcctctttt ttctacaagt ttgcaagtga cacgttaatg gaatatagct cagttggtga | 360 |
| gcgtacgact gttaatcgta gggtcatgag ttcgagtctc gttattccag taagtagcta | 420 |
| tgctacttaa ataaaaaaat cgtcaataag tcaaatgtaa ctacctttac gatcagatga | 480 |
| cggttaagat tttccctcct atctgagact gcacttctga gtgtggtctt ttttcttaa | 540 |
| aaattcatag ctaatcaaat ttcactttt acattcttt tatattagct tatagtatta | 600 |
| tgtagtaagt aaaaaatatg aaaataagtg gagtgaaaat taatgagtt taaatagtct | 660 |
| attgttgtta ttgattttg gtggtagaag cgtttgtctt acaataaaca aatatacata | 720 |
| aaaacaatta ggagagagaa catgaaaagc tattggtatg tatcgttaac acatgaatat | 780 |
| ccacagccga accgctcaac tgattcagta cgtgtctaaa ggccgcacaa taaaagtgta | 840 |
| gccttttatt ttattcctcg tgttgaaaga aattagtaat tagtagataa ttaattcaaa | 900 |
| agacagatgg aggtataa | 918 |

<210> SEQ ID NO 176
<211> LENGTH: 480
<212> TYPE: DNA
<213> ORGANISM: Enterococcus phage

<400> SEQUENCE: 176

| gtgttaatgg atggctagaa aaagagatcc acgtcgtgac caggctaaag aaacttggtt | 60 |
| aaagtcaaac ggtaaaaagg ttcttaaaga attagctaat gaattaaatg tttcagattc | 120 |
| ccaaataaga aaatggaaat cgatagataa atgggctgat gaattaaaag gtaatgttac | 180 |
| caattcaaaa agtaacgtta ctaataaagg tggagcgccg cctggaaaca aaaatgccgt | 240 |
| aggtaacaaa gggaataaaa gtgcctcgcc accaaaaaga aataagaatg cggtaaaaac | 300 |
| aggtgaatat gagacaatat ttgctgactt actatctgac gaagaaaagg acatctattc | 360 |

```
taaactgaat gatgatcctt tttttatttt ggatgaagaa ataagaatcc tgaaaattcg    420
ccaatataga atgcttaaac gcataaaaga tgcagaggct ggcttaaatg atgaagaagt    480
```